United States Patent
Lee et al.

(10) Patent No.: US 10,344,030 B2
(45) Date of Patent: Jul. 9, 2019

(54) HETEROCYCLIC COMPOUND AND ORGANIC LIGHT EMITTING DEVICE USING SAME

(71) Applicant: HEESUNG MATERIAL LTD., Yongin, Gyeonggi-do (KR)

(72) Inventors: Jung-Hyun Lee, Osan (KR); Kee-Yong Kim, Suwon (KR); Yong-Hoon An, Hwaseong (KR); Jin-Seok Choi, Suwon (KR); Dae-Hyuk Choi, Yongin (KR); Sung-Jin Eum, Yongin (KR); Joo-Dong Lee, Seongnam (KR)

(73) Assignee: HEESUNG MATERIAL LTD., Yongin (KR)

( * ) Notice: Subject to any disclaimer, the term of this patent is extended or adjusted under 35 U.S.C. 154(b) by 0 days.

(21) Appl. No.: 15/311,487

(22) PCT Filed: May 15, 2015

(86) PCT No.: PCT/KR2015/004905
§ 371 (c)(1),
(2) Date: Nov. 15, 2016

(87) PCT Pub. No.: WO2015/174784
PCT Pub. Date: Nov. 19, 2015

(65) Prior Publication Data
US 2017/0107217 A1   Apr. 20, 2017

(30) Foreign Application Priority Data

May 15, 2014   (KR) .................. 10-2014-0058651
May 15, 2014   (KR) .................. 10-2014-0058654

(51) Int. Cl.
C07D 471/04   (2006.01)
C07F 7/08    (2006.01)
(Continued)

(52) U.S. Cl.
CPC ......... C07D 471/04 (2013.01); C07D 487/04 (2013.01); C07D 491/048 (2013.01);
(Continued)

(58) Field of Classification Search
None
See application file for complete search history.

(56) References Cited

U.S. PATENT DOCUMENTS 4,024,149 A * 5/1977 Winters .............. C07D 471/04
                                                   514/292
4,356,429 A   10/1982 Tang
(Continued)

FOREIGN PATENT DOCUMENTS

WO   WO-03/004494 A1 *  1/2003

OTHER PUBLICATIONS

Kiselyov (Tetrahedron 2006, 62, p. 543).*
(Continued)

*Primary Examiner* — Jay Yang
(74) *Attorney, Agent, or Firm* — Birch, Stewart, Kolasch & Birch, LLP

(57) ABSTRACT

The present application provides a hetero-cyclic compound which may significantly improve the service life, efficiency, electrochemical stability, and thermal stability of an organic light emitting device, and an organic light emitting device in which the hetero-cyclic compound is contained in an organic compound layer.

14 Claims, 2 Drawing Sheets

(51) Int. Cl.
- C07D 487/04 (2006.01)
- C09K 11/06 (2006.01)
- H01L 51/00 (2006.01)
- C07D 491/048 (2006.01)
- C07D 495/04 (2006.01)
- C07D 495/14 (2006.01)
- C07D 519/00 (2006.01)
- H01L 51/50 (2006.01)

(52) U.S. Cl.
CPC ......... *C07D 495/04* (2013.01); *C07D 495/14* (2013.01); *C07D 519/00* (2013.01); *C07F 7/0812* (2013.01); *C09K 11/06* (2013.01); *H01L 51/006* (2013.01); *H01L 51/0061* (2013.01); *H01L 51/0067* (2013.01); *H01L 51/0072* (2013.01); *H01L 51/0094* (2013.01); *C09K 2211/1007* (2013.01); *C09K 2211/1029* (2013.01); *C09K 2211/1044* (2013.01); *C09K 2211/1059* (2013.01); *H01L 51/0058* (2013.01); *H01L 51/0073* (2013.01); *H01L 51/0074* (2013.01); *H01L 51/5012* (2013.01); *H01L 51/5016* (2013.01); *H01L 51/5056* (2013.01); *H01L 51/5072* (2013.01); *H01L 51/5092* (2013.01)

(56) References Cited

U.S. PATENT DOCUMENTS 5,457,200 A * 10/1995 Zimmermann ...... C07D 471/04 435/28
2011/0284799 A1* 11/2011 Stoessel ............... C07F 1/00 252/301.16

OTHER PUBLICATIONS

Ding et al., "Copper-catalyzed direct oxidative annulation of N-iminopyridinium ylides with terminal alkynes using $O_2$ as oxidant", Chem. Commun., 2013, vol. 49, pp. 4250-4252.
International Search Report for PCT/KR2015/004905 (PCT/ISA/210) dated Aug. 28, 2015.
Kato et al., "Development of a new cascade reaction for convergent synthesis of pyrazolo[1,5-a]quinoline derivatives under transition-metal-free conditions", Org. Biomol. Chem., 2013, vol. 11, pp. 1171-1178.
Kato et al., "Synthesis of poly-substituted pyrazolo[1,5-a]quinolines through one-pot two component cascade reaction", Tetrahedron, vol. 70, 2014, pp. 2766-2775.
Office Action of Taiwanese Patent Office in Application No. 104115513, dated Jan. 12, 2016.
Tsuchiya et al., "Thermal Rearrangements of Cyclic Amine Ylides. III.[1]) Intramolecular Cyclization of 2-Ethynylpyridine N-Imides to 3-Azaindolizine Derivatives", Chem. Pharm. Bull., vol. 31, 1983, pp. 4658-4572.
Umeda et al, "Rhodium-Catalyzed Oxidative 1:1, 1:2, and 1:4 Coupling Reactions of Phenylazoles with Internal Alkynes through the Regioselective Cleavages of Multiple C—H Bonds", J. Org. Chem. 2011, vol. 76, pp. 13-24.
Written Opinion of the International Searching Authority for PCT/KR2015/004905 (PCT/ISA/237) dated Aug. 28, 2015.
Gnichtel, H., et al, "Ring Closures of syn-(E)- and anti-(E)-(2-Quinolylmethyl)- and -(1-Isoquinolylmethyl)ketoximes to Pyrazolo[1,5-a]quinolines und Pyrazolo[5,1-a]isoquinolines," Liebigs. Ann. Chem., 1981, pp. 1751-1759.
Kiselyov, A.S., et al, "A convenient procedure for the synthesis of fused fluro isoquinolines," Tetrahedron, 2006, vol. 62, pp. 543-548.
Schweizer, E.E., et al, "Reactions of Azines. 12. Preparation and Reaction of Triphenyl[2-((phenyl(methoxycarbonyl)methylene)hydrazono)propyl]-phosphonium Bromide," J. Org. Chem, 1987, vol. 52, pp. 1810-1816.
STN on Web, RN 487063-56-9, 487063-54-7, 487062-83-9, 487062-82-8, 107769-85-7, 89877-07-6, Feb. 7, 2003.

* cited by examiner

[Figure 1]
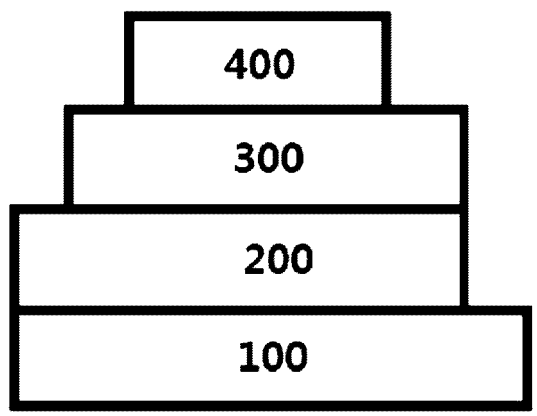
[Figure 2]
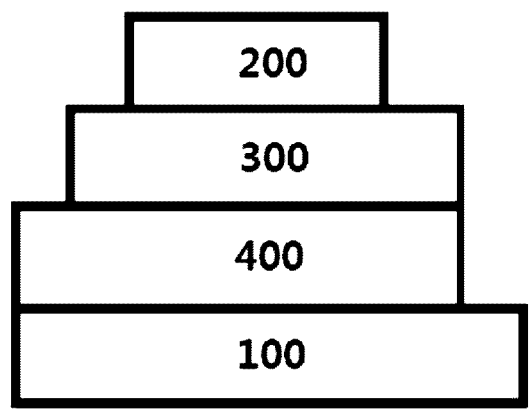

[Figure 3]
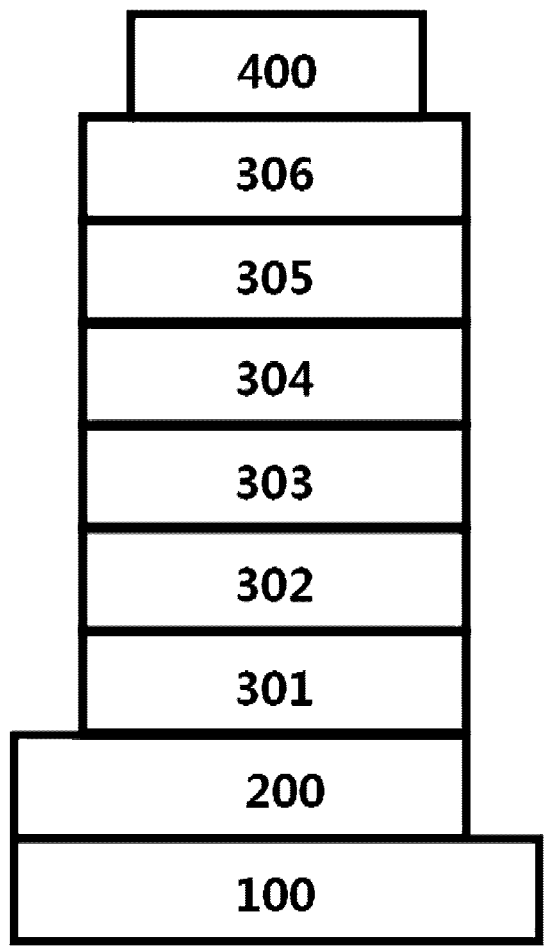

HETEROCYCLIC COMPOUND AND ORGANIC LIGHT EMITTING DEVICE USING SAME

TECHNICAL FIELD

This application claims priority to and the benefit of Korean Patent Application Nos. 10-2014-0058651 and 10-2014-0058654 filed in the Korean Intellectual Property Office on May 15, 2014, the entire contents of which are incorporated herein by reference.

The present specification relates to a hetero-cyclic compound and an organic light emitting device using the same.

BACKGROUND ART

An electroluminescence device is a kind of self-emitting type display device, and has an advantage in that the viewing angle is wide, the contrast is excellent, and the response speed is fast.

An organic light emitting device has a structure in which an organic thin film is disposed between two electrodes. When a voltage is applied to an organic light emitting device having the structure, electrons and holes injected from the two electrodes combine with each other in an organic thin film to make a pair, and then, emit light while being extinguished. The organic thin film may be composed of a single layer or multi layers, if necessary.

A material for the organic thin film may have a light emitting function, if necessary. For example, as the material for the organic thin film, it is also possible to use a compound, which may itself constitute a light emitting layer alone, or it is also possible to use a compound, which may serve as a host or a dopant of a host-dopant-based light emitting layer. In addition, as a material for the organic thin film, it is also possible to use a compound, which may perform a function such as hole injection, hole transport, electron blocking, hole blocking, electron transport or electron injection.

In order to improve the performance, service life, or efficiency of the organic light emitting device, there is a continuous need for developing a material for an organic thin film.

DETAILED DESCRIPTION OF THE INVENTION

Technical Problem

It is necessary to perform studies on an organic light emitting device including a compound having a chemical structure, which may satisfy conditions required for a material which is available for the organic light emitting device, for example, appropriate energy levels, electrochemical stability, thermal stability, and the like, and may perform various functions required for the organic light emitting device according to the substituent.

Technical Solution

An exemplary embodiment of the present application provides a hetero-cyclic compound represented by the following Formula 1.

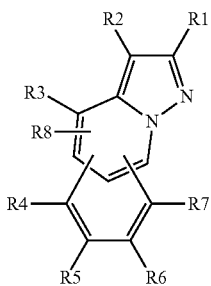

[Formula 1]

In Formula 1,

R1 to R8 are the same as or different from each other, and are each independently selected from the group consisting of hydrogen; deuterium; a halogen group; —CN; a substituted or unsubstituted, straight-chained or branched $C_1$ to $C_{60}$ alkyl group; a substituted or unsubstituted, straight-chained or branched $C_2$ to $C_{60}$ alkenyl group; a substituted or unsubstituted, straight-chained or branched $C_2$ to $C_{60}$ alkynyl group; a substituted or unsubstituted, monocyclic or polycyclic $C_3$ to $C_{60}$ cycloalkyl group; a substituted or unsubstituted, monocyclic or polycyclic $C_2$ to $C_{60}$ heterocycloalkyl group; a substituted or unsubstituted, monocyclic or polycyclic $C_6$ to $C_{60}$ aryl group; a substituted or unsubstituted, monocyclic or polycyclic $C_2$ to $C_{60}$ heteroaryl group; —SiRR'R"; —P(=O)RR'; and —NRR', and R, R', and R" are the same as or different from each other, and are each independently selected from the group consisting of hydrogen; deuterium; a substituted or unsubstituted, straight-chained or branched $C_1$ to $C_{60}$ alkyl group; a substituted or unsubstituted, monocyclic or polycyclic $C_3$ to $C_{60}$ cycloalkyl group; a substituted or unsubstituted, monocyclic or polycyclic $C_6$ to $C_{60}$ aryl group; and a substituted or unsubstituted, monocyclic or polycyclic $C_2$ to $C_{60}$ heteroaryl group.

Further, the present application provides an organic light emitting device including a positive electrode, a negative electrode, and one or more organic material layers provided between the positive electrode and the negative electrode, in which one or more layers of the organic material layers include the heterocyclic compound represented by Formula 1.

Advantageous Effects

A hetero-cyclic compound according to an exemplary embodiment of the present application may be used as a material for an organic material layer of an organic light emitting device. The hetero-cyclic compound may serve as a hole injection material, a hole transport material, a light emitting material, a hole blocking material, an electron transport material, an electron injection material, and the like in the organic light emitting device.

In particular, the hetero-cyclic compound represented by Formula 1 may be used as a material for an electron injection and/or transport layer of the organic light emitting device.

In addition, the hetero-cyclic compound represented by Formula 1 may be used as a material for a hole blocking layer of the organic light emitting device.

Furthermore, the hetero-cyclic compound represented by Formula 1 may be used as a material for a light emitting layer of the organic light emitting device.

BRIEF DESCRIPTION OF DRAWINGS

FIGS. 1 to 3 each are views schematically illustrating a stacking structure of an organic light emitting device according to an exemplary embodiment of the present application.

EXPLANATION OF REFERENCE NUMERALS AND SYMBOLS

100: Substrate
200: Positive electrode
300: Organic material layer
301: Hole injection layer
302: Hole transport layer
303: Light emitting layer
304: Hole blocking layer
305: Hole transporting layer
306: Electron injection layer
400: Negative electrode

BEST MODE

Hereinafter, the present application will be described in detail.

A hetero-cyclic compound according to an exemplary embodiment of the present application is represented by Formula 1. More specifically, the hetero-cyclic compound represented by Formula 1 may be used as a material for an organic material layer of an organic light emitting device by the structural characteristics of the core structure and the substituent as described above.

In the present application, the substituents of Formula 1 will be more specifically described as follows.

In the present specification, "substituted or unsubstituted" means to be unsubstituted or substituted with one or more substituents selected from the group consisting of deuterium; halogen; —CN; a straight-chained or branched $C_1$ to $C_{60}$ alkyl group; a straight-chained or branched $C_2$ to $C_{60}$ alkenyl group; a straight-chained or branched $C_2$ to $C_{60}$ alkynyl group; a monocyclic or polycyclic $C_3$ to $C_{60}$ cycloalkyl group; a monocyclic or polycyclic $C_2$ to $C_{60}$ heterocycloalkyl group; a monocyclic or polycyclic $C_6$ to $C_{60}$ aryl group; a monocyclic or polycyclic $C_2$ to $C_{60}$ heteroaryl group; —SiRR'R"; —P(=O)RR'; and —NRR', or to be unsubstituted or substituted with a substituent to which two or more among the substituents are bonded, or to be unsubstituted or substituted with a substituent to which two or more substituents selected from the substituents are linked. For example, "the substituent to which two or more substituents are linked" may be a biphenyl group. That is, the biphenyl group may also be an aryl group, and may be interpreted as a substituent to which two phenyl groups are linked. R, R', and R" are the same as or different from each other, and are each independently selected from the group consisting of hydrogen; deuterium; halogen; —CN; a straight-chained or branched $C_1$ to $C_{60}$ alkyl group; a monocyclic or polycyclic $C_3$ to $C_{60}$ cycloalkyl group; a monocyclic or polycyclic $C_6$ to $C_{60}$ aryl group; and a monocyclic or polycyclic $C_2$ to $C_{60}$ heteroaryl group. The substituents may also be additionally substituted.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the halogen may be fluorine, chlorine, bromine or iodine.

In the present specification, the alkyl group includes a straight-chained or branched chain having 1 to 60 carbon atoms, and may be additionally substituted with another substituent. The number of carbon atoms of the alkyl group may be 1 to 60, specifically 1 to 40, and more specifically 1 to 20. Specific examples thereof include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group, and the like, but are not limited thereto.

In the present specification, the alkenyl group includes a straight-chained or branched chain having 2 to 60 carbon atoms, and may be additionally substituted with another substituent. The number of carbon atoms of the alkenyl group may be 2 to 60, specifically 2 to 40, and more specifically 2 to 20. Specific examples thereof include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group, and the like, but are not limited thereto.

In the present specification, the alkynyl group includes a straight-chained or branched chain having 2 to 60 carbon atoms, and may be additionally substituted with another substituent. The number of carbon atoms of the alkynyl group may be 2 to 60, specifically 2 to 40, and more specifically 2 to 20.

In the present specification, the cycloalkyl group includes a monocycle or polycycle having 3 to 60 carbon atoms, and may be additionally substituted with another substituent. Here, the polycycle means a group in which a cycloalkyl group is directly linked to or fused with another cyclic group. Here, another cyclic group may also be a cycloalkyl group, but may also be another kind of cyclic group, for example, a heterocycloalkyl group, an aryl group, a heteroaryl group, and the like. The number of carbon atoms of the cycloalkyl group may be 3 to 60, specifically 3 to 40, and more specifically 5 to 20. Specific examples thereof include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group, and the like, but are not limited thereto.

In the present specification, the heterocyclcoalkyl group includes O, S, Se, N, or Si as a heteroatom, includes a monocycle or polycycle having 2 to 60 carbon atoms, and may be additionally substituted with another substituent. Here, the polycycle means a group in which a heterocycloalkyl group is directly linked to or fused with another cyclic group. Here, another cyclic group may also be a heterocycloalkyl group, but may also be another kind of cyclic group, for example, a cycloalkyl group, an aryl group, a heteroaryl group, and the like. The number of carbon atoms of the heterocycloalkyl group may be 2 to 60, specifically 2 to 40, and more specifically 3 to 20.

In the present specification, the aryl group includes a monocycle or polycycle having 6 to 60 carbon atoms, and may be additionally substituted with another substituent. Here, the polycycle means a group in which an aryl group is directly linked to or fused with another cyclic group. Here, another cyclic group may also be an aryl group, but may also be another kind of cyclic group, for example, a cycloalkyl group, a heterocycloalkyl group, a heteroaryl group, and the like. The aryl group includes a Spiro group. The number of carbon atoms of the aryl group may be 6 to 60, specifically 6 to 40, and more specifically 6 to 25. Specific examples of the aryl group include a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused cyclic group thereof, and the like, but are not limited thereto.

In the present specification, the spiro group is a group including a Spiro structure, and may have 15 to 60 carbon atoms. For example, the spiro group may include a structure in which a 2,3-dihydro-1H-indene group or a cyclohexane group is spiro-bonded to a fluorenyl group. Specifically, the following Spiro group may include any one of the groups of the following structural formulae.

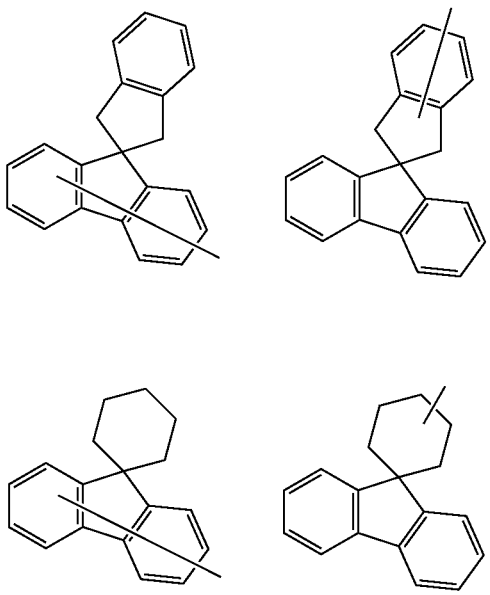

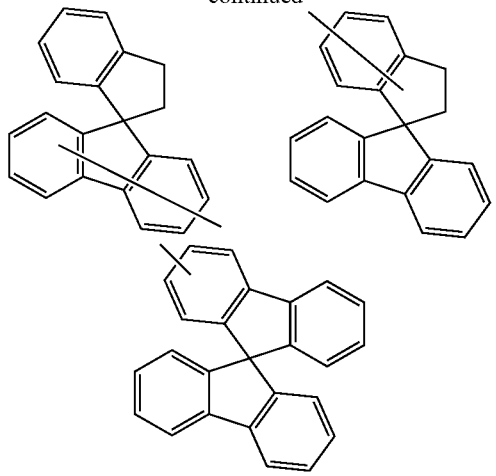

In the present specification, the heteroaryl group includes O, S, Se, N, or Si as a heteroatom, includes a monocycle or polycycle having 2 to 60 carbon atoms, and may be additionally substituted with another substituent. Here, the polycycle means a group in which a heteroaryl group is directly linked to or fused with another cyclic group. Here, another cyclic group may also be a heteroaryl group, but may also be another kind of cyclic group, for example, a cycloalkyl group, a heterocycloalkyl group, an aryl group, and the like. The number of carbon atoms of the heteroaryl group may be 2 to 60, specifically 2 to 40, and more specifically 3 to 25. Specific examples of the heteroaryl group include a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxinyl group, a triazinyl group, a tetrazinyl group, a quinolyl group, an isoquinolyl group, a quinazolinyl group, an isoquinazolinyl group, a quinozolilyl group, a naphthyridyl group, an acridinyl group, a phenanthridinyl group, an imidazopyridinyl group, a diaza naphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi (dibenzosilole), a dihydrophenazinyl group, a phenoxazinyl group, a phenanthridyl group, an imidazopyridinyl group, a thienyl group, an indolo[2,3-a] carbazolyl group, an indolo[2,3-b]carbazolyl group, an indolinyl group, a 10,11-dihydro-dibenzo[b,f]azepin group, a 9,10-dihydroacridinyl group, a phenanthrazinyl group, a phenothiazinyl group, a phthalazinyl group, a naphthylidinyl group, a phenanthrolinyl group, a benzo[c][1,2,5]thiadiazolyl group, a 5,10-dihydrodibenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group, and the like, but are not limited thereto.

In the present specification, the amine group may be selected from the group consisting of a monoalkylamine group; a monoarylamine group; a monoheteroarylamine group; —NH₂; a dialkylamine group; a diarylamine group; a diheteroarylamine group; an alkylarylamine group; an alkylheteroarylamine group; and an arylheteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group, and the like, but are not limited thereto.

In the present specification, the arylene group means that there are two bonding positions in an aryl group, that is, a divalent group. The above-described description on the aryl group may be applied, except that these are each a divalent group. Further, the heteroarylene group means that there are two bonding positions in a heteroaryl group, that is, a divalent group. The above-described description on the heteroaryl group may be applied, except that these are each a divalent group.

According to an exemplary embodiment of the present application, Formula 1 may be represented by the following Formula 2.

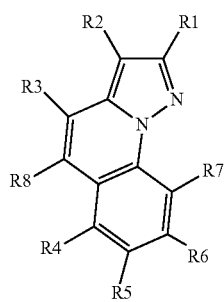

[Formula 2]

In Formula 2, R1 to R8 are the same as those defined in Formula 1.

Further, according to an exemplary embodiment of the present application, Formula 1 may be represented by the following Formula 3.

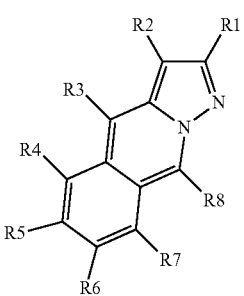

[Formula 3]

In Formula 3, R1 to R8 are the same as those defined in Formula 1.

According to an exemplary embodiment of the present application, at least one of R1 and R2 is a substituted or unsubstituted, monocyclic or polycyclic $C_6$ to $C_{60}$ aryl group; a substituted or unsubstituted, monocyclic or polycyclic $C_2$ to $C_{60}$ heteroaryl group; —SiRR'R"; —P(=O)RR'; or —NRR', and R, R', and R" are the same as or different from each other, and are each independently selected from the group consisting of hydrogen; deuterium; a substituted or unsubstituted, straight-chained or branched $C_1$ to $C_{60}$ alkyl group; a substituted or unsubstituted, monocyclic or polycyclic $C_3$ to $C_{60}$ cycloalkyl group; a substituted or unsubstituted, monocyclic or polycyclic $C_6$ to $C_{60}$ aryl group; and a substituted or unsubstituted, monocyclic or polycyclic $C_2$ to $C_{60}$ heteroaryl group.

According to an exemplary embodiment of the present application, R1 is a substituted or unsubstituted, monocyclic or polycyclic $C_6$ to $C_{60}$ aryl group; a substituted or unsubstituted, monocyclic or polycyclic $C_2$ to $C_{60}$ heteroaryl group; —SiRR'R"; —P(=O)RR'; or —NRR', and R, R', and R" are the same as those described above, and R2 is hydrogen; deuterium; or a substituted or unsubstituted, monocyclic or polycyclic $C_6$ to $C_{60}$ aryl group.

According to an exemplary embodiment of the present application, R2 is a substituted or unsubstituted, monocyclic or polycyclic $C_6$ to $C_{60}$ aryl group; a substituted or unsubstituted, monocyclic or polycyclic $C_2$ to $C_{60}$ heteroaryl group; —SiRR'R"; —P(=O)RR'; or —NRR', and R, R', and R" are the same as those described above, and R1 is hydrogen; deuterium; or a substituted or unsubstituted, monocyclic or polycyclic $C_6$ to $C_{60}$ aryl group.

According to an exemplary embodiment of the present application, R, R', and R" are the same as or different from each other, and are each independently a substituted or unsubstituted, monocyclic or polycyclic $C_6$ to $C_{60}$ aryl group, or a substituted or unsubstituted, monocyclic or polycyclic $C_2$ to $C_{60}$ heteroaryl group.

According to an exemplary embodiment of the present application, R, R', and R" are the same as or different from each other, and are each independently selected from the group consisting of a phenyl group, a biphenyl group, a naphthyl group, a pyridyl group, a pyrimidyl group, an anthracenyl group, a phenanthrenyl group, a chrysenyl group, a triphenylenyl group, a pyrenyl group, a fluorenyl group, a dimethylfluorenyl group, a carbazolyl group, a dibenzofuranyl group, and a dibenzothiophenyl group.

According to an exemplary embodiment of the present application, in Formula 1, R3 to R8 are hydrogen, deuterium, or a substituted or unsubstituted, monocyclic or polycyclic $C_6$ to $C_{30}$ aryl.

According to an exemplary embodiment of the present application, in Formula 1, R3 to R8 are hydrogen or deuterium.

According to an exemplary embodiment of the present application, in Formula 1, at least one of R1 and R2 is -(L)m-(Z)n, L is a direct bond; a substituted or unsubstituted, monocyclic or polycyclic $C_6$ to $C_{60}$ arylene group; or a substituted or unsubstituted, monocyclic or polycyclic $C_2$ to $C_{60}$ heteroarylene group, m is an integer of 0 to 3, n is an integer of 1 to 5, Z is selected from the group consisting of a substituted or unsubstituted, monocyclic or polycyclic $C_6$ to $C_{60}$ aryl group; a substituted or unsubstituted, monocyclic or polycyclic $C_2$ to $C_{60}$ heteroaryl group; —SiRR'R"; —P(=O)RR'; and —NRR', and R, R', and R" are the same as or different from each other, and are each independently selected from the group consisting of hydrogen; deuterium; a substituted or unsubstituted, straight-chained or branched $C_1$ to $C_{60}$ alkyl group; a substituted or unsubstituted, monocyclic or polycyclic $C_3$ to $C_{60}$ cycloalkyl group; a substituted or unsubstituted, monocyclic or polycyclic $C_6$ to $C_{60}$ aryl group; and a substituted or unsubstituted, monocyclic or polycyclic $C_2$ to $C_{60}$ heteroaryl group.

According to an exemplary embodiment of the present application, L is a direct bond; a substituted or unsubstituted $C_6$ to $C_{20}$ arylene group; or a substituted or unsubstituted $C_2$ to $C_{20}$ N-containing heteroarylene group.

According to an exemplary embodiment of the present application, L is a direct bond; a $C_6$ to $C_{20}$ arylene group; or a $C_2$ to $C_{20}$ N-containing heteroarylene group.

According to an exemplary embodiment of the present application, L is a direct bond, or a phenylene group; a naphthylene group; an anthracenylene group; a pyridylene group; a pyrimidylene group; or a triazinylene group, and may be further substituted with fluorine (F).

According to an exemplary embodiment of the present application, R, R', and R" are the same as or different from each other, and are each independently a substituted or unsubstituted, monocyclic or polycyclic $C_6$ to $C_{60}$ aryl group, or a substituted or unsubstituted, monocyclic or polycyclic $C_2$ to $C_{60}$ heteroaryl group.

According to an exemplary embodiment of the present application, R, R', and R" are the same as or different from each other, and are each independently selected from the group consisting of a phenyl group, a biphenyl group, a naphthyl group, a pyridyl group, a pyrimidyl group, an anthracenyl group, a phenanthrenyl group, a chrysenyl group, a triphenylenyl group, a pyrenyl group, a fluorenyl group, a dimethylfluorenyl group, a carbazolyl group, a dibenzofuranyl group, and a dibenzothiophenyl group.

According to an exemplary embodiment of the present application, Z is a substituted or unsubstituted, monocyclic or polycyclic $C_6$ to $C_{60}$ aryl group.

According to an exemplary embodiment of the present application, Z is a substituted or unsubstituted phenyl group, a substituted or unsubstituted biphenyl group, a substituted or unsubstituted naphthyl group, a substituted or unsubstituted chrysenyl group, a substituted or unsubstituted pyrenyl group, a substituted or unsubstituted triphenylenyl group, a substituted or unsubstituted anthracenyl group, a substituted or unsubstituted phenanthrenyl group, a substituted or unsubstituted fluorenyl group, or a substituted or unsubstituted spirobifluorenyl group.

According to an exemplary embodiment of the present application, Z is a substituted or unsubstituted phenyl group, a substituted or unsubstituted biphenyl group, a substituted or unsubstituted naphthyl group, a substituted or unsubstituted chrysenyl group, a substituted or unsubstituted pyrenyl group, a substituted or unsubstituted triphenylenyl group, a substituted or unsubstituted anthracenyl group, a substituted or unsubstituted phenanthrenyl group, a substituted or unsubstituted fluorenyl group, or a substituted or unsubstituted spirobifluorenyl group, the term "substituted or unsubstituted" means to be unsubstituted or substituted with at least one selected from halogen, —CN, a straight-chained or branched $C_1$ to $C_{60}$ alkyl group, a substituted or unsubstituted, monocyclic or polycyclic $C_3$ to $C_{60}$ cycloalkyl group, a monocyclic or polycyclic $C_6$ to $C_{60}$ aryl group, and a monocyclic or polycyclic $C_2$ to $C_{60}$ heteroaryl group, and the groups may be additionally substituted.

According to an exemplary embodiment of the present application, Z is a substituted or unsubstituted phenyl group, a substituted or unsubstituted biphenyl group, a substituted or unsubstituted naphthyl group, a substituted or unsubstituted chrysenyl group, a substituted or unsubstituted pyrenyl group, a substituted or unsubstituted triphenylenyl group, a substituted or unsubstituted anthracenyl group, a substituted or unsubstituted phenanthrenyl group, a substituted or unsubstituted fluorenyl group, or a substituted or unsubstituted spirobifluorenyl group, the term "substituted or unsubstituted" means to be unsubstituted or substituted with at least one selected from halogen, —CN, a methyl group, a cyclohexyl group, a phenyl group, a biphenyl group, a naphthyl group, a pyridyl group, and a carbazole group, and the groups may be additionally substituted.

According to another exemplary embodiment of the present application, Z is a substituted or unsubstituted, monocyclic or polycyclic $C_2$ to $C_{60}$ heteroaryl group, and the heteroaryl includes at least one selected from N, O, S, Si, and Se, as a heteroatom.

According to an exemplary embodiment of the present application, Z is a substituted or unsubstituted benzimidazolyl group, a substituted or unsubstituted quinolyl group, a substituted or unsubstituted isoquinolyl group, a substituted or unsubstituted naphthyridyl group, a substituted or unsubstituted quinazolinyl group, a substituted or unsubstituted quinoxalinyl group, a substituted or unsubstituted cinolinyl group, a substituted or unsubstituted benzothiazolyl group, a substituted or unsubstituted benzoxazolyl group, a substituted or unsubstituted oxadiazolyl group, a substituted or unsubstituted dibenzofuranyl group, a substituted or unsubstituted dibenzothiophenyl group, a substituted or unsubstituted pyridyl group, a substituted or unsubstituted pyrimidyl group, a substituted or unsubstituted triazinyl group, a substituted or unsubstituted pyrazolophthalazinyl group, a substituted or unsubstituted pyrazoloquinazolinyl group, a substituted or unsubstituted pyridoindazolyl group, or a substituted or unsubstituted carbazolyl group.

According to an exemplary embodiment of the present application, Z is a substituted or unsubstituted benzimidazolyl group, a substituted or unsubstituted quinolyl group, a substituted or unsubstituted isoquinolyl group, a substituted or unsubstituted naphthyridyl group, a substituted or unsubstituted quinazolinyl group, a substituted or unsubstituted quinoxalinyl group, a substituted or unsubstituted cinolinyl group, a substituted or unsubstituted benzothiazolyl group, a substituted or unsubstituted benzoxazolyl group, a substituted or unsubstituted oxadiazolyl group, a substituted or unsubstituted dibenzofuranyl group, a substituted or unsubstituted dibenzothiophenyl group, a substituted or unsubstituted pyridyl group, a substituted or unsubstituted pyrimidyl group, a substituted or unsubstituted triazinyl group, a substituted or unsubstituted pyrazolophthalazinyl group, a substituted or unsubstituted pyrazoloquinazolinyl group, a substituted or unsubstituted pyridoindazolyl group, or a substituted or unsubstituted carbazolyl group, the term "substituted or unsubstituted" means to be unsubstituted or substituted with at least one selected from halogen, —CN, a monocyclic or polycyclic $C_3$ to $C_{60}$ cycloalkyl group, a monocyclic or polycyclic $C_6$ to $C_{60}$ aryl group and a monocyclic or polycyclic $C_2$ to $C_{60}$ heteroaryl group, and the groups may be additionally substituted.

According to an exemplary embodiment of the present application, Z is a substituted or unsubstituted benzimidazolyl group, a substituted or unsubstituted quinolyl group, a substituted or unsubstituted isoquinolyl group, a substituted or unsubstituted naphthyridyl group, a substituted or unsubstituted quinazolinyl group, a substituted or unsubstituted quinoxalinyl group, a substituted or unsubstituted cinolinyl group, a substituted or unsubstituted benzothiazolyl group, a substituted or unsubstituted benzoxazolyl group, a substituted or unsubstituted oxadiazolyl group, a substituted or unsubstituted dibenzofuranyl group, a substituted or unsubstituted dibenzothiophenyl group, a substituted or unsubstituted pyridyl group, a substituted or unsubstituted pyrimidyl group, a substituted or unsubstituted triazinyl group, a substituted or unsubstituted pyrazolophthalazinyl group, a substituted or unsubstituted pyrazoloquinazolinyl group, a substituted or unsubstituted pyridoindazolyl group, or a substituted or unsubstituted carbazolyl group, the term "substituted or unsubstituted" means to be unsubstituted or substituted with at least one selected from halogen, —CN, a cyclohexyl group, a phenyl group, a naphthyl group, and a pyridyl group, and the groups may be additionally substituted.

According to another exemplary embodiment of the present application, Z is

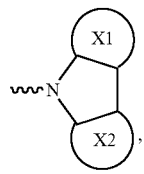

and X1 and X2 are the same as or different from each other, and are each independently a substituted or unsubstituted, monocyclic or polycyclic $C_6$ to $C_{60}$ aromatic hydrocarbon ring; or a substituted or unsubstituted, monocyclic or polycyclic $C_2$ to $C_{60}$ aromatic hetero ring.

According to an exemplary embodiment of the present application,

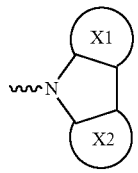

is represented by any one of the following structures.

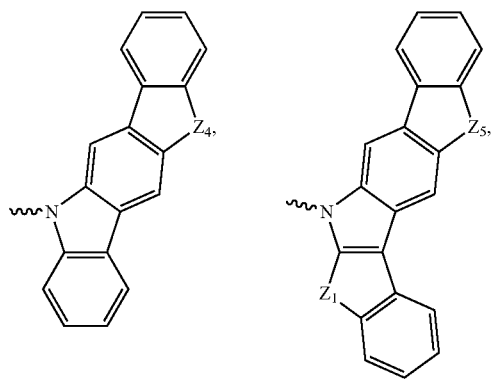

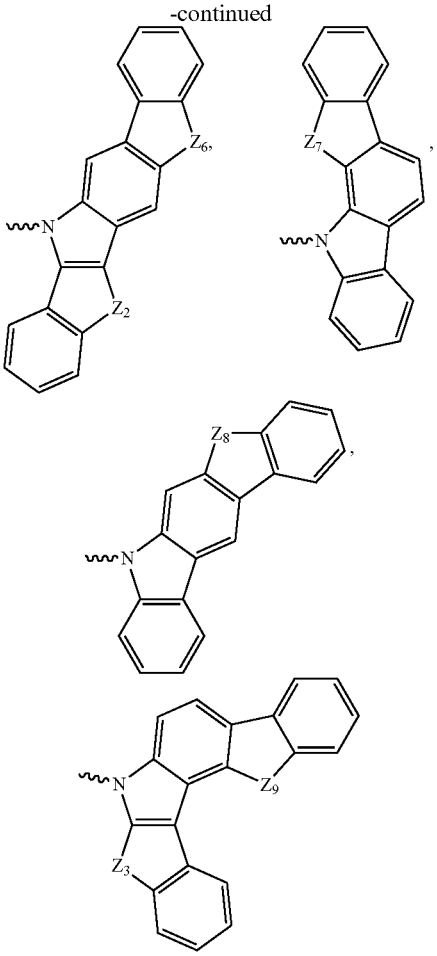

In the structures, $Z_1$ to $Z_3$ are the same as or different from each other, and are each independently S or O, $Z_4$ to $Z_9$ are the same as or different from each other, and are each independently CY'Y", NY', S, or O, and Y' and Y" are the same as or different from each other, and are each independently hydrogen; deuterium; a substituted or unsubstituted, straight-chained or branched $C_1$ to $C_{60}$ alkyl group; or a substituted or unsubstituted, monocyclic or polycyclic $C_6$ to $C_{60}$ aryl group.

According to an exemplary embodiment of the present application, Y' and Y" are the same as or different from each other, and are each independently hydrogen, deuterium, a methyl group, a phenyl group, or a naphthyl group.

According to another exemplary embodiment of the present application, Z is —SiRR'R", and R, R', and R" are the same as or different from each other, and are each independently selected from the group consisting of a substituted or unsubstituted, straight-chained or branched $C_1$ to $C_{60}$ alkyl group; a substituted or unsubstituted, monocyclic or polycyclic $C_6$ to $C_{60}$ aryl group; and a substituted or unsubstituted, monocyclic or polycyclic $C_2$ to $C_{60}$ heteroaryl group.

According to an exemplary embodiment of the present application, Z is —SiRR'R", and R, R', and R" are the same as or different from each other, and are a monocyclic or polycyclic $C_6$ to $C_{60}$ aryl group.

According to an exemplary embodiment of the present application, Z is —SiRR'R", and R, R', and R" are the same as or different from each other, and are a phenyl group or a biphenyl group.

According to another exemplary embodiment of the present application, Z is —P(=O)RR', and R and R' are the same as or different from each other, and are each independently selected from the group consisting of a substituted or unsubstituted, straight-chained or branched $C_1$ to $C_{60}$ alkyl group; a substituted or unsubstituted, monocyclic or polycyclic $C_6$ to $C_{60}$ aryl group; and a substituted or unsubstituted, monocyclic or polycyclic $C_2$ to $C_{60}$ heteroaryl group.

According to an exemplary embodiment of the present application, Z is —P(=O)RR', and R and R' are the same as or different from each other, and are a monocyclic or polycyclic $C_6$ to $C_{60}$ aryl group.

According to an exemplary embodiment of the present application, Z is —P(=O)RR', and R and R' are a phenyl group or a biphenyl group.

According to another exemplary embodiment of the present application, Z is —NRR', and R and R' are the same as or different from each other, and are each independently selected from the group consisting of a substituted or unsubstituted, straight-chained or branched $C_1$ to $C_{60}$ alkyl group; a substituted or unsubstituted, monocyclic or polycyclic $C_6$ to $C_{60}$ aryl group; and a substituted or unsubstituted, monocyclic or polycyclic $C_2$ to $C_{60}$ heteroaryl group.

According to an exemplary embodiment of the present application, Z is —NRR', and R and R' are the same as or different from each other, and are a monocyclic or polycyclic $C_6$ to $C_{60}$ aryl group, or a substituted or unsubstituted, monocyclic or polycyclic $C_2$ to $C_{60}$ heteroaryl group.

According to an exemplary embodiment of the present application, Z is —NRR', and R and R' may be selected from the group consisting of a phenyl group, a biphenyl group, a naphthyl group, a fluorenyl group, a dimethylfluorenyl group, a dibenzofuranyl group, a dibenzothiophenyl group, and a carbazole group.

The compound of Formula 1 may include two or more core structures.

According to an exemplary embodiment of the present application, Formula 1 is represented by the following Formula 4 or 5.

[Formula 4]

[Formula 5]

In Formulae 4 and 5,

A and A' are each independently selected from the group consisting of a direct bond; a substituted or unsubstituted, straight-chained or branched $C_2$ to $C_{60}$ alkylene group; a substituted or unsubstituted, straight-chained or branched $C_2$ to $C_{60}$ alkenylene group; a substituted or unsubstituted, straight-chained or branched $C_2$ to $C_{60}$ alkynylene group; a substituted or unsubstituted, monocyclic or polycyclic $C_3$ to $C_{60}$ cycloalkylene group; a substituted or unsubstituted, monocyclic or polycyclic $C_2$ to $C_{60}$ heterocycloalkylene group; a substituted or unsubstituted, monocyclic or polycyclic $C_6$ to $C_{60}$ arylene group; and a substituted or unsubstituted, monocyclic or polycyclic $C_2$ to $C_{60}$ heteroarylene group, and R2 to R8 are the same as those defined in Formula 1.

According to an exemplary embodiment of the present application, A and A' in Formulae 4 and 5 are each independently selected from the group consisting of a direct bond; a substituted or unsubstituted, monocyclic or polycyclic $C_6$ to $C_{60}$ arylene group; and a monocyclic or polycyclic $C_2$ to $C_{60}$ heteroarylene group.

According to an exemplary embodiment of the present application, A and A' in Formulae 4 and 5 are each independently a direct bond; a substituted or unsubstituted $C_6$ to $C_{60}$ arylene group; or a substituted or unsubstituted $C_6$ to $C_{60}$ heteroarylene group, and may be further substituted with a straight-chained or branched $C_1$ to $C_{20}$ alkyl group; or a substituted or unsubstituted, monocyclic or polycyclic $C_6$ to $C_{20}$ aryl group.

According to an exemplary embodiment of the present application, A and A' in Formulae 4 and 5 are each independently a direct bond, a phenylene group, or a biphenylylene group.

According to an exemplary embodiment of the present application, Formula 1 may be selected from the following compounds.

Compound 1-1-1

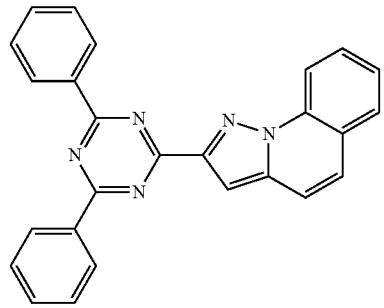

Compound 1-1-2

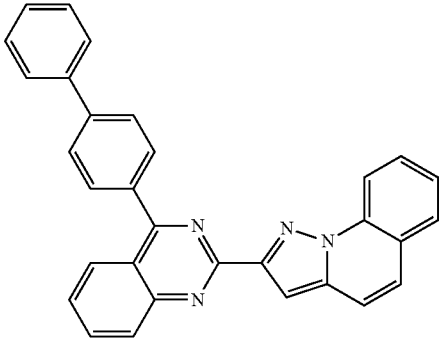

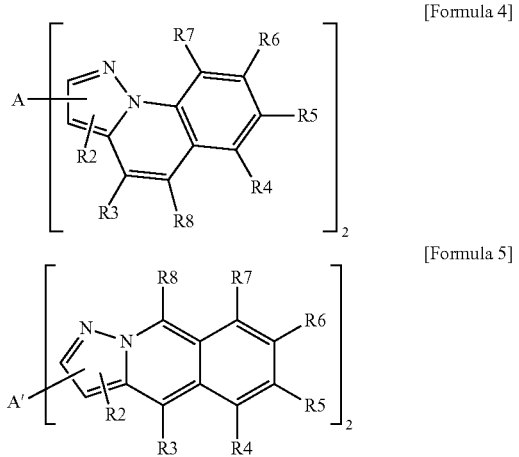

Compound 1-1-3
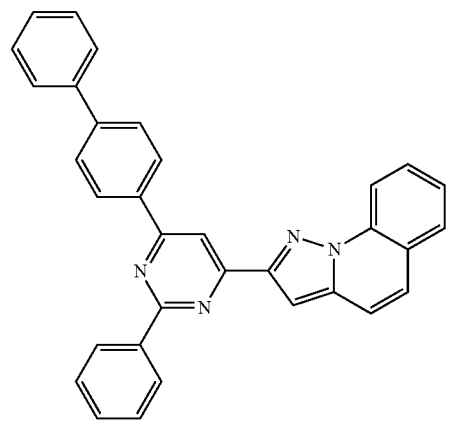
Compound 1-1-4
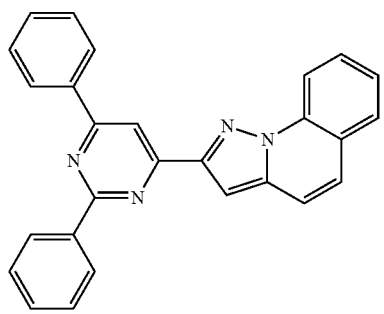
Compound 1-1-5
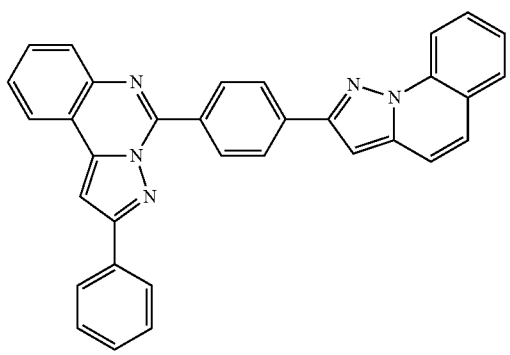
Compound 1-1-6
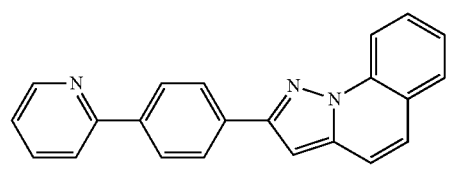
Compound 1-1-7
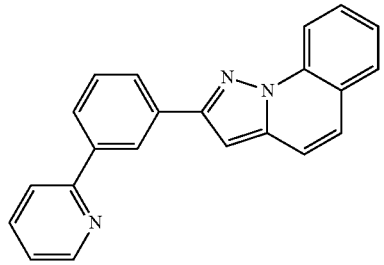
Compound 1-1-8
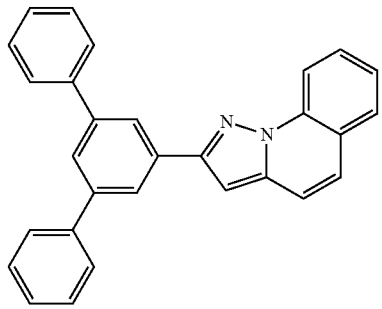
Compound 1-1-9
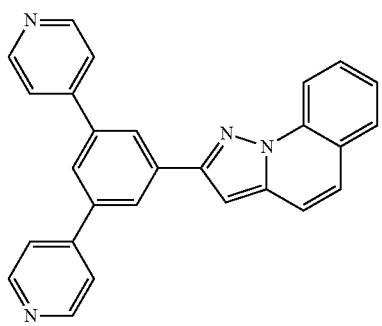
Compound 1-1-10
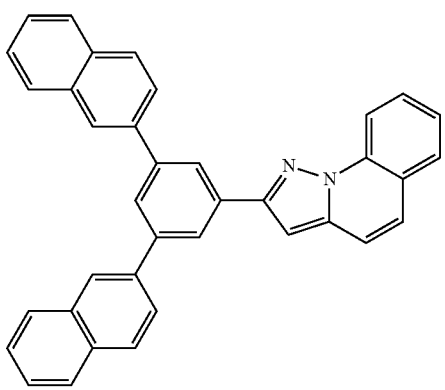
Compound 1-1-11
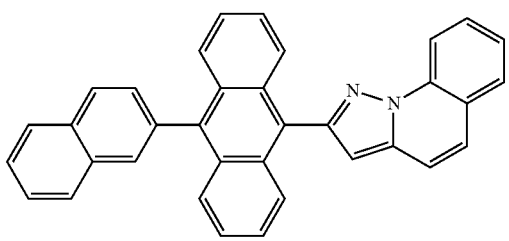
Compound 1-1-12
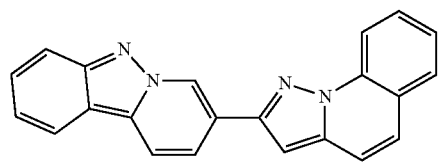

Compound 1-1-13
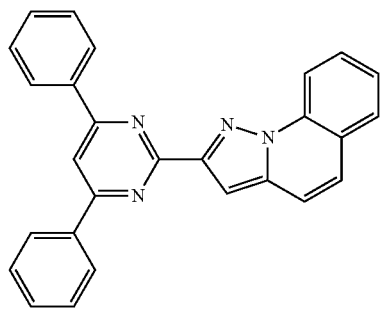
Compound 1-1-14
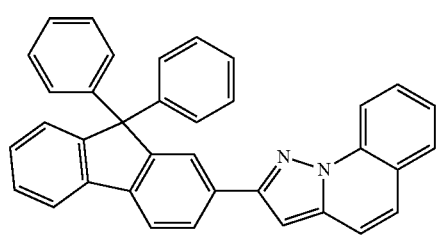
Compound 1-1-15
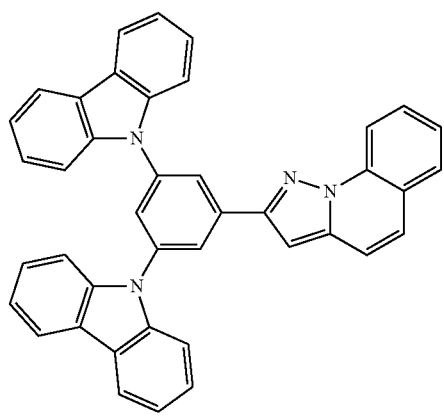
Compound 1-1-16
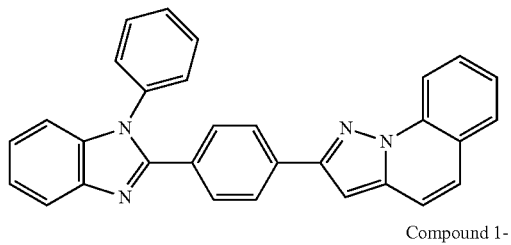
Compound 1-1-17
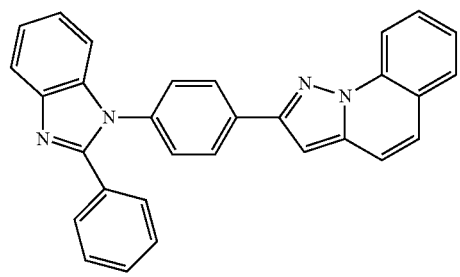
Compound 1-1-18
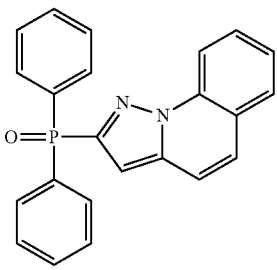
Compound 1-1-19
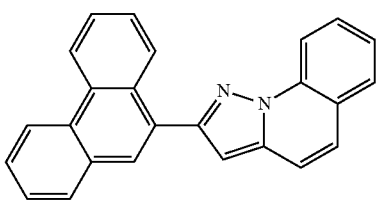
Compound 1-1-20
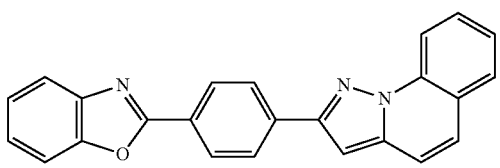
Compound 1-1-21
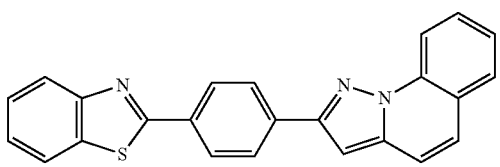
Compound 1-1-22
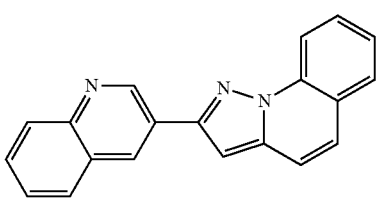
Compound 1-1-23
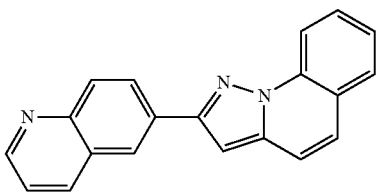
Compound 1-1-24
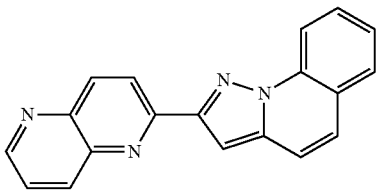

Compound 1-1-25
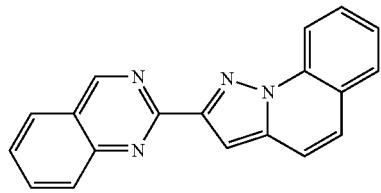
Compound 1-1-26
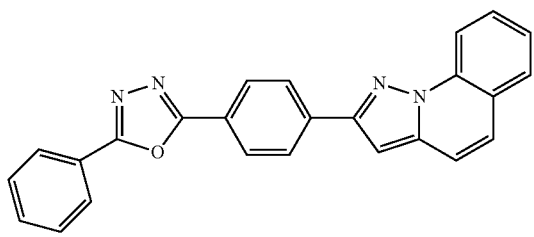
Compound 1-1-27
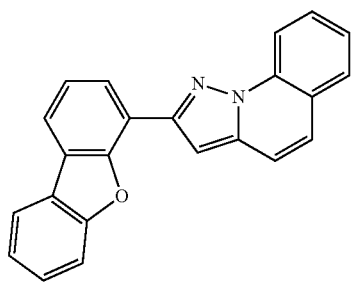
Compound 1-1-28
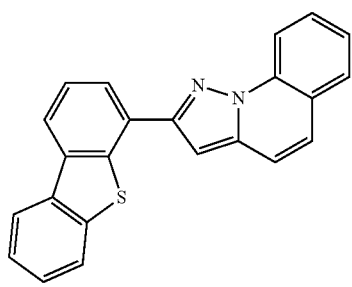
Compound 1-1-29
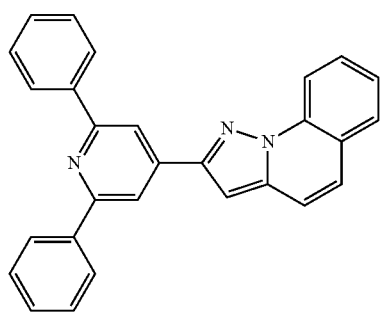
Compound 1-1-30
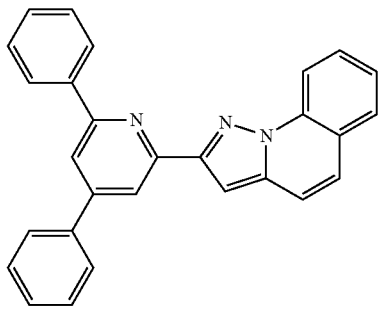
Compound 1-1-31
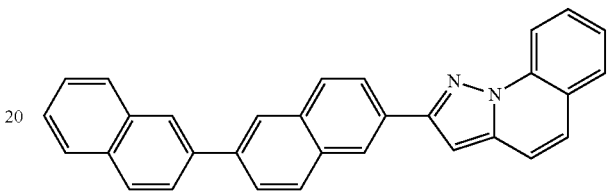
Compound 1-1-32
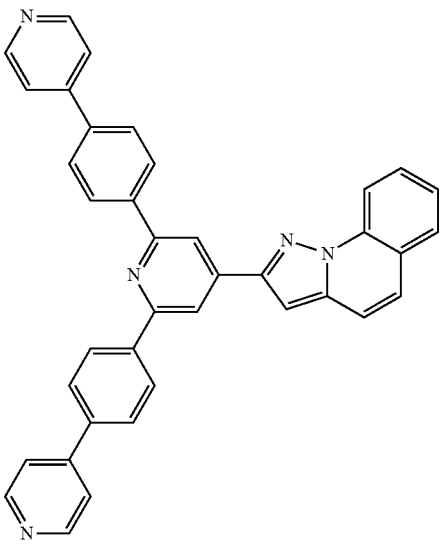
Compound 1-1-33
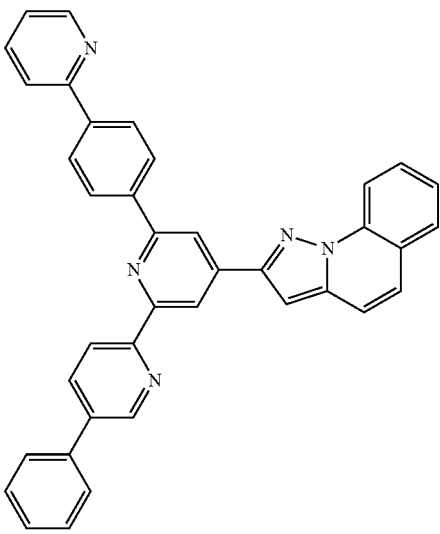

Compound 1-1-34
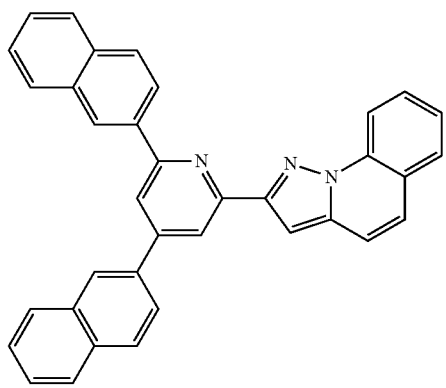
Compound 1-1-35
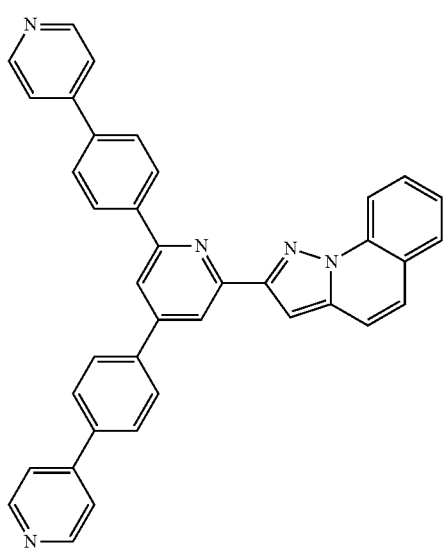
Compound 1-1-36
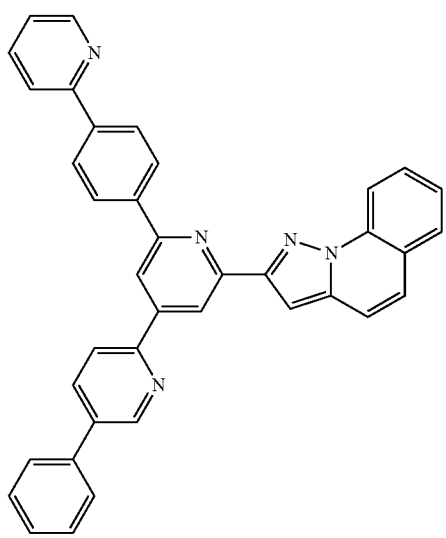
Compound 1-1-37
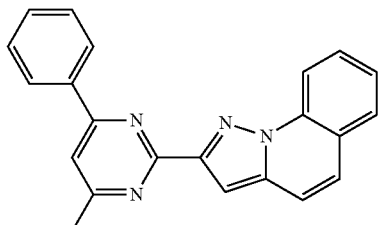
Compound 1-1-38
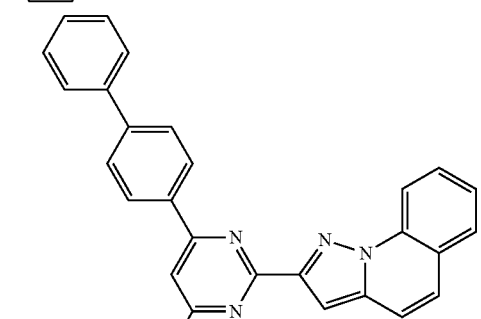
Compound 1-1-39
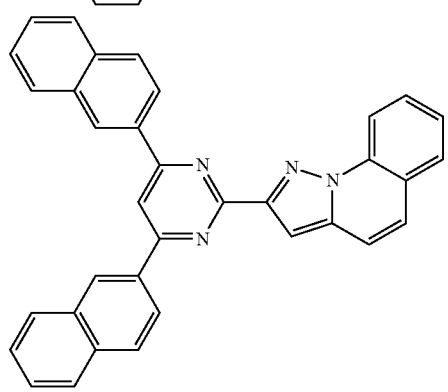
Compound 1-1-40
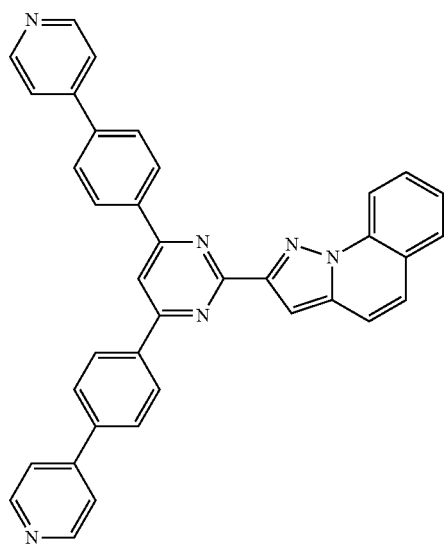

Compound 1-1-41
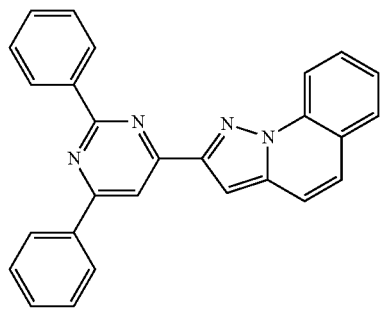
Compound 1-1-42
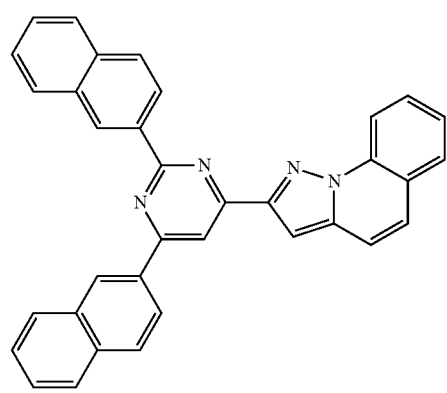
Compound 1-1-43
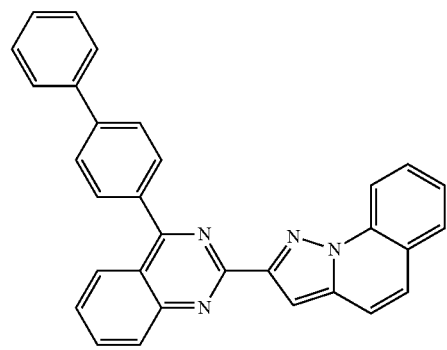
Compound 1-1-44
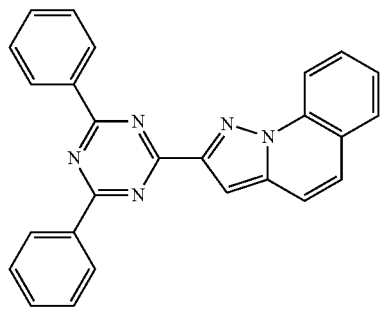
Compound 1-1-45
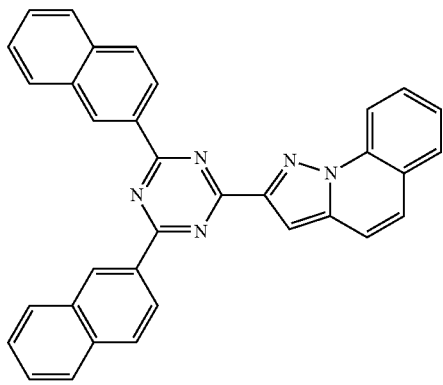
Compound 1-1-46
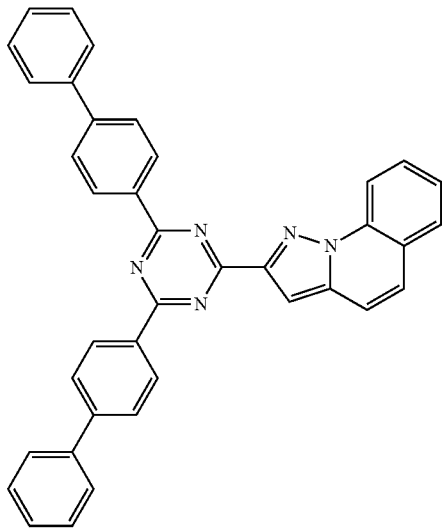
Compound 1-1-47
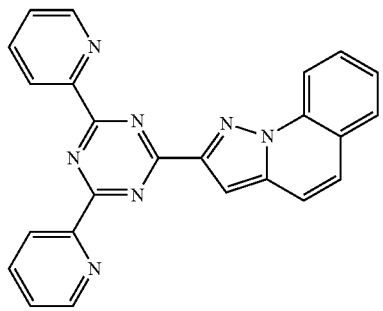
Compound 1-1-48
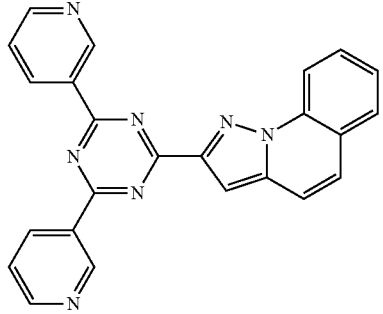

Compound 1-1-49
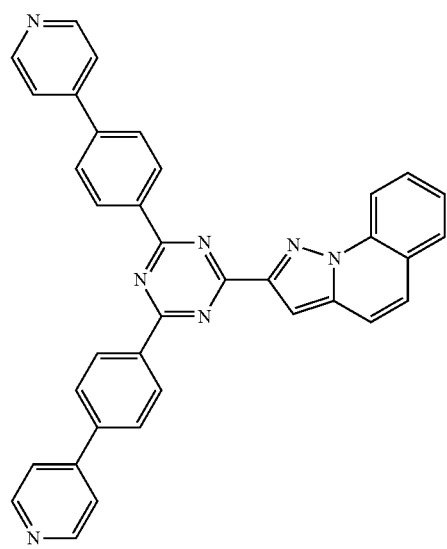
Compound 1-1-50
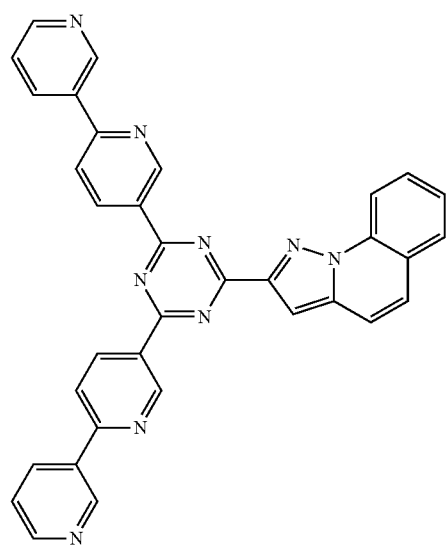
Compound 1-1-51
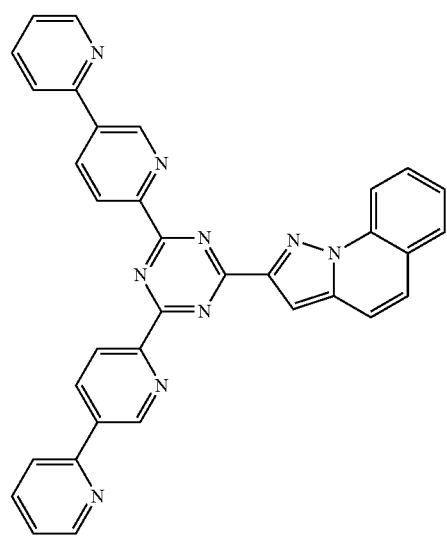
Compound 1-1-52
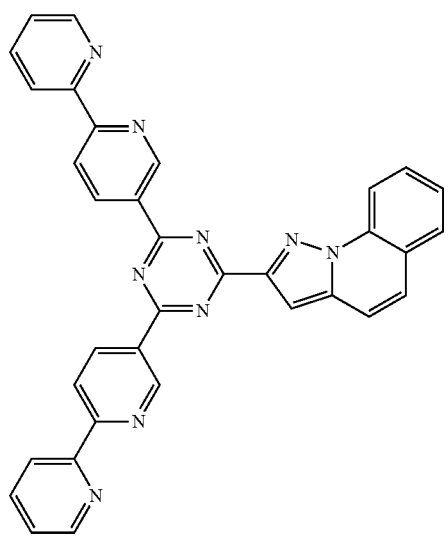
Compound 1-1-53
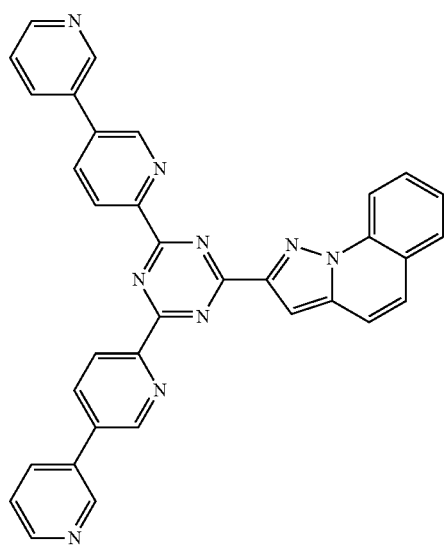
Compound 1-1-54
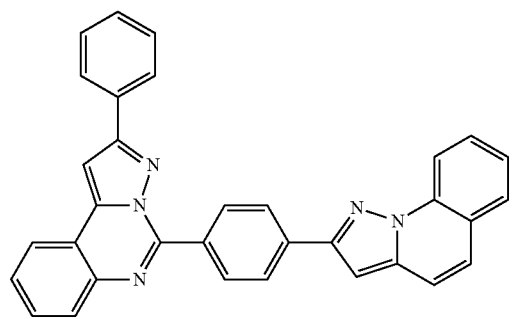

Compound 1-1-55
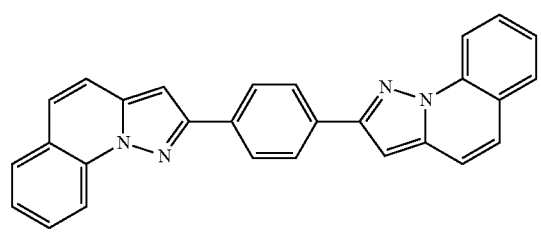
Compound 1-1-56
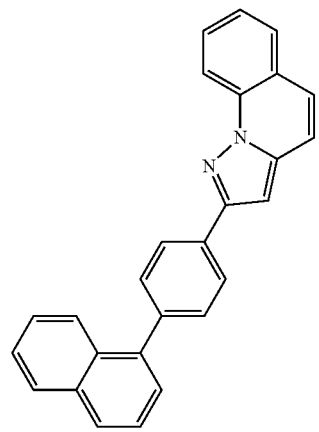
Compound 1-1-57
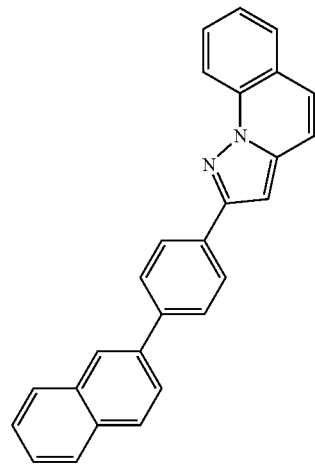
Compound 1-1-58
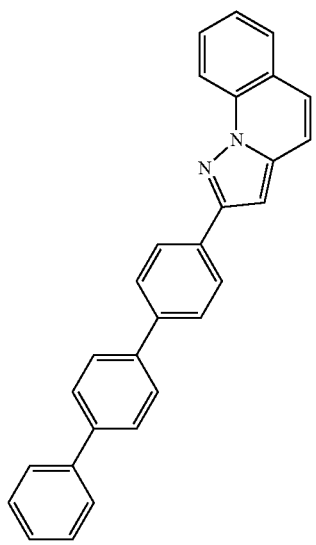
Compound 1-1-59
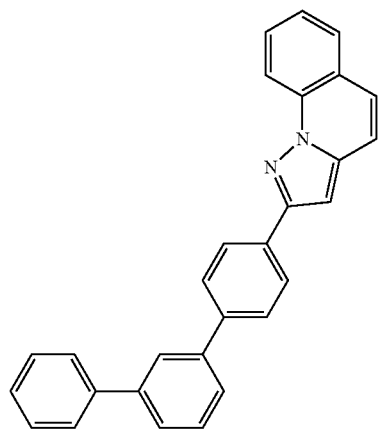
Compound 1-1-60
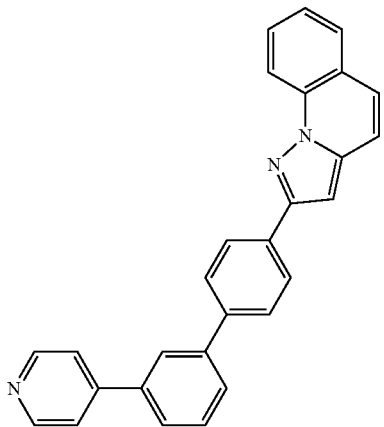

Compound 1-1-61
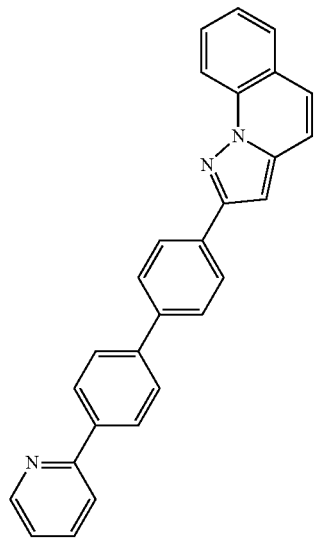
Compound 1-1-62
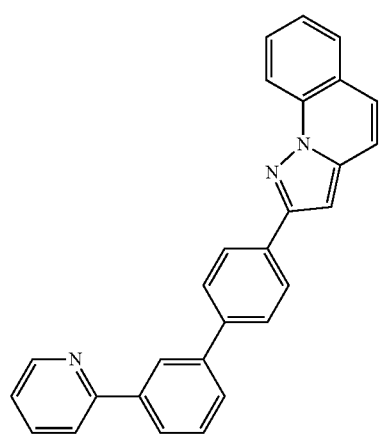
Compound 1-1-63
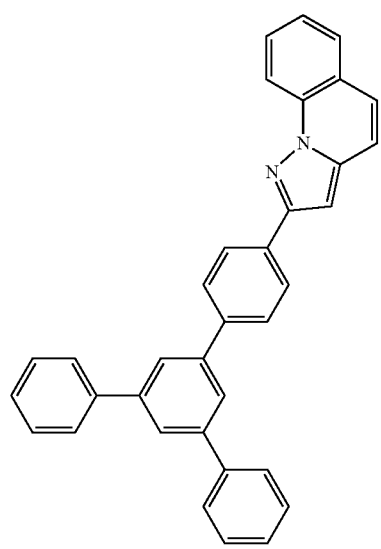
Compound 1-1-64
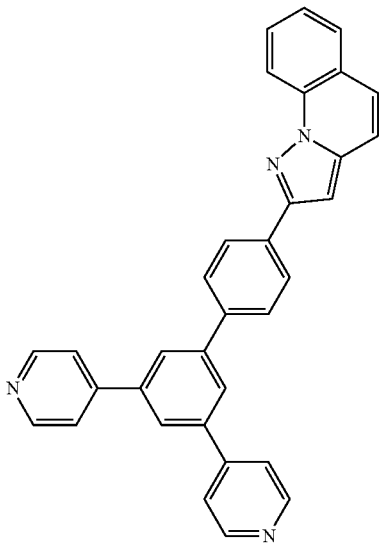
Compound 1-1-65
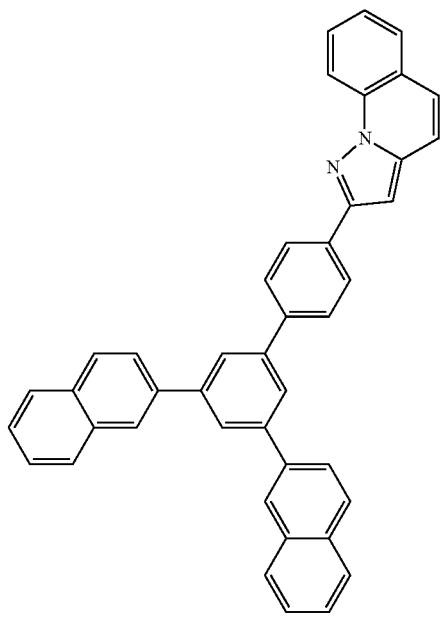

Compound 1-1-66
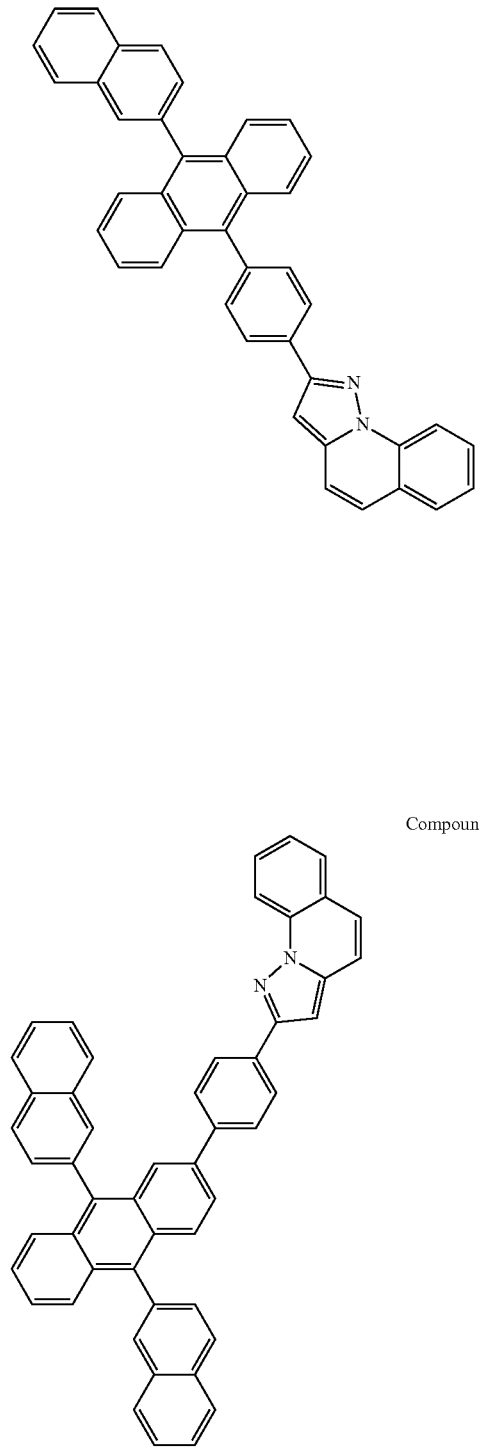
Compound 1-1-67
Compound 1-1-68
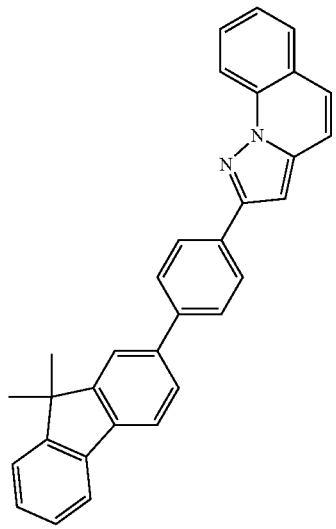
Compound 1-1-69
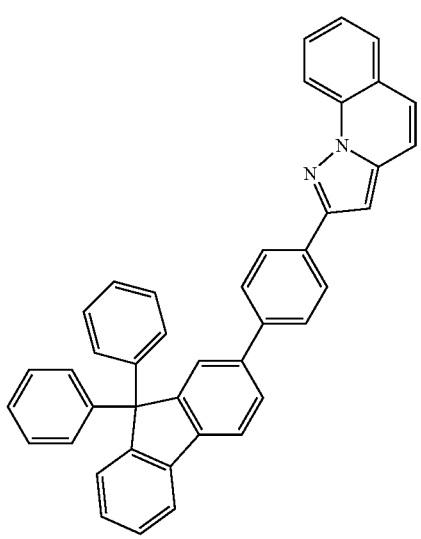
Compound 1-1-70
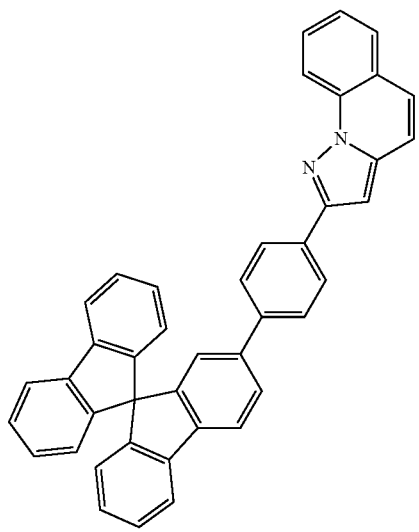

Compound 1-1-71
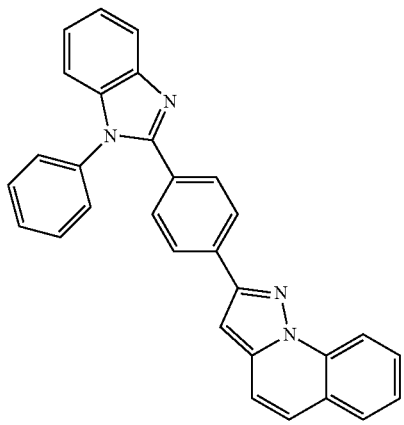
Compound 1-1-72
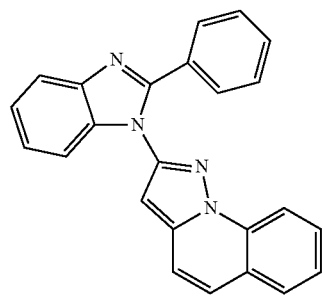
Compound 1-1-73
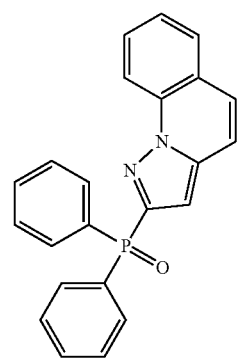
Compound 1-1-74
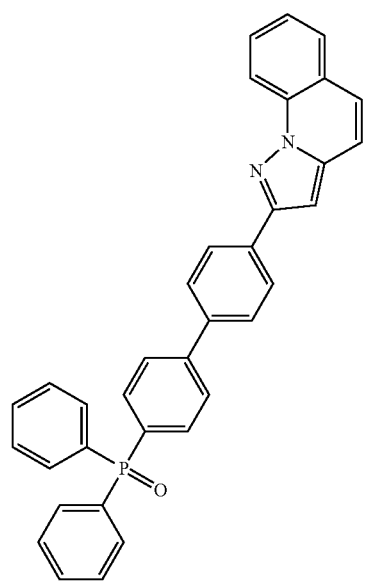
Compound 1-1-75
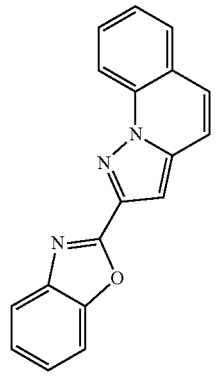
Compound 1-1-76
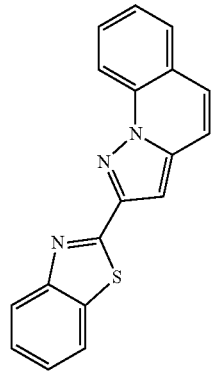
Compound 1-1-77
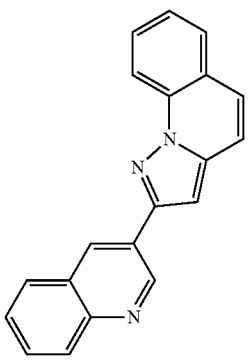
Compound 1-1-78
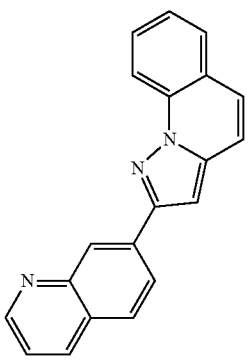

Compound 1-1-79
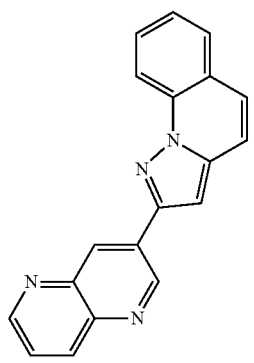
Compound-1-1-80
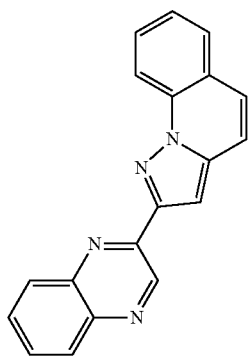
Compound 1-1-81
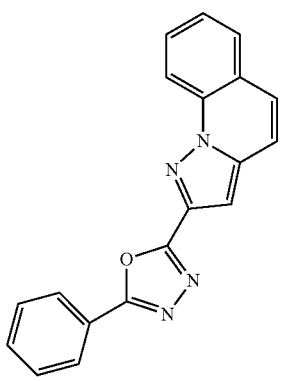
Compound 1-1-82
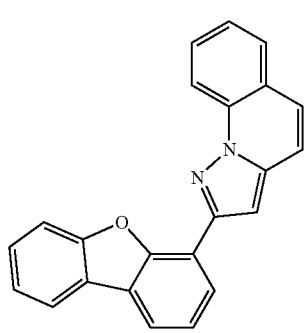
Compound 1-1-83
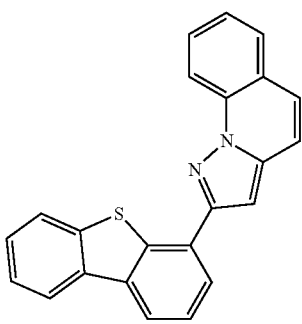
Compound 1-1-84
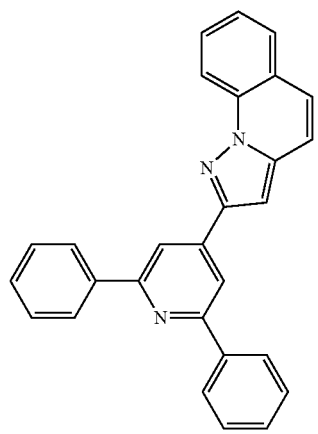
Compound 1-1-85
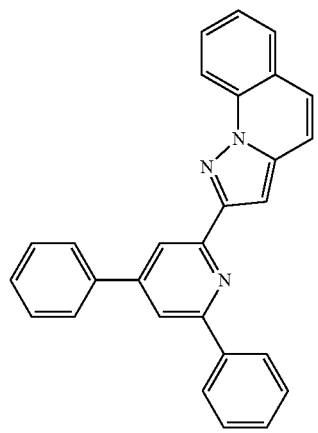
Compound 1-1-86
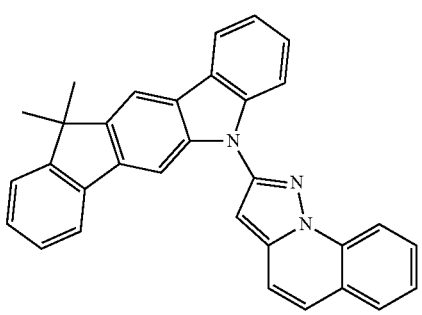

Compound 1-1-87
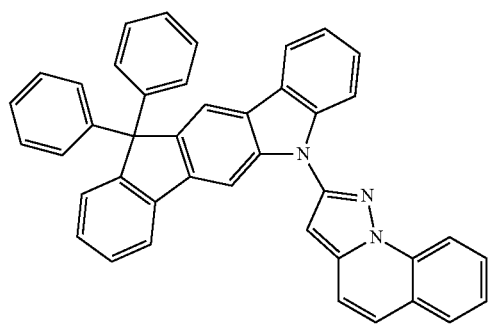
Compound 1-1-88
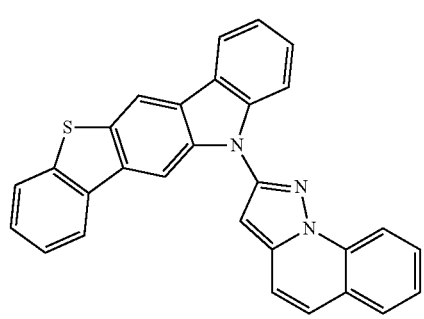
Compound 1-1-89
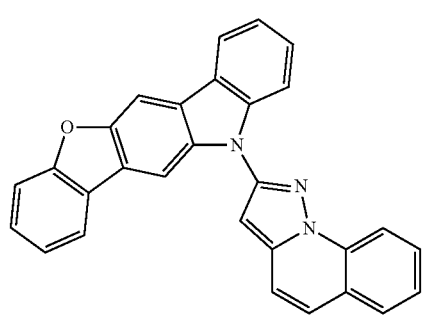
Compound 1-1-90
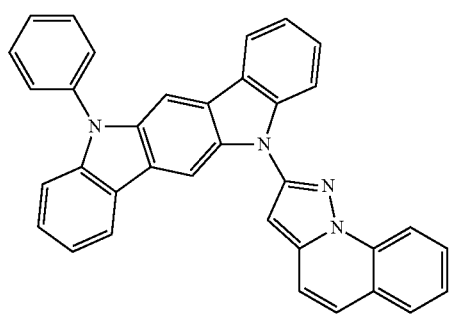
Compound 1-1-91
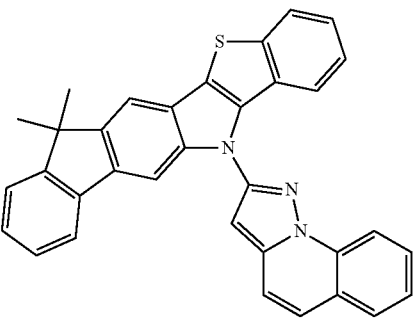
Compound 1-1-92
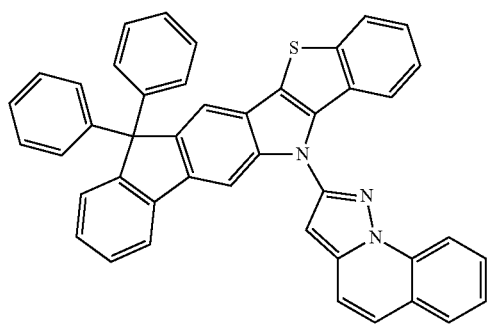
Compound 1-1-93
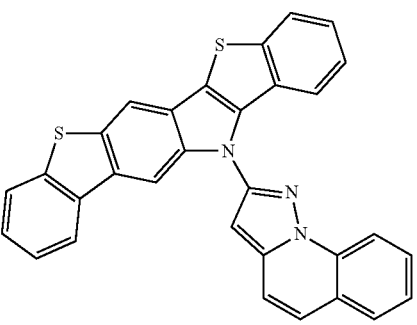
Compound 1-1-94
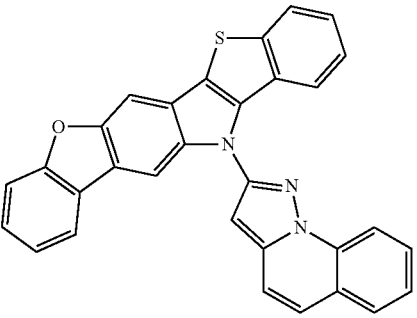

-continued
Compound 1-1-95
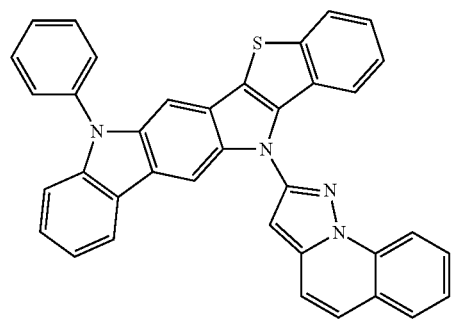
Compound 1-1-96
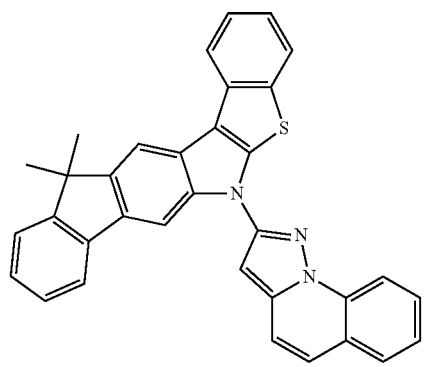
Compound 1-1-97
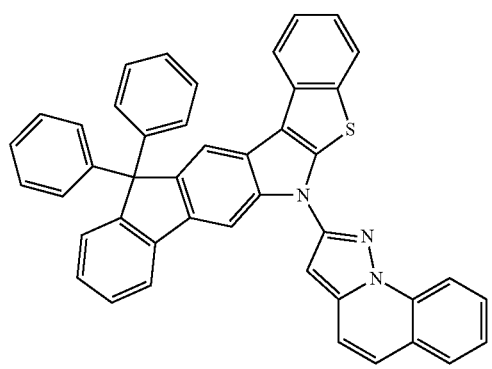
Compound 1-1-98
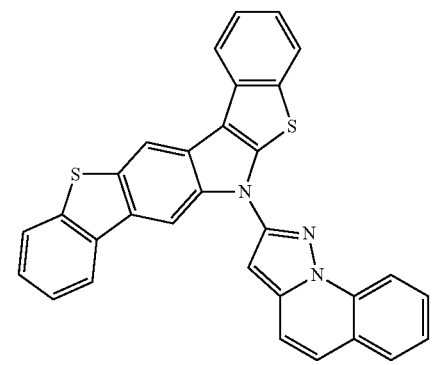
-continued
Compound 1-1-99
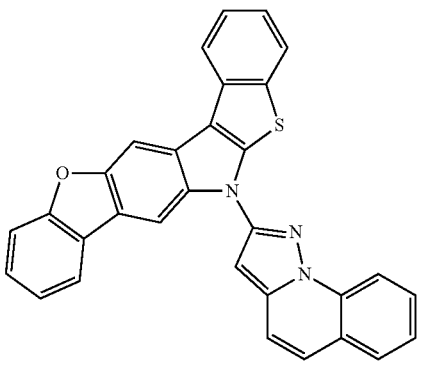
Compound 1-1-100
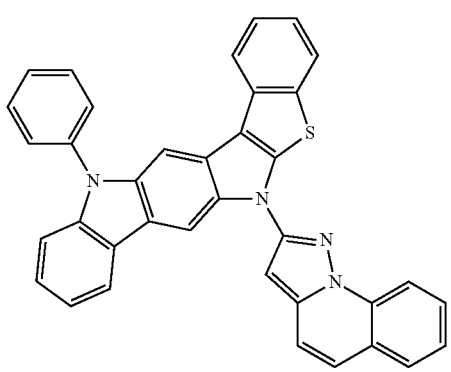
Compound 1-1-101
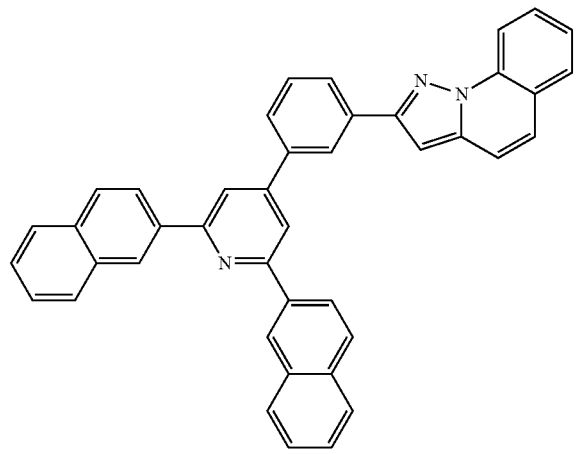

-continued
Compound 1-1-102
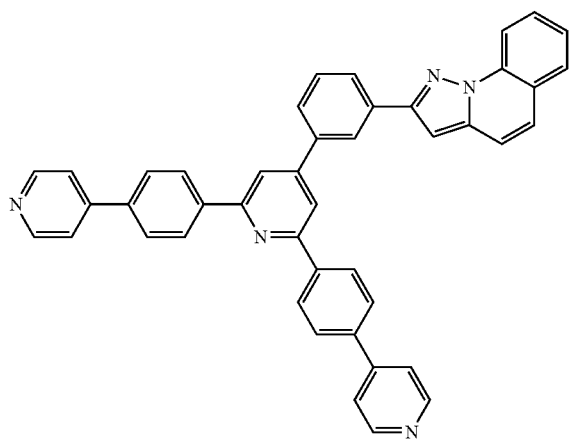
Compound 1-1-103
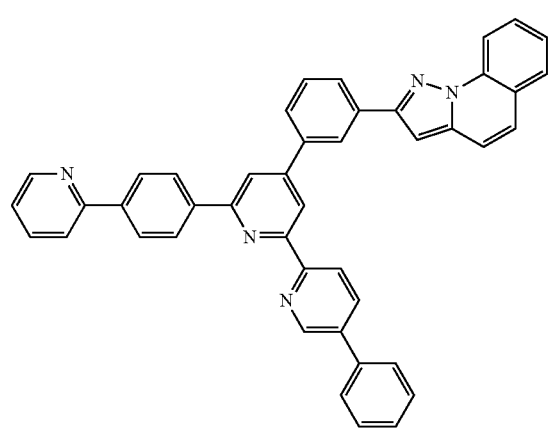
Compound 1-1-104
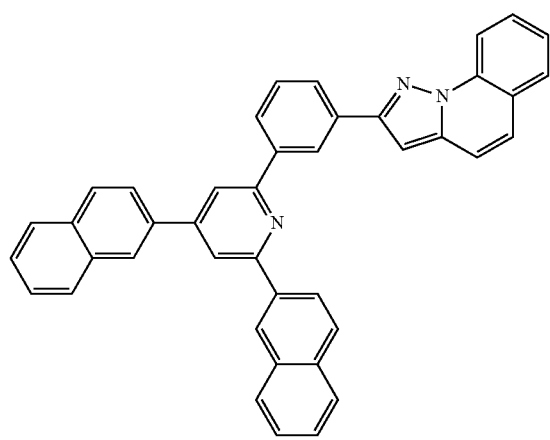
Compound 1-1-105
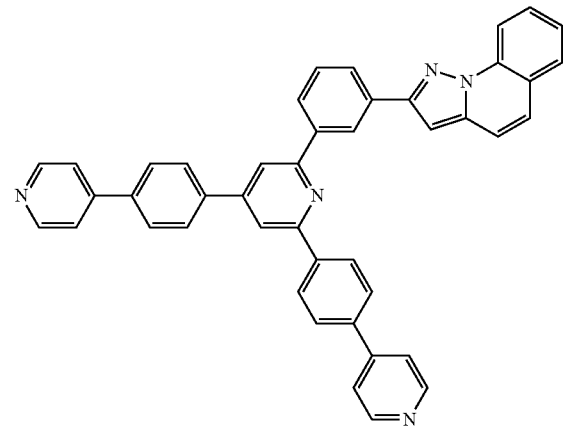
Compound 1-1-106
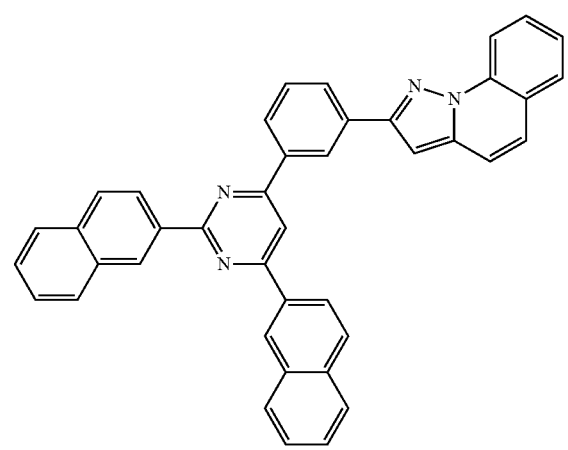
Compound 1-1-107
Compound 1-1-108
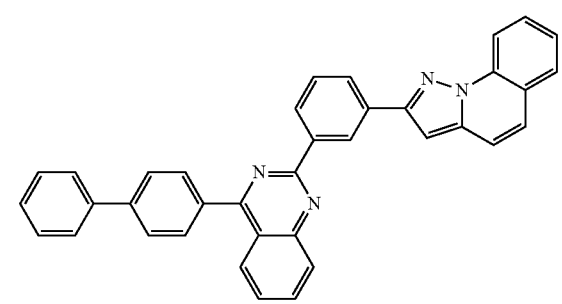

Compound 1-1-109
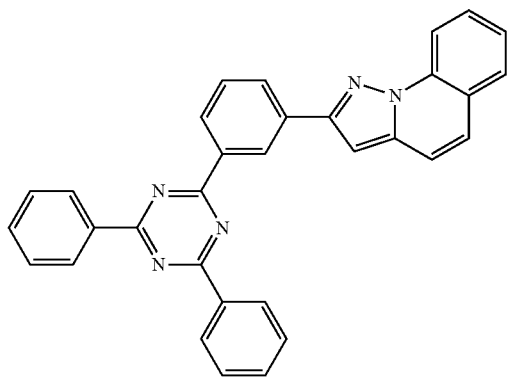
Compound 1-1-110
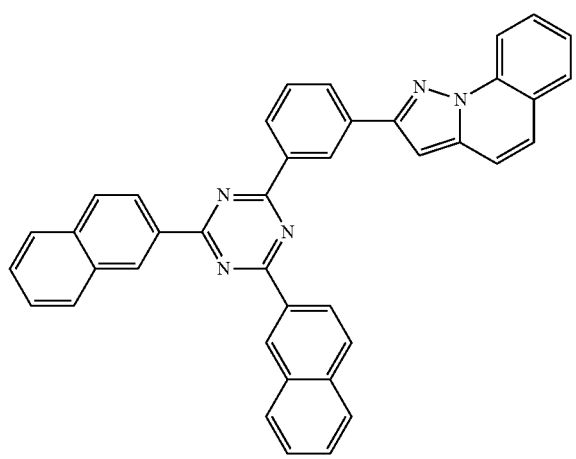
Compound 1-1-111
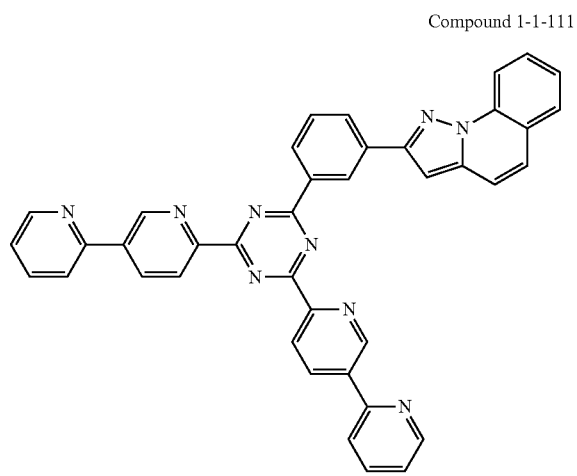
Compound 1-1-112
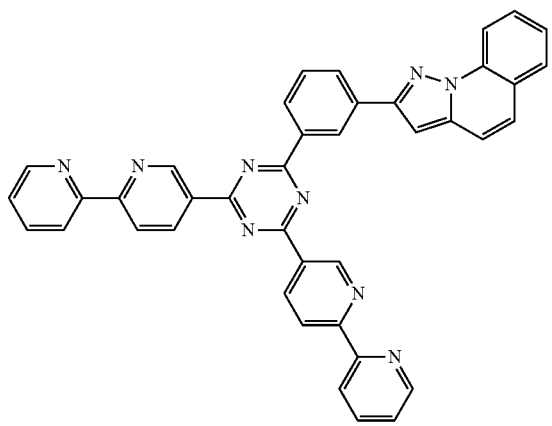
Compound 1-1-113
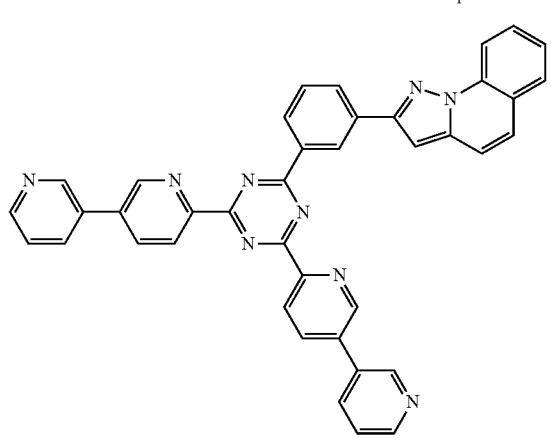
Compound 1-1-114
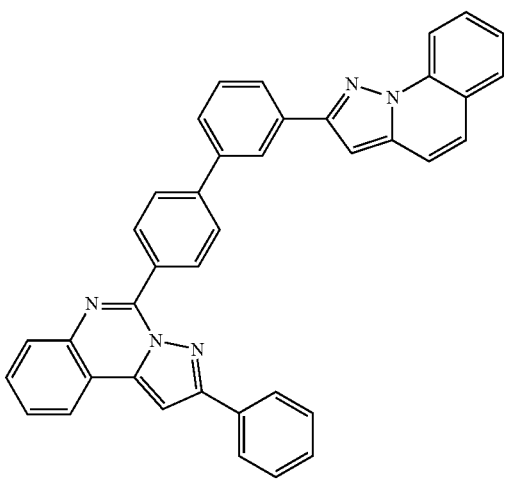

Compound 1-1-115
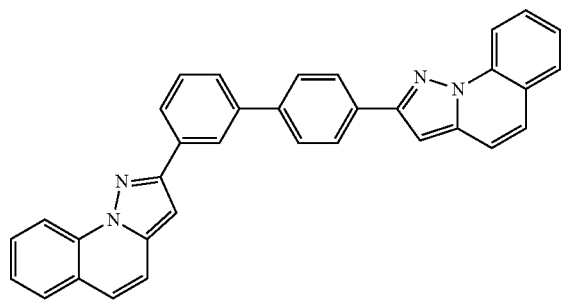
Compound 1-1-116
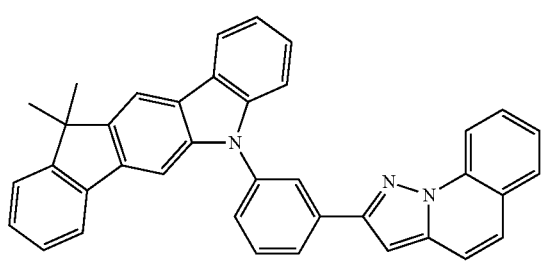
Compound 1-1-117
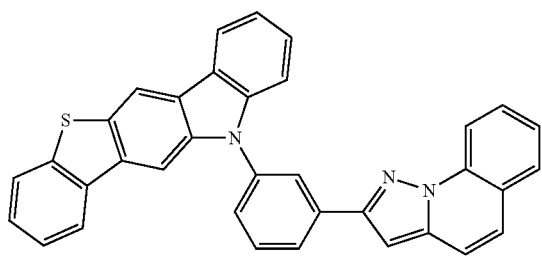
Compound 1-1-118
Compound 1-1-119
Compound 1-1-120
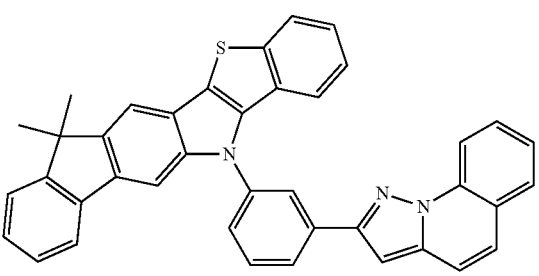
Compound 1-1-121
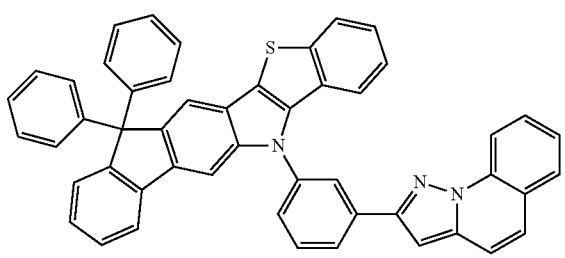
Compound 1-1-122
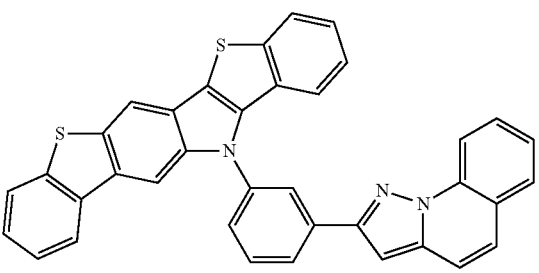
Compound 1-1-123
Compound 1-1-124
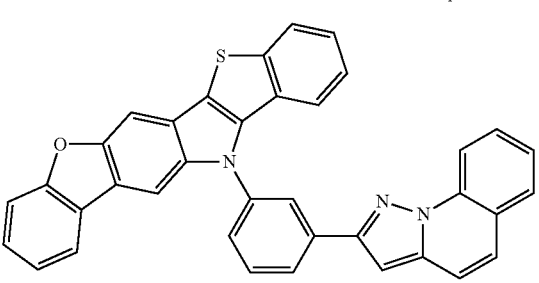

Compound 1-1-125
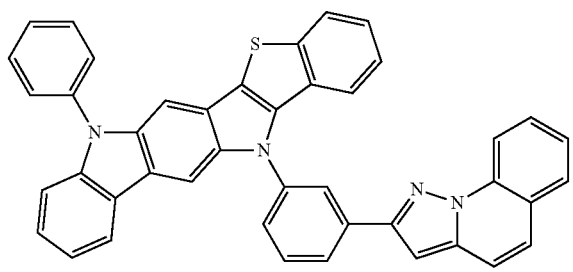
Compound 1-1-126
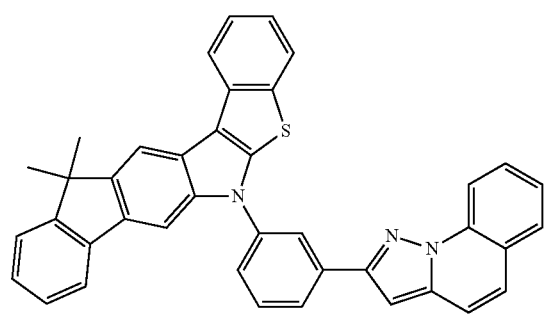
Compound 1-1-127
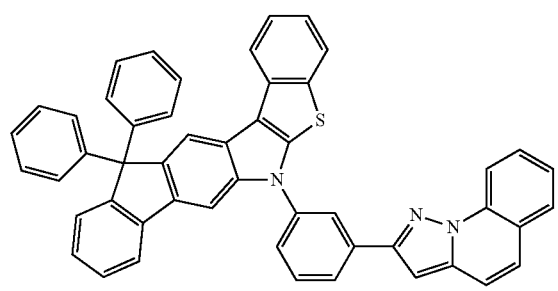
Compound 1-1-128
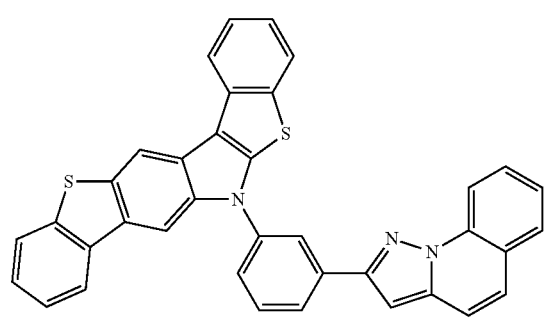
Compound 1-1-129
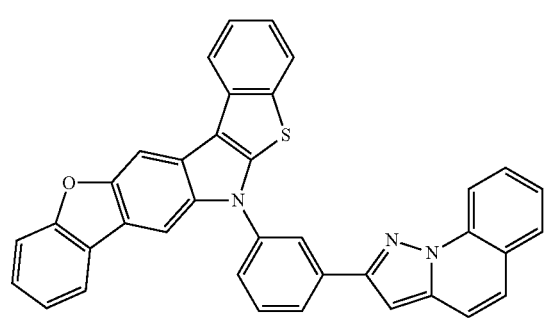
Compound 1-1-130
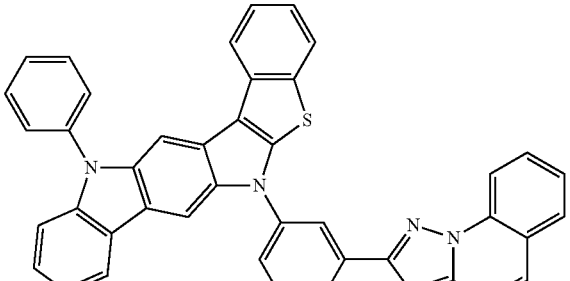
Compound 1-1-131
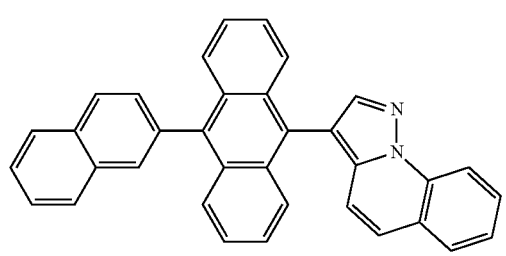
Compound 1-1-132
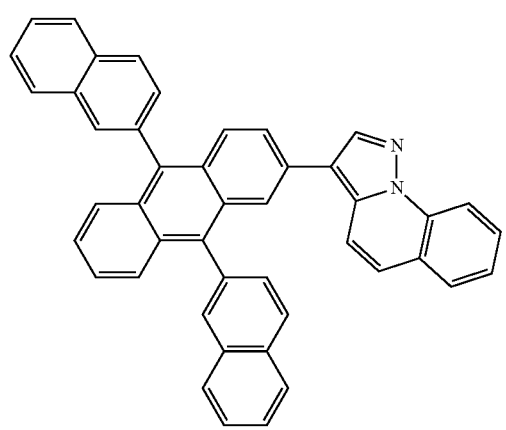
Compound 1-1-133
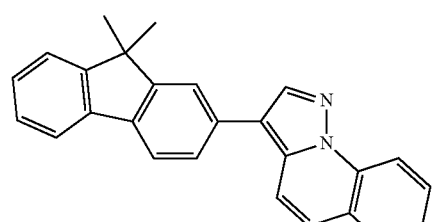
Compound 1-1-134
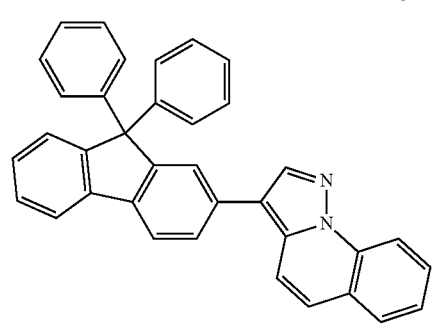

Compound 1-1-135
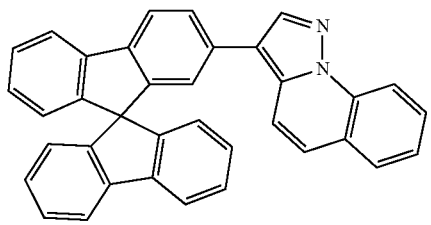
Compound 1-1-136
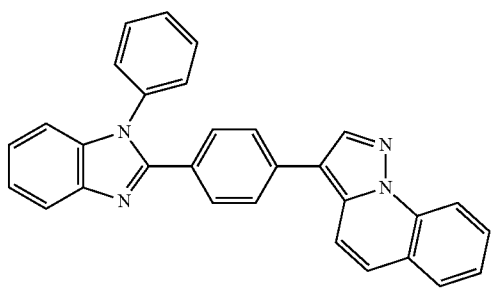
Compound 1-1-137
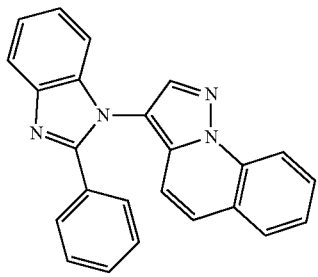
Compound 1-1-138
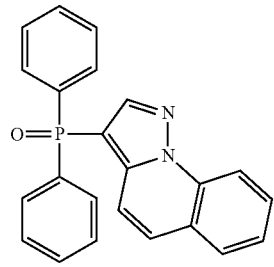
Compound 1-1-139
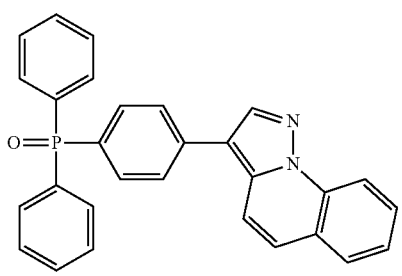
Compound 1-1-140
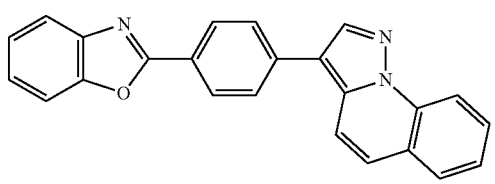
Compound 1-1-141
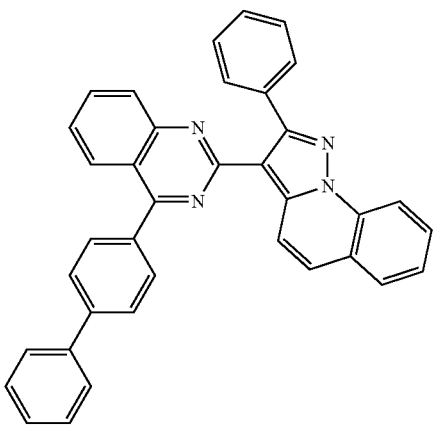
Compound 1-1-142
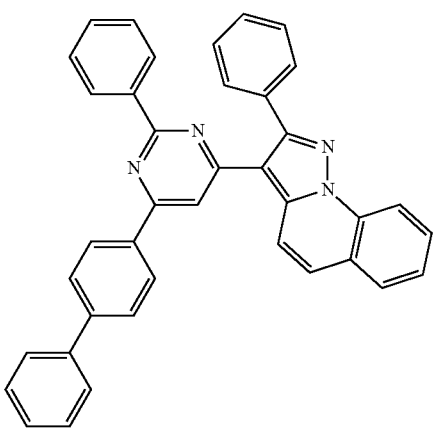
Compound 1-1-143
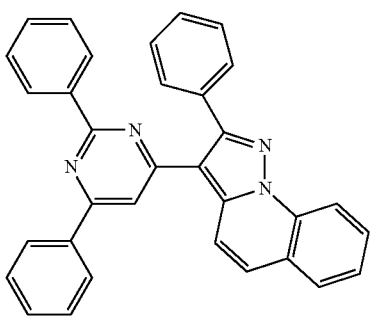
Compound 1-1-144
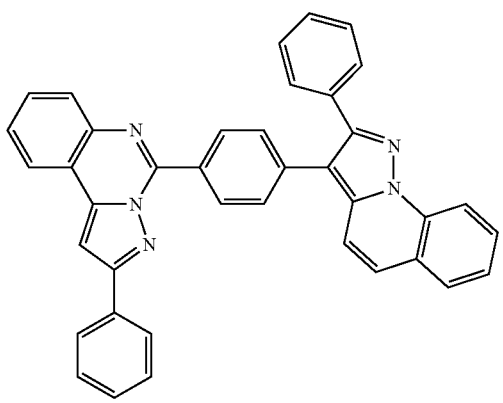

Compound 1-1-145
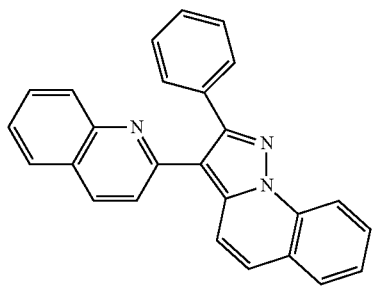
Compound 1-1-150
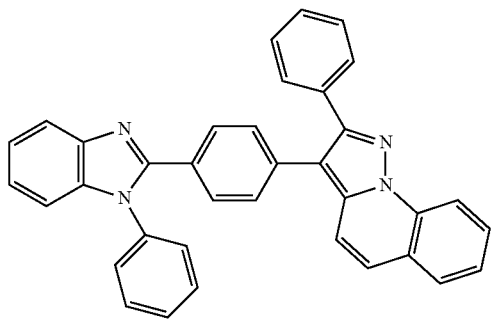
Compound 1-1-146
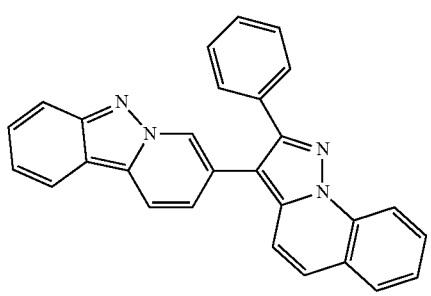
Compound 1-1-147
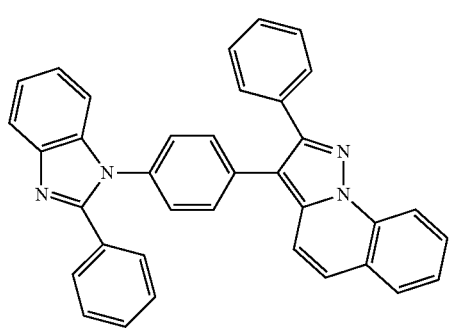
Compound 1-1-151

Compound 1-1-148
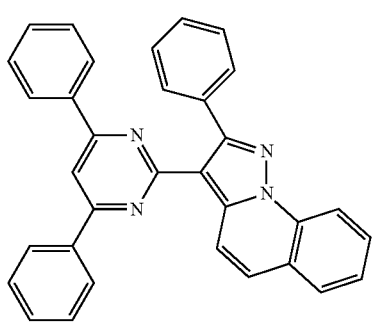
Compound 1-1-152
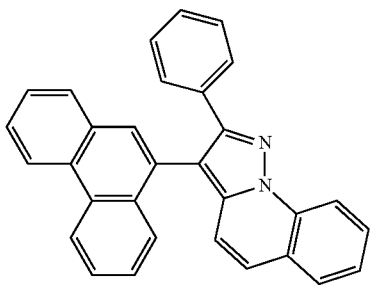
Compound 1-1-149
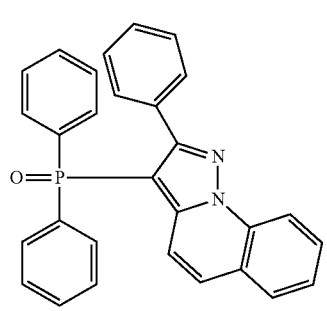
Compound 1-1-153
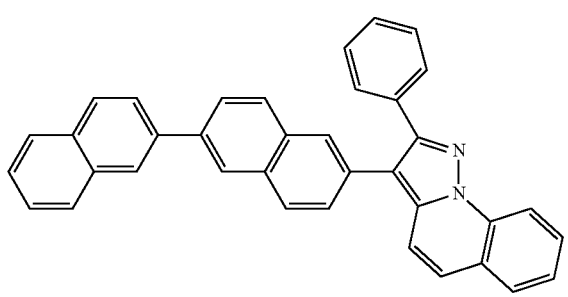

Compound 1-1-154
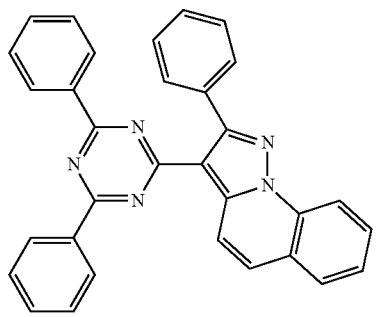
Compound 1-1-159
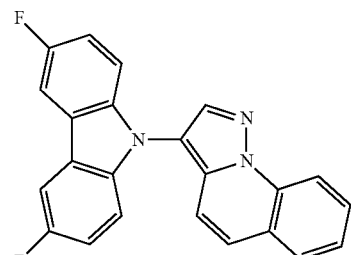
Compound 1-1-155
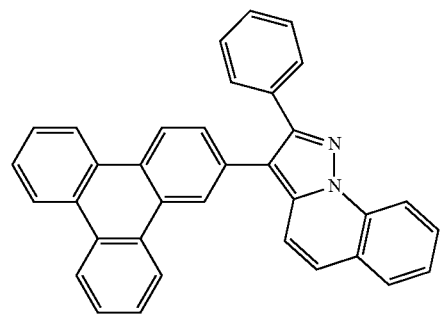
Compound 1-1-160
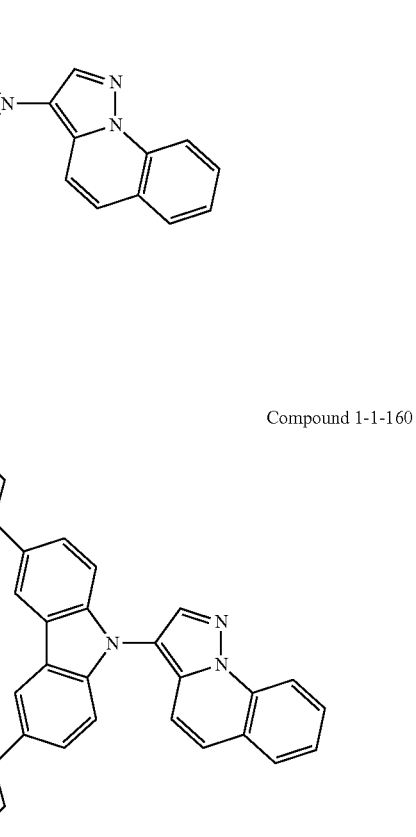
Compound 1-1-156
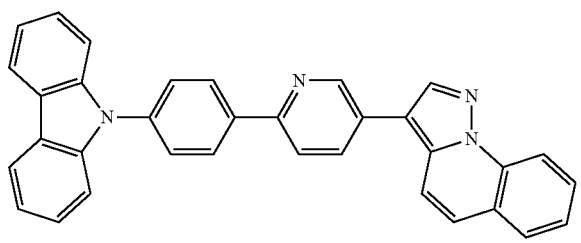
Compound 1-1-157
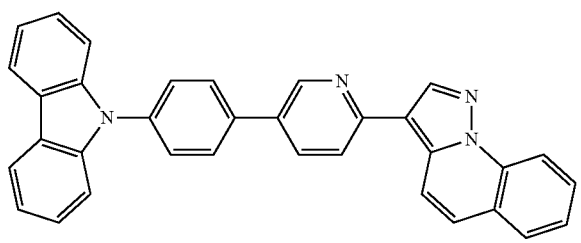
Compound 1-1-161
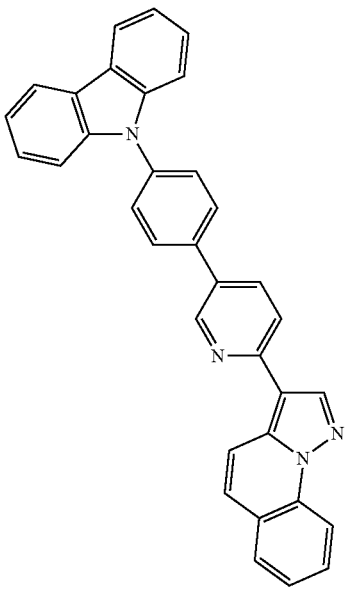
Compound 1-1-158

Compound 1-1-162
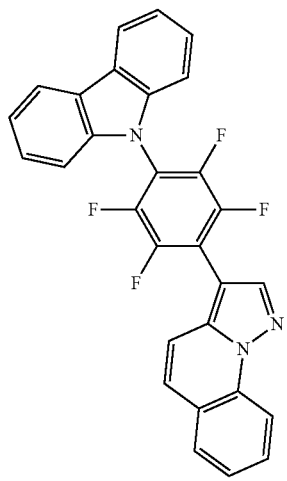
Compound 1-1-165
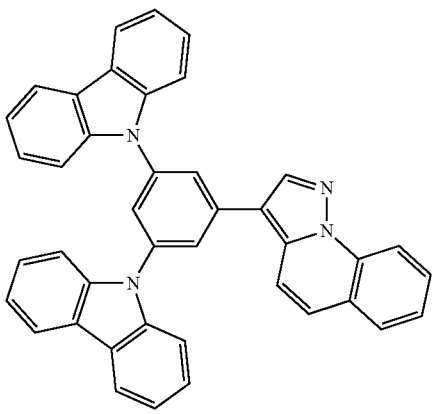
Compound 1-1-163
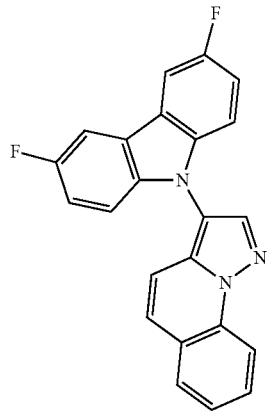
Compound 1-1-166
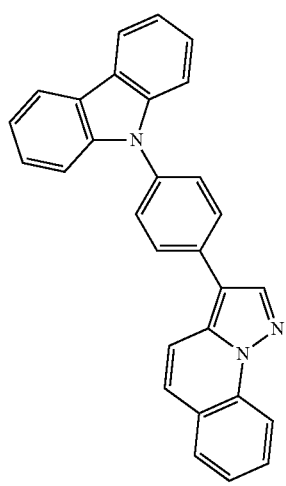
Compound 1-1-164
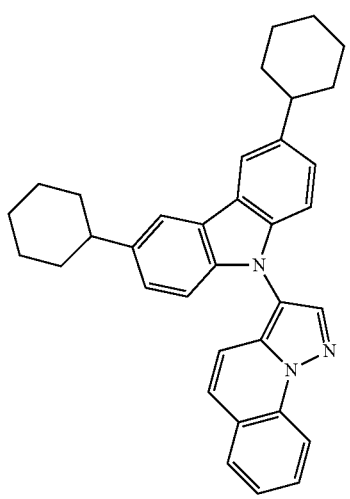
Compound-1-1-167
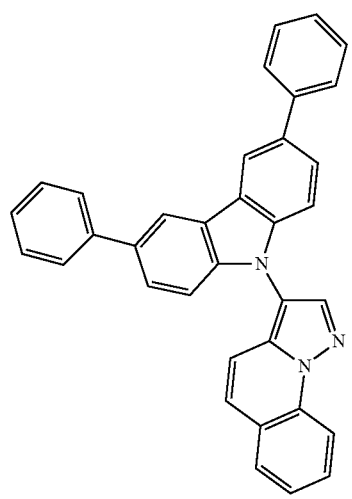

Compound 1-1-168
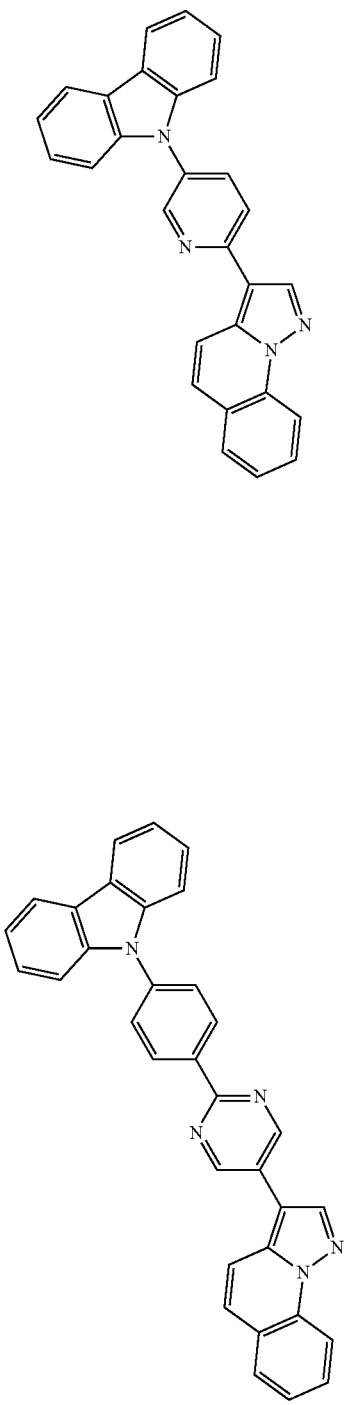
Compound 1-1-169
Compound 1-1-170
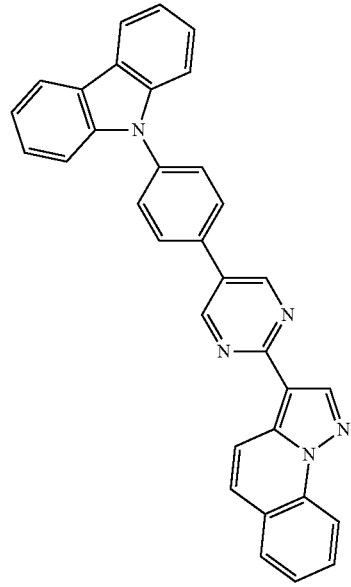
Compound 1-1-171
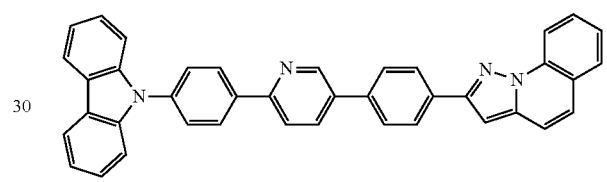
Compound 1-1-172

Compound 1-1-173
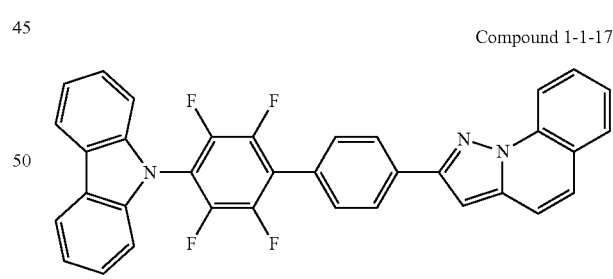
Compound 1-1-174
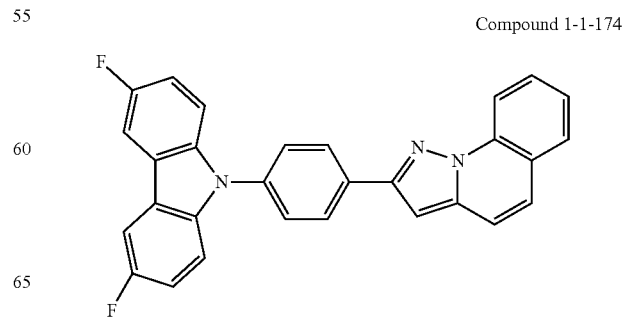

Compound 1-1-175
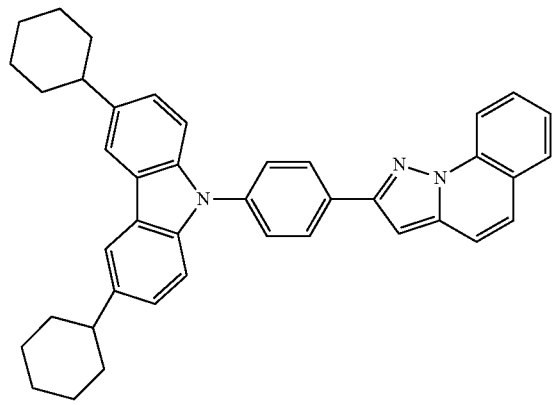
Compound 1-1-176
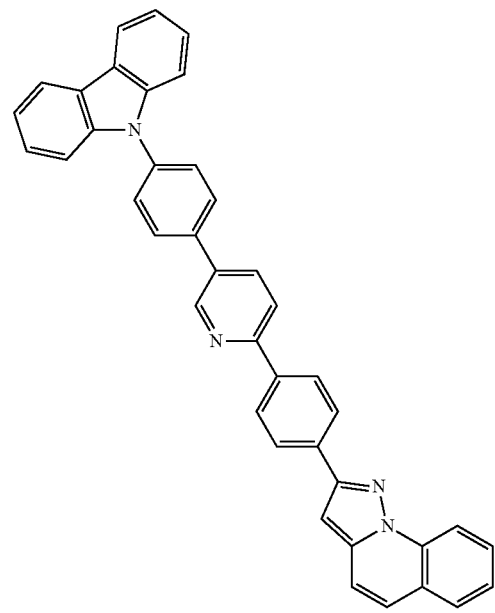
Compound 1-1-177
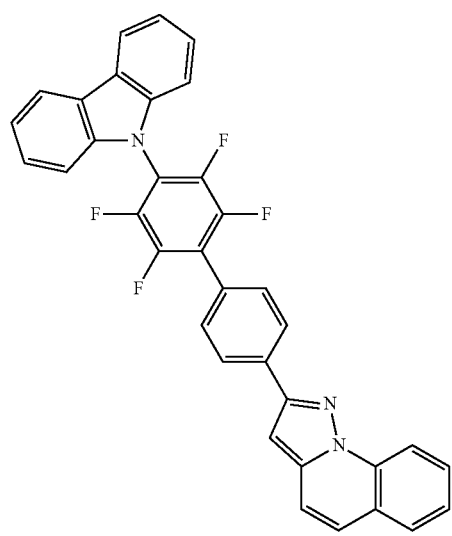
Compound-1-1-178
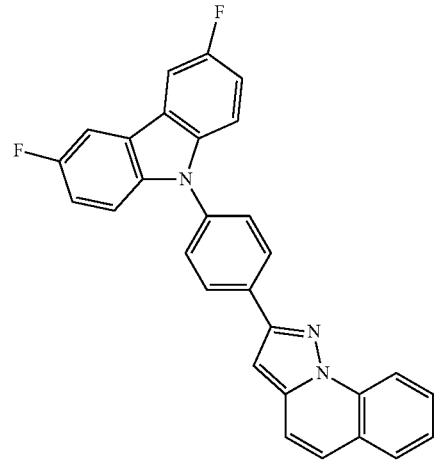
Compound 1-1-179
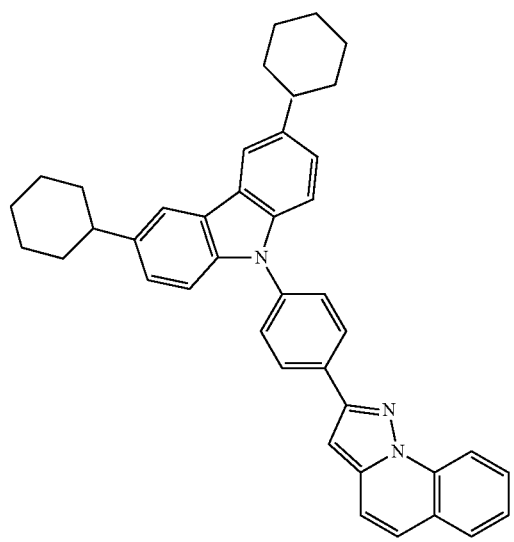
Compound-1-1-180
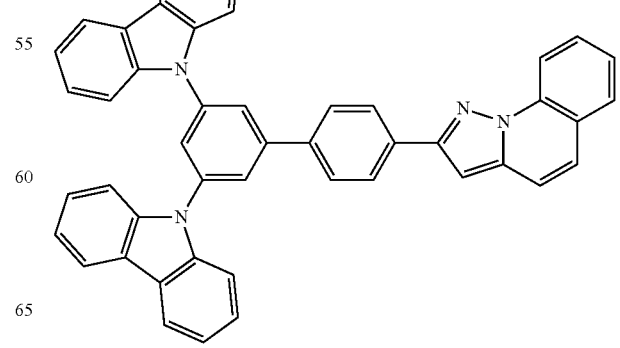

Compound-1-1-181
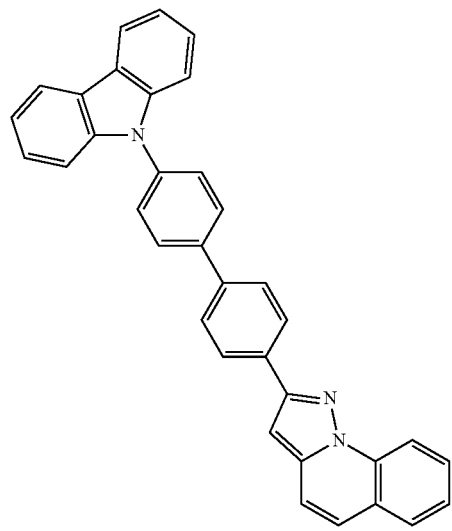
Compound 1-1-182
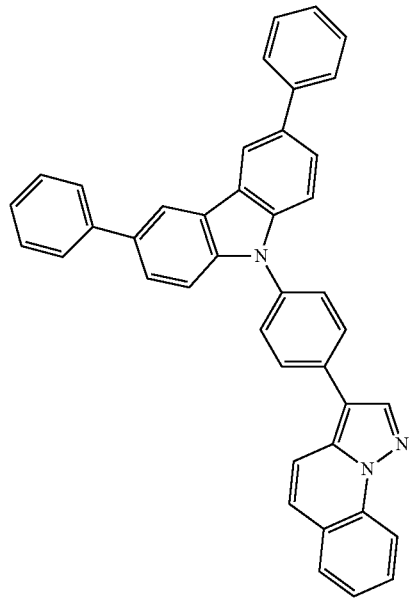
Compound 1-1-183
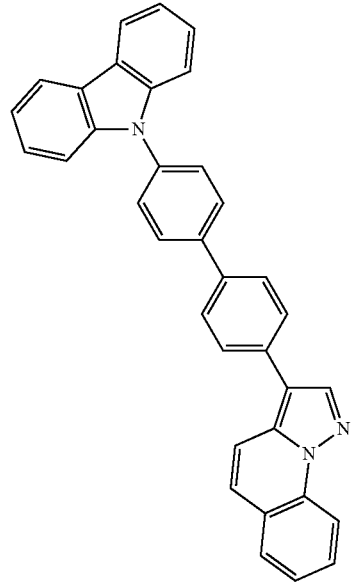
Compound-1-1-184
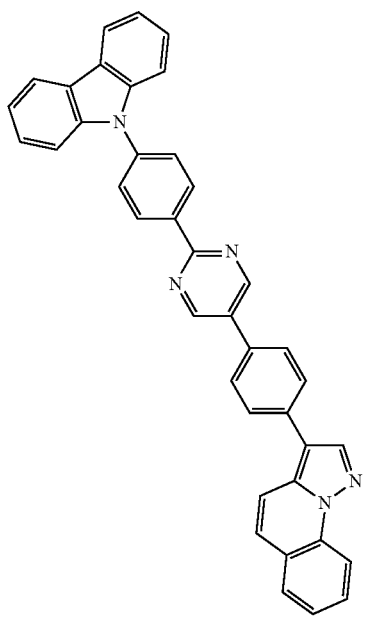

Compound 1-1-185
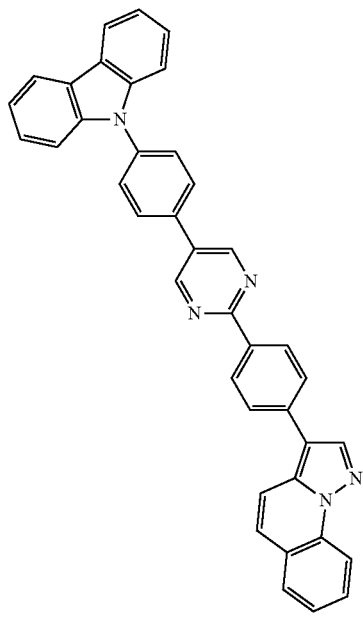
Compound 1-1-186
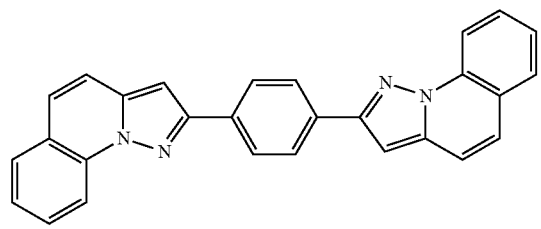
Compound 1-1-187
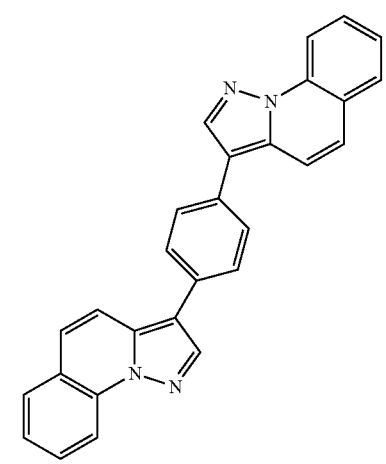
Compound 1-1-188
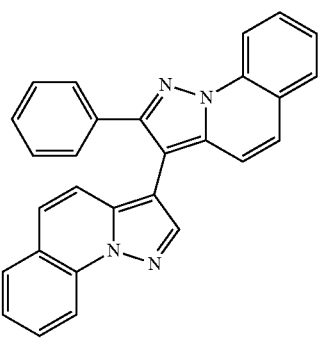
Compound 1-1-189
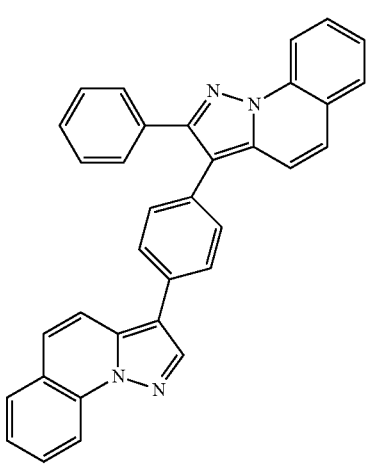
Compound 1-1-190
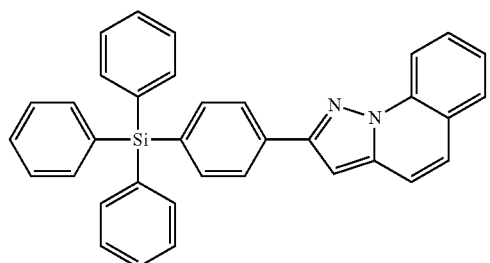
Compound 1-1-191
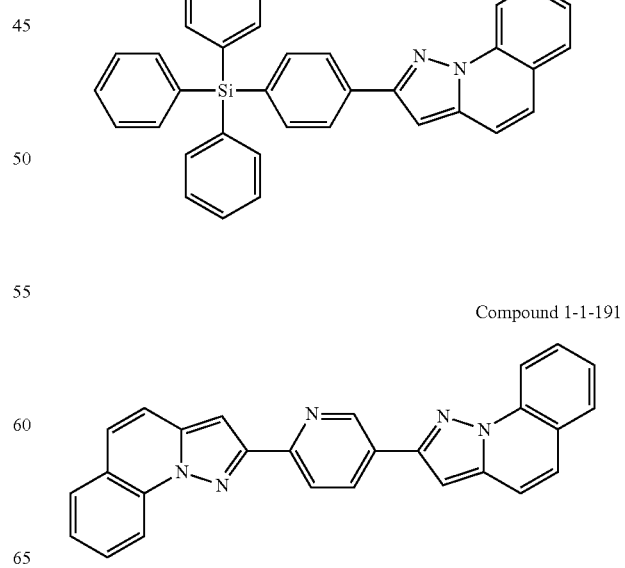

Compound 1-1-192
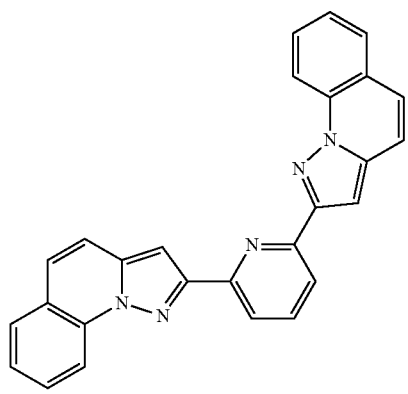
Compound 1-1-195
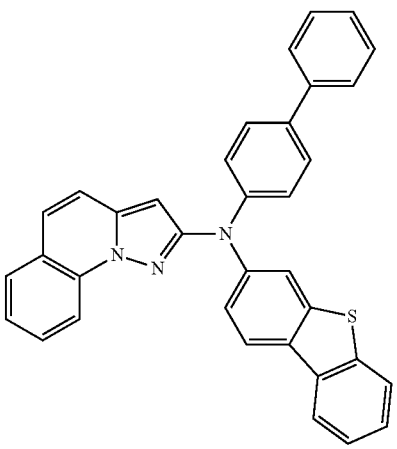
Compound 1-1-193
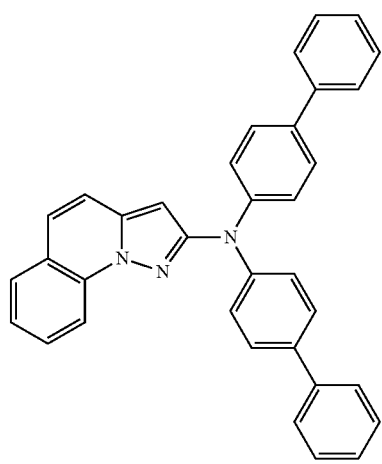
Compound 1-1-196
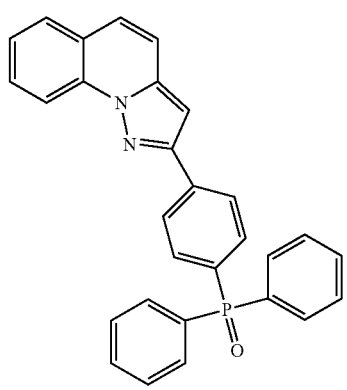
Compound 1-1-194
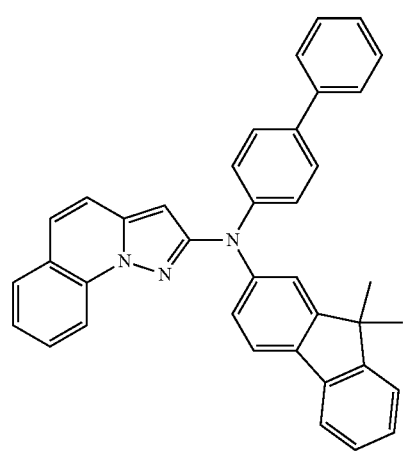
Compound 1-1-197
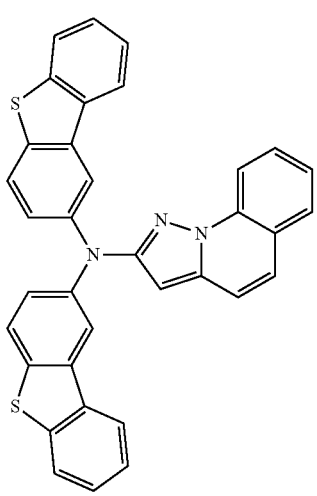

Compound 1-1-198
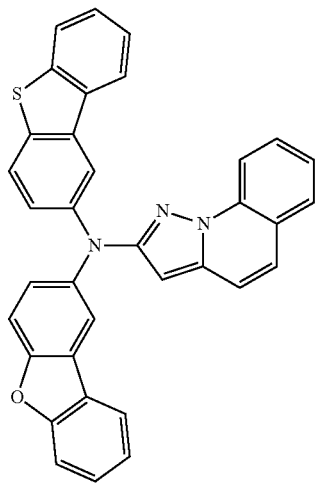
Compound 1-1-201
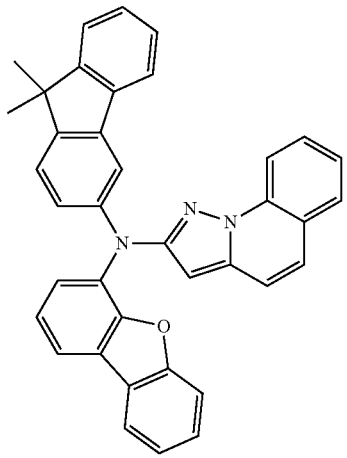
Compound 1-1-199
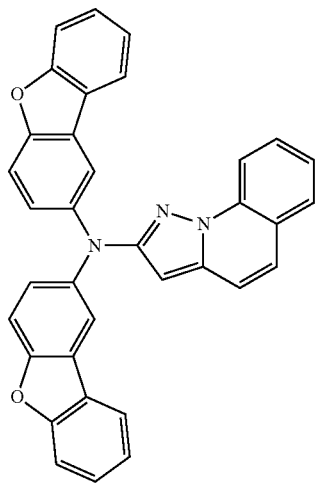
Compound 1-1-202
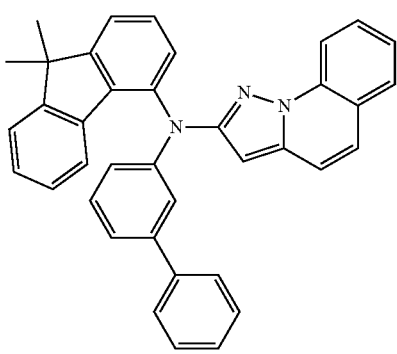
Compound 1-1-200
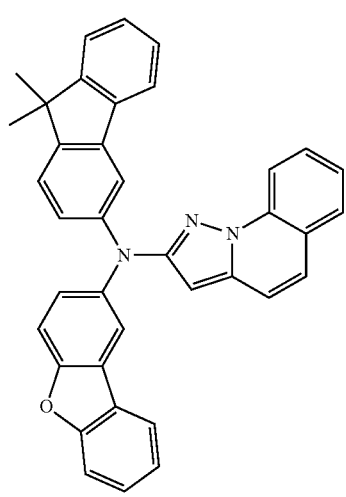
Compound 1-1-203
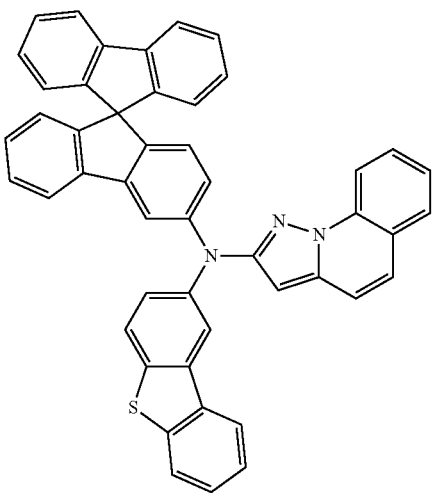

-continued
Compound 1-1-204
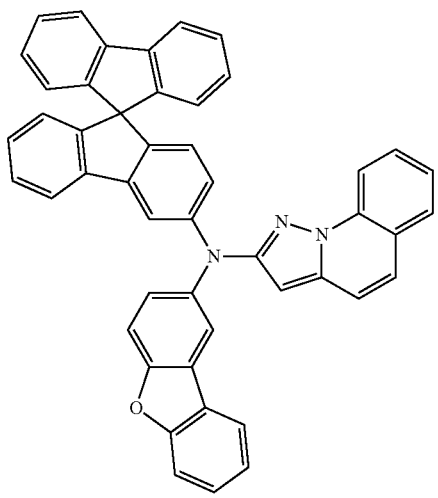
Compound 1-1-205
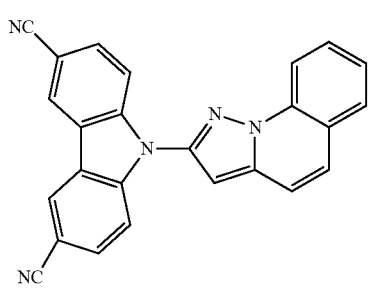
Compound 1-1-206
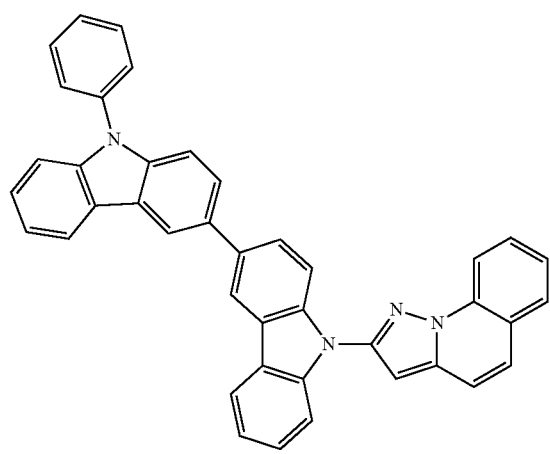
-continued
Compound 1-1-207
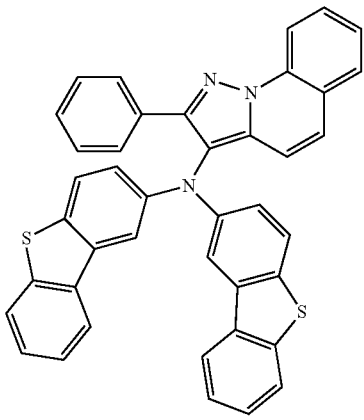
Compound 1-1-208
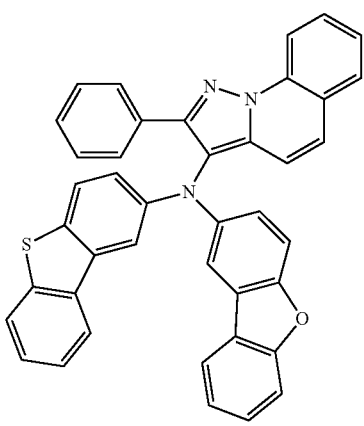
Compound 1-1-209
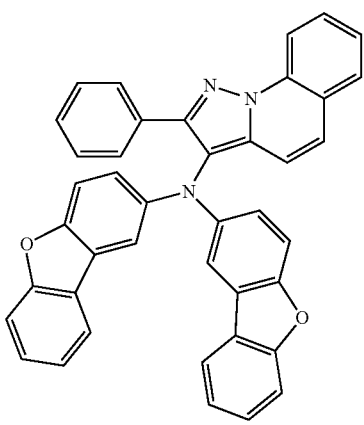

Compound 1-1-210
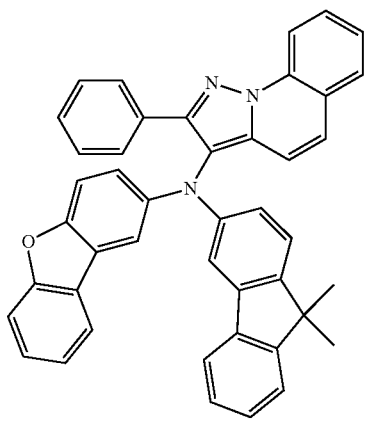
Compound 1-1-211
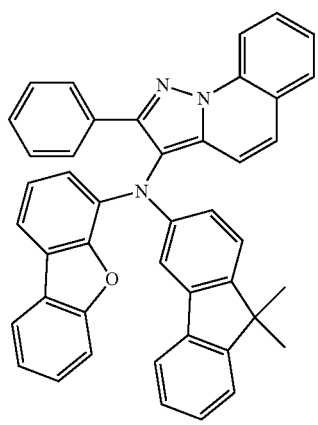
Compound 1-1-212
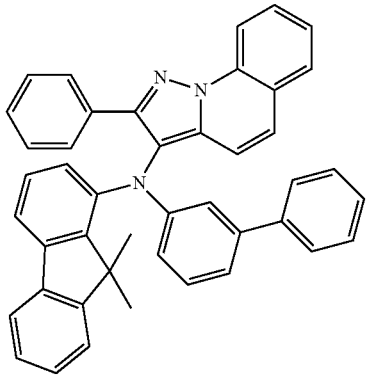
Compound 1-1-213
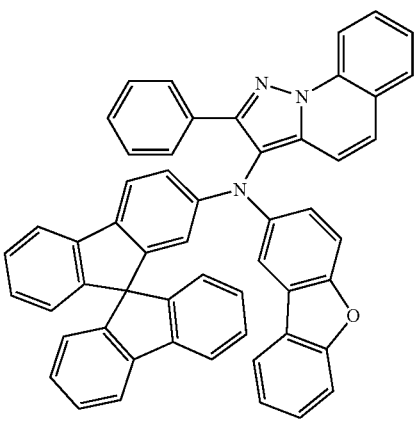
Compound 1-1-214
Compound 1-1-215
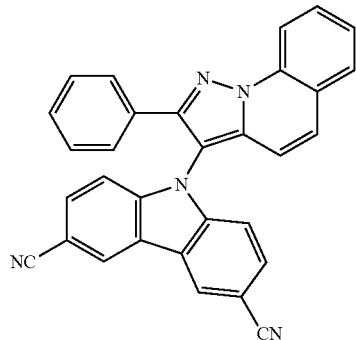

Compound 1-1-216
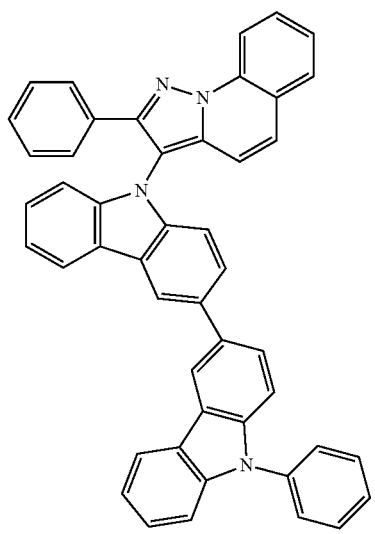
According to an exemplary embodiment of the present application, Formula 1 may be selected from the following compounds.
Compound 2-1-1
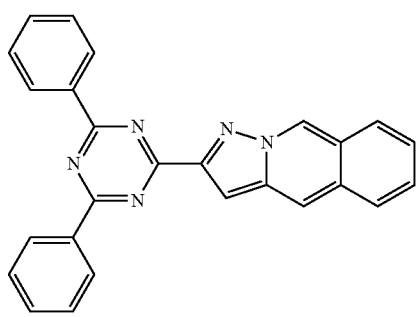
Compound 2-1-2
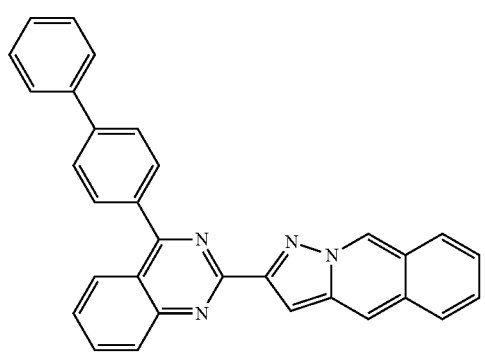
Compound 2-1-3
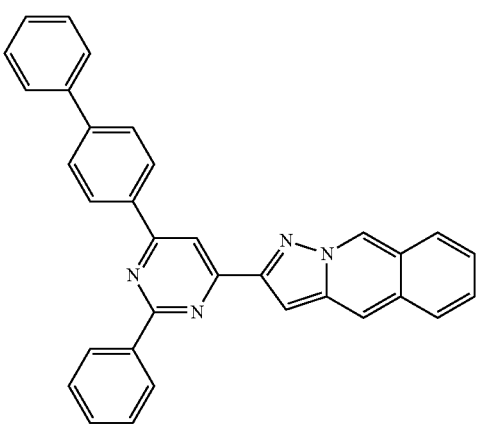
Compound 2-1-4
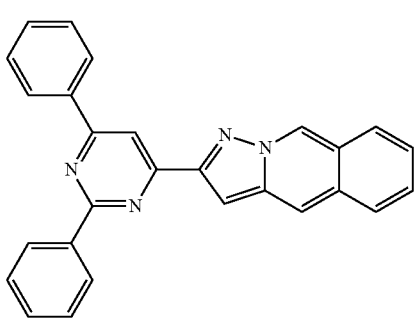
Compound 2-1-5
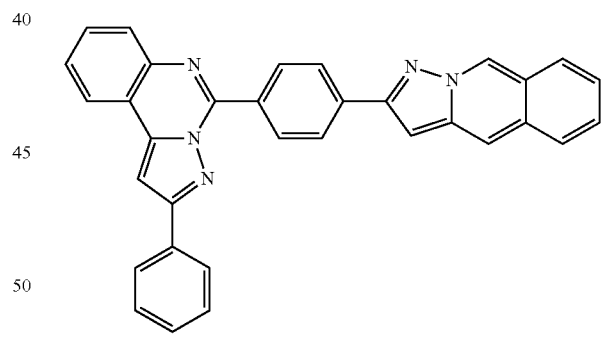
Compound 2-1-6
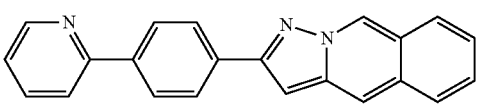
Compound 2-1-7

Compound 2-1-8
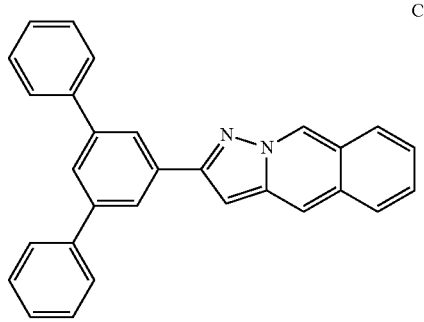
Compound 2-1-9
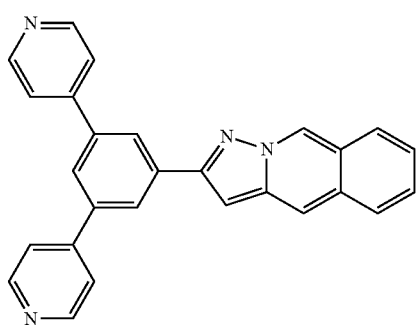
Compound 2-1-10
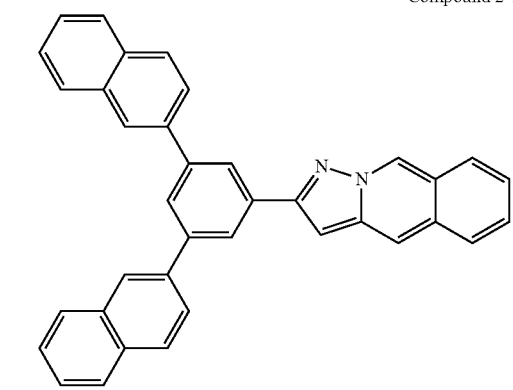
Compound 2-1-11
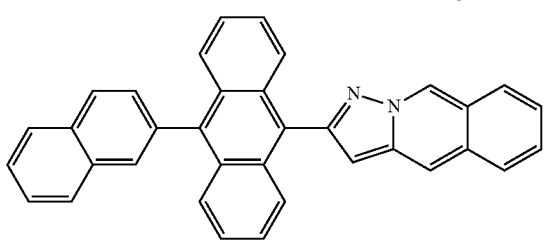
Compound 2-1-12
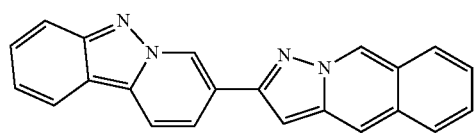
Compound 2-1-13
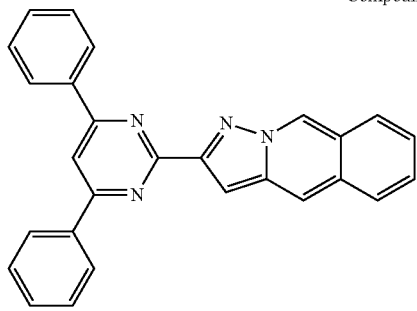
Compound 2-1-14
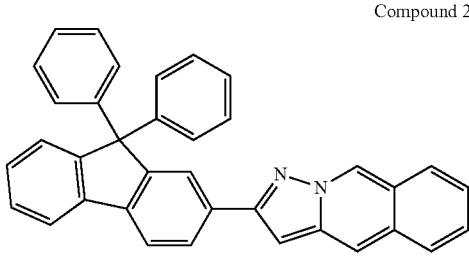
Compound 2-1-15
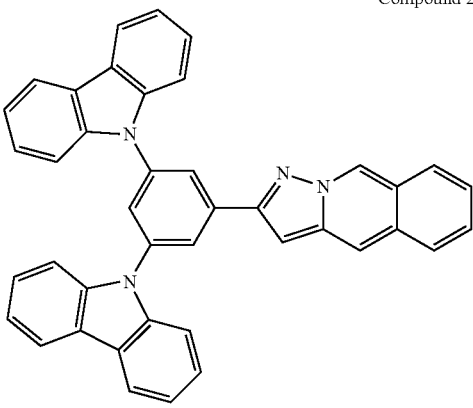
Compound 2-1-16
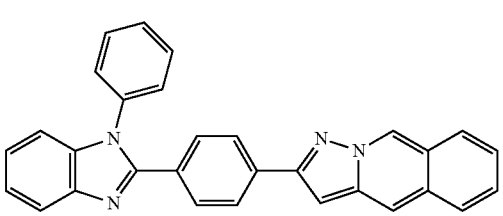
Compound 2-1-17
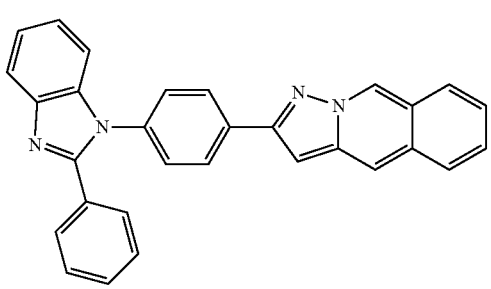

Compound 2-1-18
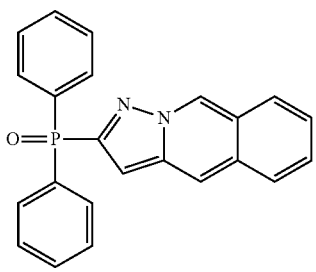
Compound 2-1-19
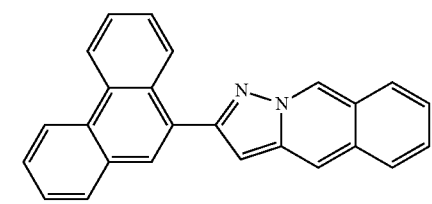
Compound 2-2-20
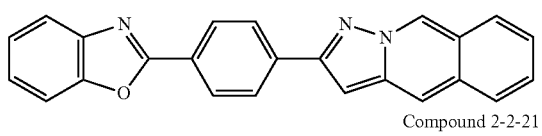
Compound 2-2-21
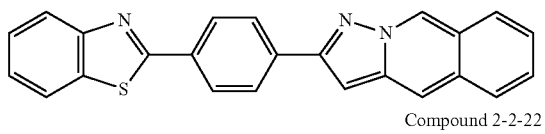
Compound 2-2-22
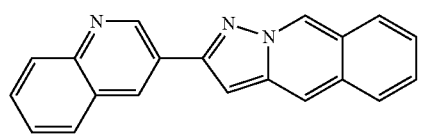
Compound 2-2-23
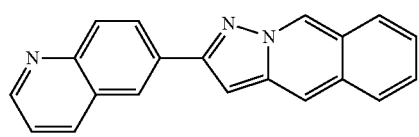
Compound 2-2-24
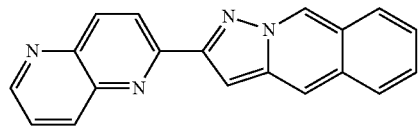
Compound 2-2-25
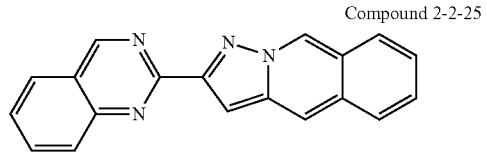
Compound 2-2-26
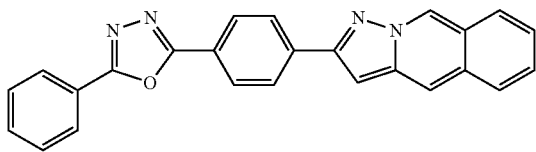
Compound 2-2-27
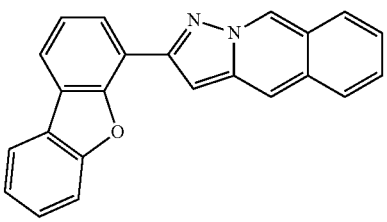
Compound 2-2-28
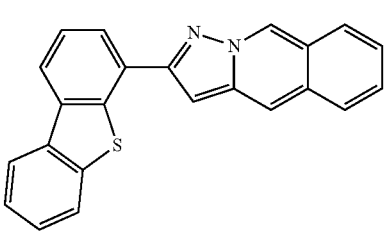
Compound 2-1-29
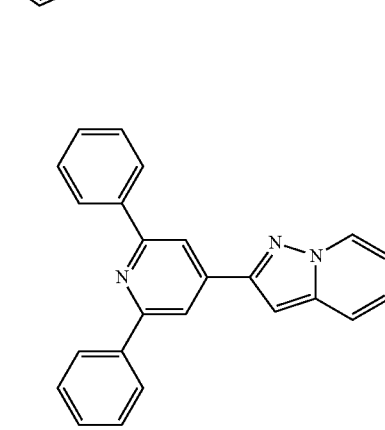
Compound 2-1-30
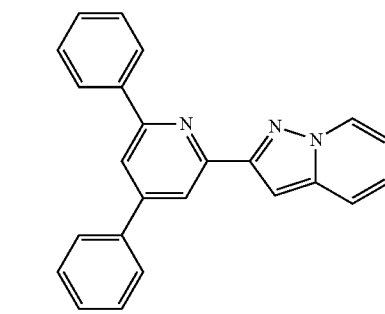
Compound 2-1-31
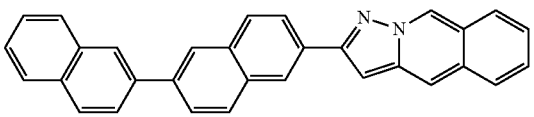

Compound 2-1-32
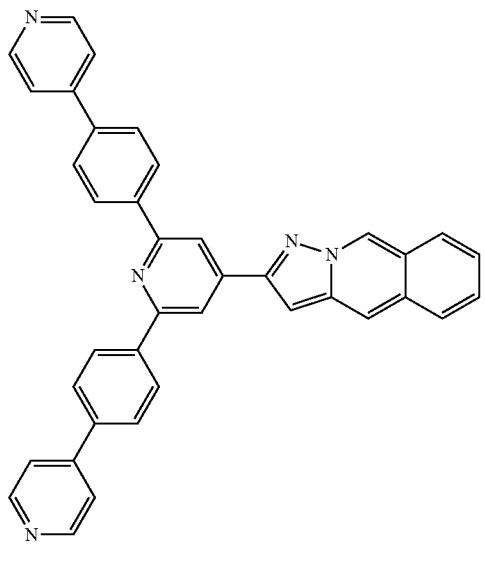
Compound 2-1-33
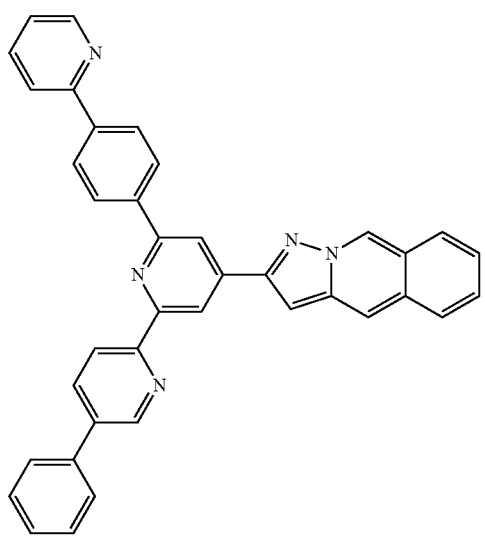
Compound 2-1-34
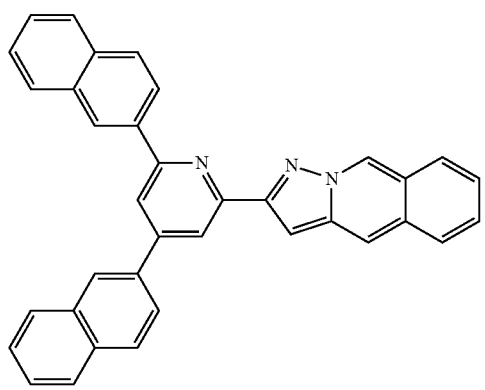
Compound 2-1-35
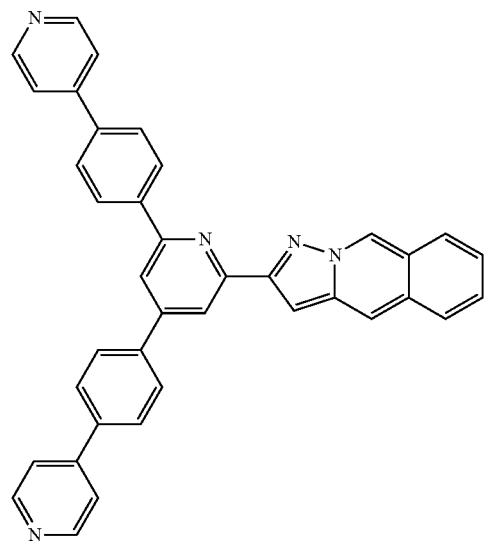
Compound 2-1-36
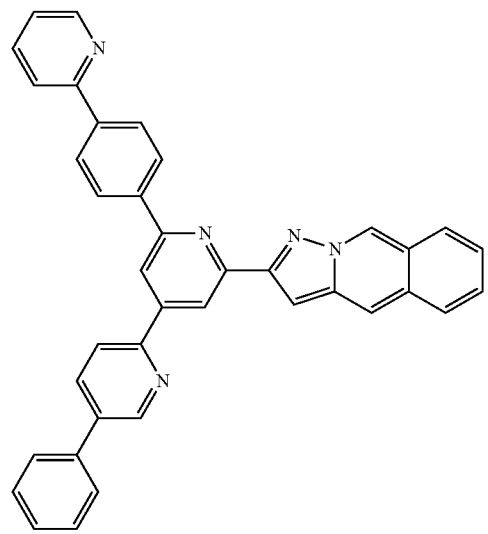
Compound 2-1-37
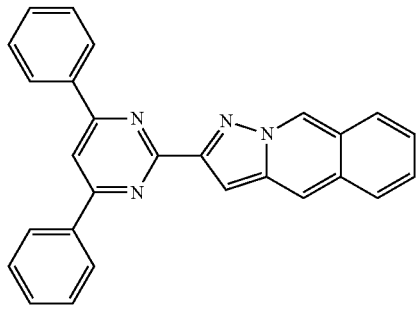

Compound 2-1-38
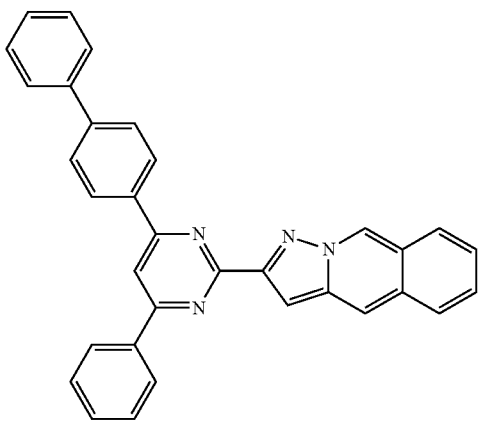
Compound 2-1-39
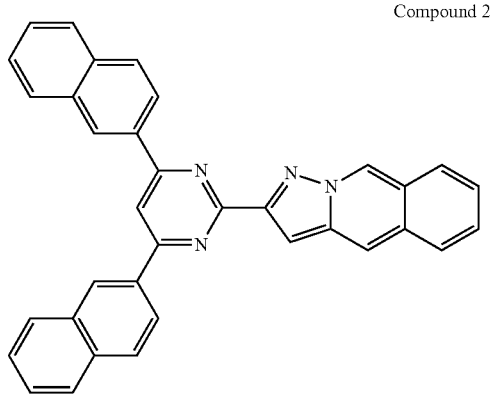
Compound 2-1-40
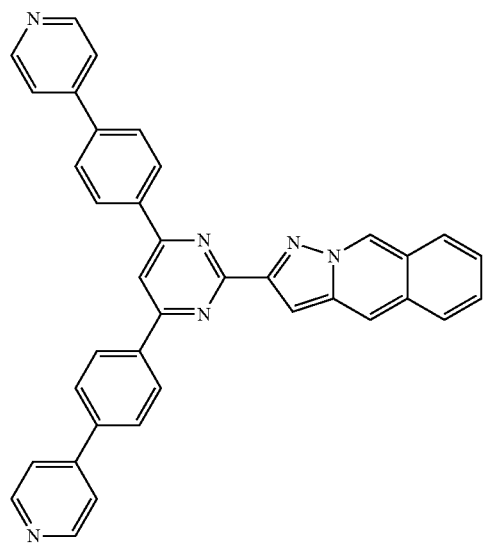
Compound 2-1-41
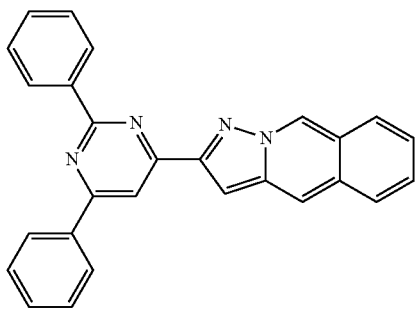
Compound 2-1-42
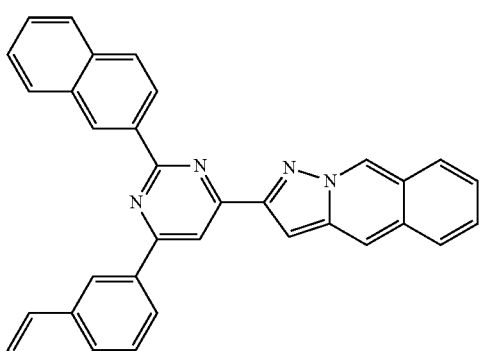
Compound 2-1-43
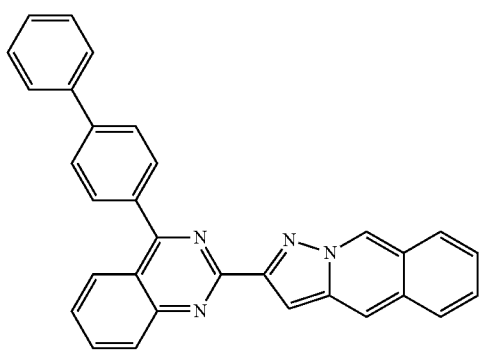
Compound 2-1-44
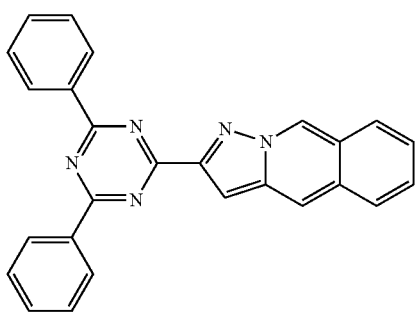

Compound 2-1-45
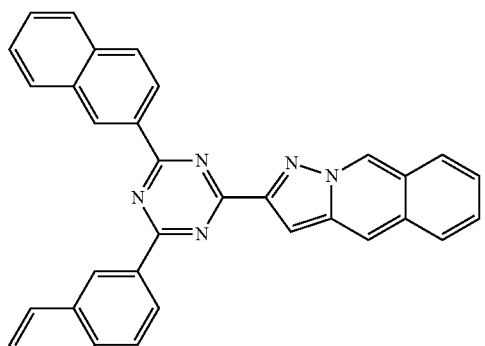
Compound 2-1-46
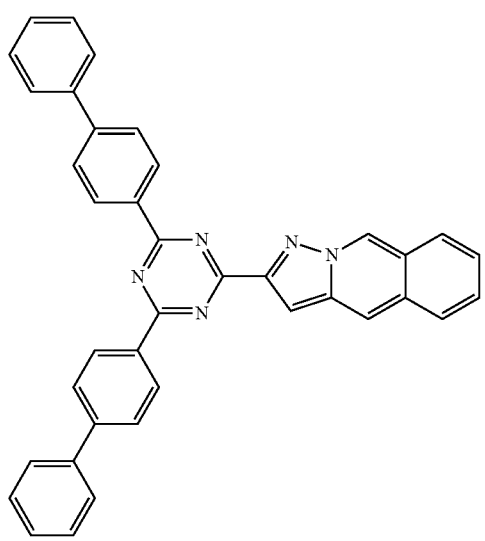
Compound 2-1-47
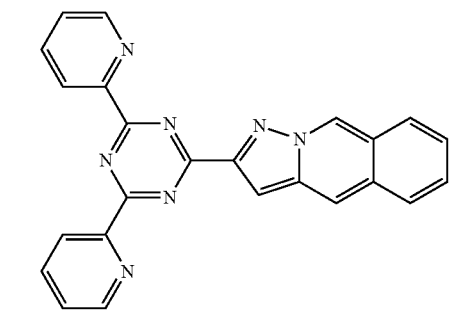
Compound 2-1-48
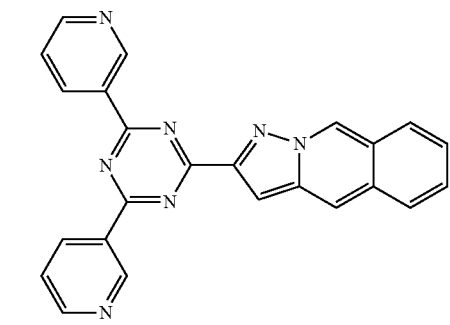
Compound 2-1-49
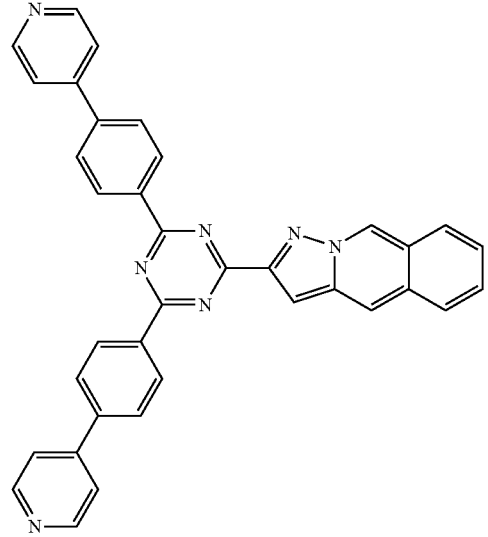
Compound 2-1-50
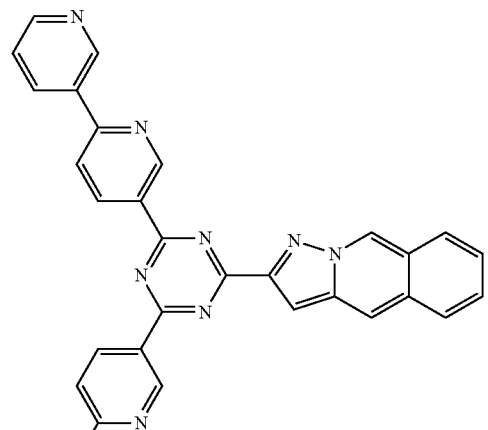
Compound 2-1-51
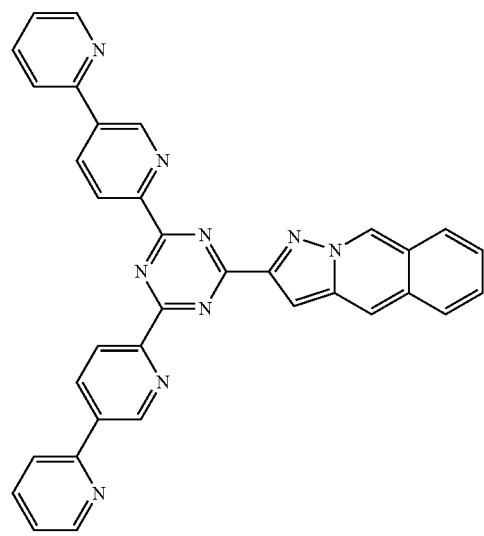

Compound 2-1-52
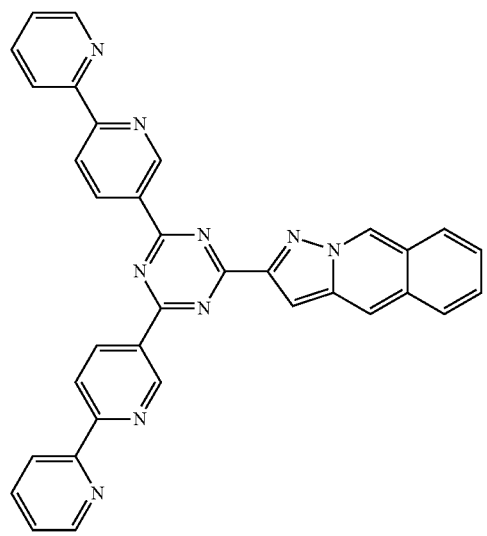
Compound 2-1-56
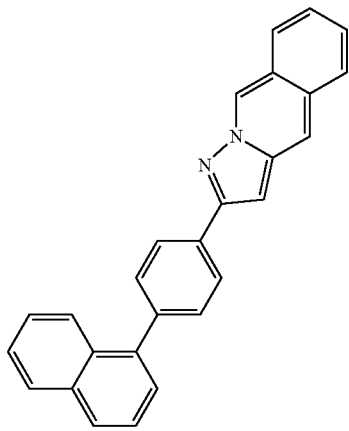
Compound 2-1-53
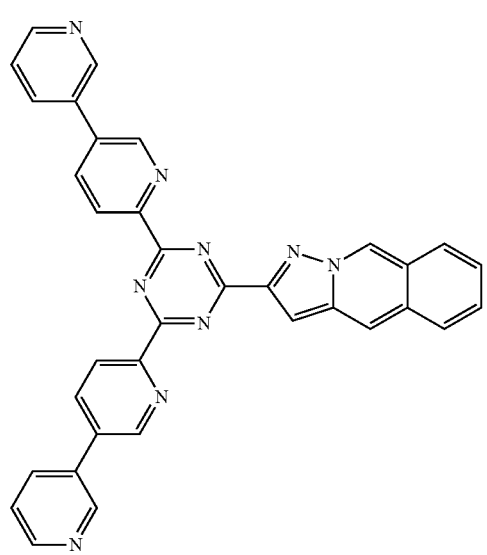
Compound 2-1-57
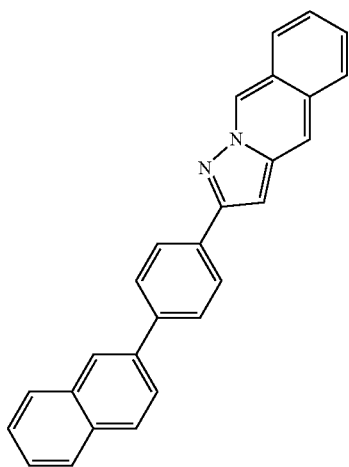
Compound 2-1-54
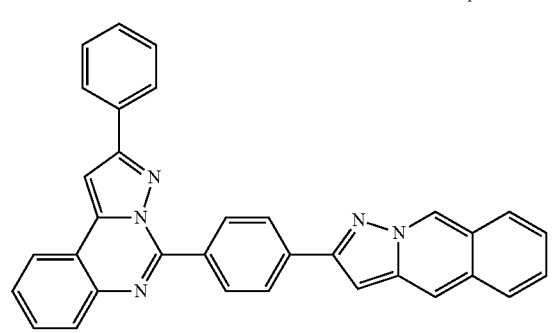
Compound 2-1-58
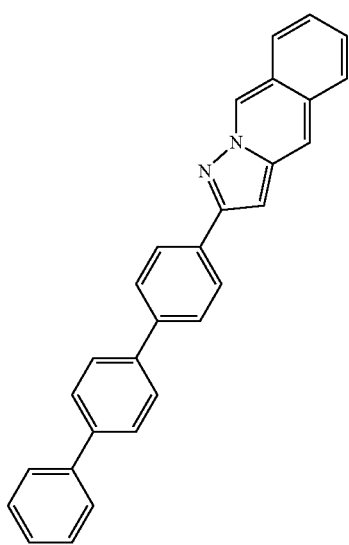
Compound 2-1-55
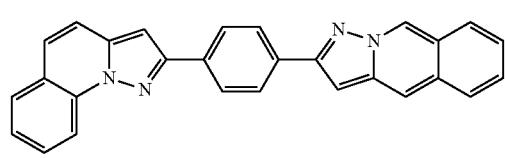

Compound 2-1-59
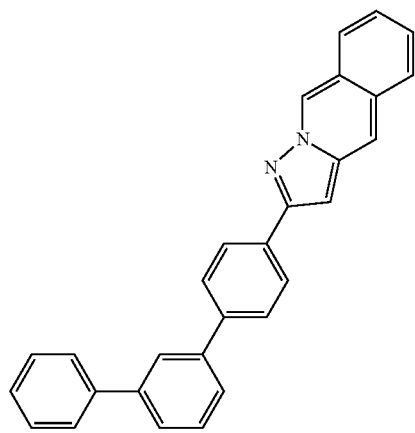
Compound 2-1-60
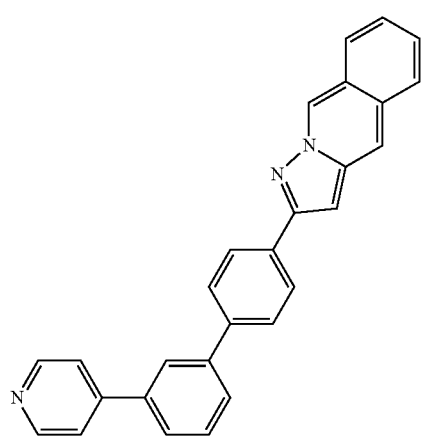
Compound 2-1-61
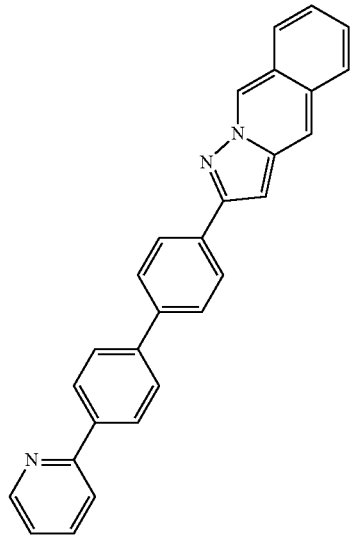
Compound 2-1-62
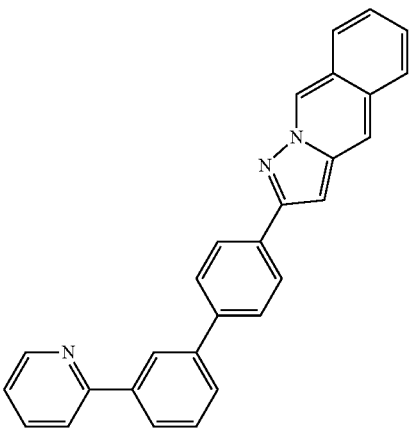
Compound 2-1-63
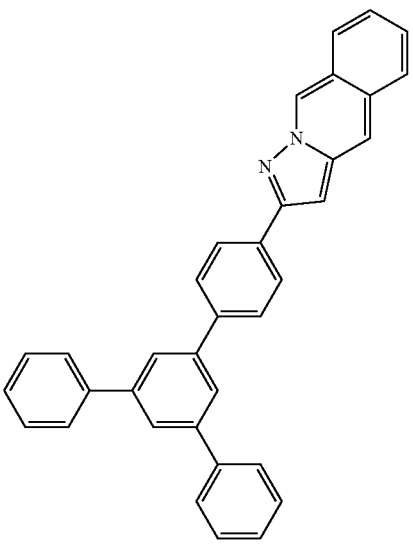
Compound 2-1-64
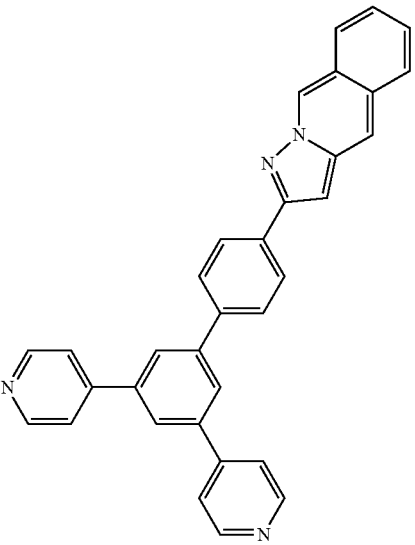

Compound 2-1-65
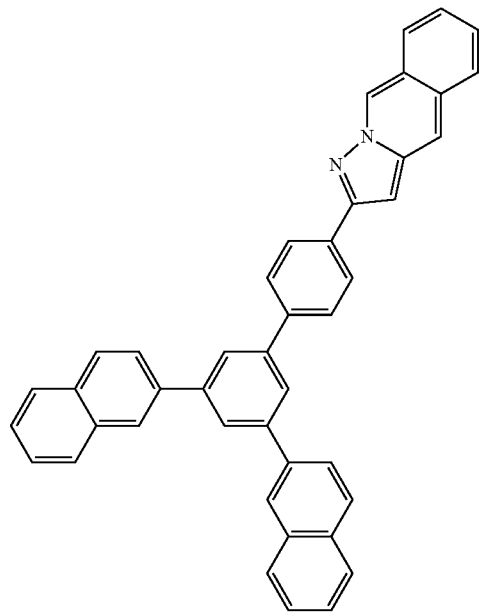
Compound 2-1-67
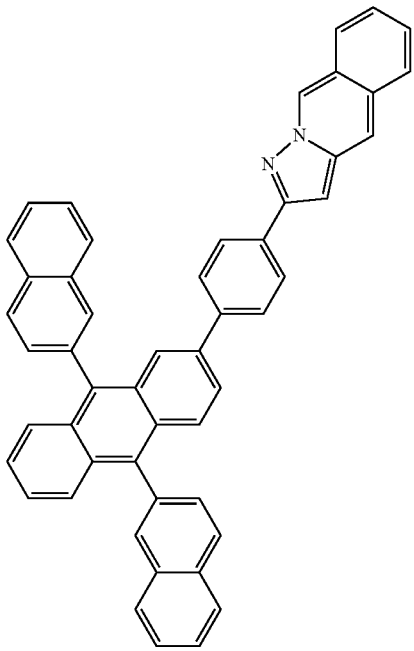
Compound 2-1-66
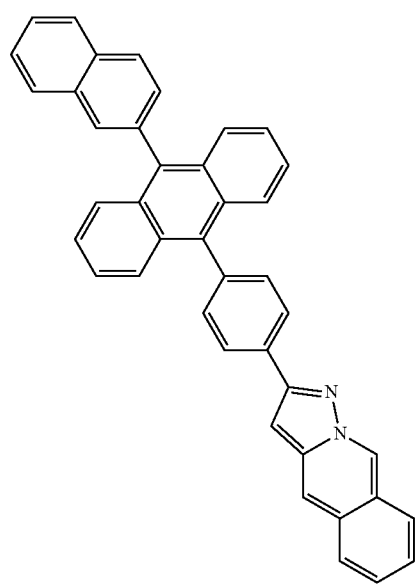
Compound 2-1-68
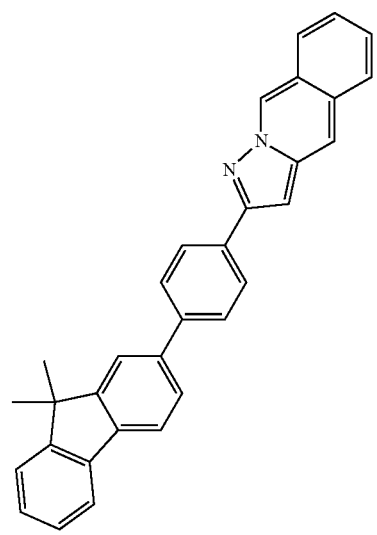

Compound 2-1-69
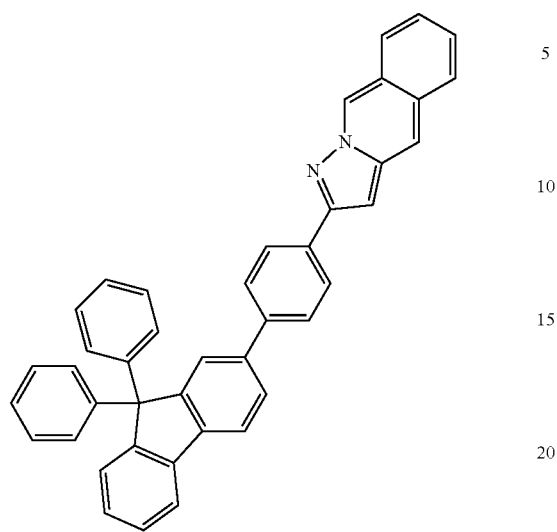
Compound 2-1-70
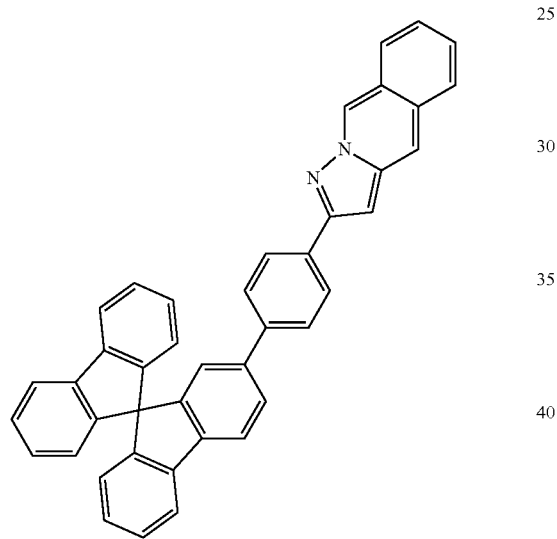
Compound 2-1-71
Compound 2-1-72
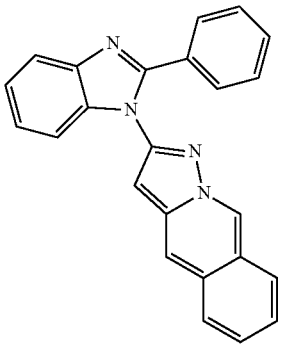
Compound 2-1-73
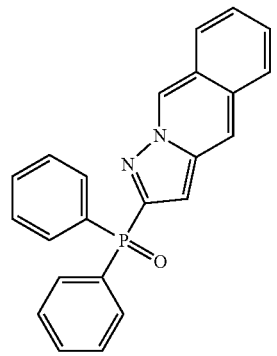
Compound 2-1-74
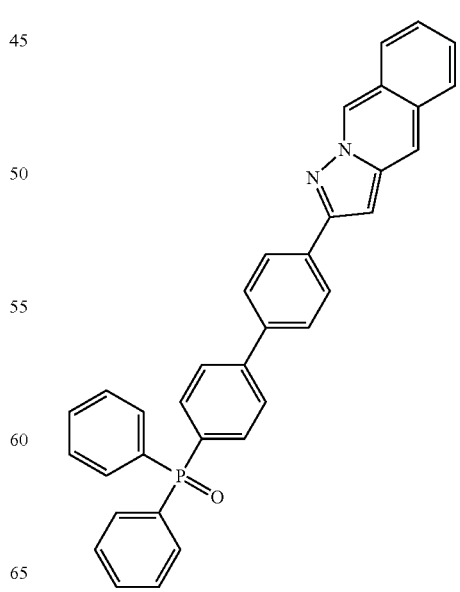

Compound 2-1-75
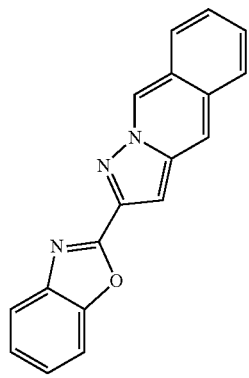
Compound 2-1-80
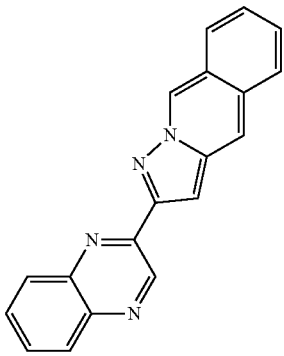
Compound 2-1-76
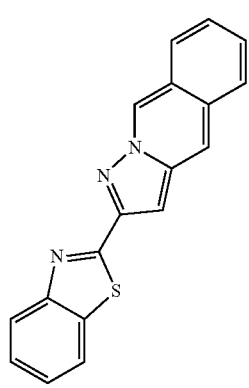
Compound 2-1-81
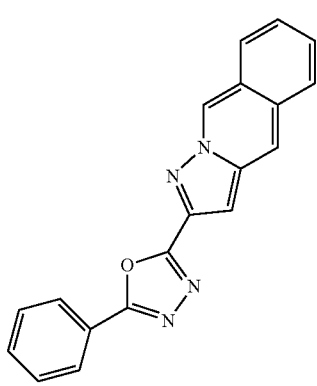
Compound 2-1-77
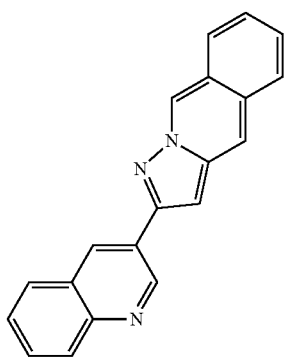
Compound 2-1-82
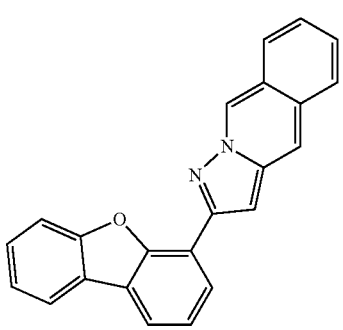
Compound 2-1-79
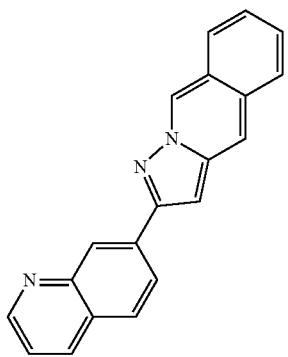
Compound 2-1-83
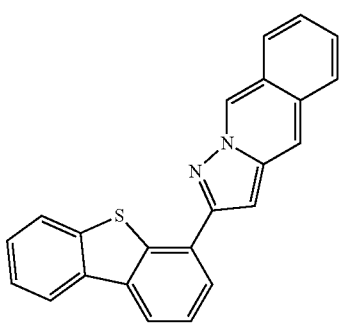

Compound 2-1-84
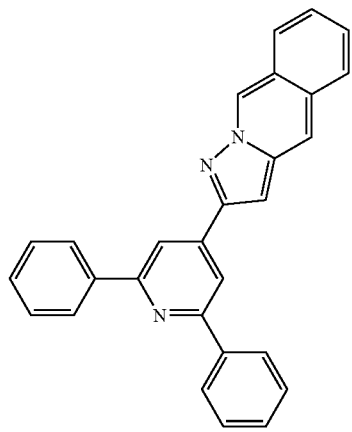
Compound 2-1-85
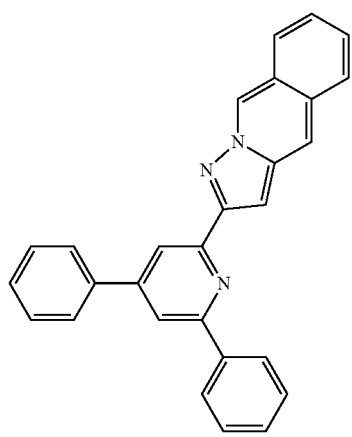
Compound 2-1-86
Compound 2-1-87
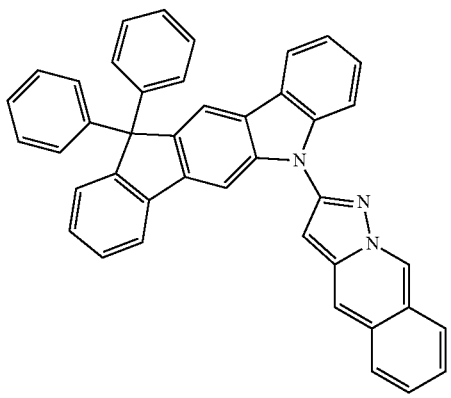
Compound 2-1-88
Compound 2-1-89
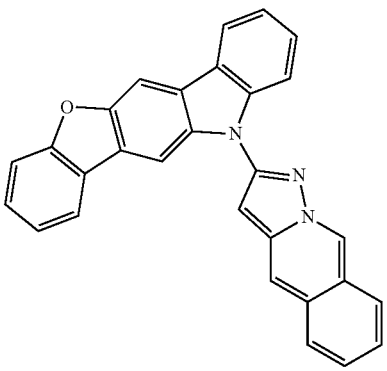
Compound 2-1-90
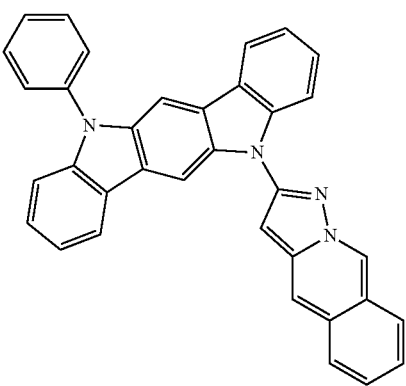

Compound 2-1-91
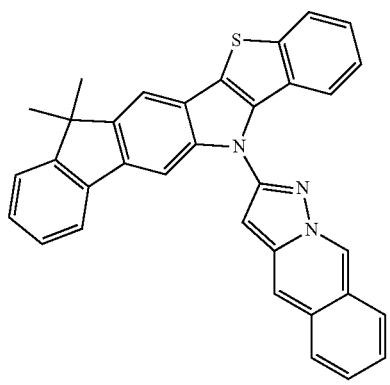
Compound 2-1-92
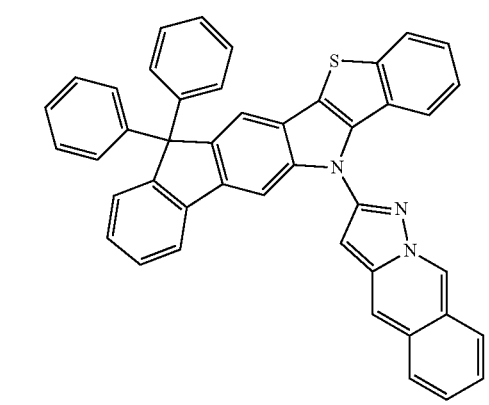
Compound 2-1-93
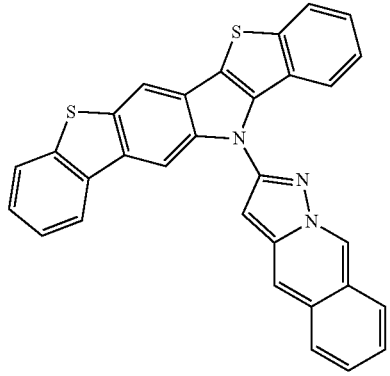
Compound 2-1-94
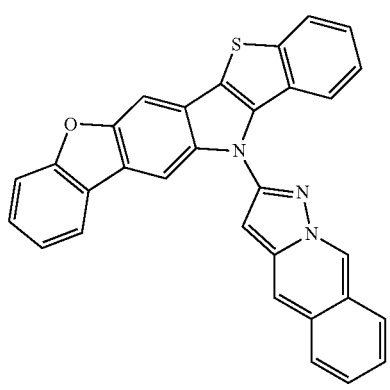
Compound 2-1-95
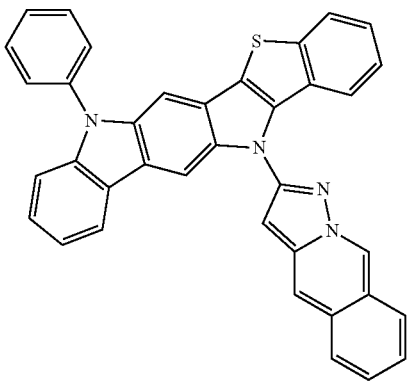
Compound 2-1-96
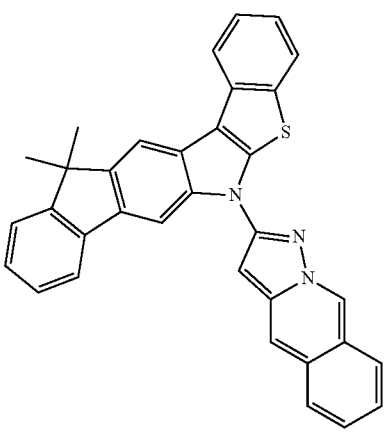
Compound 2-1-97
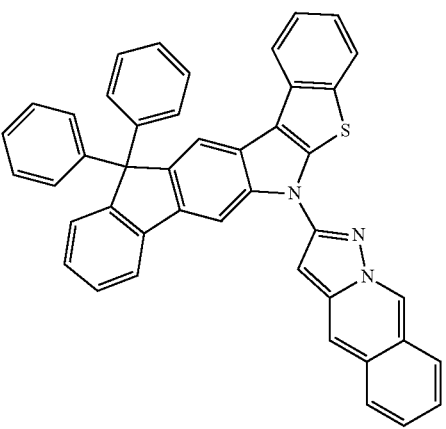

Compound 2-1-98
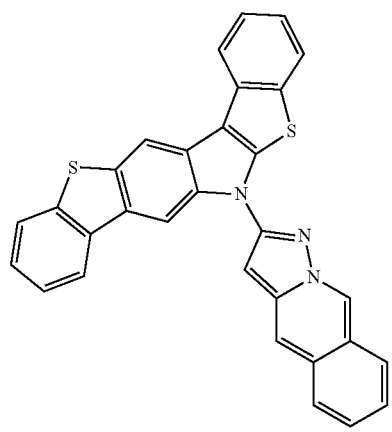
Compound 2-1-99
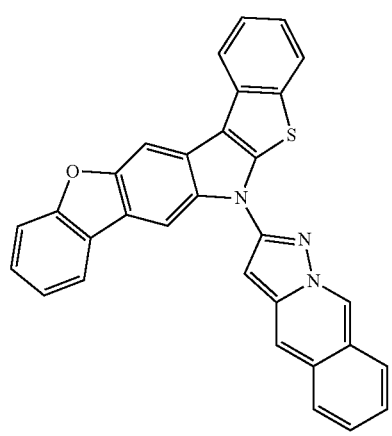
Compound 2-1-100
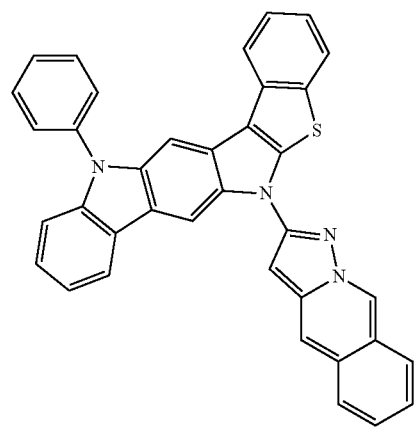
Compound 2-1-101
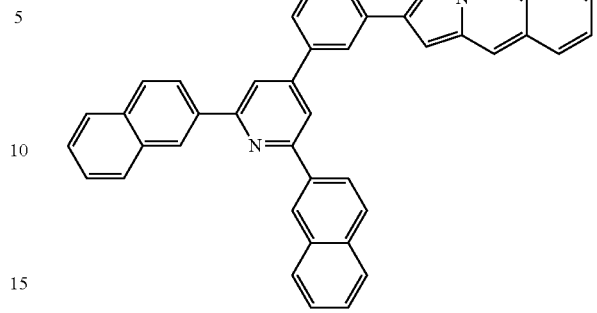
Compound 2-1-102
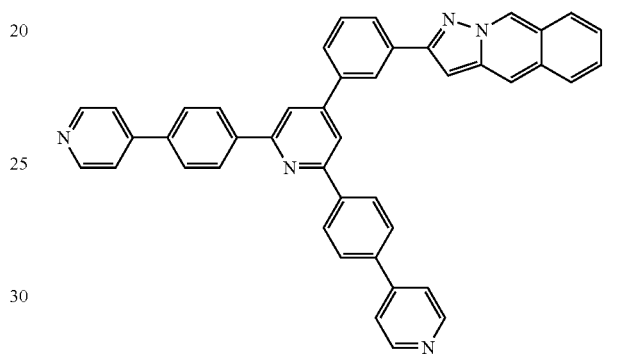
Compound 2-1-103
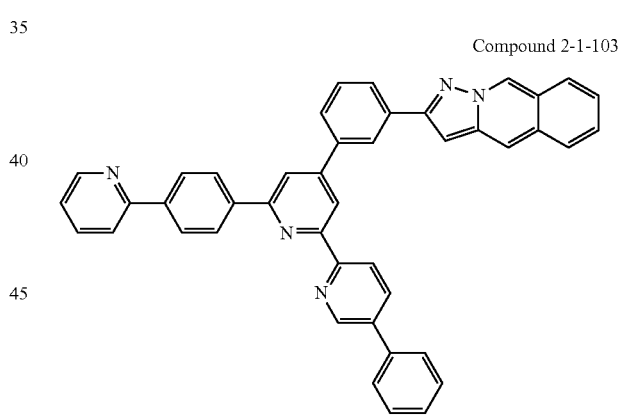
Compound 2-1-104
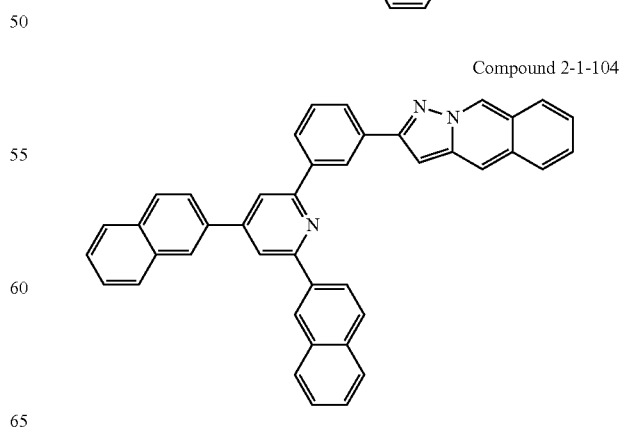

Compound 2-1-105
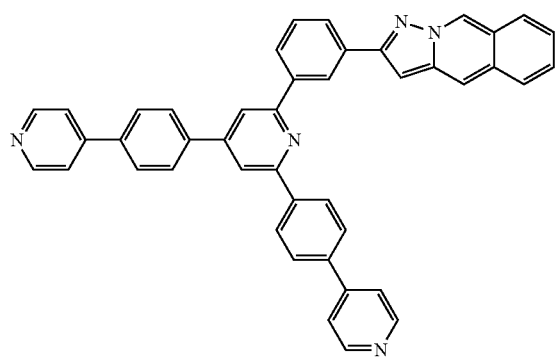
Compound 2-1-106
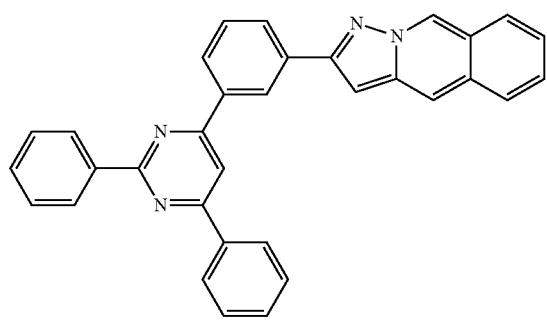
Compound 2-1-107
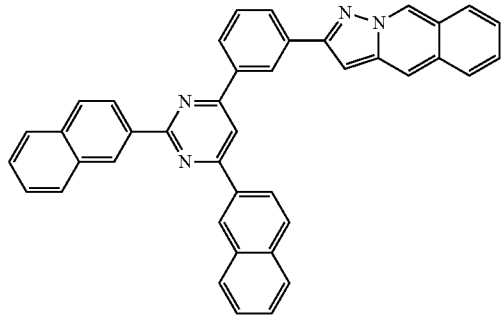
Compound 2-1-108
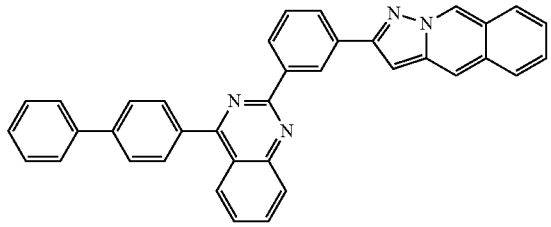
Compound 2-1-109
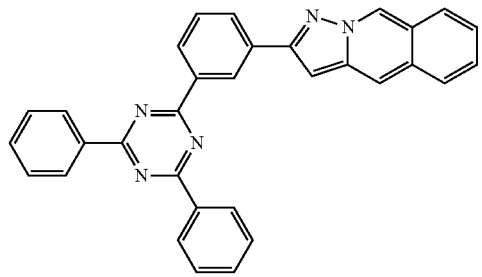
Compound 2-1-110
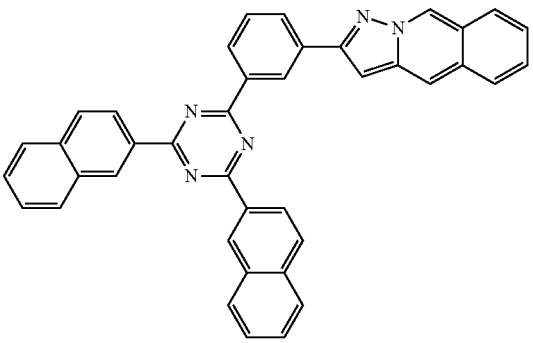
Compound 2-1-111
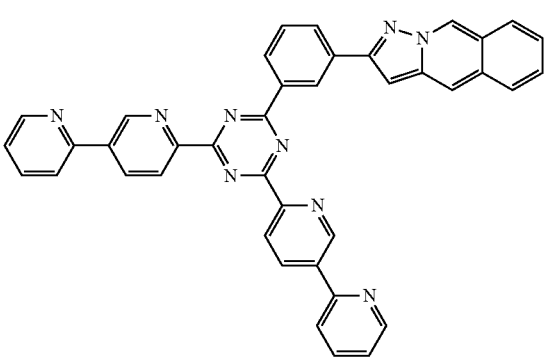
Compound 2-1-112
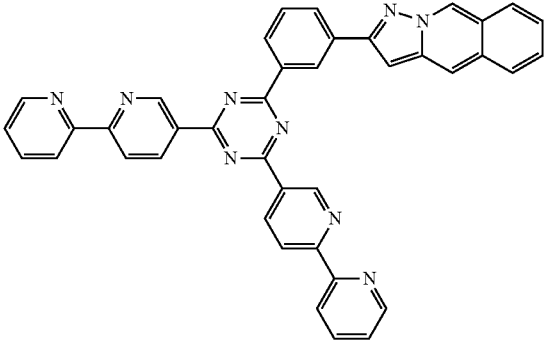
Compound 2-1-113
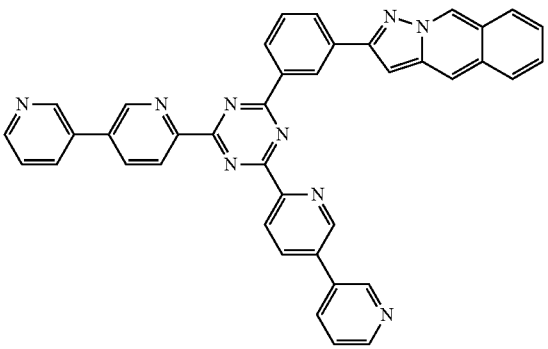

Compound 2-1-114
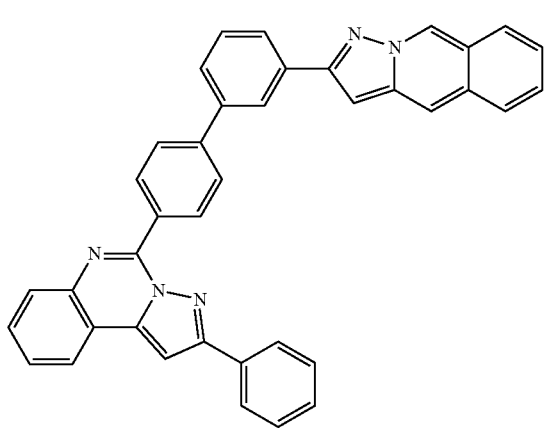
Compound 2-1-115
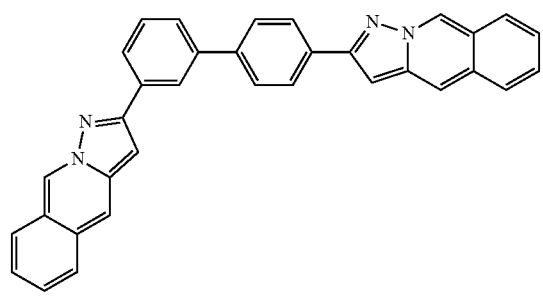
Compound 2-1-116
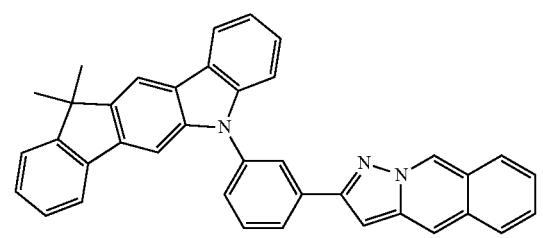
Compound 2-1-117
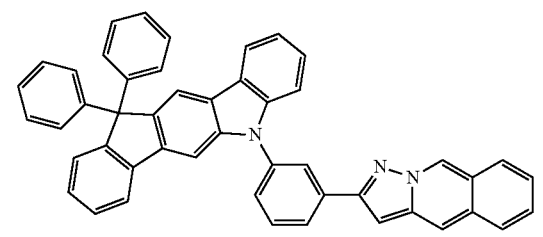
Compound 2-1-118
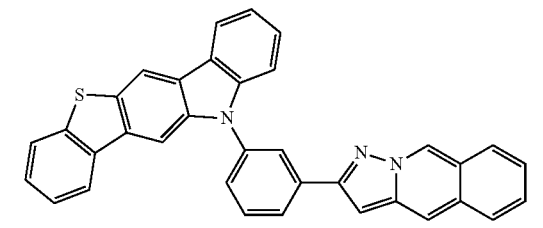
Compound 2-1-119
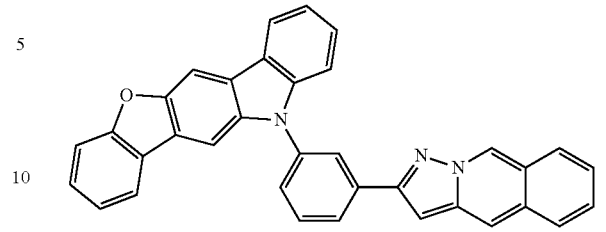
Compound 2-1-120
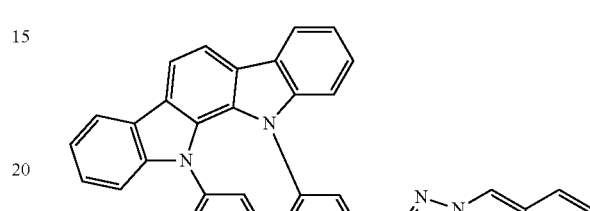
Compound 2-1-121
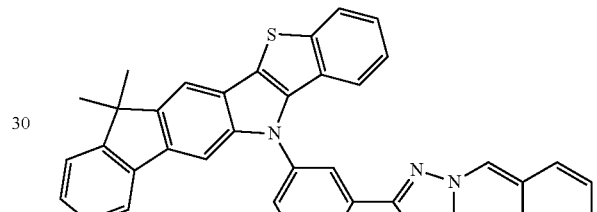
Compound 2-1-122

Compound 2-1-123

Compound 2-1-124
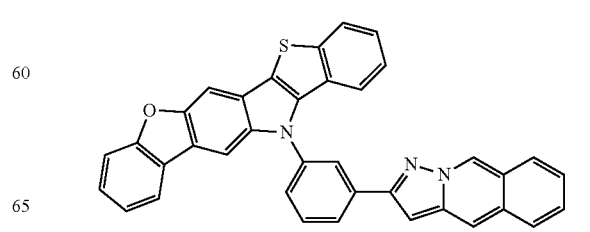

-continued
Compound 2-1-125
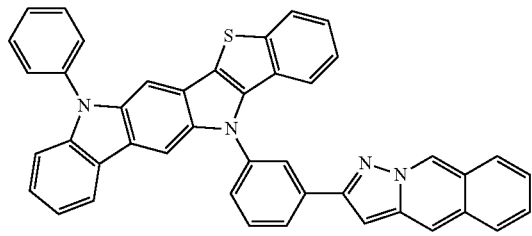
Compound 2-1-126
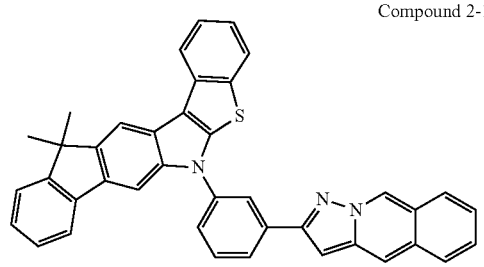
Compound 2-1-127
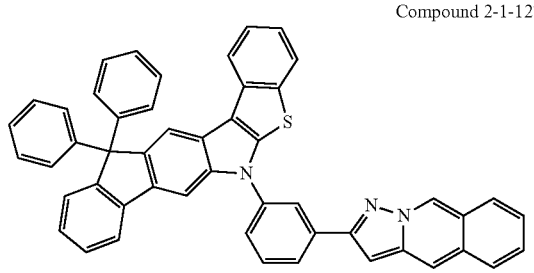
Compound 2-1-128
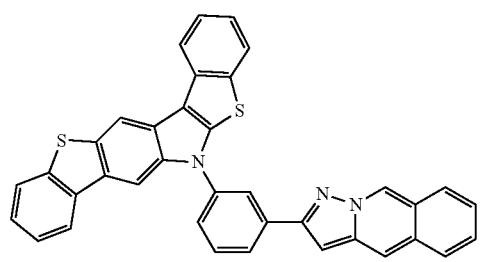
Compound 2-1-129
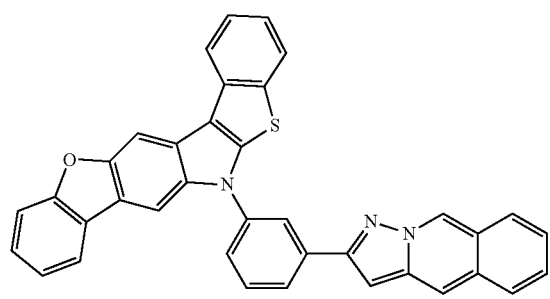
-continued
Compound 2-1-130
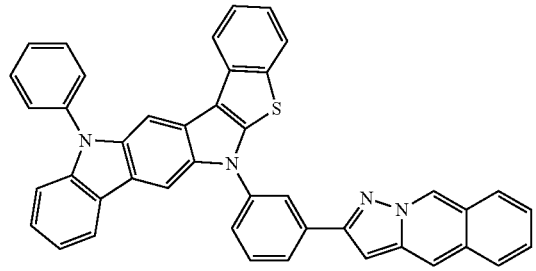
Compound 2-1-131
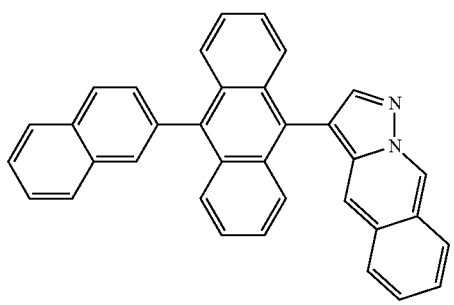
Compound 2-1-132
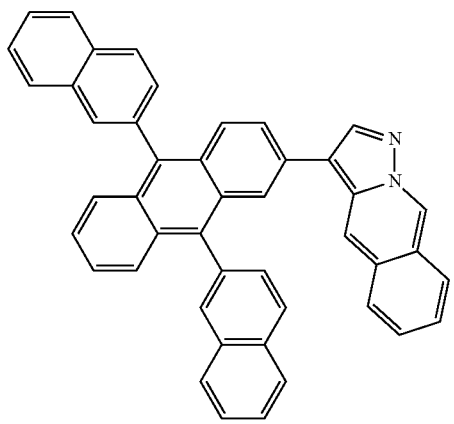
Copound 2-1-133
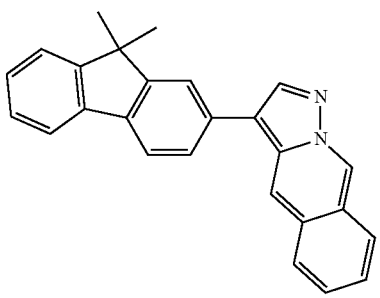

Compound 2-1-134
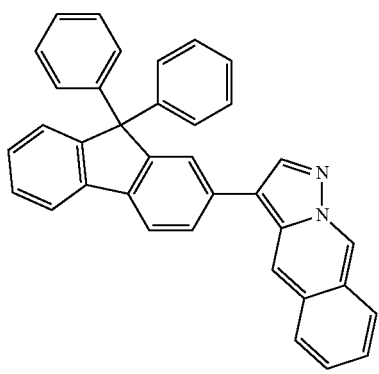
Compound 2-1-135
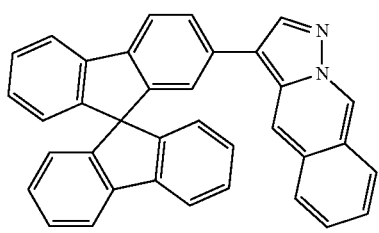
Compound 2-1-136
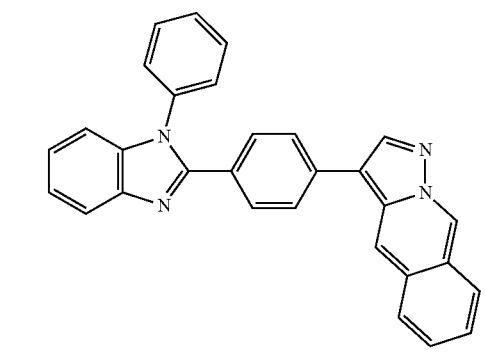
Compound 2-1-137
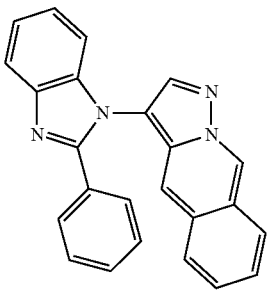
Compound 2-1-138
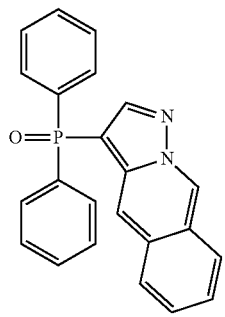
Compound 2-1-139
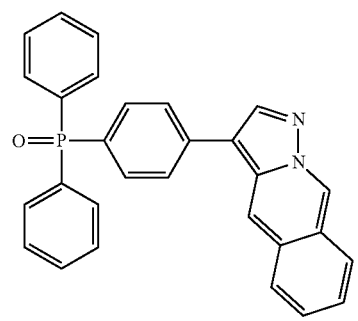
Compound 2-1-140
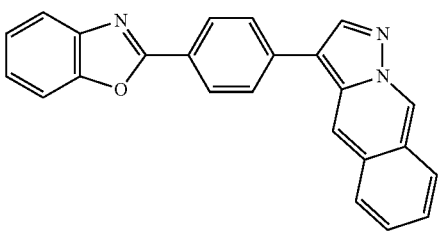
Compound 2-1-141
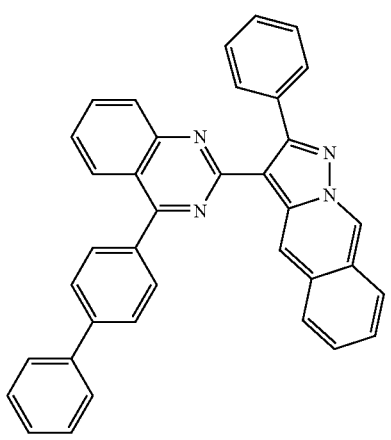
Compound 2-1-142
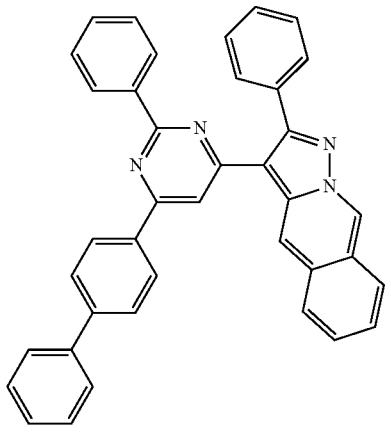

Compound 2-1-143
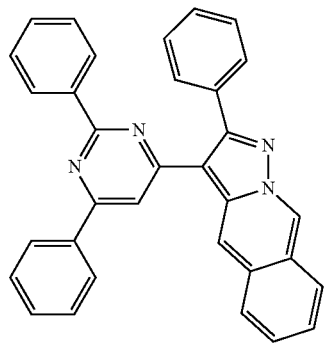
Compound 2-1-147
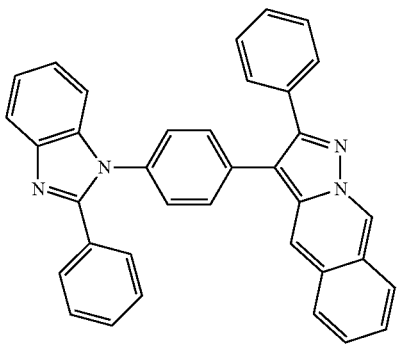
Compound 2-1-144
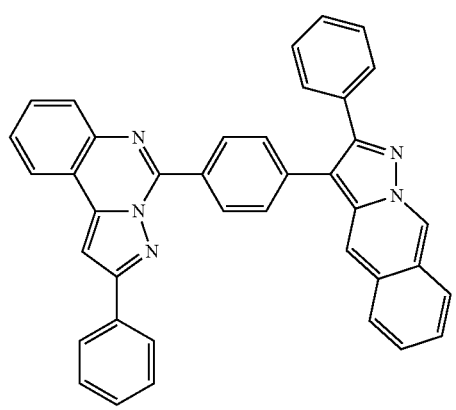
Compound 2-1-148
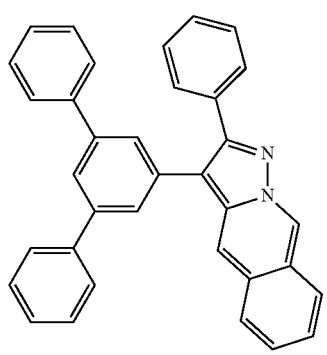
Compound 2-1-145
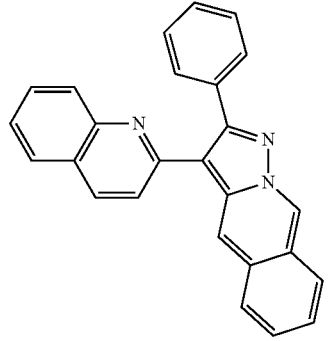
Compound 2-1-149
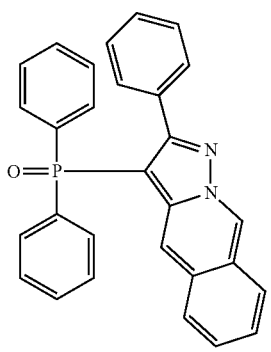
Compound 2-1-146
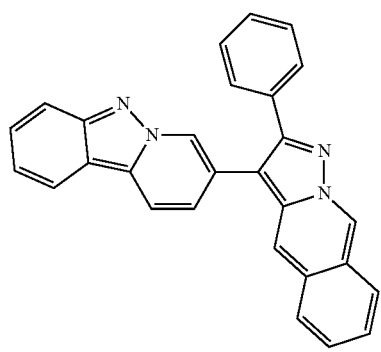
Compound 2-1-150
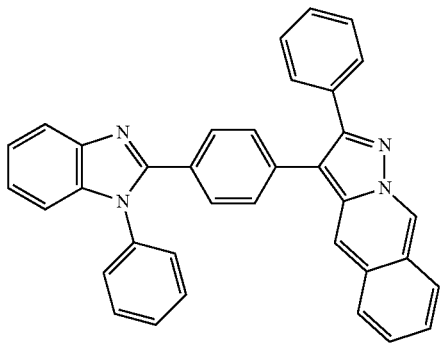

Compond 2-1-151
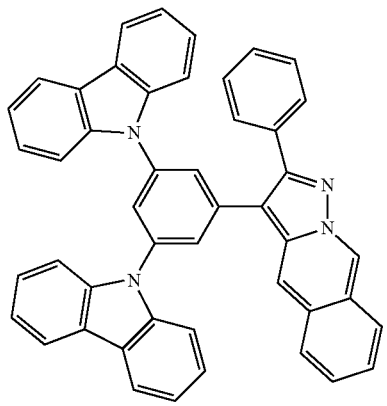
Compond 2-1-152
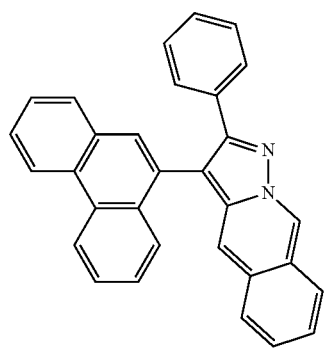
Compond 2-1-153
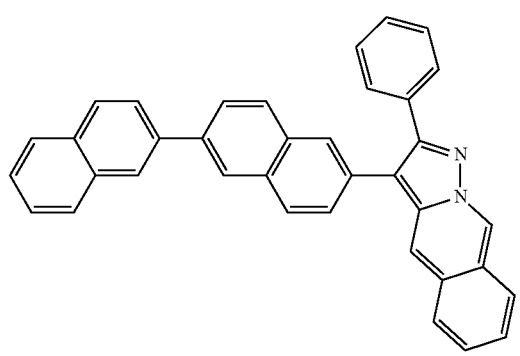
Compond 2-1-154
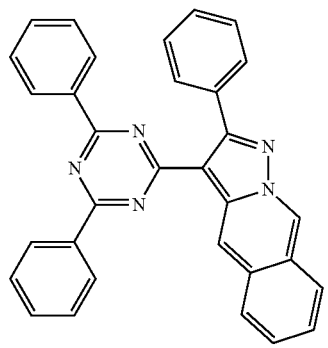
Compond 2-1-155
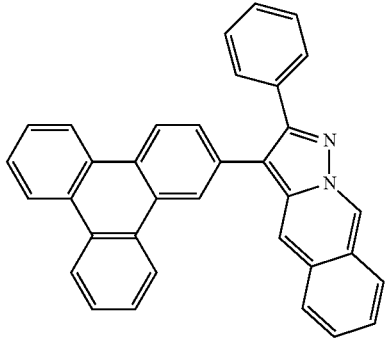
Compond 2-1-156
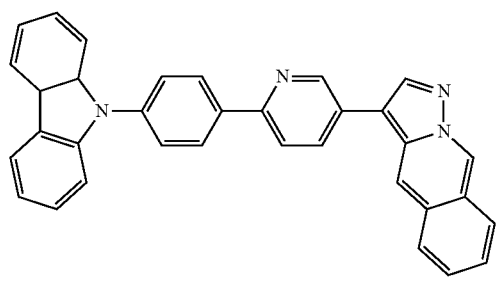
Compond 2-1-157
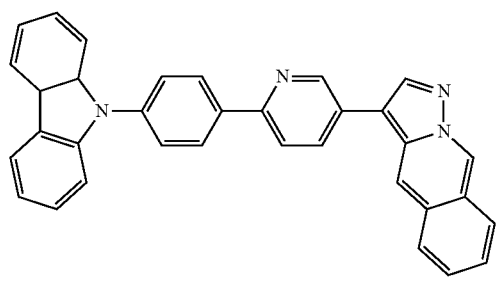
Compond 2-1-158
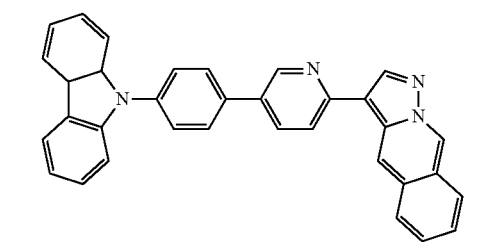
Compond 2-1-159
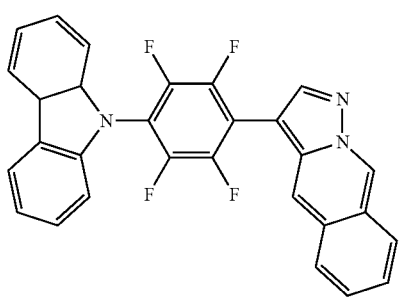

Compound 2-1-160
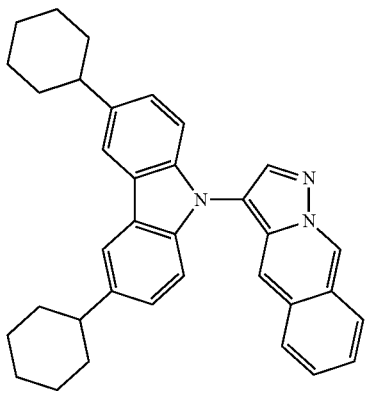
Compound 2-1-161
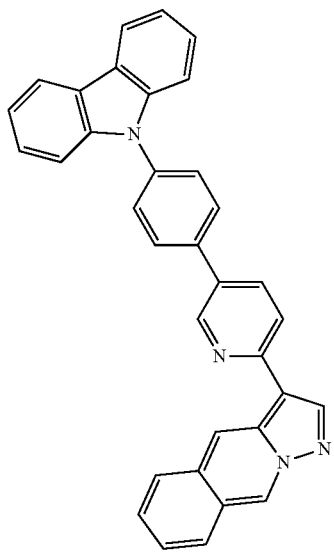
Compound 2-1-162
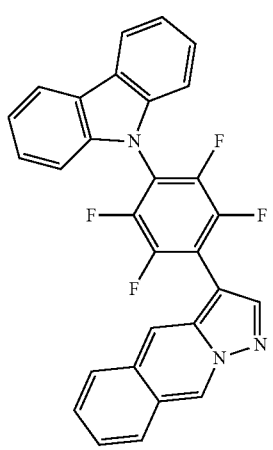
Compound 2-1-163
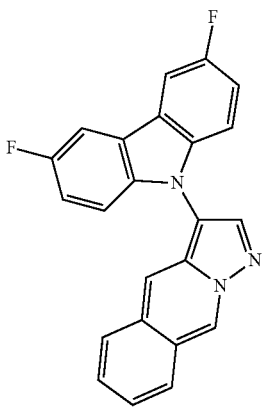
Compound 2-1-164
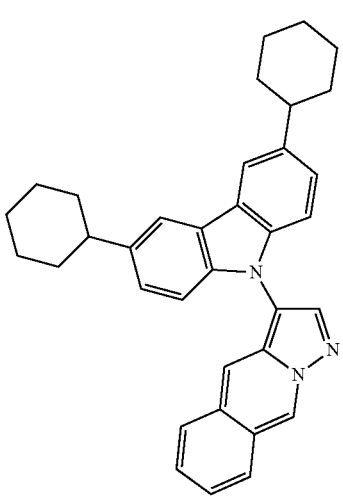
Compound 2-1-165
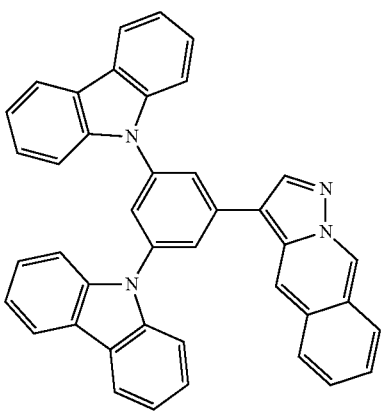

Compound 2-1-166
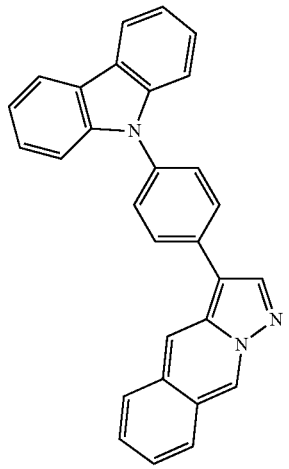
Compound 2-1-169
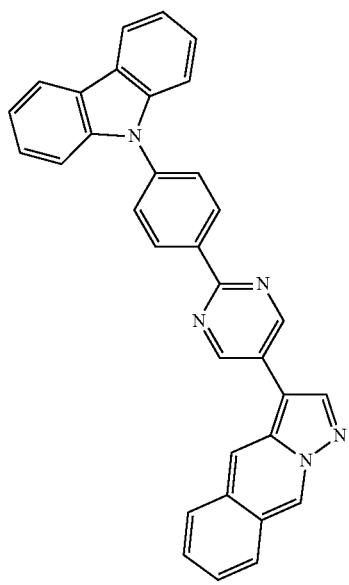
Compound 2-1-167
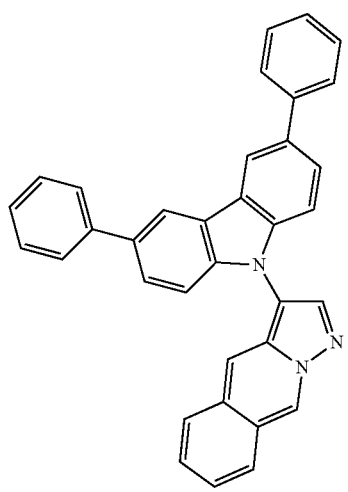
Compound 2-1-170
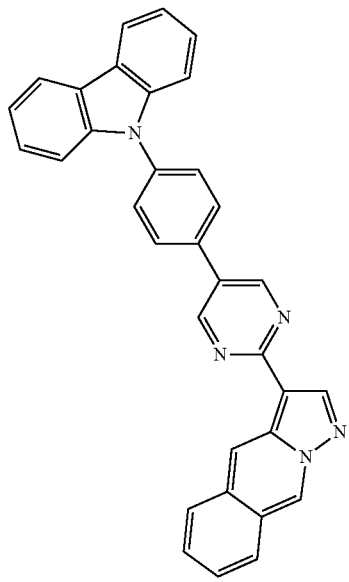
Compound 2-1-168
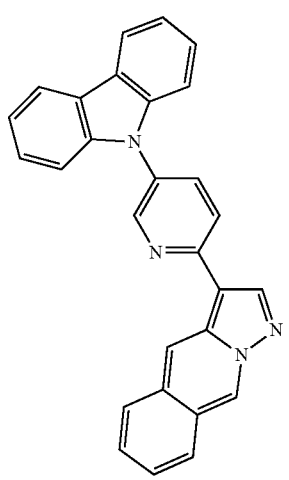
Compound 2-1-171
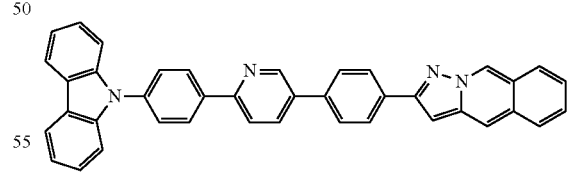
Compound 2-1-172
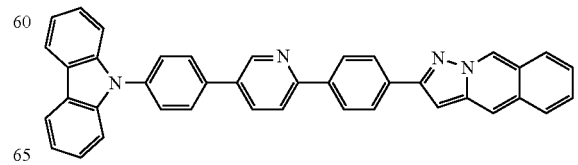

Compound 2-1-173
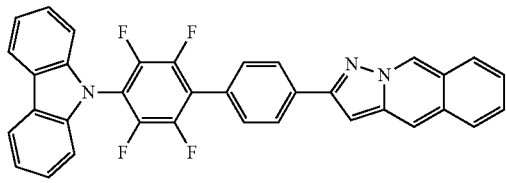
Compound 2-1-174
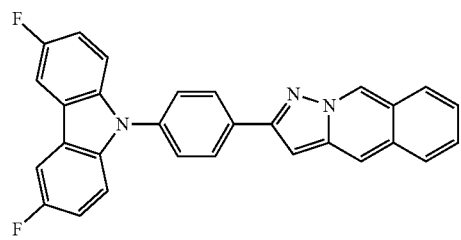
Compound 2-1-175
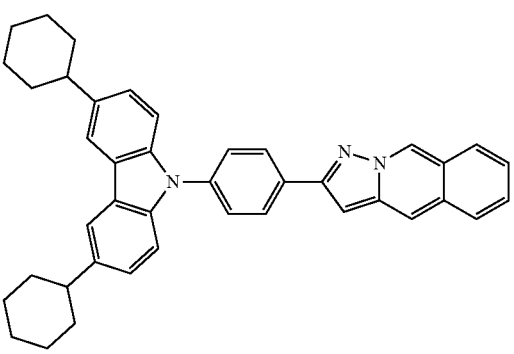
Compound 2-1-176
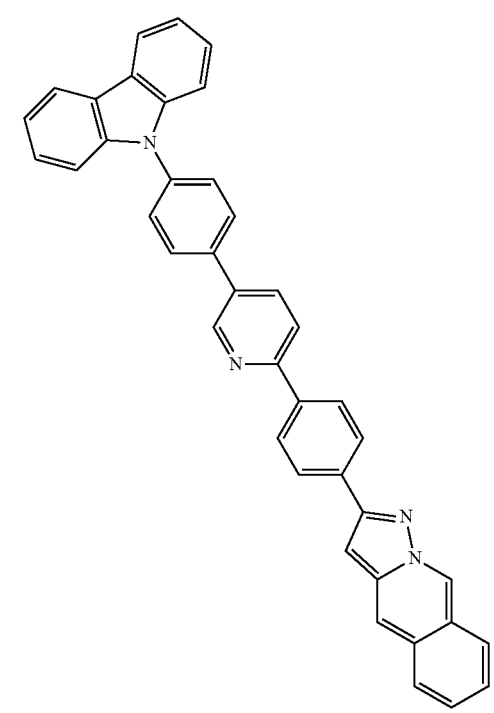
Compound 2-1-177
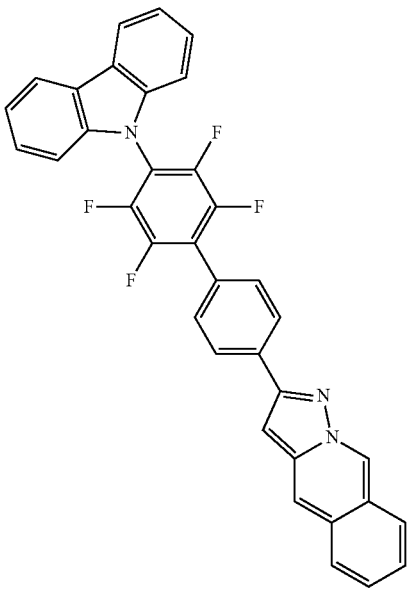
Compound 2-1-178
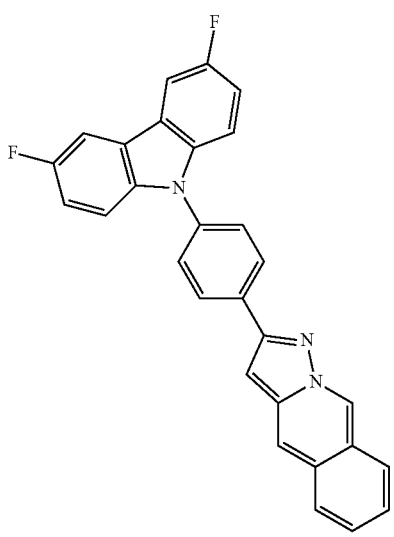

Compound 2-1-179
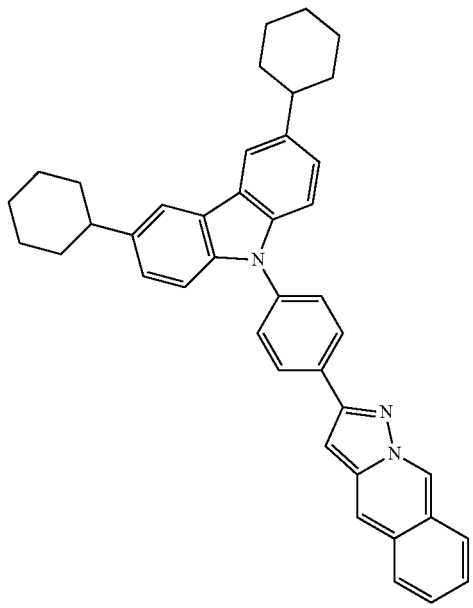
Compound 2-1-180
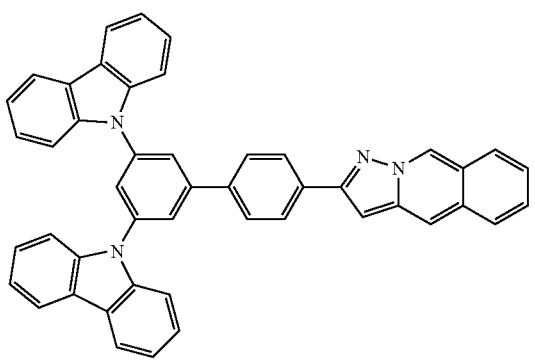
Compound 2-1-181
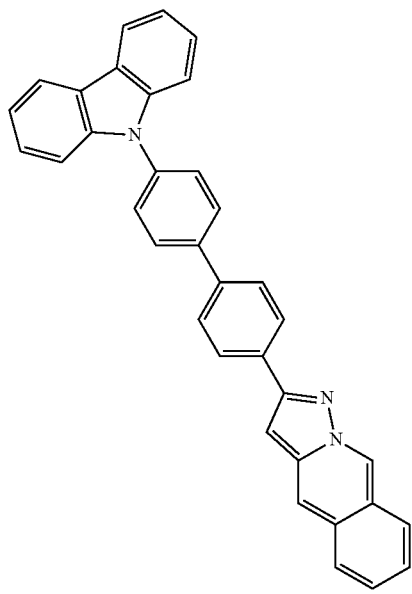
Compound 2-1-182
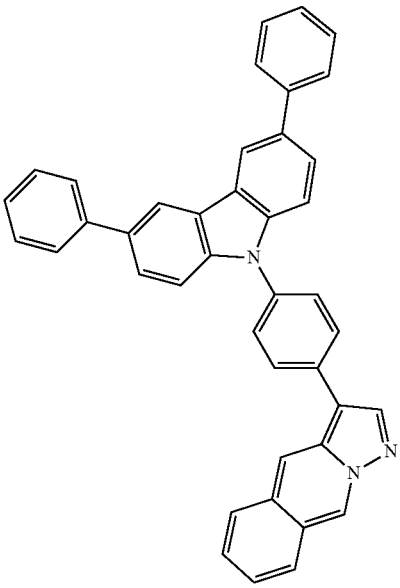
Compound 2-1-183
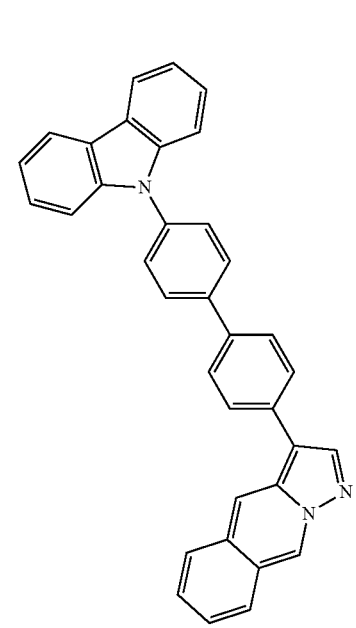

Compound 2-1-184
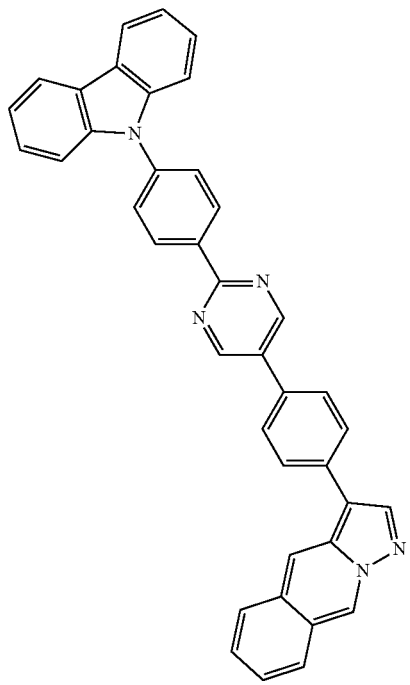
Compound 2-1-185
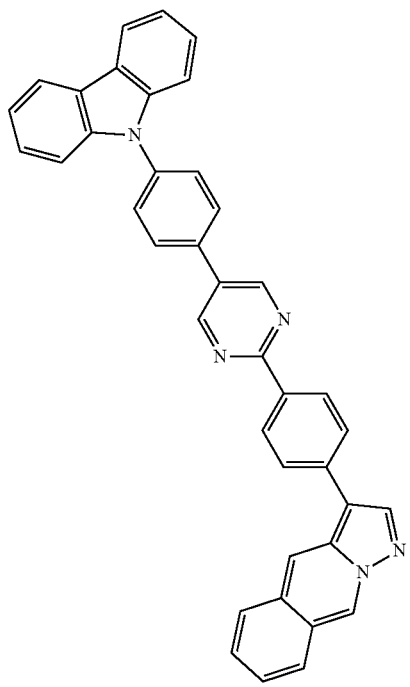
Compound 2-1-186
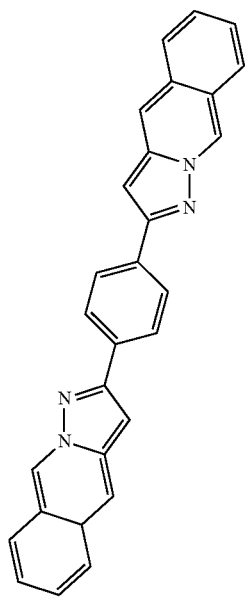
Compound 2-1-187
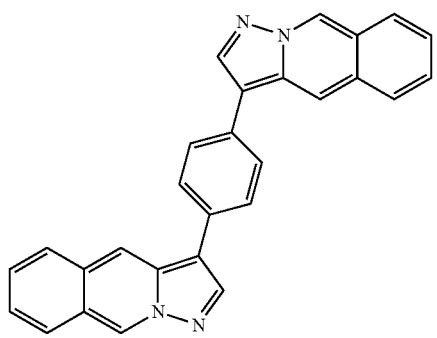
Compound 2-1-188
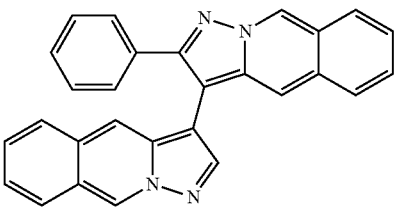
Compound 2-1-189
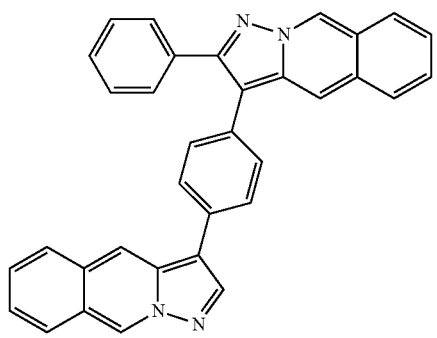

Compound 2-1-190
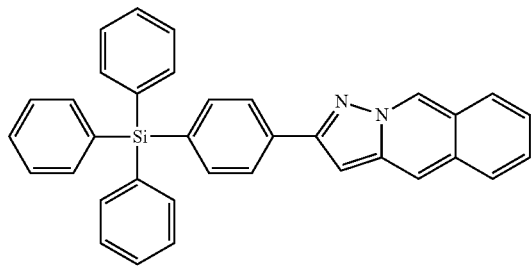
Compound 2-1-191
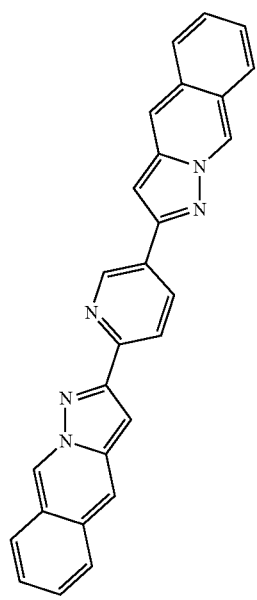
Compound 2-1-192
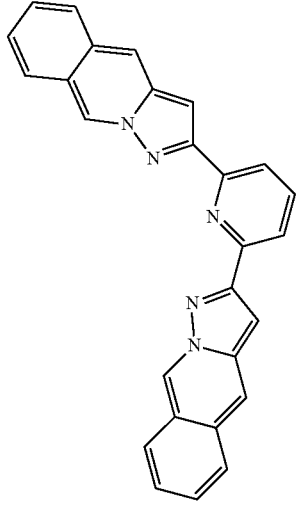
Compound 2-1-193
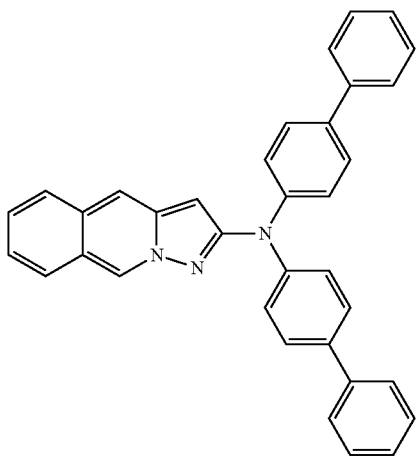
Compound 2-1-194
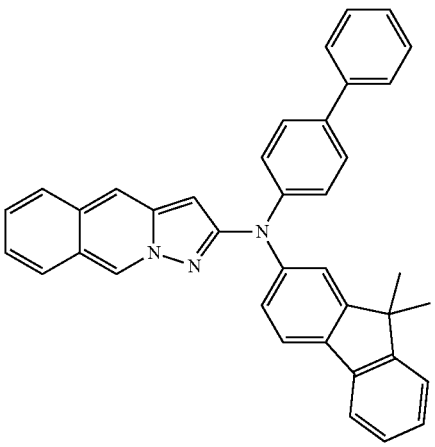
Compound 2-1-195
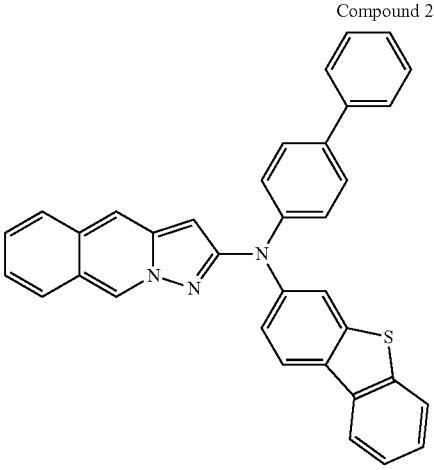

Compound 2-1-196
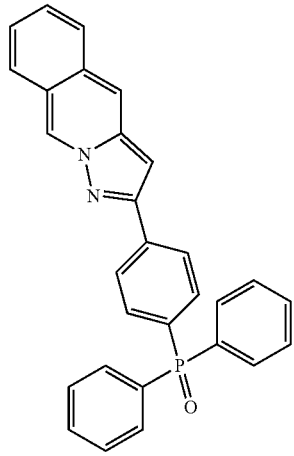
Compound 2-1-199
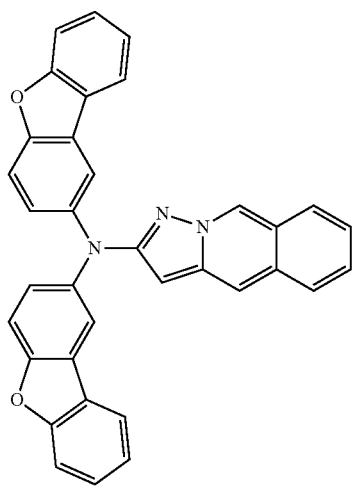
Compound 2-1-197
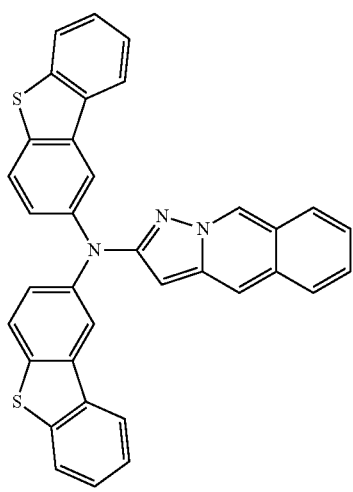
Comppind 2-1-200
Compound 2-1-198
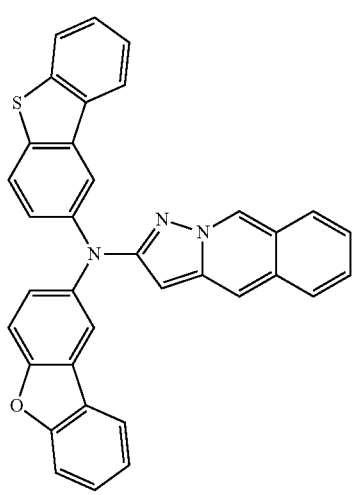
Compound 2-1-201
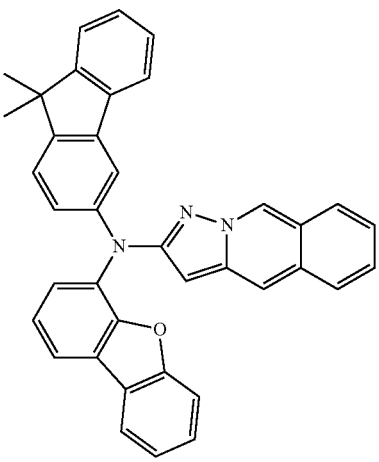

Compound 2-1-202
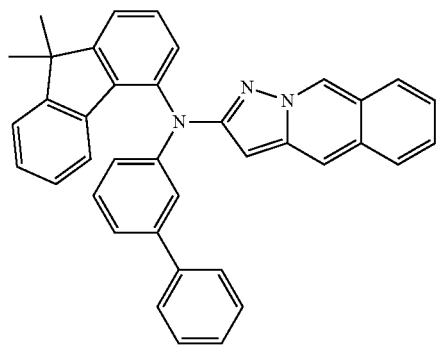
Compound 2-1-203
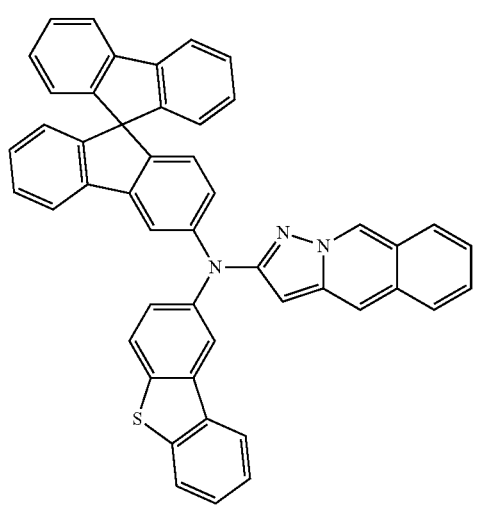
Compound 2-1-203
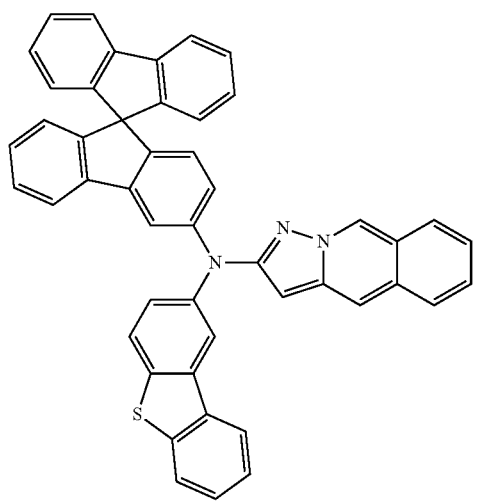
Compound 2-1-204
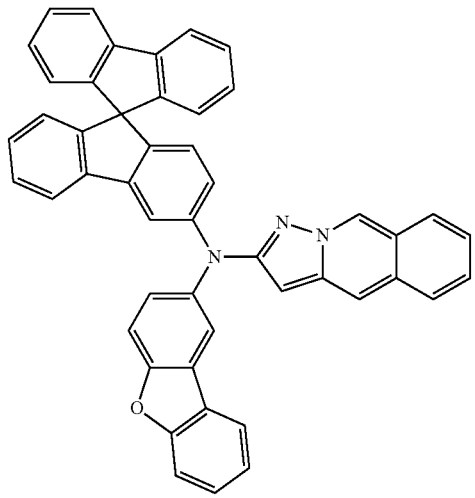
Compound 2-1-205
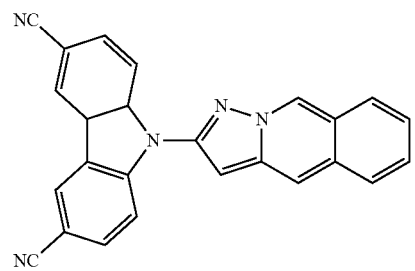
Compound 2-1-206
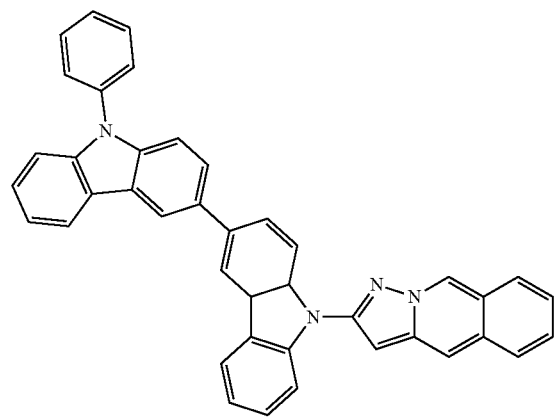
Compound 2-1-207
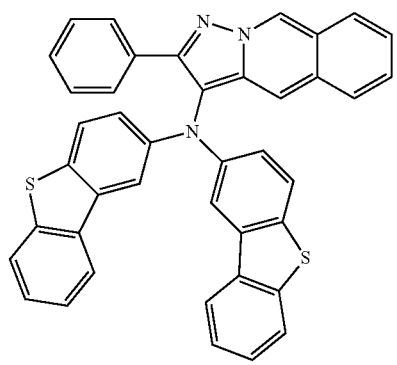

Compound 2-1-208
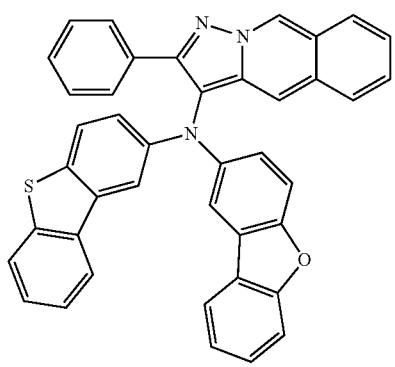
Compound 2-1-212
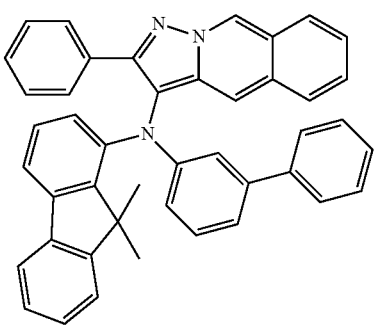
Compound 2-1-209
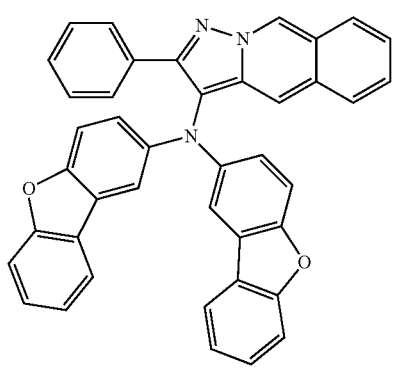
Compound 2-1-213
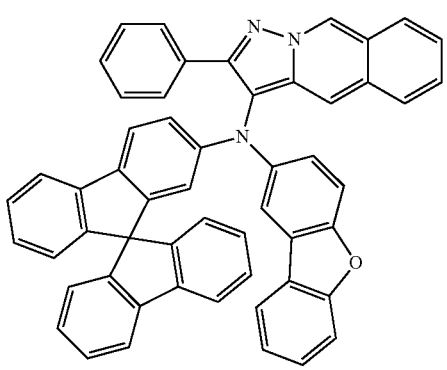
Compound 2-1-210
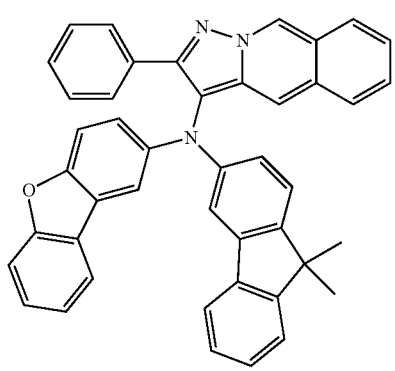
Compound 2-1-214
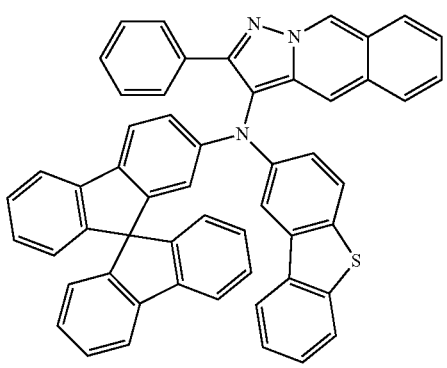
Compound 2-1-211
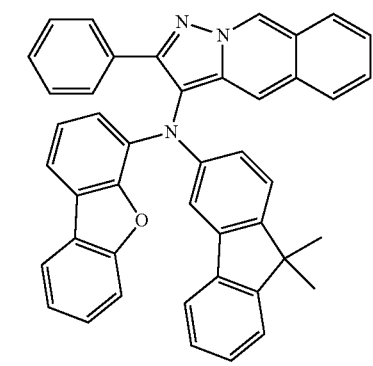
Compound 2-1-215
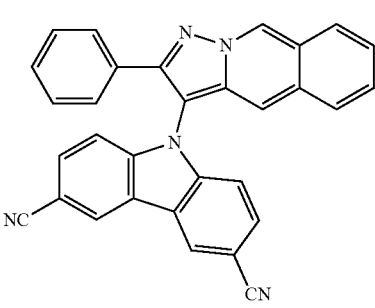

Compound 2-1-216

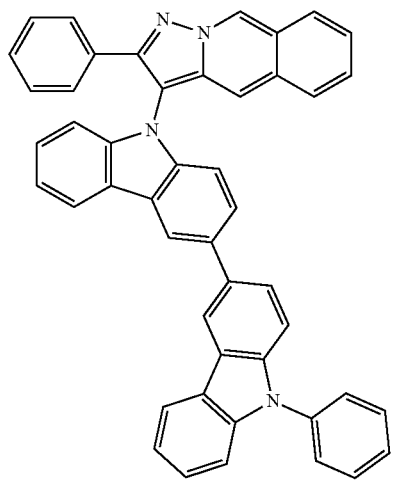

The above-described compounds may be prepared based on the Preparation Examples to be described below. Representative examples will be described in the Preparation Examples to be described below, but if necessary, a substituent may be added or excluded, and the position of the substituent may be changed. Further, a starting material, a reactant, reaction conditions, and the like may be changed based on the technology known in the art.

For example, in the compound of Formula 1, a core structure may be prepared as in the following Formula 1 or 2. The substituent may be bonded by a method known in the art, and the kinds and position of the substituent and the number of substituents may be changed according to the technology known in the art.

[Formula 1]

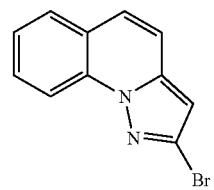

[Formula 2]

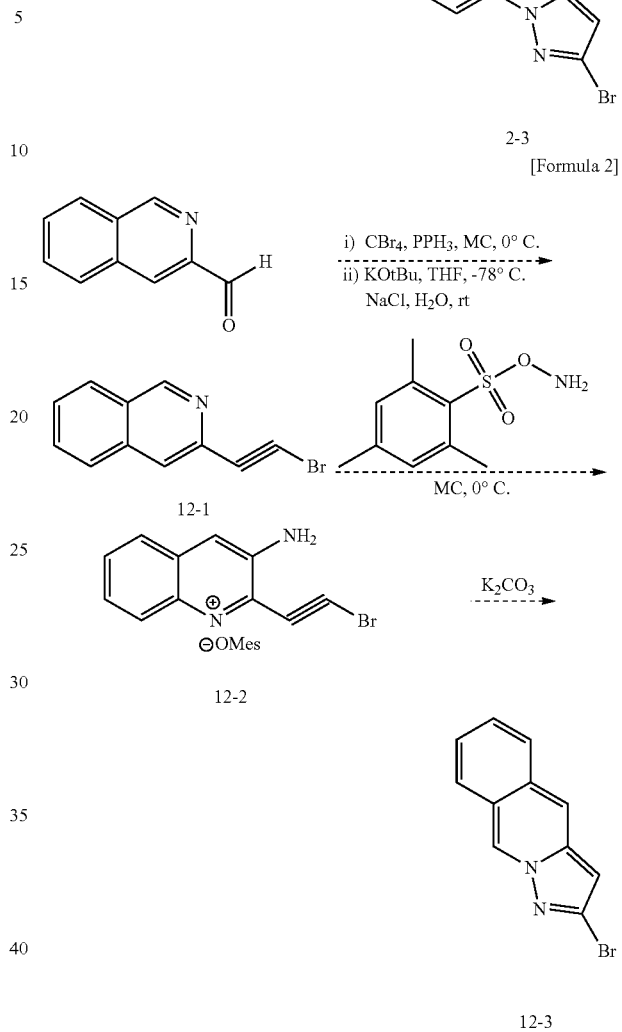

The specific preparation method will be described in more detail in the Preparation Examples to be described below.

Another exemplary embodiment of the present application provides an organic light emitting device including the above-described compound of Formula 1. Specifically, the organic light emitting device according to the present application includes a positive electrode, a negative electrode, and one or more organic material layers provided between the positive electrode and the negative electrode, and one or more of the organic material layers include the compound of Formula 1.

FIGS. 1 to 3 illustrate the stacking sequence of the electrodes and the organic material layers of the organic light emitting device according to exemplary embodiments of the present application. However, the scope of the present application is not intended to be limited by these drawings, and the structure of the organic light emitting device known in the art may also be applied to the present application.

According to FIG. 1, an organic light emitting device in which a positive electrode 200, an organic material layer 300, and a negative electrode 400 are sequentially stacked on a substrate 100 is illustrated. However, the organic light emitting device is not limited to such a structure, and as in FIG. 2, an organic light emitting device in which a negative electrode, an organic material layer, and a positive electrode are sequentially stacked may also be implemented.

FIG. 3 exemplifies a case where the organic material layer is a multilayer. The organic light emitting device according to FIG. 3 includes a hole injection layer 301, a hole transport layer 302, a light emitting layer 303, a hole blocking layer 304, an electron transport layer 305, and an electron injection layer 306. However, the scope of the present application is not limited by the stacking structure as described above, and if necessary, the other layers except for the light emitting layer may be omitted, and another necessary functional layer may be further added.

The organic light emitting device according to the present application may be manufactured by the materials and methods known in the art, except that one or more layers of the organic material layers include the compound of Formula 1.

The compound of Formula 1 may alone constitute one or more layers of the organic material layers of the organic light emitting device. However, the compound of Formula 1 may be mixed with another material, if necessary, to constitute an organic material layer.

The compound of Formula 1 may be used as a hole injection material, a hole transport material, a light emitting material, a hole blocking material, an electron transport material, an electron injection material, and the like in the organic light emitting device.

For example, the compound according to an exemplary embodiment of the present application may be used as a material for an electron injection layer, an electron transport layer, or a layer which injects and transports electrons simultaneously in the organic light emitting device.

In addition, the compound according to an exemplary embodiment of the present application may be used as a material for a light emitting layer of an organic light emitting device. Specifically, the compound may also be used alone as a light emitting material, and as a host material or a dopant material of the light emitting layer.

Furthermore, the compound according to an exemplary embodiment of the present application may be used as a phosphorescent host material of an organic light emitting device. In this case, the compound according to an exemplary embodiment of the present application is included along with a phosphorescent dopant.

Further, the compound according to an exemplary embodiment of the present application may be used as a material for a hole blocking layer of an organic light emitting device.

In the organic light emitting device according to the present application, materials other than the compound of Formula 1 will be exemplified below, but these materials are provided only for exemplification and are not for limiting the scope of the present application, and may be replaced with materials publicly known in the art.

As a material for the positive electrode, materials having a relatively large work function may be used, and a transparent conductive oxide, a metal or a conductive polymer, and the like may be used.

As a material for the negative electrode, materials having a relatively small work function may be used, and a metal, a metal oxide, or a conductive polymer, and the like may be used.

As a hole injection material, a publicly-known hole injection material may also be used, and it is possible to use, for example, a phthalocyanine compound such as copper phthalocyanine disclosed in U.S. Pat. No. 4,356,429 or starburst-type amine derivatives described in the document [Advanced Material, 6, p. 677 (1994)], for example, TCTA, m-MTDATA, m-MTDAPB, polyaniline/dodecylbenzene-sulfonic acid (Pani/DBSA) or poly(3,4-ethylenedioxythiophene)/poly(4-styrenesulfonate) (PEDOT/PSS), which is a soluble conductive polymer, polyaniline/camphor sulfonic acid (Pani/CSA) or polyaniline/poly(4-styrene-sulfonate) (PANI/PSS), and the like.

As the hole transport material, a pyrazoline derivative, an arylamine-based derivative, a stilbene derivative, a triphenyldiamine derivative, and the like may be used, and a low-molecular weight or polymer material may also be used.

As the electron transport material, it is possible to use an oxadiazole derivative, anthraquinodimethane and a derivative thereof, benzoquinone and a derivative thereof, naphthoquinone and a derivative thereof, anthraquinone and a derivative thereof, tetracyanoanthraquinodimethane and a derivative thereof, a fluorenone derivative, diphenyldicyanoethylene and a derivative thereof, a diphenoquinone derivative, a metal complex of 8-hydroxyquinoline and a derivative thereof, and a low-molecular weight material and a polymer material may also be used.

As the electron injection material, for example, LiF is typically used in the art, but the present application is not limited thereto.

As the light emitting material, a red, green, or blue light emitting material may be used, and if necessary, two or more light emitting materials may be mixed and used. Further, as the light emitting material, a fluorescent material may also be used, but a phosphorescent material may also be used. As the light emitting material, it is also possible to use alone a material which emits light by combining holes and electrons each injected from the positive electrode and the negative electrode, but materials in which a host material and a dopant material work together to emit light may also be used.

When the compound according to the present application is used as a phosphorescent host material, those known in the art may be used as a phosphorescent dopant material to be used together.

For example, phosphorescent dopant materials represented by LL'MX, LL'L"M, LMXX', $L_2MX$, and $L_3M$ may be used, but the scope of the present application is not limited by these examples.

Here, L, L', L", X, and X' are bidentate ligands different from each other, and M is a metal forming an octahedral complex.

M may be iridium, platinum, osmium, and the like.

L is an anionic, bidendate ligand coordinated on M by $sp^2$ carbon and a heteroatom, and X may perform a function of trapping electrons or holes. Non-limiting examples of L include 2-(1-naphthyl)benzoxazole, (2-phenylbezoxazole), (2-phenylbenzothiazole), (7,8-benzoquinoline), (thienylpyrizine), phenylpyridine, benzothienylpyrizine, 3-methoxy-2-phenylpyridine, thienylpyrizine, tolylpyridine, and the like. Non-limiting examples of X include acetylacetonate (acac), hexafluoroacetylacetonate, salicylidene, picolinate, 8-hydroxyquinolinate, and the like.

More specific examples thereof will be shown below, but the present application is not limited only to these examples.

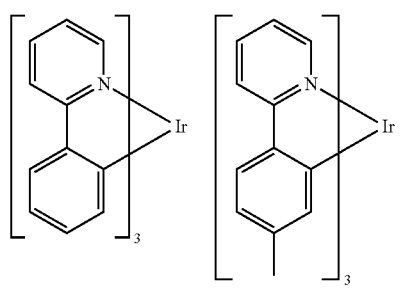
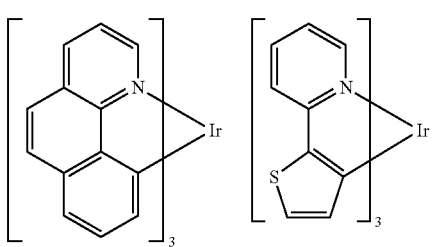
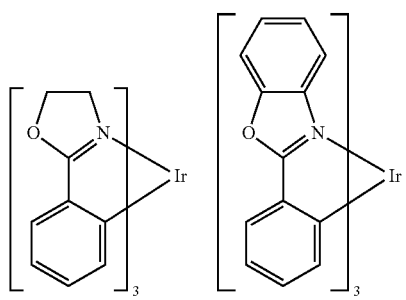
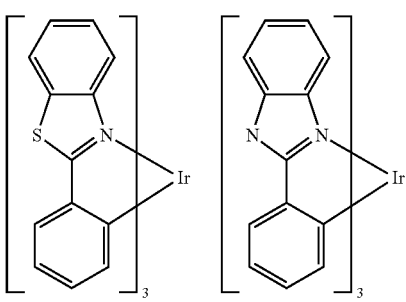
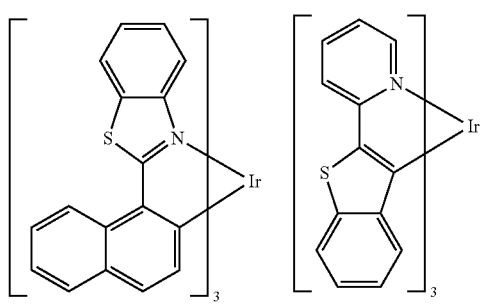
-continued
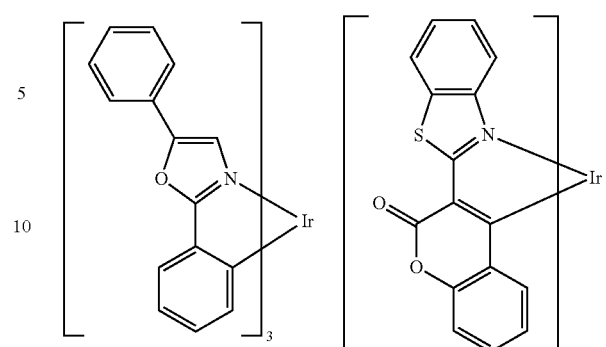
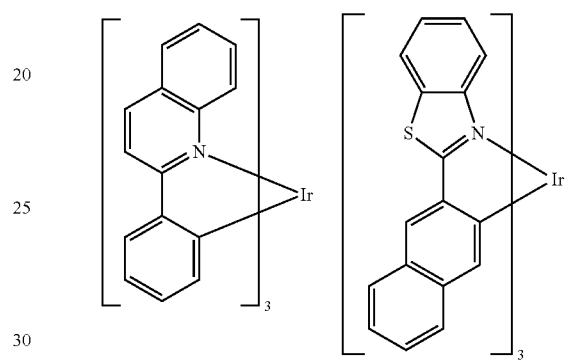
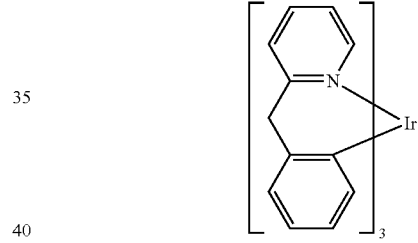
MODE FOR INVENTION
Hereinafter, the present application will be described in more detail through the Examples, but these are provided only for exemplifying the present application, and are not for limiting the scope of the present application.
EXAMPLE
<Preparation Example 1> Preparation of Compound 1-1-18
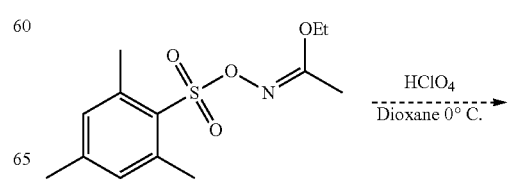

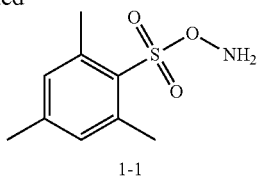

1-1

Preparation of Compound 1-1

Ethyl-o-sulfonylacetohydroxyamine (13.26 g, 46.47 mmol) was dissolved in 12 mL of 1,4-dioxane in a one-neck round bottom flask, and then the resulting solution was maintained at 0° C. Perchloric acid (70%, 5.40 mL) was slowly added dropwise thereto for 2 minutes while maintaining the temperature, and the resulting mixture was stirred for 5 minutes. The mixed solution, in which the reaction was terminated, was extracted with $H_2O$/ether and dried over $MgSO_4$, and then filtered. Solid Compound 1-1 (9.33 g, 93%) was obtained by performing distillation under reduced pressure.

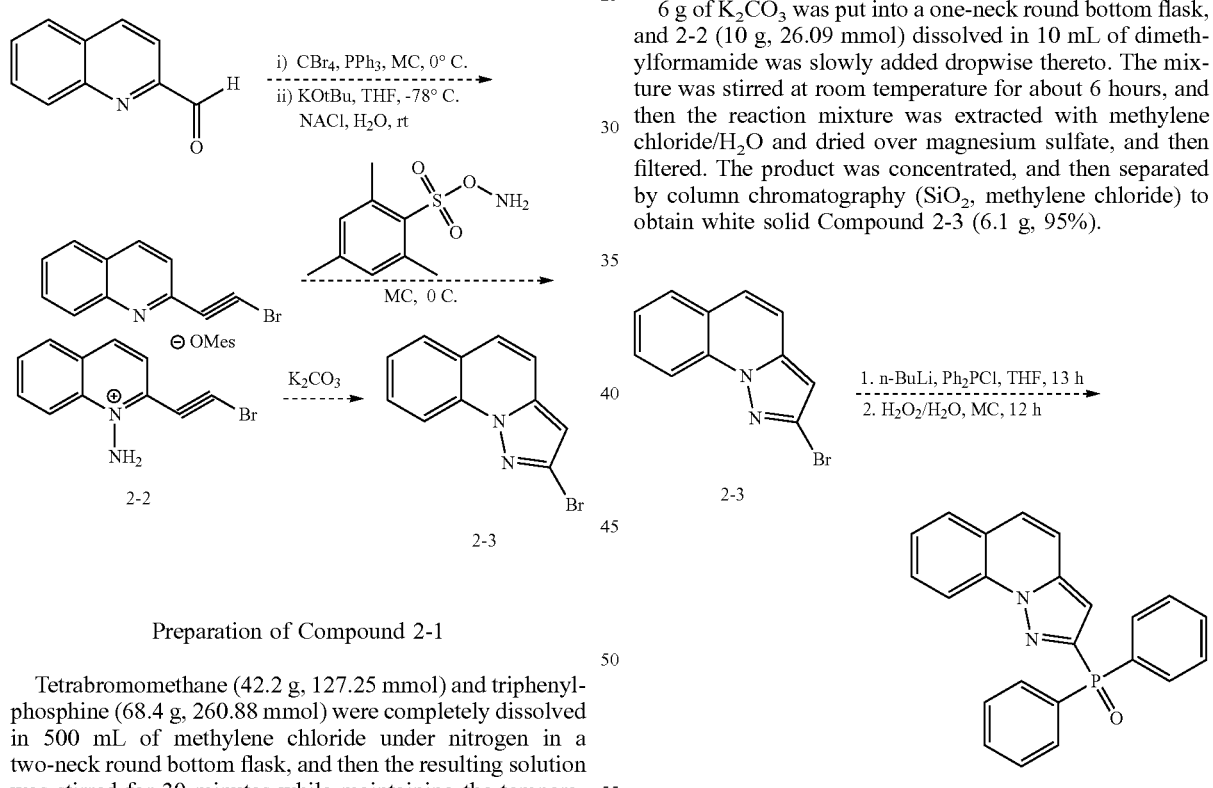

Preparation of Compound 2-1

Tetrabromomethane (42.2 g, 127.25 mmol) and triphenylphosphine (68.4 g, 260.88 mmol) were completely dissolved in 500 mL of methylene chloride under nitrogen in a two-neck round bottom flask, and then the resulting solution was stirred for 30 minutes while maintaining the temperature at 0° C. Thereafter, quinoline-2-carbaldehyde (10 g, 63.63 mmol) was slowly added dropwise thereto for 10 minutes, and then the resulting mixture was stirred for 1 hour while maintaining the temperature at 0° C. After the reaction was terminated, the reaction mixture was extracted with methylene chloride/$H_2O$ and dried over magnesium sulfate, and then filtered. A solid was produced by concentrating the mixture and then using hexane and filtered to produce a resulting solid (19.5 g, 62.3 mmol, 98%), and the resulting solid was completely dissolved in 200 mL of tetrahydrofuran, and then KOtBu (118 g, 1.06 mol) was slowly added thereto while maintaining the temperature at −78° C. Thereafter, 100 ML of brine was added thereto, the resulting mixture was cooled to room temperature, the reaction was terminated, and then the reaction mixture was extracted with ethyl ether/$H_2O$ and dried over $MgSO_4$, and then filtered. After the mixture was concentrated, hexane was used to produce a solid, and the solid was filtered to obtain ivory-colored solid Compound 2-1 (14.2 g, 98%).

Preparation of Compound 2-2

1-1 (10 g, 46.45 mmol) was completely dissolved in 50 mL of methylene chloride in a one-neck round bottom flask, and then the resulting solution was maintained at 0° C., 2-1 (9.70 g, 41.81 mmol) was completely dissolved in 50 mL of methylene chloride, and the resulting solution was slowly added dropwise thereto. After the mixture was stirred for about 10 minutes, 300 mL of ethyl ether was added thereto, and the resulting mixture was stirred for 30 minutes. A white solid was produced and filtered, and then recrystallization was performed with ethyl acetate/methanol to obtain white solid Compound 2-2 (15.7 g, 88%).

Preparation of Compound 2-3

6 g of $K_2CO_3$ was put into a one-neck round bottom flask, and 2-2 (10 g, 26.09 mmol) dissolved in 10 mL of dimethylformamide was slowly added dropwise thereto. The mixture was stirred at room temperature for about 6 hours, and then the reaction mixture was extracted with methylene chloride/$H_2O$ and dried over magnesium sulfate, and then filtered. The product was concentrated, and then separated by column chromatography ($SiO_2$, methylene chloride) to obtain white solid Compound 2-3 (6.1 g, 95%).

Preparation of Compound 1-1-18

Compound 2-3 (10 g, 40.47 mmol) was dissolved in anhydrous tetrahydrofuran (50 ml) under nitrogen in a one-neck round bottom flask, and then the resulting solution was cooled to −78° C. n-butyllithium (2.5 M in hexane) (21 ml, 52.61 mmol) was slowly added dropwise thereto, and then the resulting mixture was stirred for 1 hour. Chlorodiphenylphosphine (11.61 ml, 52.61 mol) was added dropwise to the solution, and the resulting solution was stirred at room temperature for 12 hours. The reaction mixture was extracted with methylene chloride/H₂O, and then distilled under reduced pressure. The reaction mixture was dissolved in methylene chloride (250 ml), and then the resulting solution was stirred along with 20 ml of a 30% H₂O₂ aqueous solution at room temperature for 12 hours. The reaction mixture was extracted with methylene chloride/H₂O, and then the concentrated mixture was separated by column chromatography (SiO₂, methylene chloride:methanol=25:1) to obtain yellow solid Compound 1-1-18 (4.03 g, 27%).

<Preparation Example 2> Preparation of Compound 1-1-86

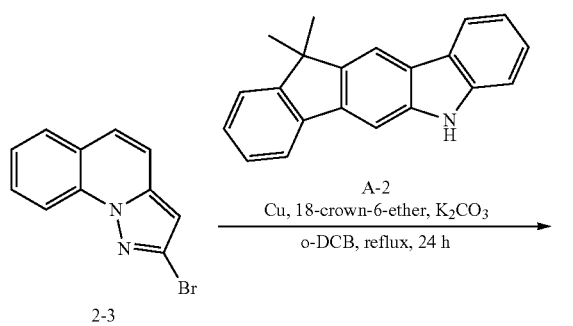

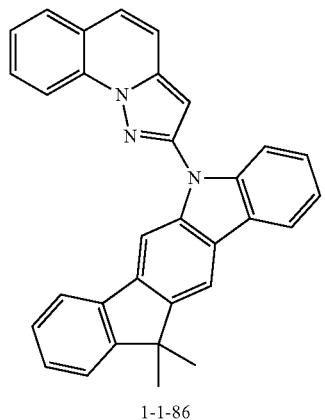

1-1-86

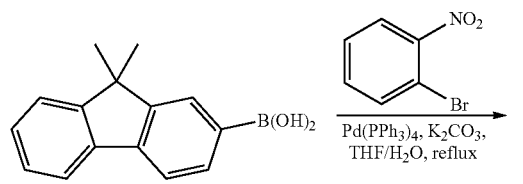

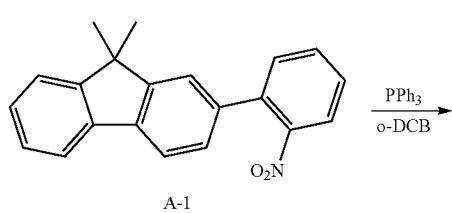

A-1

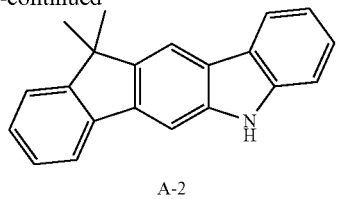

A-2

Preparation of Compound A-1

A mixture of 9,9-dimethyl-9H-fluoren-2-yl)boronic acid (25.9 g, 0.108 mol), 1-bromo-2-nitrobenzene (20 g, 0.099 mol), tetra(triphenylphosphine) palladium (5.7 g, 4.95 mmol), potassium carbonate (27.3 g, 0.198 mol), and tetrahydrofuran (250 ml)/H₂O (50 ml) was refluxed and stirred for 24 hours in a one-neck round bottom flask. The aqueous layer was removed, and then the organic layer was dried over MgSO₄. The organic layer was concentrated, and then separated by column chromatography (SiO₂, hexane:methylene chloride=2:1) to obtain yellow solid Compound A-1 (21 g, 61%).

Preparation of Compound A-2

A mixture of 1-1 (20 g, 0.0634 mmol), triphenylphosphine (49.8 g, 0.190 mol), and ortho-dichlorobenzene (300 ml) was refluxed and stirred under nitrogen for 18 hours in a one-neck round bottom flask. o-DCB was distilled under reduced pressure and removed, and then separated by column chromatography (SiO₂, hexane:methylene chloride=3:1) to obtain white solid Compound A-2 (6.6 g, 36%).

Preparation of Compound 1-1-86

A mixture of 2-3 (6.0 g, 24.28 mmol), A-2 (6.19 g, 21.85 mmol), Cu (0.15 g, 2.43 mmol), 18-crown-6-ether (0.64 g, 2.43 mmol), potassium carbonate (10.1 g, 72.84 mmol), and ortho-dichlorobenzene (80 ml) was refluxed and stirred under nitrogen for 24 hours in a one-neck round bottom flask. Ortho-dichlorobenzene was distilled under reduced pressure and removed, and then separated by column chromatography (SiO₂, hexane:methylene chloride=4:1) to obtain white solid Compound 1-1-86 (6.2 g, 57%).

<Preparation Example 3> Preparation of Compound 1-1-37

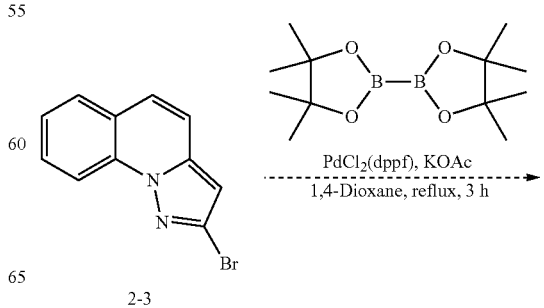

2-3

-continued

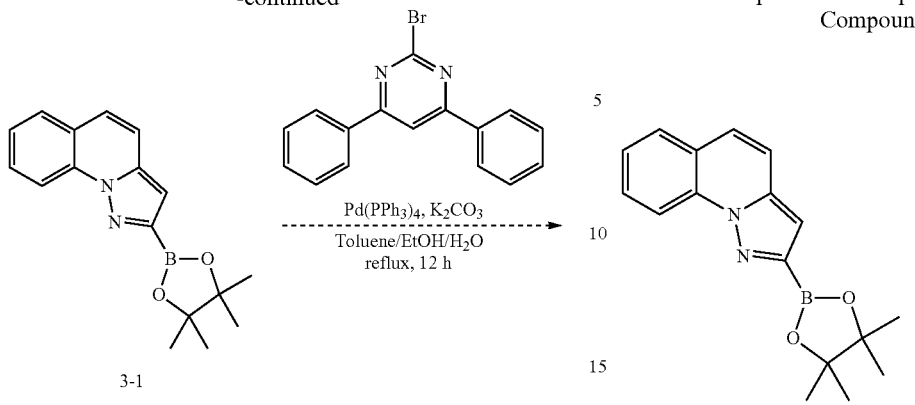

3-1

1-1-37

Preparation of Compound 3-1

A mixed solution of Compound 2-3 (6.0 g, 24.28 mmol), bis(pinacolato)diboron (7.4 g, 28.14 mmol), potassium acetate (4.77 g, 48.56 mmol), $PdCl_2(dppf)$ (0.8 g, 1.21 mmol), and 1,4-dioxane (120 ml) was refluxed and stirred under nitrogen for 3 hours in a two-neck round bottom flask. The reaction mixture cooled to room temperature was extracted with methylene chloride/$H_2O$ and dried over magnesium sulfate, and then filtered. After the mixture was concentrated, hexane was used to produce a solid, and the solid was filtered to obtain ivory-colored solid Compound 3-1 (6.1 g, 86%).

Preparation of Compound 1-1-37

A mixed solution of Compound 3-1 (6.0 g, 20.40 mmol), 2-bromo-4,6-diphenylpyrimidine (6.98 g, 22.44 mmol), potassium acetate (5.64 g, 40.8 mmol), tetra(triphenylphosphine) palladium (1.18 g, 1.02 mmol), and toluene/ethanol (EtOH)/$H_2O$ (60 ml/12 ml/12 ml) was refluxed and stirred under nitrogen for 12 hours in a two-neck round bottom flask. The solvent was filtered from the reaction mixture, and the solid was washed sequentially with 100 ml of toluene, 150 ml of hexane, and 150 ml of methanol to obtain white solid Compound 1-1-37 (7.1 g, 88%).

<Preparation Example 4> Preparation of Compound 1-1-63

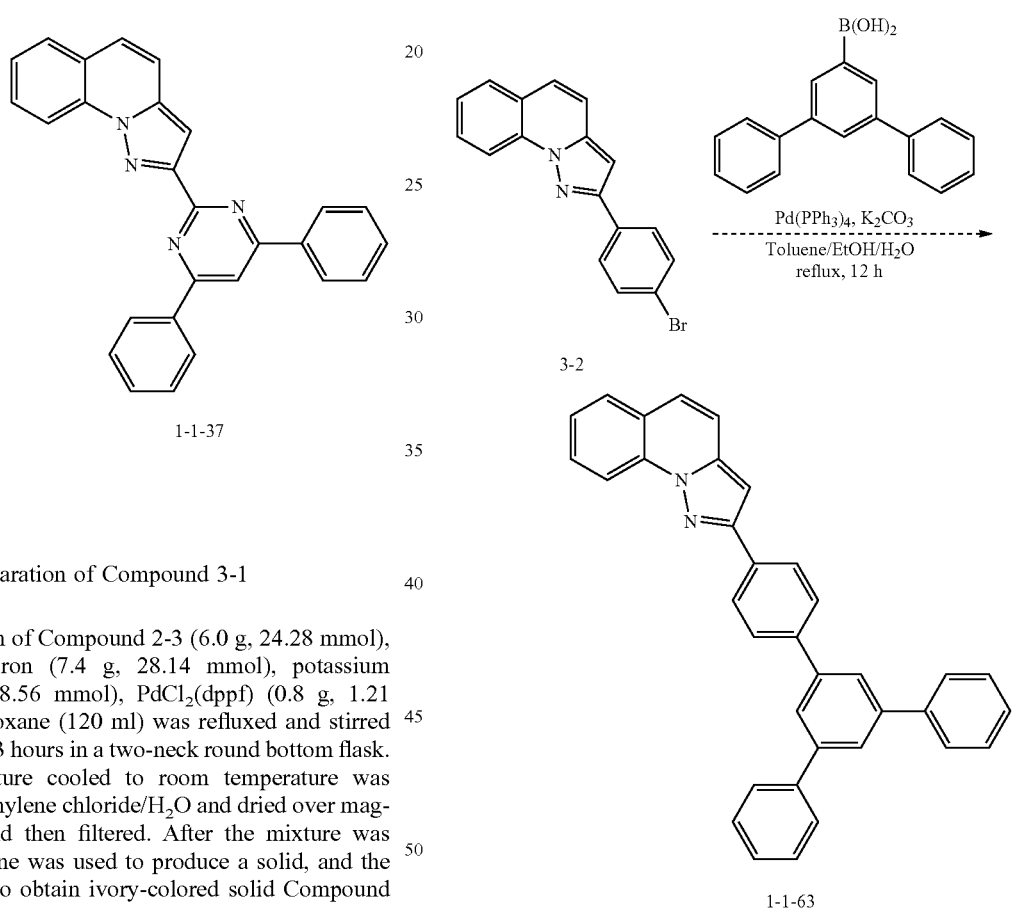

1-1-63

Preparation of Compound 3-2

A mixed solution of Compound 3-1 (6.0 g, 20.40 mmol), 1-iodo-4-bromobenzene (6.35 g, 22.44 mol), potassium carbonate (5.64 g, 40.8 mmol), $Pd(PPh_3)_4$ (1.18 g, 1.02 mmol), and toluene/ethanol/$H_2O$ (60 ml/12 ml/12 ml) was refluxed and stirred for 6 hours in a one-neck round bottom flask. The solvent was filtered from the reaction mixture, and the solid was washed sequentially with 100 ml of toluene, 150 ml of hexane, and 150 ml of methanol to obtain white solid Compound 3-2 (4.0 g, 61%).

Preparation of Compound 1-1-63

A mixed solution of Compound 3-2 (4.0 g, 12.38 mmol), [1,1':3',1''-terphenyl]-5'-ylboronic acid (3.73 g, 13.61 mmol), potassium carbonate (3.42 g, 24.76 mmol), tetra(triphenylphosphine) palladium (0.72 g, 0.62 mmol), and toluene/ethanol/$H_2O$ (40 ml/8 ml/8 ml) was refluxed and stirred under nitrogen for 12 hours in a two-neck round bottom flask. The solvent was filtered from the reaction mixture, and the solid was washed sequentially with 50 ml of toluene, 80 ml of hexane, and 80 ml of methanol to obtain white solid Compound 1-1-63 (5.4 g, 93%).

Compound 3-2 has a form in which bromophenyl is substituted at the R1 position in the core structure of Formula 2. In Preparation Example 4, bromine (Br) of Compound 3-2 was substituted with terphenyl to prepare Compound 1-1-63.

For example, the person skilled in the art may modify Preparation Example 4 to introduce another substituent instead of terphenyl. When Compound 3-2 is used instead of Compound 2-3 in the preparation of Compound 1-1-18, it is possible to obtain a structure into which a diphenyl phosphoryl-substituted phenyl is introduced (Compound 1-1-196). That is, it is possible to prepare a compound including a phosphine-based substituent which has an arylene linking group in the core structure of Formula 2. For example, Compounds 1-1-74 and 1-1-139 are compounds including a phosphine-based substituent which has an arylene linking group.

Further, a substituent such as terphenyl may be directly introduced into the core structure of Formula 2 by using Compound 2-3 of Preparation Example 1 instead of Compound 3-2 of Preparation Example 4.

<Preparation Example 5> Preparation of Compound 1-1-180

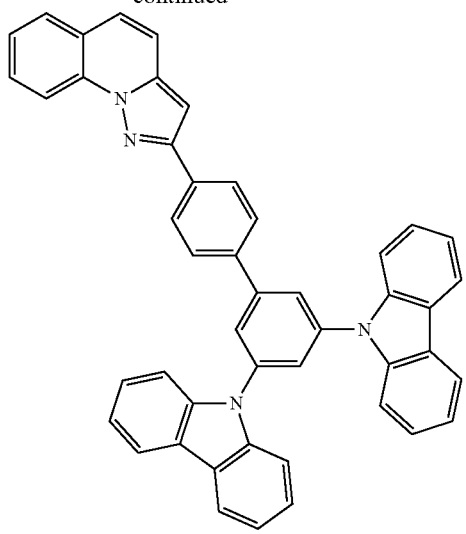

1-1-180

A mixed solution of Compound 3-2 (5.0 g, 15.47 mmol), 3,5-di(9H-carbazol-9-yl)phenyl)boronic acid (7.7 g, 17.02 mmol), $K_2CO_3$ (4.28 g, 30.94 mmol), tetra(triphenylphosphine) palladium (0.89 g, 0.77 mmol), and toluene/ethanol/$H_2O$ (100 ml/20 ml/20 ml) was refluxed and stirred under nitrogen for 12 hours in a two-neck round bottom flask. The reaction mixture cooled to room temperature was extracted with methylene chloride/$H_2O$ and dried over magnesium sulfate, and then filtered. The product was concentrated, and then separated by column chromatography ($SiO_2$, hexane:methylene chloride=2:1) to obtain white solid Compound 1-1-180 (6.64 g, 66%).

<Preparation Example 6> Preparation of Compound 1-1-109

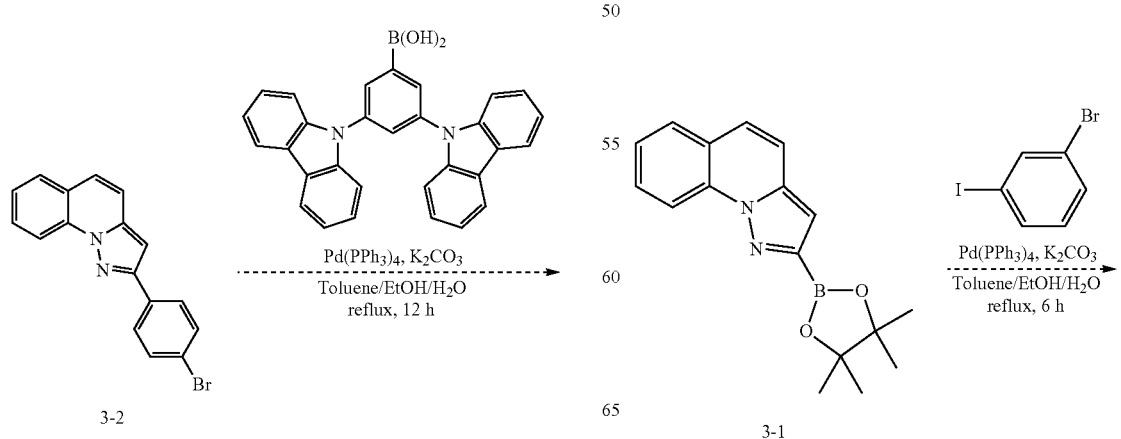

-continued

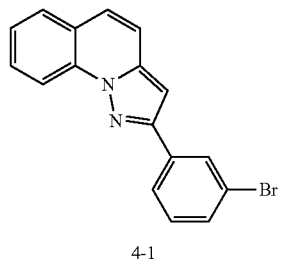

4-1

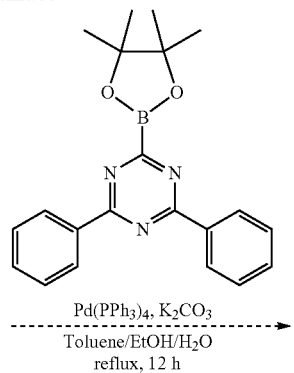

Pd(PPh₃)₄, K₂CO₃
Toluene/EtOH/H₂O
reflux, 12 h

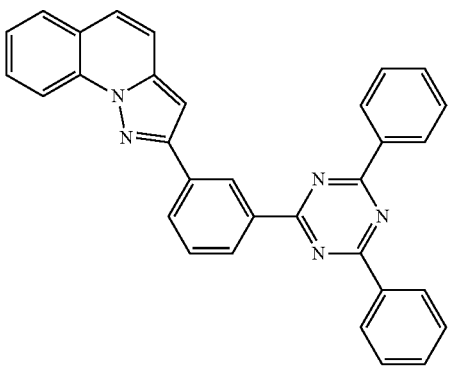

1-1-109

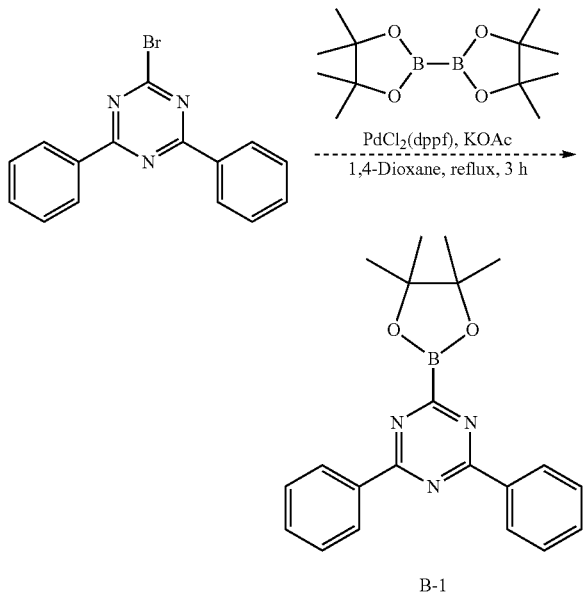

B-1

Preparation of Compound B-1

A mixed solution of 2-bromo-4,6-diphenyl-1,3,5-triazine (10.0 g, 32.03 mmol), bis(pinacolato) diboron (9.76 g, 38.44 mmol), potassium acetate (6.29 g, 64.06 mmol), PdCl₂dppf (dppf: 1,1'-bis(diphenylphosphino)ferrocene) (1.17 g, 1.60 mmol), and 1,4-dioxane (100 ml) was refluxed and stirred under nitrogen for 3 hours in a two-neck round bottom flask. The reaction mixture cooled to room temperature was extracted with methylene chloride/H₂O and dried over magnesium sulfate, and then filtered. After the mixture was concentrated, hexane was used to produce a solid, and the solid was filtered to obtain ivory-colored solid Compound B-1 (19.67 g, 83%).

Preparation of Compound 4-1

A mixed solution of Compound 3-1 (8.0 g, 27.20 mmol), 1-iodo-3-bromobenzene (8.46 g, 29.92 mmol), potassium carbonate (7.52 g, 54.5 mmol), Pd(PPh₃)₄ (1.57 g, 1.36 mmol), and toluene/ethanol/H₂O (80 ml/16 ml/16 ml) was refluxed and stirred for 6 hours in a one-neck round bottom flask. The solvent was filtered from the reaction mixture, and the solid was washed sequentially with 100 ml of toluene, 150 ml of hexane, and 150 ml of methanol to obtain white solid Compound 4-1 (5.0 g, 57%).

Preparation of Compound 1-1-109

A mixed solution of Compound 4-1 (5.0 g, 15.47 mmol), 2,4-diphenyl-6-(4,4,5,5-tetramethyl-1,3,2-dioxaborolan-2-yl)-1,3,5-triazine (6.67 g, 18.56 mmol), potassium carbonate (4.28 g, 30.94 mmol), tetra(triphenylphosphine) palladium (0.89 g, 0.77 mol), and toluene/ethanol/H₂O (100 ml/20 ml/20 ml) was refluxed and stirred under nitrogen for 12 hours in a two-neck round bottom flask. The reaction mixture cooled to room temperature was extracted with methylene chloride/H₂O and dried over magnesium sulfate, and then filtered. The product was concentrated, and then separated by column chromatography (SiO₂, hexane:methylene chloride=4:1) to obtain white solid Compound 1-1-109 (6.0 g, 82%).

<Preparation Example 7> Preparation of Compound 1-1-120

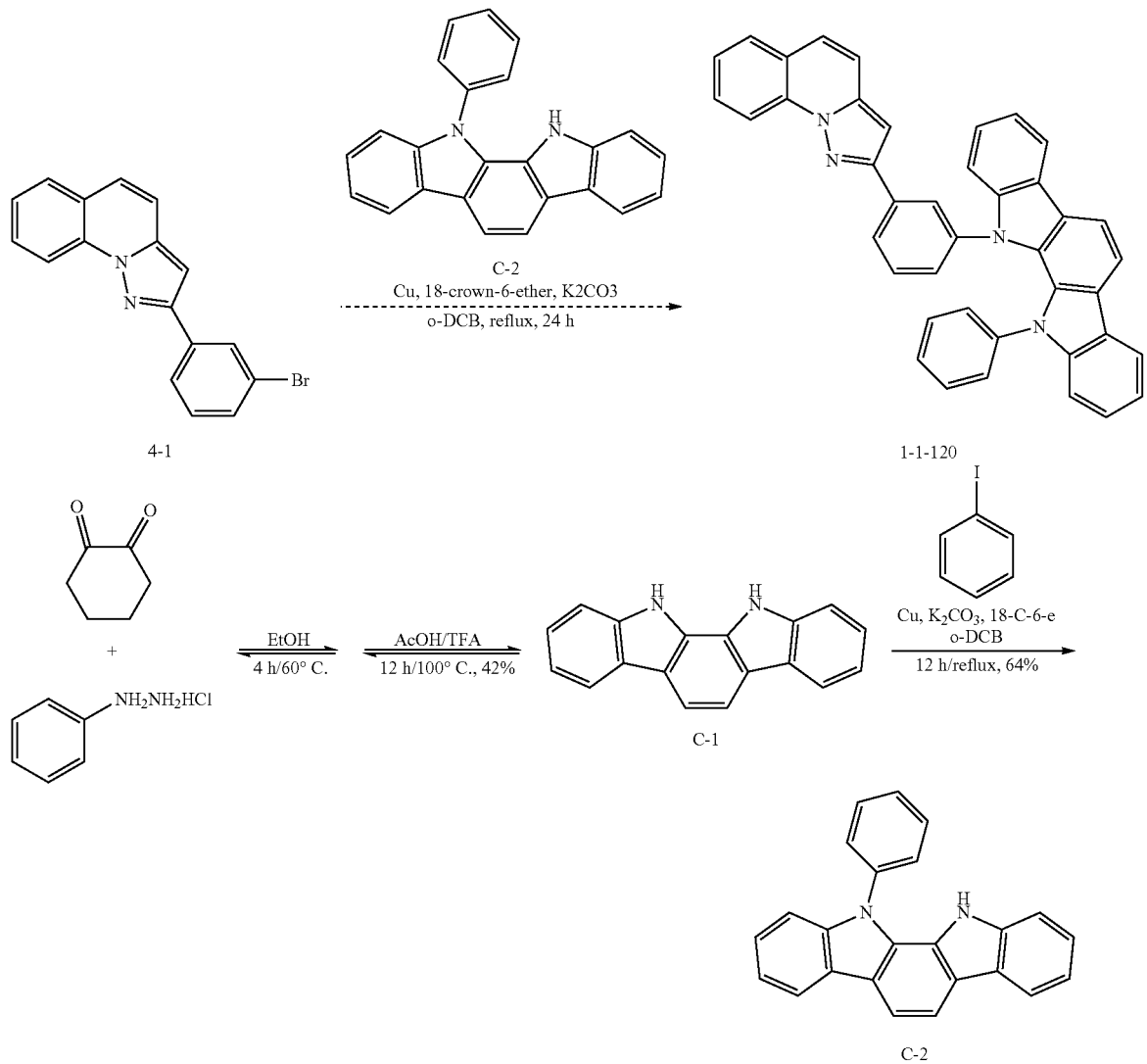

Preparation of Compound C-1

Sulfuric acid (1.4 mL, 0.0374 mol) was slowly added dropwise to a mixture of 1,2-dicyclohexanone (30.0 g, 0.374 mol), phenylhydrazine hydrochloride (77.37 g, 0.749 mol), and ethanol (1,000 ml) under nitrogen in a one-neck round bottom flask, and then the resulting mixture was stirred at 60° C. for 4 hours. The solution cooled to room temperature was filtered to obtain a yellow brown solid (69 g, 93%). Trifluoroacetic acid (46.5 mL, 0.6 mol) was added to a mixture of the solid (68.9 g, 0.25 mol) and acetic acid (700 ml) in a one-neck round bottom flask, and the resulting mixture was stirred at 100° C. for 12 hours. The solution cooled to room temperature was washed with acetic acid and hexane and filtered to obtain ivory-colored solid C-1 (27.3 g, 42%).

Preparation of Compound C-2

A mixture of C-1 (2.1 g, 0.0082 mol), iodobenzene (2.5 g, 0.013 mol), Cu (0.312 g, 0.0049), 18-crown-6-ether (0.433 g, 0.0016 mol), potassium carbonate (3.397 g, 0.0246 mol), and ortho-dichlorobenzene (20 ml) was refluxed and stirred under nitrogen for 12 hours in a two-neck round bottom flask. The solution cooled to room temperature was extracted with methylene chloride/H$_2$O and concentrated, and separated by column chromatography (SiO$_2$, hexane: ethyl acetate=10:1) to obtain white solid compound C-2 (1.76 g, 64%).

Preparation of Compound 1-1-120

A mixture of 4-1 (6.0 g, 24.28 mmol), C-2 (9.69 g, 29.14 mmol), Cu (0.15 g, 2.43 mmol), 18-crown-6-ether (0.64 g, 2.43 mmol), potassium carbonate (6.71 g, 48.56 mmol), and ortho-dichlorobenzene (60 ml) was refluxed and stirred under nitrogen for 24 hours in a one-neck round bottom flask. Ortho-dichlorobenzene was distilled under reduced pressure and removed, and then separated by column chromatography (SiO$_2$, hexane:methylene chloride=3:1) to obtain white solid Compound 1-1-120 (6.7 g, 48%).

<Preparation Example 8> Preparation of Compound 1-1-154

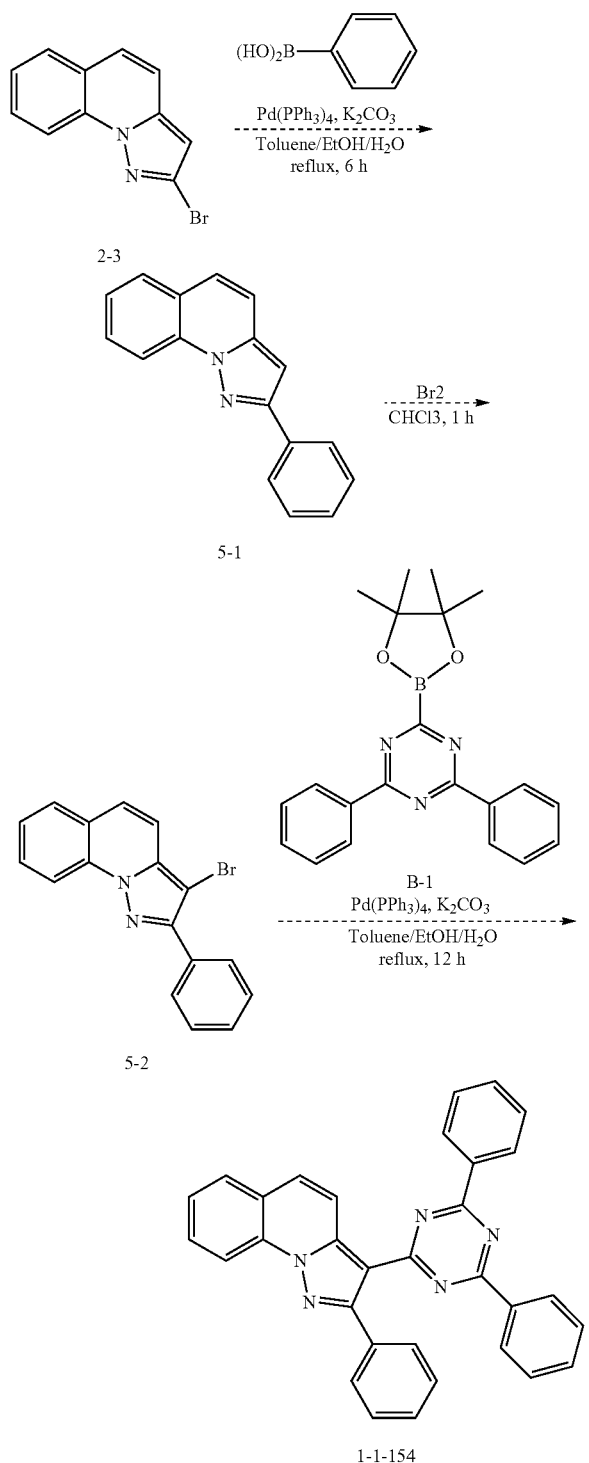

Preparation of Compound 5-1

A mixed solution of Compound 2-3 (6.0 g, 24.28 mmol), phenyl boronic acid (3.55 g, 29.14 mmol), potassium carbonate (6.71 g, 48.56 mmol), tetra(triphenylphosphine) palladium (1.40 g, 1.21 mmol), and toluene/ethanol/$H_2O$ (60 ml/12 ml/12 ml) was refluxed and stirred for 6 hours in a one-neck round bottom flask. The solvent was filtered from the reaction mixture, and the solid was washed sequentially with 50 ml of toluene, 80 ml of hexane, and 80 ml of methanol to obtain white solid Compound 5-1 (5.6 g, 95%).

Preparation of Compound 5-2

100 mL of $CHCl_3$ and $br_2$ (2.1 mL, 40.94 mmol) were put into a one-neck round bottom flask, the resulting mixture was stirred for 10 minutes, and then the temperature was maintained at 0° C. Compound 5-1 (5 g, 20.47 mmol) dissolved in 50 mL of chloroform was slowly added dropwise thereto. The reaction was terminated after about 1 hour, and the product was extracted with methylene chloride/$H_2O$ and concentrated, and then washed with a small amount of EA and hexane to obtain solid Compound 5-2 (6.2 g, 94%).

Preparation of Compound 1-1-154

A mixed solution of Compound 5-2 (6.0 g, 18.56 mmol), 2,4-diphenyl-6-(4,4,5,5-tetramethyl-1,3,2-dioxaborolan-2-yl)-1,3,5-triazine (8.0 g, 22.28 mmol), potassium carbonate (5.13 g, 37.12 mmol), tetra(triphenylphosphine) palladium (1.07 g, 0.93 mmol), and toluene/EtOH/$H_2O$ (60 ml/12 ml/12 ml) was refluxed and stirred for 12 hours in a one-neck round bottom flask. The solution cooled to room temperature was extracted with methylene chloride/$H_2O$ and concentrated, and separated by column chromatography ($SiO_2$, hexane:methylene chloride=3:1) to obtain white solid Compound 1-1-154 (6.88 g, 78%).

<Preparation Example 9> Preparation of Compound 1-1-186

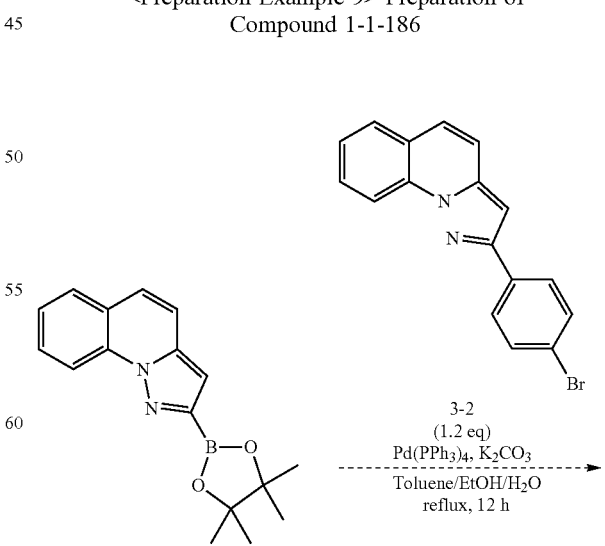

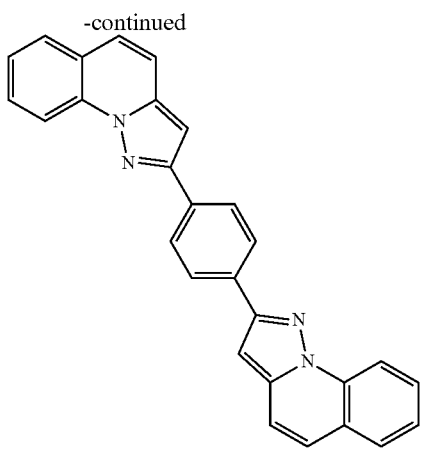

1-1-186

A mixed solution of Compound 3-1 (6.0 g, 20.4 mmol), 3-2 (7.9 g, 24.48 mmol), potassium carbonate (8.46 g, 61.2 mmol), tetra(triphenylphosphine) palladium (1.18 g, 1.02 mmol), and toluene/ethanol/H₂O (60 ml/12 ml/12 ml) was refluxed and stirred for 12 hours in a one-neck round bottom flask. The solution cooled to room temperature was extracted with methylene chloride/H₂O and concentrated, and separated by column chromatography (SiO₂, hexane: methylene chloride=4:1) to obtain white solid Compound 1-1-186 (5.26 g, 64%).

<Preparation Example 10> Preparation of Compound 1-1-190

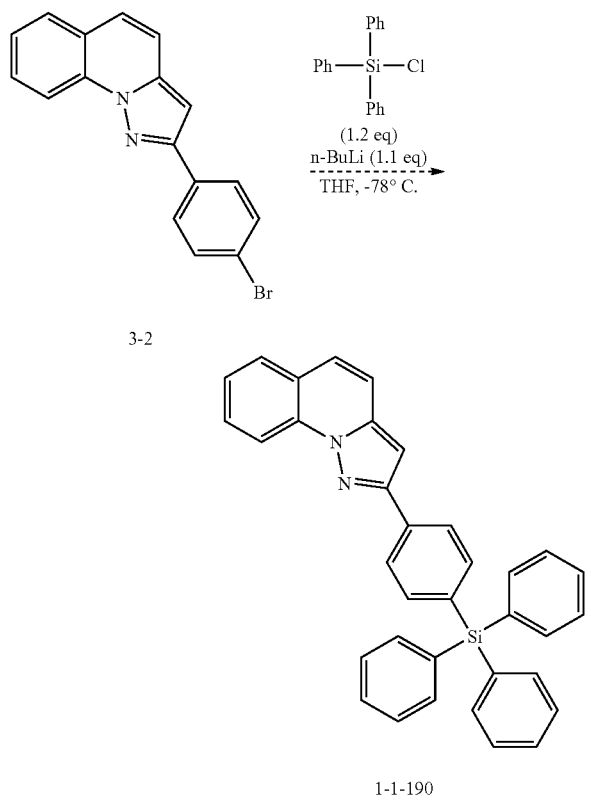

1-1-190

Compound 3-2 (10 g, 30.94 mmol) was completely dissolved in 200 mL of tetrahydrofuran in a one-neck round bottom flask, and then n-butyllithium (6.6 mL, 32.04 mmol) was slowly added dropwise thereto while maintaining the temperature at −78° C. The resulting mixture was stirred for about 30 minutes, and then chlorotriphenylsilane (10.03 g, 34.03 mmol) was slowly added dropwise thereto, the reaction was terminated after about 1 hour, and the product was extracted with methylene chloride/H₂O and concentrated, and separated by column chromatography (SiO₂, hexane: methylene chloride=4:1) to obtain white solid Compound 1-1-190 (5.29 g, 34%).

<Preparation Example 11> Preparation of Compound 1-1-192

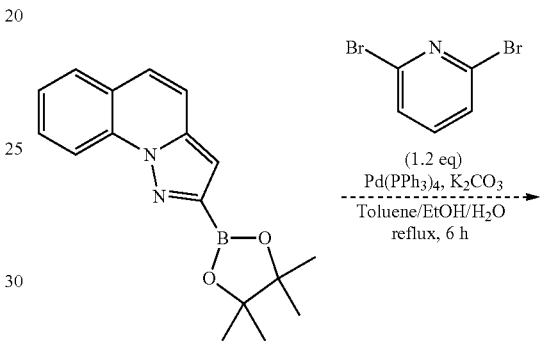

3-1

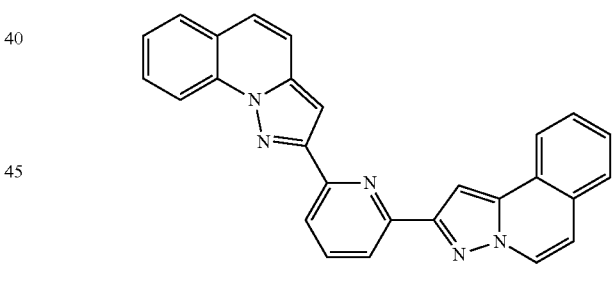

1-1-192

A mixed solution of Compound 3-1 (6.0 g, 20.4 mmol), 2,6-dibromopyridine (5.8 g, 24.48 mmol), potassium carbonate (8.46 g, 61.2 mmol), tetra(triphenylphosphine) palladium (1.18 g, 1.02 mmol), and toluene/ethanol/H₂O (60 ml/12 ml/12 ml) was refluxed and stirred for 6 hours in a one-neck round bottom flask. The solution cooled to room temperature was extracted with methylene chloride/H₂O and concentrated, and separated by column chromatography (SiO₂, hexane:methylene chloride=2:1) to obtain white solid Compound 1-1-192 (6.60 g, 78%).

<Preparation Example 12> Preparation of Compound 1-1-193

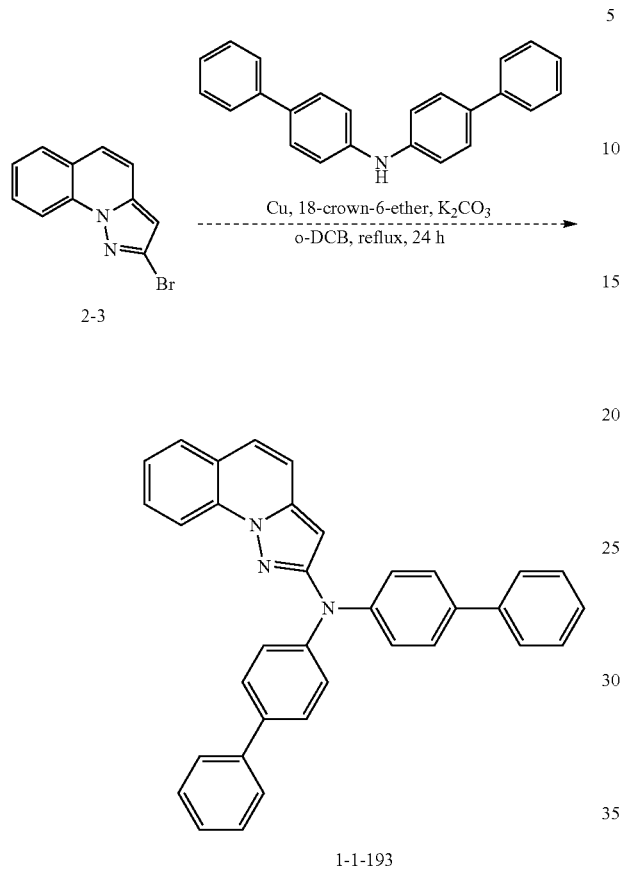

1-1-193

A mixture of 2-3 (6.0 g, 24.28 mmol), di([1,1'-biphenyl]-4-yl)amine) (7.0 g, 21.85 mmol), Cu (0.15 g, 2.43 mmol), 18-crown-6-ether (0.64 g, 2.43 mmol), potassium carbonate (10.1 g, 72.84 mmol), and ortho-dichlorobenzene (80 ml) was refluxed and stirred under nitrogen for 24 hours in a one-neck round bottom flask. Ortho-dichlorobenzene was distilled under reduced pressure and removed, and then separated by column chromatography (SiO$_2$, hexane:methylene chloride=5:1) to obtain white solid Compound 1-1-193 (5.5 g, 46%).

<Preparation Example 13> Preparation of Compound 1-1-200

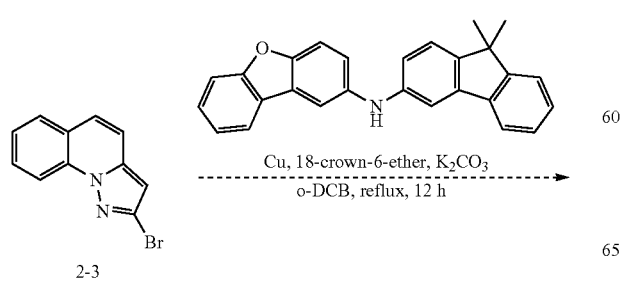

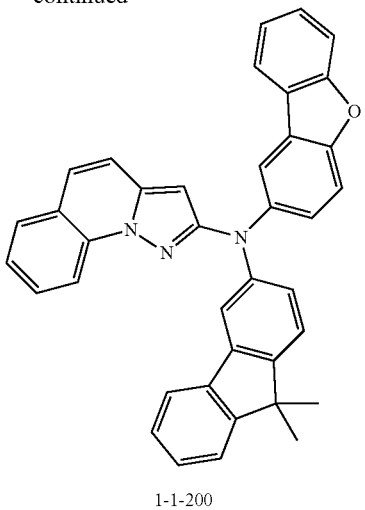

1-1-200

An o-DCB (80 ml) mixture of 2-3 (6.0 g, 24.28 mmol), a reagent (8.2 g, 21.85 mmol), Cu (0.15 g, 2.43 mmol), 18-crown-6-ether (0.79 g, 2.43 mmol), and K$_2$CO$_3$ (10.1 g, 72.84 mmol) was refluxed and stirred under nitrogen for 12 hours in a one-neck round bottom flask. o-DCB was distilled under reduced pressure and removed, and then separated by column chromatography (SiO$_2$, hexane:MC=4:1) to obtain white solid Compound 1-1-200 (10.8 g, 82%).

<Preparation Example 14> Preparation of Compound 1-1-201

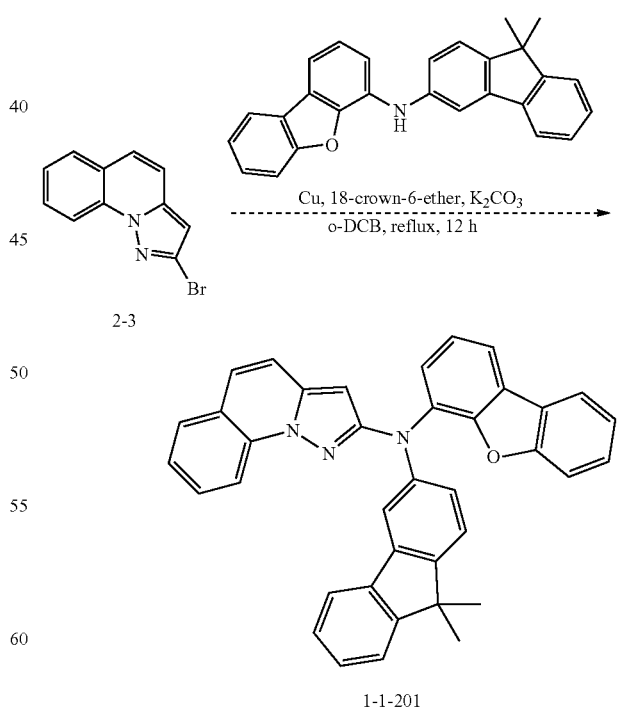

1-1-201

A product (10.1 g, 77%) was prepared in the same manner as in the method for preparing Compound 1-1-200 of Preparation Example 13, except that N-(9,9-dimethyl-9H- fluoren-3-yl)dibenzo[b,d]furan-4-amine was used instead of N-(9,9-dimethyl-9H-fluoren-3-yl)dibenzo[b,d]furan-2-amine in the method.

<Preparation Example 15> Preparation of Compound 1-1-202

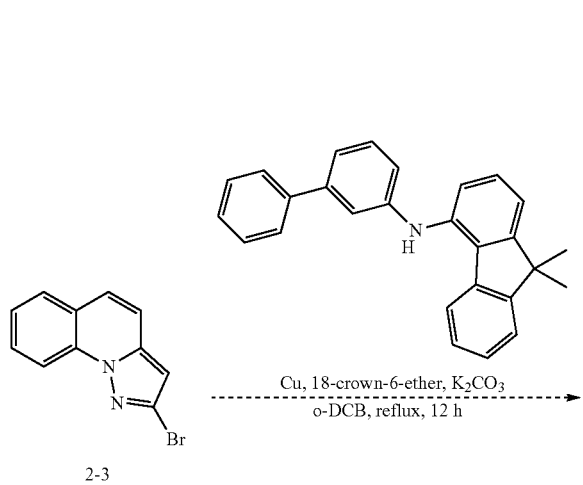

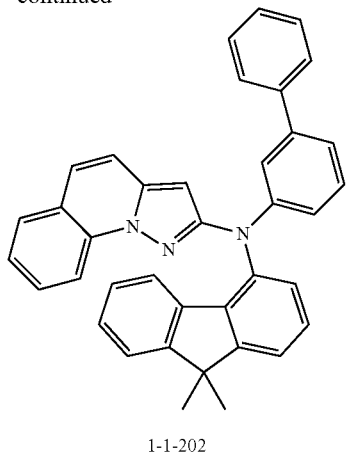

1-1-202

A product (10.4 g, 49%) was prepared in the same manner as in the method for preparing Compound 1-1-200 of Preparation Example 13, except that N-([1,1'-biphenyl]-3-yl)-9,9-dimethyl-9H-fluoren-4-amine was used instead of N-(9,9-dimethyl-9H-fluoren-3-yl)dibenzo[b,d]furan-2-amine in the method.

<Preparation Example 16> Preparation of Compound 1-1-203

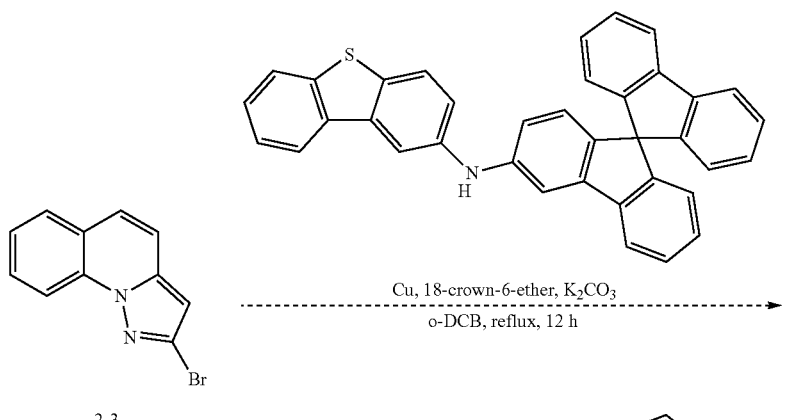

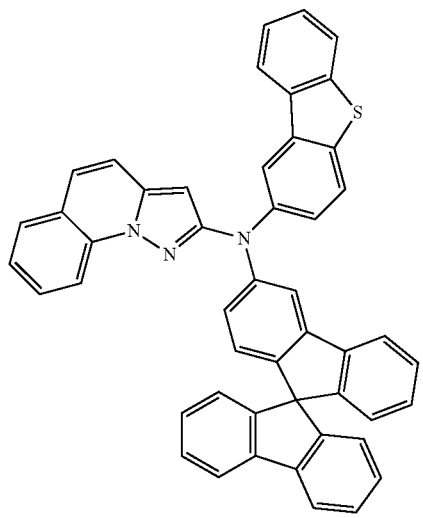

1-1-203

A product (15.1 g, 55%) was prepared in the same manner as in the method for preparing Compound 1-1-200 of Preparation Example 13, except that N-(9,9'-spirobi[fluoren]-3-yl)dibenzo[b,d]thiophen-2-amine was used instead of N-(9,9-dimethyl-9H-fluoren-3-yl)dibenzo[b,d]furan-2-amine in the method.

<Preparation Example 17> Preparation of Compound 1-1-204

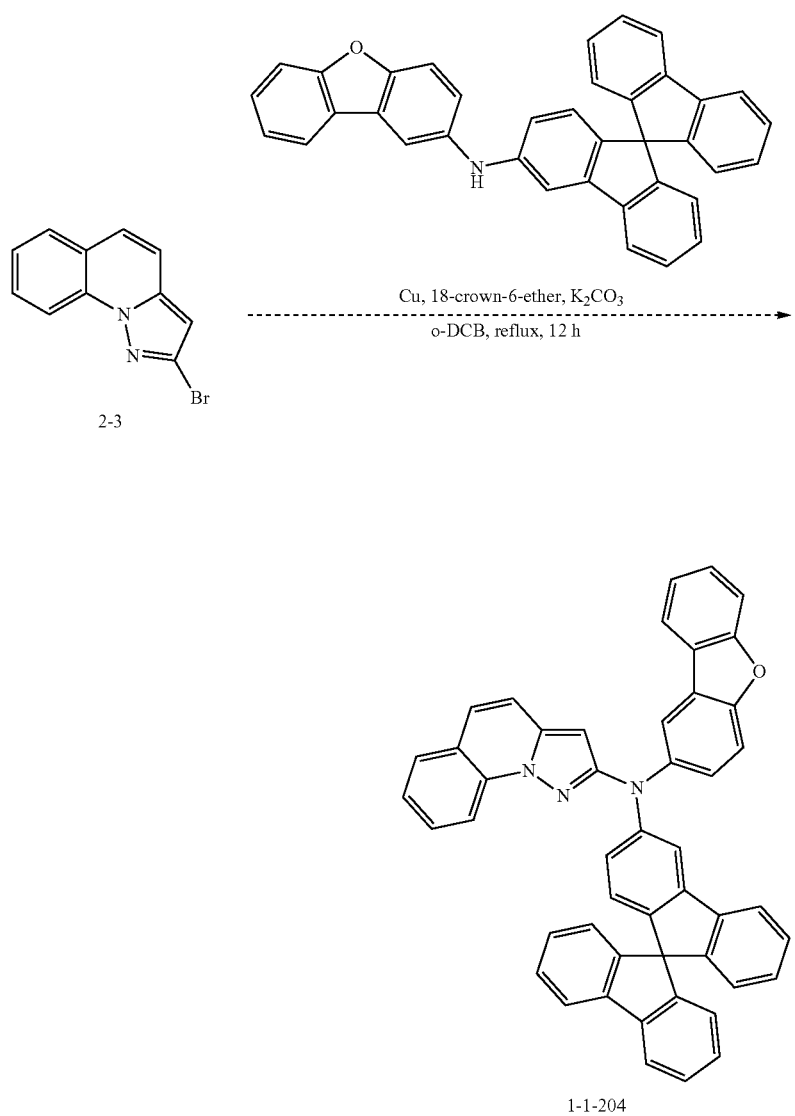

A product (11.8 g, 44%) was prepared in the same manner as in the method for preparing Compound 1-1-200 of Preparation Example 13, except that N-(9,9'-spirobi[fluoren]-3-yl)dibenzo[b,d]furan-2-amine was used instead of N-(9,9-dimethyl-9H-fluoren-3-yl)dibenzo[b,d]furan-2-amine in the method.

<Preparation Example 18> Preparation of Compound 1-1-206

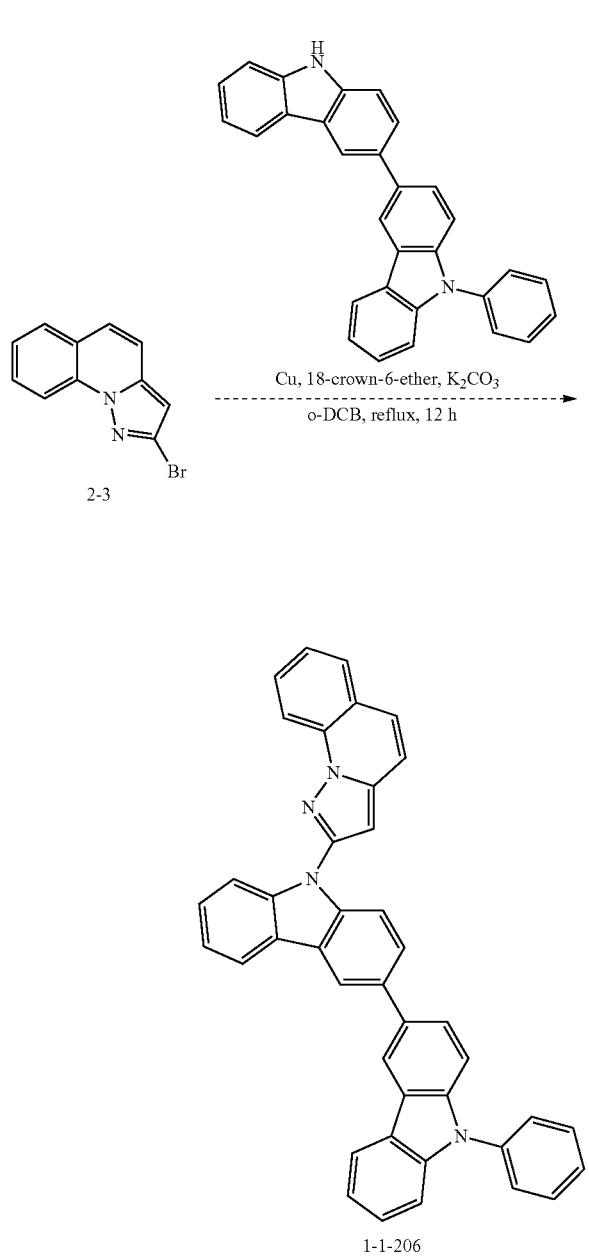

<Preparation Example 19> Preparation of Compound 1-1-207

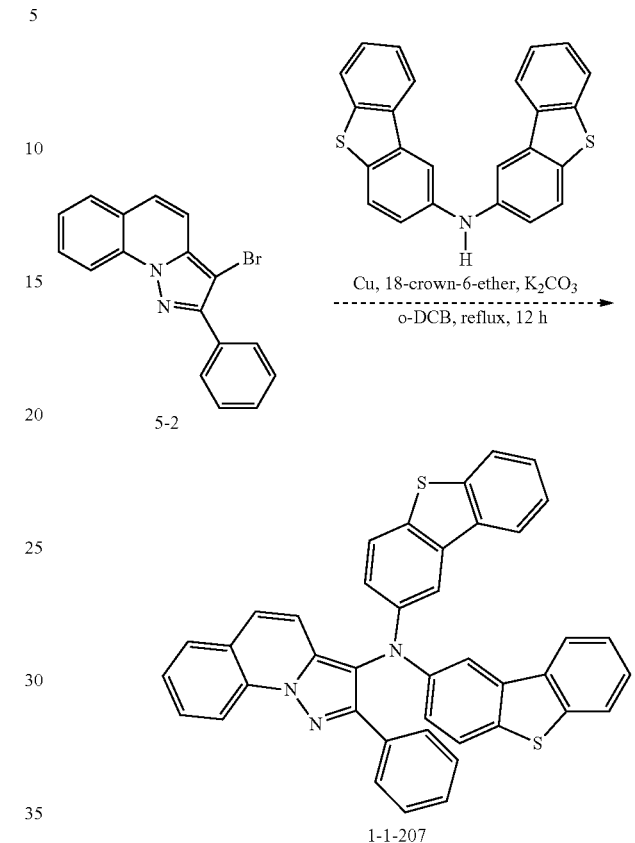

An o-DCB (80 ml) mixture of 5-2 (10.0 g, 30.94 mmol), a reagent (12.9 g, 34.04 mmol), Cu (0.19 g, 3.09 mmol), 18-crown-6-ether (1.0 g, 3.09 mmol), and $K_2CO_3$ (12.8 g, 92.82 mmol) was refluxed and stirred under nitrogen for 12 hours in a one-neck round bottom flask. o-DCB was distilled under reduced pressure and removed, and then separated by column chromatography ($SiO_2$, hexane:MC=3:1) to obtain white solid Compound 1-1-207 (14.8 g, 77%).

<Preparation Example 20> Preparation of Compound 1-1-208

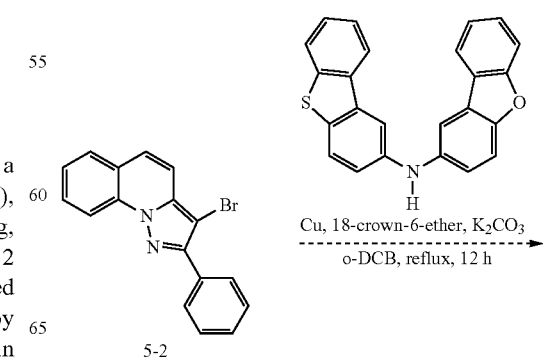

An o-DCB (80 ml) mixture of 2-3 (6.0 g, 24.28 mmol), a reagent (8.9 g, 21.85 mmol), Cu (0.15 g, 2.43 mmol), 18-crown-6-ether (0.79 g, 2.43 mmol), and $K_2CO_3$ (10.1 g, 72.84 mmol) was refluxed and stirred under nitrogen for 12 hours in a one-neck round bottom flask. o-DCB was distilled under reduced pressure and removed, and then separated by column chromatography ($SiO_2$, hexane:MC=4:1) to obtain white solid Compound 1-1-206 (8.4 g, 60%).

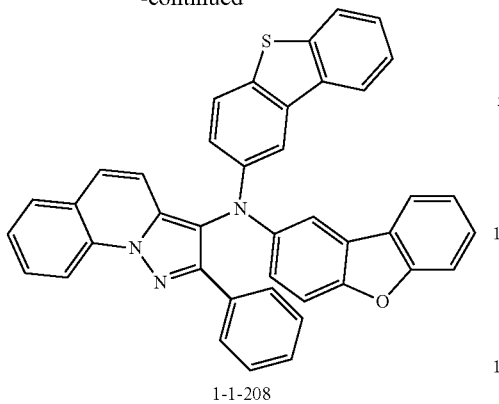

1-1-208

A product (12.4 g, 66%) was prepared in the same manner as in the method for preparing Compound 1-1-207 of Preparation Example 19, except that N-(dibenzo[b,d]thiophen-2-yl)dibenzo[b,d]furan-2-amine was used instead of bis(dibenzo[b,d]thiophen-2-yl)amine in the method.

<Preparation Example 21> Preparation of Compound 1-1-210

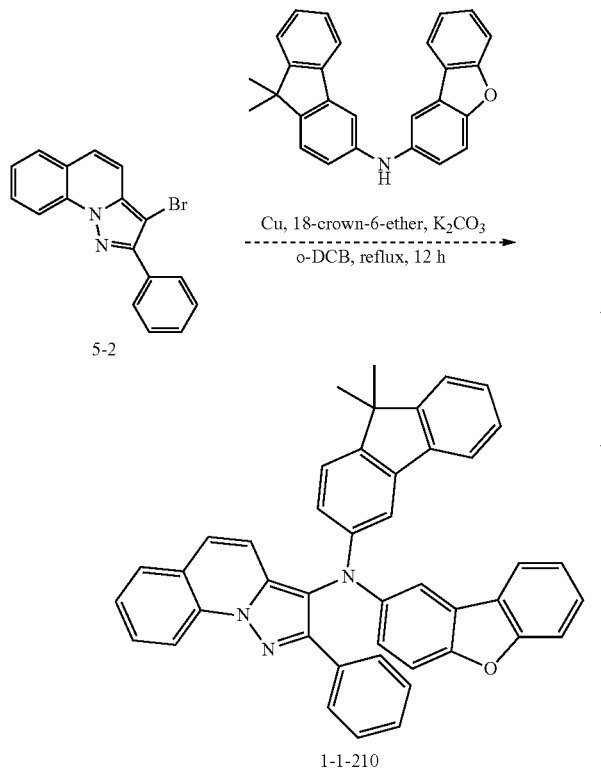

1-1-210

A product (13.6 g, 71%) was prepared in the same manner as in the method for preparing Compound 1-1-207 of Preparation Example 19, except that N-(9,9-dimethyl-9H-fluoren-3-yl)dibenzo[b,d]furan-2-amine was used instead of bis(dibenzo[b,d]thiophen-2-yl)amine in the method.

<Preparation Example 22> Preparation of Compound 1-1-213

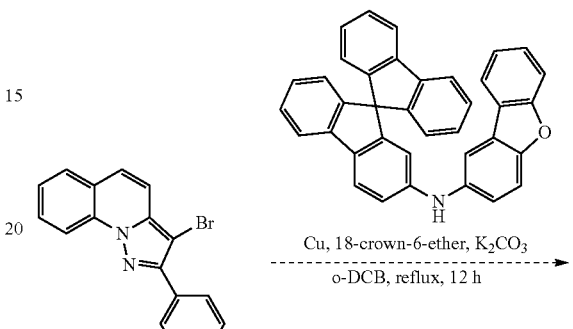

1-1-213

A product (12.1 g, 53%) was prepared in the same manner as in the method for preparing Compound 1-1-207 of Preparation Example 19, except that N-(9,9'-spirobi[fluoren]-2-yl)dibenzo[b,d]furan-2-amine was used instead of bis(dibenzo[b,d]thiophen-2-yl)amine in the method.

Compounds 1-1-1 to 1-1-216 may be prepared by modifying the bonded substituent based on Preparation Examples 1 to 22.

Compounds were prepared in the same manner as in the Preparation Examples, and the synthesis confirmation results thereof are shown in Tables 1 and 2. Table 1 is about the measurement values of $^1$H NMR (CDCl$_3$, 200 Mz), and Table 2 is about the measurement values of field desorption mass spectrometry (FD-MS).

TABLE 1

| Compound | $^1$H NMR(CDCl$_3$, 200 Mz) |
|---|---|
| 1-1-18 | δ = 6.40(1H, s), 7.29(1H, d), 7.51(6H, s), 7.69~7.84(6H, m), 8.08~8.11(2H, m), 8.46(1H, d) |

TABLE 1-continued

| Compound | $^1$H NMR(CDCl$_3$, 200 Mz) |
|---|---|
| 1-1-37 | δ = 6.40(1H, s), 7.29(1H, d), 7.49~7.55(6H, m), 7.69(1H, t), 7.84~7.94(5H, m), 8.08~8.11(2H, m), 8.46(1H, d) |
| 1-1-63 | δ = 6.66(1H, s), 7.29(1H, d), 7.41~7.49(6H, m), 7.75~7,85(8H, m), 8.04~8.11(5H, m), 8.30(2H, m), 8.46(1H, d) |
| 1-1-86 | δ = 1.69(6H, s), 6.40(1H, s), 7.20(1H, t), 7.29(1H, d), 7.38(1H, t), 7.50~7.58(3H, m), 7.69~7.84(4H, m), 8.08~8.19(3H, m), 8.46(1H, d), 9.01(1H, d) |
| 1-1-109 | δ = 6.66(1H, s), 7.29(1H, d), 7.50(6H, m), 7.69~7.94(5H, m), 8.08~8.11(2H, m), 8.36~8.46(6H, m) |
| 1-1-120 | δ = 6.66(1H, s), 7.16(2H, m), 7.35(3H, m), 7.50~7.69(9H, m), 7.80~7.84(2H, m), 7.94(2H, m), 8.08~8.12(3H, m), 8.21(1H, s), 8.46(1H, d), 8.55(2H, m) |
| 1-1-154 | δ = 7.29(1H, d), 7.50~7.53(9H, m), 7.669(1H, t), 7.84(3H, m), 8.08~8.11(2H, m), 8.36(4H, m), 8.46(1H, d) |
| 1-1-180 | δ = 6.66(1H, s), 7.16~7.35(7H, m), 7.50~7.58(5H, m), 7.69~7.94(4H, m), 8.11~8.30(7H, m), 8.46(1H, d), 8.55(2H, m) |
| 1-1-186 | δ = 6.66(2H, s), 7.29(2H, d), 7.69(2H, t), 7.84(2H, t), 8.08~8.11(4H, m), 8.30(4H, s), 8.46(2H, d) |
| 1-1-190 | δ = 6.66(1H, s), 7.29(1H, d), 7.38~7.46(15H, m), 7.65(2H, m), 7.87(2H, m), 8.08~8.11(2H, m), 8.46(1H, d) |
| 1-1-192 | δ = 6.40(2H, s), 7.29(2H, d), 7.69~7.84(4H, m), 8.08~8.12(5H, m), 8.46~8.50(4H, m) |
| 1-1-193 | δ = 6.40(1H, s), 7.29~7.55(15H, m), 7.75(4H, m), 8.08~8.11(2H, m), 8.46(1H, d) |
| 1-1-200 | δ = 1.69(6H, s), 6.40(1H, s), 6.97~7.06(2H, d), 7.28~7.69(11H, m), 7.84~7.90(2H, m), 7.98(1H, d), 8.08~8.19(2H, m), 8.22(1H, s), 8.46(1H, d) |
| 1-1-206 | δ = 6.40(1H, s), 7.16~7.35(4H, m), 7.58~7.94(14H, m), 8.08~8.19(4H, m), 8.30(1H, d), 8.46(1H, d), 8.55(1H, d) |
| 1-1-207 | δ = 7.29(1H, d), 7.41~7.56(9H, m), 7.69(1H, t), 7.84~7.93(9H, m), 8.08~8.11(2H, m), 8.45~8.46(3H, m) |

TABLE 2

| Compound | FD-MS |
|---|---|
| 1-1-1 | m/z = 399.15 (C26H17N5 = 399.46) |
| 1-1-2 | m/z = 448.17 (C31H20N4 = 448.53) |
| 1-1-3 | m/z = 474.18 (C33H22N4 = 474.57) |
| 1-1-4 | m/z = 398.15 (C27H18N4 = 398.47) |
| 1-1-5 | m/z = 487.18 (C33H21N5 = 487.57) |
| 1-1-6 | m/z = 321.13 (C22H15N3 = 321.38) |
| 1-1-7 | m/z = 321.13 (C22H15N3 = 321.38) |
| 1-1-8 | m/z = 396.16 (C29H20N2 = 396.49) |
| 1-1-9 | m/z = 398.15 (C27H18N4 = 398.47) |
| 1-1-10 | m/z = 496.19 (C37H24N2 = 496.61) |
| 1-1-11 | m/z = 470.18 (C35H22N2 = 470.57) |
| 1-1-12 | m/z = 334.12 (C22H14N4 = 334.38) |
| 1-1-13 | m/z = 398.15 (C27H18N4 = 398.47) |
| 1-1-14 | m/z = 484.19 (C36H24N2 = 484.63) |
| 1-1-15 | m/z = 574.22 (C41H26N4 = 574.69) |
| 1-1-16 | m/z = 436.17 (C30H20N4 = 436.52) |
| 1-1-17 | m/z = 436.17 (C30H20N4 = 436.52) |
| 1-1-18 | m/z = 368.11 (C23H17N2OP = 368.38) |
| 1-1-19 | m/z = 344.13 (C25H16N2 = 344.42) |
| 1-1-20 | m/z = 361.12 (C24H15N3O = 361.40) |
| 1-1-21 | m/z = 377.10 (C24H15N3S = 377.47) |
| 1-1-22 | m/z = 295.11 (C20H13N3 = 295.34) |
| 1-1-23 | m/z = 295.11 (C20H13N3 = 295.34) |
| 1-1-24 | m/z = 295.11 (C20H12N4 = 295.33) |
| 1-1-25 | m/z = 295.11 (C20H12N4 = 295.33) |
| 1-1-26 | m/z = 388.13 (C25H16N4O = 388.43) |
| 1-1-27 | m/z = 334.11 (C23H14N2O = 334.38) |
| 1-1-28 | m/z = 350.09 (C23H14N2S = 350.44) |
| 1-1-29 | m/z = 397.16 (C28H19N3 = 397.48) |
| 1-1-30 | m/z = 397.16 (C28H19N3 = 397.48) |
| 1-1-31 | m/z = 420.16 (C31H20N2 = 420.51) |
| 1-1-32 | m/z = 551.21 (C38H25N5 = 551.65) |
| 1-1-33 | m/z = 551.21 (C38H25N5 = 551.65) |
| 1-1-34 | m/z = 497.19 (C36H23N2 = 497.60) |
| 1-1-35 | m/z = 551.21 (C38H25N5 = 551.65) |
| 1-1-36 | m/z = 551.21 (C38H25N5 = 551.65) |
| 1-1-37 | m/z = 398.15 (C27H18N4 = 398.47) |
| 1-1-38 | m/z = 474.18 (C33H22N4 = 474.57) |
| 1-1-39 | m/z = 498.18 (C35H22N4 = 198.59) |
| 1-1-40 | m/z = 552.21 (C37H24N6 = 552.64) |

TABLE 2-continued

| Compound | FD-MS |
|---|---|
| 1-1-41 | m/z = 398.15 (C27H18N4 = 398.47) |
| 1-1-42 | m/z = 498.18 (C35H22N4 = 198.59) |
| 1-1-43 | m/z = 448.17 (C31H20N4 = 448.53) |
| 1-1-44 | m/z = 399.15 (C26H17N5 = 399.46) |
| 1-1-45 | m/z = 499.18 (C34H21N5 = 499.58) |
| 1-1-46 | m/z = 551.21 (C38H25N5 = 551.65) |
| 1-1-47 | m/z = 401.14 (C24H15N7 = 401.43) |
| 1-1-48 | m/z = 401.14 (C24H15N7 = 401.43) |
| 1-1-49 | m/z = 553.20 (C36H23N7 = 553.63) |
| 1-1-50 | m/z = 555.19 (C34H21N9 = 555.61) |
| 1-1-51 | m/z = 555.19 (C34H21N9 = 555.61) |
| 1-1-52 | m/z = 555.19 (C34H21N9 = 555.61) |
| 1-1-53 | m/z = 555.19 (C34H21N9 = 555.61) |
| 1-1-54 | m/z = 487.18 (C33H21N5 = 487.57) |
| 1-1-55 | m/z = 410.15 (C28H18N4 = 410.48) |
| 1-1-56 | m/z = 370.15 (C27H18N2 = 370.45) |
| 1-1-57 | m/z = 370.15 (C27H18N2 = 370.45) |
| 1-1-58 | m/z = 396.19 (C29H20N2 = 396.49) |
| 1-1-59 | m/z = 396.19 (C29H20N2 = 396.49) |
| 1-1-60 | m/z = 397.16 (C28H19N3 = 397.48) |
| 1-1-61 | m/z = 397.16 (C28H19N3 = 397.48) |
| 1-1-62 | m/z = 397.16 (C28H19N3 = 397.48) |
| 1-1-63 | m/z = 427.19 (C35H24N2 = 427.59) |
| 1-1-64 | m/z = 474.18 (C33H22N4 = 474.57) |
| 1-1-65 | m/z = 572.23 (C43H28N2 = 572.72) |
| 1-1-66 | m/z = 546.21 (C41H26N2 = 546.67) |
| 1-1-67 | m/z = 672.26 (C51H32N2 = 672.83) |
| 1-1-68 | m/z = 436.19 (C32H24N2 = 436.56) |
| 1-1-69 | m/z = 560.23 (C42H28N2 = 560.70) |
| 1-1-70 | m/z = 558.21 (C42H26N2 = 558.68) |
| 1-1-71 | m/z = 436.17 (C30H20N4 = 436.52) |
| 1-1-72 | m/z = 360.14 (C24H16N4 = 360.42) |
| 1-1-73 | m/z = 368.11 (C32H17N2OP = 368.38) |
| 1-1-74 | m/z = 520.17 (C35H25N2OP = 250.57) |
| 1-1-75 | m/z = 285.09 (C18H11N3O = 280.31) |
| 1-1-76 | m/z = 301.07 (C18H11N3S = 301.37) |
| 1-1-77 | m/z = 295.11 (C20H13N3 = 295.34) |
| 1-1-78 | m/z = 295.11 (C20H13N3 = 295.34) |
| 1-1-79 | m/z = 296.11 (C19H12N4 = 296.33) |
| 1-1-80 | m/z = 296.11 (C19H12N4 = 296.33) |
| 1-1-81 | m/z = 312.10 (C19H12N4O = 312.33) |
| 1-1-82 | m/z = 334.11 (C23H14N2O = 334.38) |
| 1-1-83 | m/z = 350.09 (C23H14N2S = 350.44) |
| 1-1-84 | m/z = 379.16 (C28H19N3 = 379.48) |
| 1-1-85 | m/z = 379.16 (C28H19N3 = 379.48) |
| 1-1-86 | m/z = 449.19 (C32H23N3 = 449.56) |
| 1-1-87 | m/z = 573.22 (C42H27N3 = 573.70) |
| 1-1-88 | m/z = 439.11 (C29H17N3S = 439.53) |
| 1-1-89 | m/z = 423.14 (C29H17N3O = 423.48) |
| 1-1-90 | m/z = 498.18 (C35H22N4 = 498.59) |
| 1-1-91 | m/z = 505.16 (C34H23N3S = 505.64) |
| 1-1-92 | m/z = 629.19 (C44H27N3S = 629.78) |
| 1-1-93 | m/z = 495.09 (C31H17N3S2 = 495.62) |
| 1-1-94 | m/z = 479.11 (C31H17N3OS = 479.56) |
| 1-1-95 | m/z = 554.16 (C37H22N4S = 554.67) |
| 1-1-96 | m/z = 505.16 (C34H23N3S = 505.64) |
| 1-1-97 | m/z = 629.19 (C44H27N3S = 629.78) |
| 1-1-98 | m/z = 495.09 (C31H17N3S2 = 495.62) |
| 1-1-99 | m/z = 497.11 (C31H147N3OS = 497.56) |
| 1-1-100 | m/z = 554.16 (C37H22N4S = 554.67) |
| 1-1-101 | m/z = 573.22 (C42H27N3 = 573.70) |
| 1-1-102 | m/z = 627.24 (C44H29N5 = 627.75) |
| 1-1-103 | m/z = 627.24 (C44H29N5 = 627.75) |
| 1-1-104 | m/z = 573.22 (C43H27N3 = 573.70) |
| 1-1-105 | m/z = 627.24 (C44H29N5 = 627.75) |
| 1-1-106 | m/z = 474.18 (C33H22N4 = 474.57) |
| 1-1-107 | m/z = 574.22 (C41H26N4 = 574.69) |
| 1-1-108 | m/z = 524.20 (C37H24N4 = 524.63) |
| 1-1-109 | m/z = 475.18 (C32H21N5 = 475.55) |
| 1-1-110 | m/z = 575.21 (C40H25N5 = 575.67) |
| 1-1-111 | m/z = 631.22 (C40H25N9 = 631.70) |
| 1-1-112 | m/z = 631.22 (C40H25N9 = 631.70) |
| 1-1-113 | m/z = 631.22 (C40H25N9 = 631.70) |
| 1-1-114 | m/z = 563.21 (C39H25N5 = 563.66) |
| 1-1-115 | m/z = 486.18 (C34H22N4 = 486.58) |
| 1-1-116 | m/z = 525.22 (C38H27N3 = 525.65) |
| 1-1-117 | m/z = 649.25 (C48H31N3 = 649.80) |
| 1-1-118 | m/z = 515.15 (C35H21N3S = 515.63) |

TABLE 2-continued

| Compound | FD-MS |
|---|---|
| 1-1-119 | m/z = 499.17 (C35H21N3O = 499.57) |
| 1-1-120 | m/z = 574.22 (C41H26N4 = 574.69) |
| 1-1-121 | m/z = 581.19 (C40H27N3S = 581.74) |
| 1-1-122 | m/z = 705.22 (C50H31N3S = 705.88) |
| 1-1-123 | m/z = 571.12 (C37H21N3S2 = 571.72) |
| 1-1-124 | m/z = 555.14 (C37H21N3OS = 555.65) |
| 1-1-125 | m/z = 630.19 (C43H26N4S = 630.77) |
| 1-1-126 | m/z = 581.19 (C40H27N3S = 581.74) |
| 1-1-127 | m/z = 705.22 (C50H31N3S = 705.88) |
| 1-1-128 | m/z = 571.12 (C37H21N3S2 = 571.72) |
| 1-1-129 | m/z = 555.14 (C37H21N3OS = 555.65) |
| 1-1-130 | m/z = 630.19 (C43H26N4S = 630.77) |
| 1-1-131 | m/z = 470.18 (C35H22N2 = 470.57) |
| 1-1-132 | m/z = 596.23 (C45H28N2 = 596.73) |
| 1-1-133 | m/z = 360.16 (C26H20N0 = 360.46) |
| 1-1-134 | m/z = 484.19 (C36H24N2 = 484.60) |
| 1-1-135 | m/z = 482.18 (C36H22N2 = 482.59) |
| 1-1-136 | m/z = 436.17 (C30H20N4 = 436.52) |
| 1-1-137 | m/z = 360.14 (C24H16N4 = 360.42) |
| 1-1-138 | m/z = 368.11 (C23H17N2OP = 368.38) |
| 1-1-139 | m/z = 444.14 (C29H21N2OP = 444.47) |
| 1-1-140 | m/z = 361.12 (C24H15N3O = 361.40) |
| 1-1-141 | m/z = 524.20 (C37H24N4 = 524.63) |
| 1-1-142 | m/z = 550.22 (C39H26N4 = 550.66) |
| 1-1-143 | m/z = 474.18 (C33H22N4 = 474.57) |
| 1-1-144 | m/z = 563.21 (C39H25N5 = 563.66) |
| 1-1-145 | m/z = 371.14 (C26H17N3 = 371.44) |
| 1-1-146 | m/z = 410.15 (C28H18N4 = 410.48) |
| 1-1-147 | m/z = 512.20 (C36H24N4 = 512.62) |
| 1-1-148 | m/z = 474.18 (C33H22N4 = 474.57) |
| 1-1-149 | m/z = 444.14 (C29H21N2OP = 444.47) |
| 1-1-150 | m/z = 512.20 (C36H24N4 = 512.62) |
| 1-1-151 | m/z = 650.25 (C47H30N4 = 650.78) |
| 1-1-152 | m/z = 420.16 (C31H20N2 = 420.51) |
| 1-1-153 | m/z = 496.19 (C37H24N2 = 496.61) |
| 1-1-154 | m/z = 475.18 (C32H21N5 = 475.55) |
| 1-1-155 | m/z = 470.18 (C35H22N2 = 470.57) |
| 1-1-156 | m/z = 468.18 (C34H22N4 = 468.58) |
| 1-1-157 | m/z = 486.18 (C34H22N4 = 486.58) |
| 1-1-158 | m/z = 481.12 (C29H15N3F4 = 481.45) |
| 1-1-159 | m/z = 369.11 (C23H13N3F2 = 369.37) |
| 1-1-160 | m/z = 497.28 (C35H35N3 = 497.69) |
| 1-1-161 | m/z = 486.18 (C34H22N4 = 486.58) |
| 1-1-162 | m/z = 481.12 (C29H15N3F4 = 481.45) |
| 1-1-163 | m/z = 369.11 (C23H13N3F2 = 369.37) |
| 1-1-164 | m/z = 497.28 (C35H35N3 = 497.69) |
| 1-1-165 | m/z = 574.22 (C41H26N4 = 574.69) |
| 1-1-166 | m/z = 409.16 (C29H19N3 = 409.49) |
| 1-1-167 | m/z = 485.19 (C35H23N3 = 485.59) |
| 1-1-168 | m/z = 410.15 (C28H18N4 = 410.48) |
| 1-1-169 | m/z = 487.18 (C33H21N5 = 487.57) |
| 1-1-170 | m/z = 487.18 (C33H21N5 = 487.57) |
| 1-1-171 | m/z = 562.22 (C40H26N4 = 562.68) |
| 1-1-172 | m/z = 562.22 (C40H26N4 = 562.68) |
| 1-1-173 | m/z = 557.15 (C35H19N3F4 = 557.55) |
| 1-1-174 | m/z = 445.14 (C29H17N3F2 = 445.47) |
| 1-1-175 | m/z = 573.31 (C41H39N3 = 574.78) |
| 1-1-176 | m/z = 562.22 (C40H26N4 = 562.68) |
| 1-1-177 | m/z = 557.15 (C35H19N3F4 = 557.55) |
| 1-1-178 | m/z = 445.14 (C29H17N3F2 = 445.47) |
| 1-1-179 | m/z = 573.31 (C41H39N3 = 573.78) |
| 1-1-180 | m/z = 650.25 (C47H30N4 = 650.78) |
| 1-1-181 | m/z = 485.19 (C35H23N3 = 485.59) |
| 1-1-182 | m/z = 561.22 (C41H27N3 = 561.69) |
| 1-1-183 | m/z = 485.19 (C35H23N3 = 485.59) |
| 1-1-184 | m/z = 563.21 (C39H25N5 = 563.66) |
| 1-1-185 | m/z = 563.21 (C39H25N5 = 563.66) |
| 1-1-186 | m/z = 334.12 (C22H14N4 = 334.38) |
| 1-1-187 | m/z = 410.15 (C28H18N4 = 410.48) |
| 1-1-188 | m/z = 410.15 (C28H18N4 = 410.48) |
| 1-1-189 | m/z = 486.18 (C34H22N4 = 486.58) |
| 1-1-190 | m/z = 502.19 (C35H26N2Si = 502.69) |
| 1-1-191 | m/z = 411.15 (C27H17N5 = 411.47) |
| 1-1-192 | m/z = 411.15 (C27H17N5 = 411.47) |
| 1-1-193 | m/z = 487.20 (C35H25N3 = 487.61) |
| 1-1-194 | m/z = 527.24 (C38H29N3 = 527.67) |
| 1-1-195 | m/z = 517.16 (C35H23N3S = 517.65) |
| 1-1-196 | m/z = 444.46 (C29H21N2OP = 444.14) |

TABLE 2-continued

| Compound | FD-MS |
|---|---|
| 1-1-197 | m/z = 547.12 (C35H21N3S2 = 547.69) |
| 1-1-198 | m/z = 531.14 (C35H21N3SO = 531.63) |
| 1-1-199 | m/z = 515.16 (C35H21N3O2 = 515.57) |
| 1-1-200 | m/z = 541.22 (C38H27N3O = 541.65) |
| 1-1-201 | m/z = 541.22 (C38H27N3O = 541.65) |
| 1-1-202 | m/z = 527.24 (C38H29N3 = 527.67) |
| 1-1-203 | m/z = 679.21 (C48H29N3S = 679.84) |
| 1-1-204 | m/z = 663.23 (C48H29N3O = 663.78) |
| 1-1-205 | m/z = 383.12 (C25H13N5 = 383.41) |
| 1-1-206 | m/z = 574.22 (C41H26N4 = 574.69) |
| 1-1-207 | m/z = 623.15 (C41H25N3S2 = 623.79) |
| 1-1-208 | m/z = 607.17 (C41H25N3SO = 607.73) |
| 1-1-209 | m/z = 591.19 (C41H25N3O2 = 591.67) |
| 1-1-210 | m/z = 617.25 (C44H31N3O = 617.75) |
| 1-1-211 | m/z = 617.25 (C44H31N3O = 617.75) |
| 1-1-212 | m/z = 603.27 (C44H33N3 = 603.77) |
| 1-1-213 | m/z = 739.26 (C54H33N3O = 739.88) |
| 1-1-214 | m/z = 755.24 (C54H33N3S = 755.94) |
| 1-1-215 | m/z = 459.15 (C31H17N5 = 459.51) |
| 1-1-216 | m/z = 650.25 (C47H30N4 = 650.78) |

<Preparation Example 23> Preparation of Compound 2-1-18

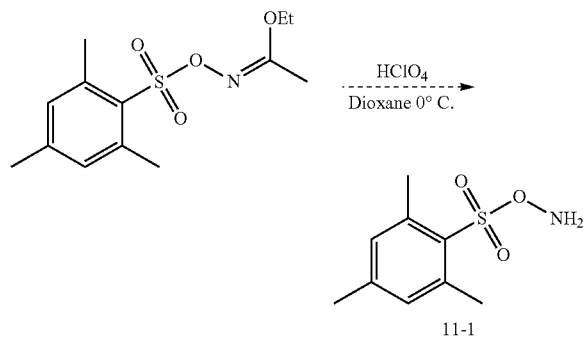

Preparation of Compound 11-1

Ethyl-o-sulfonylacetohydroxyamine (13.26 g, 46.47 mmol) was dissolved in 12 mL of 1,4-dioxane in a one-neck round bottom flask, and the temperature was maintained at 0° C. Perchloric acid (70%, 5.40 mL) was slowly added dropwise thereto for 2 minutes while maintaining the temperature, and the resulting mixture was stirred for 5 minutes. The mixed solution, in which the reaction was terminated, was extracted with H₂O/ether and dried over MgSO₄, and then filtered. Solid Compound 11-1 (9.33 g, 93%) was obtained by performing distillation under reduced pressure.

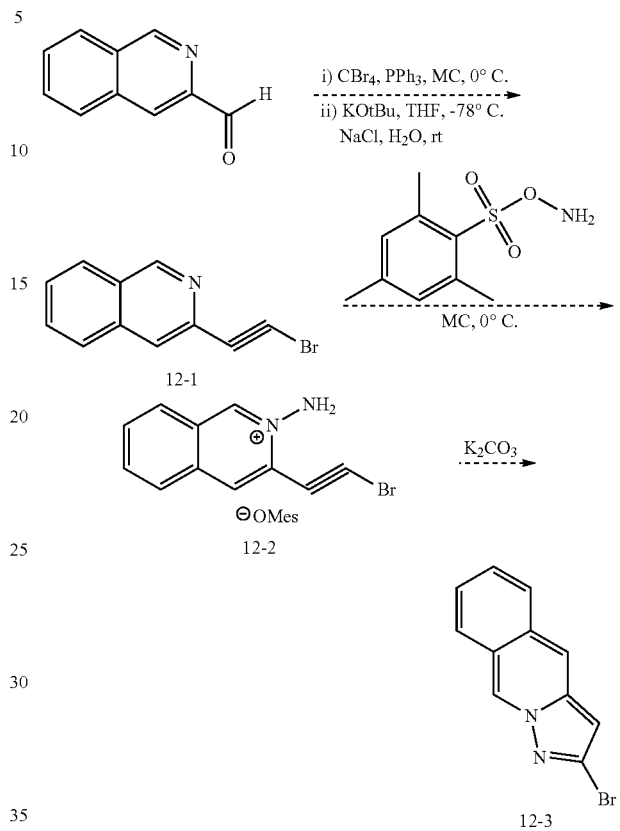

Preparation of Compound 12-1

Tetrabromomethane (42.2 g, 127.25 mol) and triphenylphosphine (68.4 g, 260.88 mol) were completely dissolved in 500 mL of methylene chloride under nitrogen in a two-neck round bottom flask, and then the resulting solution was stirred for 30 minutes while maintaining the temperature at 0° C. Thereafter, isoquinoline-3-carbaldehyde (10 g, 63.63 mmol) was slowly added dropwise thereto for 10 minutes, and then the resulting mixture was stirred for 1 hour while maintaining the temperature at 0° C. After the reaction was terminated, the reaction mixture was extracted with methylene chloride/H₂O and dried over magnesium sulfate, and then filtered. A solid was produced by concentrating the mixture and then using hexane, and filtered to produce a resulting solid (19.5 g, 62.3 mmol, 98%), and the resulting solid was completely dissolved in 200 mL of tetrahydrofuran, and then KOtBu (118 g, 1.06 mol) was slowly added thereto while maintaining the temperature at −78° C. Thereafter, 100 ML of brine was added thereto, the resulting mixture was cooled to room temperature, the reaction was terminated, and then the reaction mixture was extracted with ethyl ether/H₂O and dried over MgSO₄, and then filtered. After the mixture was concentrated, hexane was used to produce a solid, and the solid was filtered to obtain ivory-colored solid Compound 12-1 (14.3 g, 99%).

Preparation of Compound 12-2

11-1 (10 g, 46.45 mmol) was completely dissolved in 50 mL of methylene chloride in a one-neck round bottom flask, and then the temperature was maintained at 0° C., 12-1 (9.70 g, 41.81 mmol) was completely dissolved in 50 mL of methylene chloride, and the resulting solution was slowly added dropwise thereto. After the mixture was stirred for about 10 minutes, 300 mL of ethyl ether was added thereto, and the resulting mixture was stirred for 30 minutes. A white solid was produced and filtered, and then recrystallization was performed with ethyl acetate/methanol to obtain white solid Compound 12-2 (16.4 g, 92%).

Preparation of Compound 12-3

6 g of K₂CO₃ was put into a one-neck round bottom flask, and 12-2 (10 g, 26.09 mmol) dissolved in 10 mL of dimethylformamide was slowly added dropwise thereto. The mixture was stirred at room temperature for about 6 hours, and then the reaction mixture was extracted with methylene chloride/H₂O and dried over magnesium sulfate, and then filtered. The product was concentrated, and then separated by column chromatography (SiO₂, methylene chloride) to obtain white solid Compound 12-3 (6.1 g, 95%).

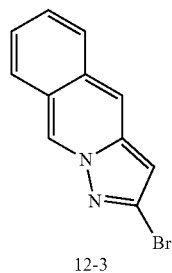

Preparation of Compound 2-1-18

Compound 12-3 (10 g, 40.47 mmol) was dissolved in anhydrous tetrahydrofuran (THF) (50 ml) under nitrogen in a one-neck round bottom flask, and then the resulting solution was cooled to −78° C. n-butyllithium (2.5 M in hexane) (21 ml, 52.61 mmol) was slowly added dropwise thereto, and then the resulting mixture was stirred for 1 hour. Chlorodiphenylphosphine (11.61 ml, 52.61 mol) was added dropwise to the solution, and the resulting solution was stirred at room temperature for 12 hours. The reaction mixture was extracted with methylene chloride/H₂O, and then distilled under reduced pressure. The reaction mixture was dissolved in methylene chloride (250 ml), and then the resulting solution was stirred along with 20 ml of a 30% H₂O₂ aqueous solution at room temperature for 12 hours. The reaction mixture was extracted with methylene chloride/H₂O, and then the concentrated mixture was separated by column chromatography (SiO₂, methylene chloride:methanol=25:1) to obtain yellow solid Compound 2-1-18 (5.52 g, 37%).

<Preparation Example 24> Preparation of Compound 2-1-86

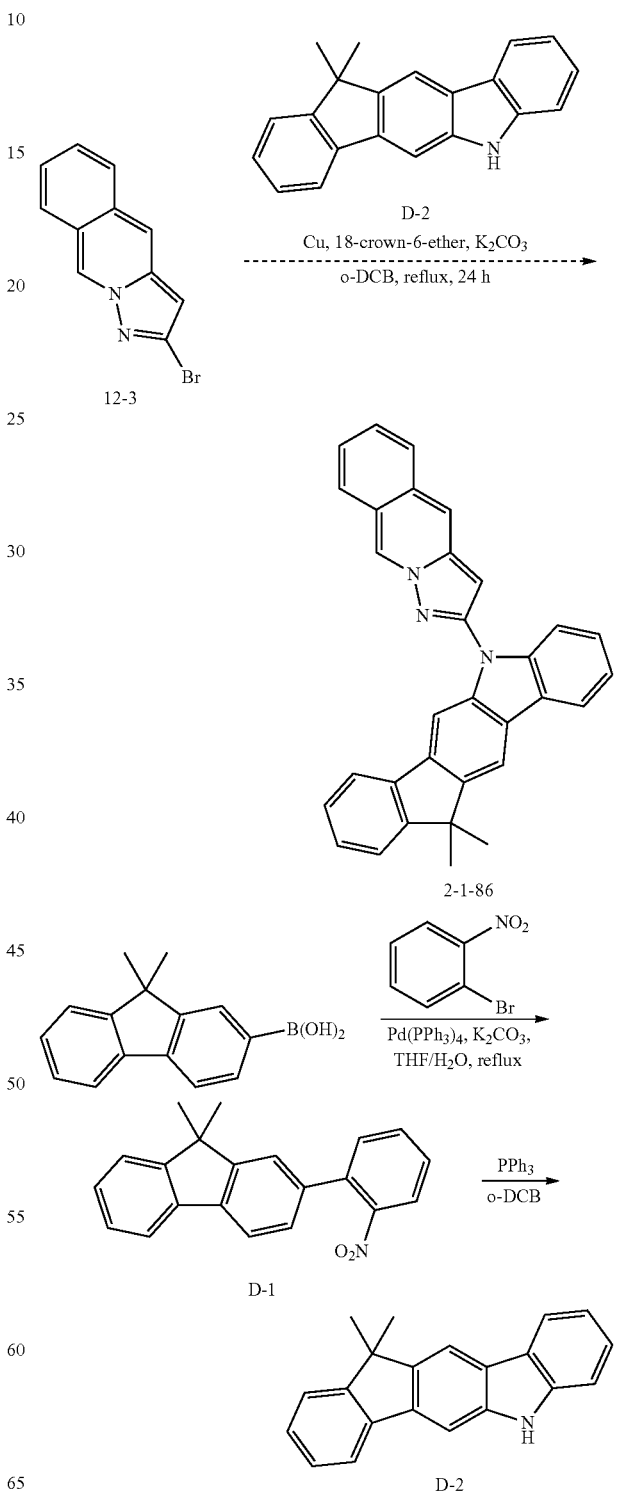

Preparation of Compound D-1

A mixture of (9,9-dimethyl-9H-fluoren-2-yl)boronic acid (25.9 g, 0.108 mol), 1-bromo-2-nitrobenzene (20 g, 0.099 mol), tetra(triphenylphosphine) palladium (5.7 g, 4.95 mmol), potassium carbonate (27.3 g, 0.198 mol), and tetrahydrofuran (250 ml)/H$_2$O (50 ml) was refluxed and stirred for 24 hours in a one-neck round bottom flask. The aqueous layer was removed, and then the organic layer was dried over MgSO$_4$. The organic layer was concentrated, and then separated by column chromatography (SiO$_2$, hexane:methylene chloride=2:1) to obtain yellow solid Compound D-1 (21 g, 61%).

Preparation of Compound D-2

A mixture of D-1 (20 g, 0.0634 mmol), triphenylphosphine (49.8 g, 0.190 mol), and ortho-dichlorobenzene (300 ml) was refluxed and stirred under nitrogen for 18 hours in a one-neck round bottom flask. o-DCB was distilled under reduced pressure and removed, and then separated by column chromatography (SiO$_2$, hexane:methylene chloride=3:1) to obtain white solid Compound D-2 (6.6 g, 36%).

Preparation of Compound 2-1-86

A mixture of 12-3 (6.0 g, 24.28 mmol), D-2 (6.19 g, 21.85 mmol), Cu (0.15 g, 2.43 mmol), 18-crown-6-ether (0.64 g, 2.43 mmol), potassium carbonate (10.1 g, 72.84 mmol), and ortho-dichlorobenzene (80 ml) was refluxed and stirred under nitrogen for 24 hours in a one-neck round bottom flask. Ortho-dichlorobenzene was distilled under reduced pressure and removed, and then separated by column chromatography (SiO$_2$, hexane:methylene chloride=4:1) to obtain white solid Compound 2-1-86 (6.4 g, 64%).

<Preparation Example 25> Preparation of Compound 2-1-37

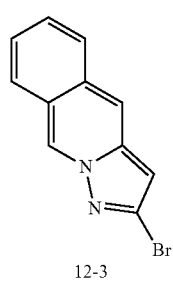
12-3

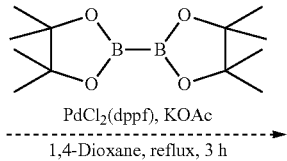
PdCl$_2$(dppf), KOAc
1,4-Dioxane, reflux, 3 h

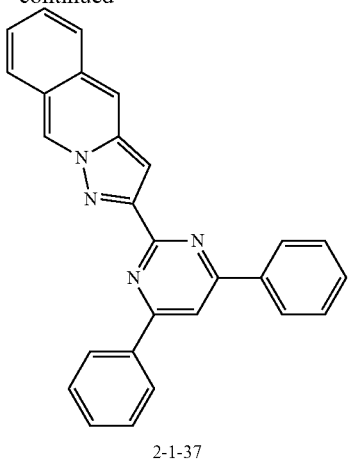
2-1-37

Preparation of Compound 13-1

A mixed solution of Compound 12-3 (6.0 g, 24.28 mmol), bis(pinacolato) diboron (7.4 g, 29.14 mmol), potassium acetate (4.77 g, 48.56 mmol), PdCl$_2$(dppf) (0.8 g, 1.21 mmol), and 1,4-dioxane (120 ml) was refluxed and stirred under nitrogen for 3 hours in a two-neck round bottom flask. The reaction mixture cooled to room temperature was extracted with methylene chloride/H$_2$O and dried over magnesium sulfate, and then filtered. After the mixture was concentrated, hexane was used to produce a solid, and the solid was filtered to obtain ivory-colored solid Compound 13-1 (6.2 g, 88%).

Preparation of Compound 2-1-37

A mixed solution of Compound 13-1 (6.0 g, 20.40 mmol), 2-bromo-4,6-diphenylpyrimidine (6.98 g, 22.44 mmol), potassium carbonate (5.64 g, 40.8 mmol), tetra(triphenylphosphine) palladium (1.18 g, 1.02 mmol), and toluene/ethanol (EtOH)/H$_2$O (60 ml/12 ml/12 ml) was refluxed and stirred under nitrogen for 12 hours in a two-neck round bottom flask. The solvent was filtered from the reaction mixture, and the solid was washed sequentially with 100 ml of toluene, 150 ml of hexane, and 150 ml of methanol to obtain white solid Compound 2-1-37 (7.1 g, 88%).

<Preparation Example 26> Preparation of Compound 2-1-63

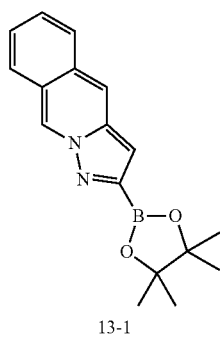
13-1

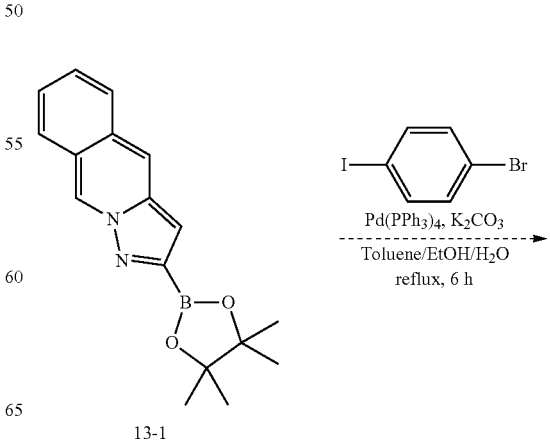

175
-continued

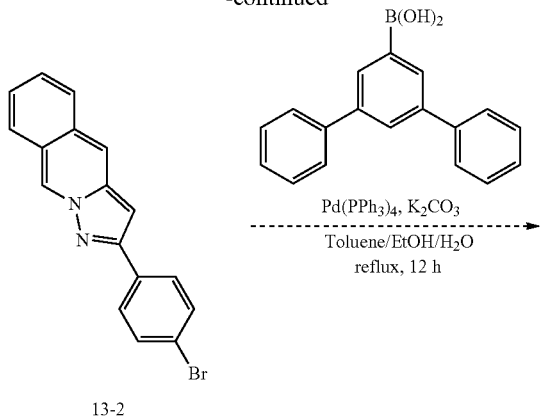

13-2

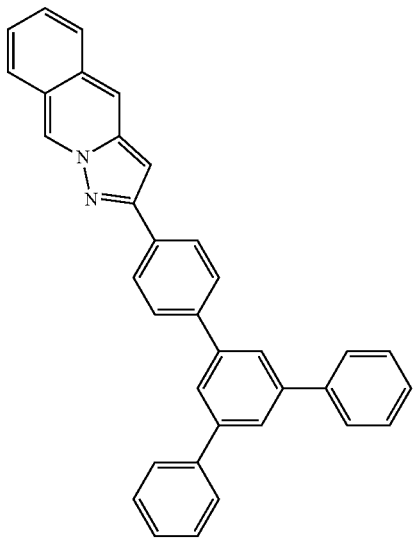

2-1-63

Preparation of Compound 13-2

A mixed solution of Compound 13-1 (6.0 g, 20.40 mmol), 1-iodo-4-bromobenzene (6.35 g, 22.44 mmol), potassium carbonate (5.64 g, 40.8 mmol), tetra(triphenylphosphine) palladium (Pd(PPh$_3$)$_4$) (1.18 g, 1.02 mmol), and toluene/ethanol/H$_2$O (60 ml/12 ml/12 ml) was refluxed and stirred for 6 hours in a one-neck round bottom flask. The solvent was filtered from the reaction mixture, and the solid was washed sequentially with 100 ml of toluene, 150 ml of hexane, and 150 ml of methanol to obtain white solid Compound 13-2 (3.6 g, 55%).

176

Preparation of Compound 2-1-63

A mixed solution of Compound 13-2 (4.0 g, 12.38 mmol), [1,1';3',1"-terphenyl]-5'-ylboronic acid (3.73 g, 13.61 mmol), potassium carbonate (3.42 g, 24.76 mmol), tetra(triphenylphosphine) palladium (0.72 g, 0.62 mmol), and toluene/ethanol/H$_2$O (40 ml/8 ml/8 ml) was refluxed and stirred under nitrogen for 12 hours in a two-neck round bottom flask. The solvent was filtered from the reaction mixture, and the solid was washed sequentially with 50 ml of toluene, 80 ml of hexane, and 80 ml of methanol to obtain white solid Compound 2-1-63 (4.5 g, 77%).

Compound 13-2 has a form in which bromophenyl is substituted at the R1 position in the core structure of Formula 3. In Preparation Example 26, bromine (Br) of Compound 13-2 was substituted with terphenyl to prepare Compound 2-1-63.

For example, the person skilled in the art may modify Preparation Example 26 to introduce another substituent instead of terphenyl. When Compound 13-2 is used instead of Compound 12-3 in the preparation of Compound 2-1-18, it is possible to obtain a structure into which a diphenyl phosphoryl-substituted phenyl is introduced (Compound 2-1-196).

That is, it is possible to prepare a compound including a phosphine-based substituent which has an arylene linking group in the core structure of Formula 3. For example, Compounds 2-1-74 and 2-1-139 are compounds including a phosphine-based substituent which has an arylene linking group.

Further, a substituent such as terphenyl may be directly introduced into the core structure of Formula 3 by using Compound 12-3 of Preparation Example 23 instead of Compound 13-2 of Preparation Example 26.

<Preparation Example 27> Preparation of Compound 2-1-180

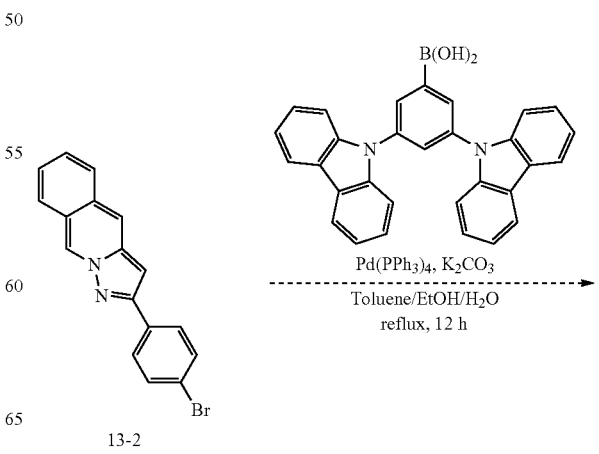

13-2

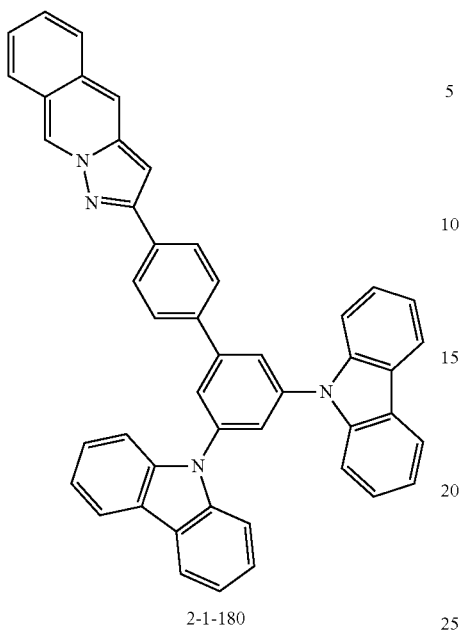

2-1-180

A mixed solution of Compound 13-2 (5.0 g, 15.47 mmol), (3,5-di(9H-carbazol-9-yl)phenyl)boronic acid (7.7 g, 17.02 mmol), $K_2CO_3$ (4.28 g, 30.94 mmol), tetra(triphenylphosphine) palladium (0.89 g, 0.77 mmol), and toluene/ethanol/$H_2O$ (100 ml/20 ml/20 ml) was refluxed and stirred under nitrogen for 12 hours in a two-neck round bottom flask. The reaction mixture cooled to room temperature was extracted with methylene chloride/$H_2O$ and dried over magnesium sulfate, and then filtered. The resulting product was concentrated, and then separated by column chromatography ($SiO_2$, hexane:methylene chloride=2:1) to obtain white solid Compound 2-1-180 (7.85 g, 78%).

<Preparation Example 28> Preparation of Compound 2-1-109

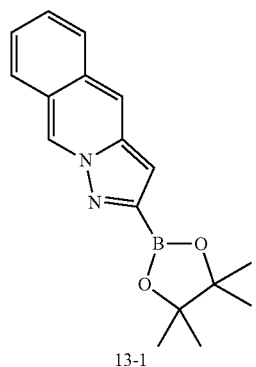

13-1

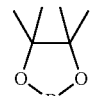

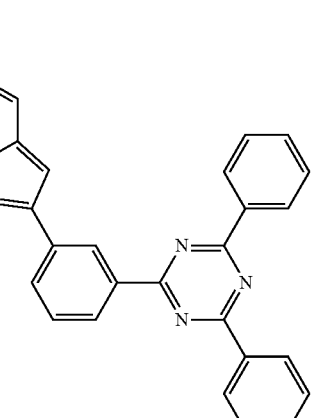

14-1

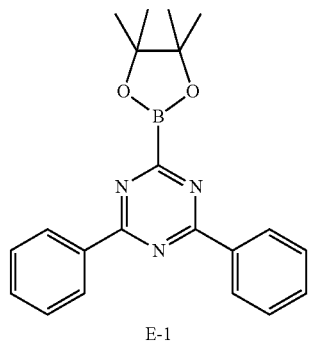

2-1-109

Preparation of Compound E-1

A mixed solution of 2-bromo-4,6-diphenyl-1,3,5-triazine (10.0 g, 32.03 mmol), bis(pinacolato) diboron (9.76 g, 38.44 mol), potassium acetate (6.29 g, 64.06 mmol), $PdCl_2$dppf (dppf: 1,1'-bis(diphenylphosphino)ferrocene) (1.17 g, 1.60 mmol), and 1,4-dioxane was refluxed and stirred under nitrogen for 3 hours in a two-neck round bottom flask. The reaction mixture cooled to room temperature was extracted with methylene chloride/H₂O and dried over magnesium sulfate, and then filtered. After the mixture was concentrated, hexane was used to produce a solid, and the solid was filtered to obtain ivory-colored solid Compound E-1 (19.67 g, 83%).

Preparation of Compound 14-1

A mixed solution of Compound 13-1 (8.0 g, 27.20 mmol), 1-iodo-3-bromobenzene (8.46 g, 29.92 mmol), potassium carbonate (7.52 g, 54.5 mmol), Pd(PPh₃)₄ (1.57 g, 1.36 mmol), and toluene/ethanol/H₂O (80 ml/16 ml/16 ml) was refluxed and stirred for 6 hours in a one-neck round bottom flask. The solvent was filtered from the reaction mixture, and the solid was washed sequentially with 100 ml of toluene, 150 ml of hexane, and 150 ml of methanol to obtain white solid Compound 14-1 (6.1 g, 69%).

Preparation of Compound 2-1-109

A mixed solution of Compound 14-1 (5.0 g, 15.47 mmol), 2,4-diphenyl-6-(4,4,5,5-tetramethyl-1,3,2-dioxaborolan-2-yl)-1,3,5-triazine (6.67 g, 18.56 mmol), potassium carbonate (4.28 g, 30.94 mol), tetra(triphenylphosphine) palladium (0.89 g, 0.77 mol), and toluene/ethanol/H₂O (100 ml/20 ml/20 ml) was refluxed and stirred under nitrogen for 12 hours in a two-neck round bottom flask. The reaction mixture cooled to room temperature was extracted with methylene chloride/H₂O and dried over magnesium sulfate, and then filtered. The resulting product was concentrated, and then separated by column chromatography (SiO₂, hexane:methylene chloride=4:1) to obtain white solid Compound 2-1-109 (6.0 g, 82%).

Compound 2-1-120m

<Preparation Example 29> Preparation of

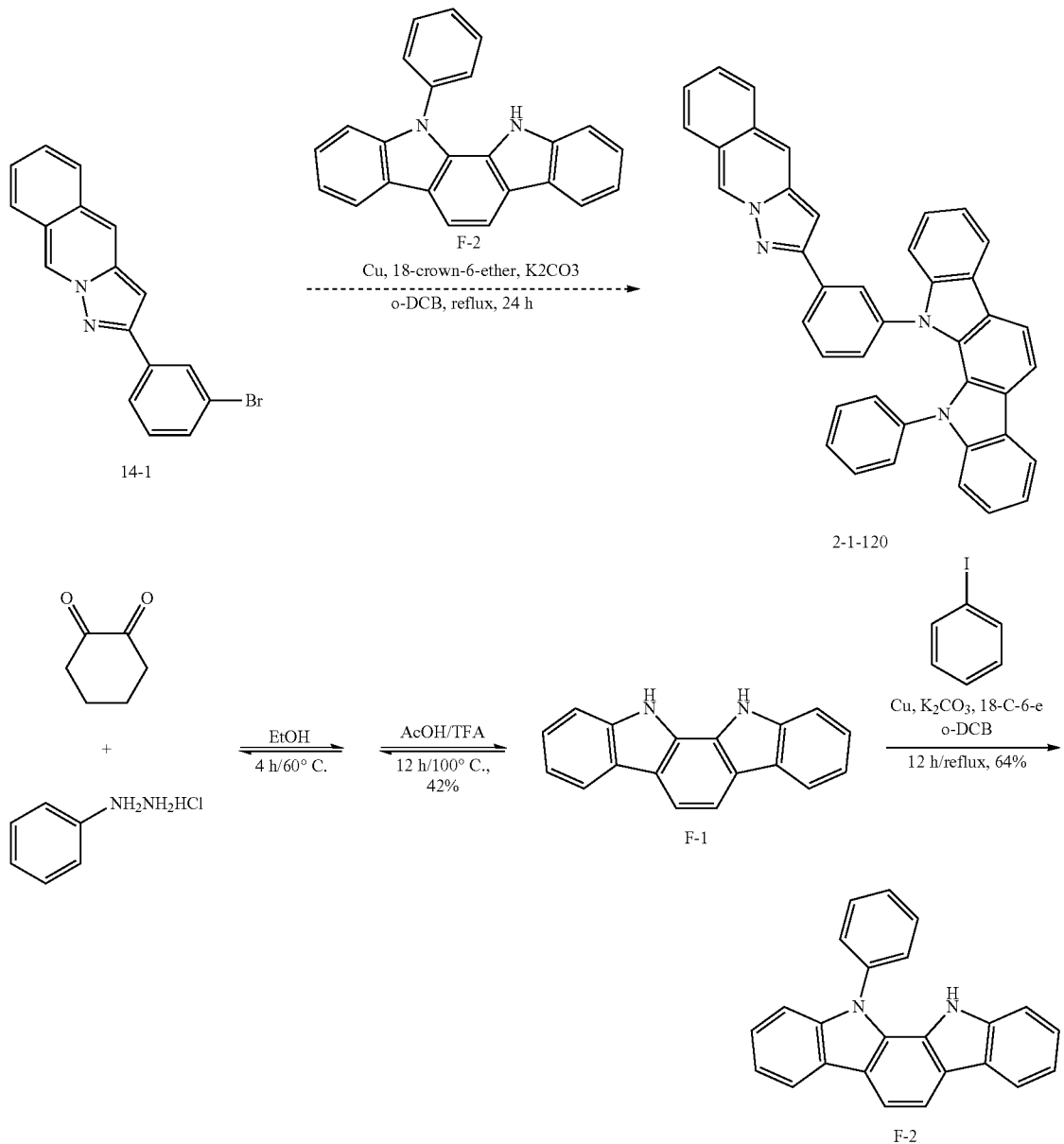

Preparation of Compound F-1

Sulfuric acid (1.4 mL, 0.0374 mol) was slowly added dropwise to a mixture of 1,2-dicyclohexanone (30.0 g, 0.374 mol), phenylhydrazine hydrochloride (77.37 g, 0.749 mol), and ethanol (1,000 ml) under nitrogen in a one-neck round bottom flask, and then the resulting mixture was stirred at 60° C. for 4 hours. The solution cooled to room temperature was filtered to obtain a yellow brown solid (69 g, 93%). Trifluoroacetic acid (46.5 mL, 0.6 mol) was put into a mixture of the solid (68.9 g, 0.25 mol) and acetic acid (700 ml) in a one-neck round bottom flask, and the resulting mixture was stirred at 100° C. for 12 hours. The solution cooled to room temperature was washed with acetic acid and hexane and filtered to obtain ivory-colored solid F-1 (27.3 g, 42%).

Preparation of Compound F-2

A mixture of F-1 (2.1 g, 0.0082 mol), iodobenzene (2.5 g, 0.013 mol), Cu (0.312 g, 0.0049), 18-crown-6-ether (0,433 g, 0.0016 mol), potassium carbonate (3.397 g, 0.0246 mol), and ortho-dichlorobenzene (20 ml) was refluxed and stirred under nitrogen for 12 hours in a two-neck round bottom flask. The solution cooled to room temperature was extracted with methylene chloride/H$_2$O and concentrated, and separated by column chromatography (SiO$_2$, hexane:ethyl acetate=10:1) to obtain white solid Compound F-2 (1.76 g, 64%).

Preparation of Compound 2-1-120

A mixture of 14-1 (6.0 g, 24.28 mmol), F-2 (9.69 g, 29.14 mmol), Cu (0.15 g, 2.43 mmol), 18-crown-6-ether (0.64 g, 2.43 mmol), potassium carbonate (6.71 g, 48.56 mmol), and ortho-dichlorobenzene (60 ml) was refluxed and stirred under nitrogen for 24 hours in a one-neck round bottom flask. Ortho-dichlorobenzene was distilled under reduced pressure and removed, and then separated by column chromatography (SiO$_2$, hexane:methylene chloride=3:1) to obtain white solid Compound 2-1-120 (6.7 g, 48%).

<Preparation Example 30> Preparation of Compound 2-1-154

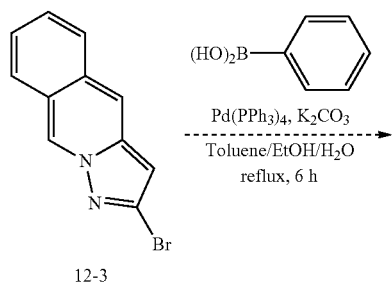

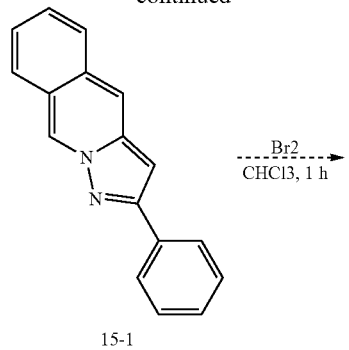

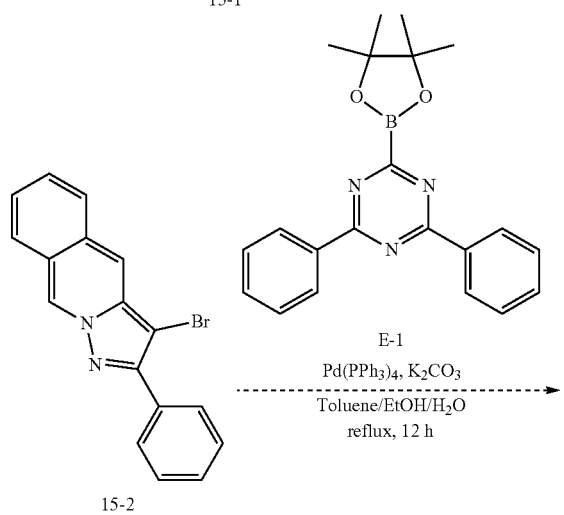

Preparation of Compound 15-1

A mixed solution of Compound 12-3 (6.0 g, 24.28 mmol), phenyl boronic acid (3.55 g, 29.14 mmol), potassium carbonate (6.71 g, 48.56 mmol), tetra(triphenylphosphine) palladium (1.40 g, 1.21 mmol), and toluene/ethanol/H$_2$O (60 ml/12 ml/12 ml) was refluxed and stirred for 6 hours in a one-neck round bottom flask. The solvent was filtered from the reaction mixture, and the solid was washed sequentially with 50 ml of toluene, 80 ml of hexane, and 80 ml of methanol to obtain white solid Compound 15-1 (5.8 g, 98%).

Preparation of Compound 15-2

100 mL of CHCl$_3$ and br$_2$ (2.1 mL, 40.94 mmol) were put into a one-neck round bottom flask, the resulting mixture was stirred for 10 minutes, and then the temperature was maintained at 0° C. Compound 15-1 (5 g, 20.47 mmol) dissolved in 50 mL of chloroform was slowly added dropwise thereto. The reaction was terminated after about 1 hour, and the product was extracted with methylene chloride/H$_2$O and concentrated, and then washed with a small amount of EA and hexane to obtain solid Compound 15-2 (6.4 g, 97%).

Preparation of Compound 2-1-154

A mixed solution of Compound 15-2 (6.0 g, 18.56 mmol), 2,4-diphenyl-6-(4,4,5,5-tetramethyl-1,3,2-dioxaborolan-2-yl)-1,3,5-triazine (8.0 g, 22.28 mmol), potassium carbonate (5.13 g, 37.12 mmol), tetra(triphenylphosphine) palladium (1.07 g, 0.93 mmol), and toluene/EtOH/H$_2$O (60 ml/12 ml/12 ml) was refluxed and stirred for 12 hours in a one-neck round bottom flask. The solution cooled to room temperature was extracted with methylene chloride/H$_2$O and concentrated, and separated by column chromatography (SiO$_2$, hexane:methylene chloride=3:1) to obtain white solid Compound 2-1-154 (7.76 g, 88%).

<Preparation Example 31> Preparation of Compound 2-1-186

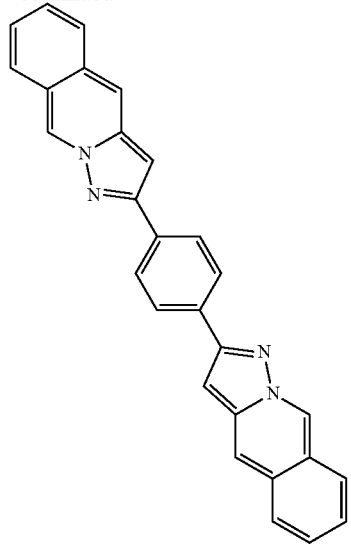

2-1-186

A mixed solution of Compound 13-1 (6.0 g, 20.4 mmol), 13-2 (7.9 g, 24.48 mmol), potassium carbonate (8.46 g, 61.2 mmol), tetra(triphenylphosphine) palladium (1.18 g, 1.02 mmol), and toluene/ethanol/H$_2$O (60 ml/12 ml/12 ml) was refluxed and stirred for 12 hours in a one-neck round bottom flask. The solution cooled to room temperature was extracted with methylene chloride/H$_2$O and concentrated, and separated by column chromatography (SiO$_2$, hexane:methylene chloride=4:1) to obtain white solid Compound 2-1-186 (5.49 g, 72%).

<Preparation Example 32> Preparation of Compound 2-1-190

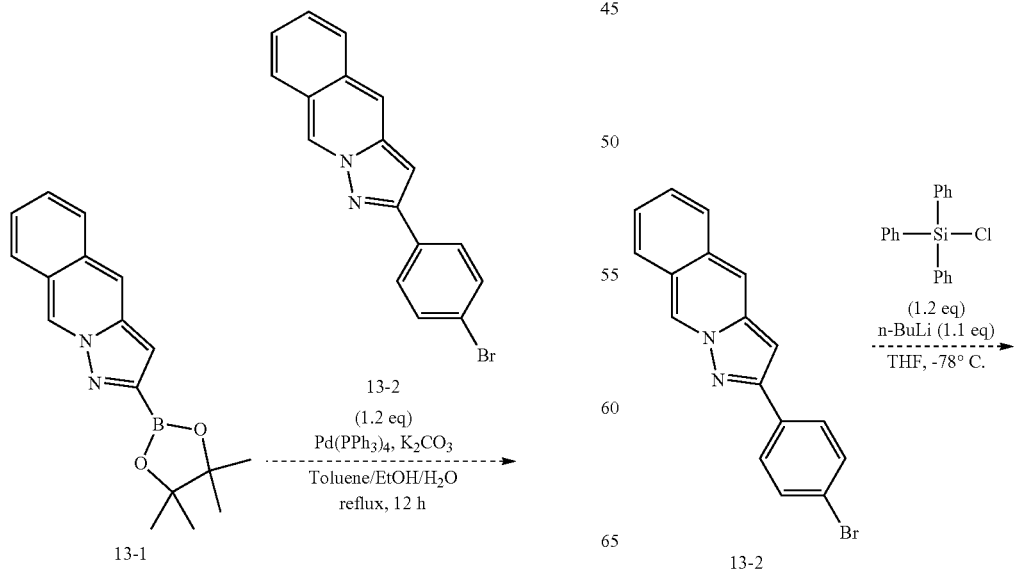

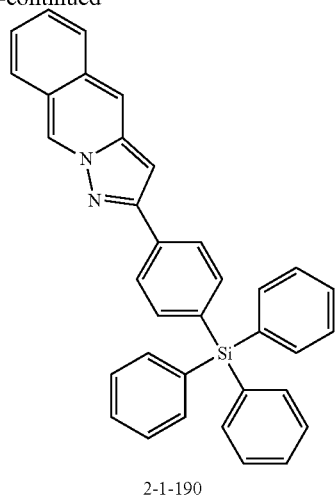

2-1-190

Compound 13-2 (10 g, 30.94 mmol) was completely dissolved in 200 mL of tetrahydrofuran in a one-neck round bottom flask, and then n-butyllithium (6.6 mL, 32.04 mmol) was slowly added dropwise thereto while maintaining the temperature at −78° C. The resulting mixture was stirred for about 30 minutes, and then chlorotriphenylsilane (10.03 g, 34.03 mmol) was slowly added dropwise thereto, the reaction was terminated after about 1 hour, and the product was extracted with methylene chloride/$H_2O$ and concentrated, and separated by column chromatography ($SiO_2$, hexane:methylene chloride 4:1) to obtain white solid Compound 2-1-190 (5.76 g, 37%).

<Preparation Example 33> Preparation of Compound 2-1-192

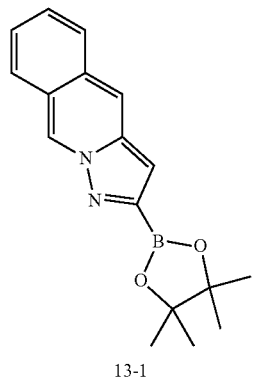

13-1

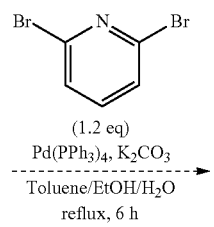

(1.2 eq)
Pd(PPh$_3$)$_4$, K$_2$CO$_3$
Toluene/EtOH/H$_2$O
reflux, 6 h

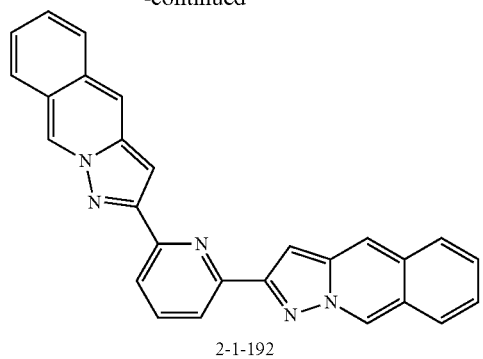

2-1-192

A mixed solution of Compound 13-1 (6.0 g, 20.4 mmol), 2,6-dibromopyridine (5.8 g, 24.48 mmol), potassium carbonate (8.46 g, 61.2 mmol), tetra(triphenylphosphine) palladium (1.18 g, 1.02 mmol), and toluene/ethanol/$H_2O$ (60 ml/12 ml/12 ml) was refluxed and stirred for 6 hours in a one-neck round bottom flask. The solution cooled to room temperature was extracted with methylene chloride/$H_2O$ and concentrated, and separated by column chromatography ($SiO_2$, hexane:methylene chloride=2:1) to obtain white solid Compound 2-1-192 (5.58 g, 66%).

<Preparation Example 34> Preparation of Compound 2-1-193

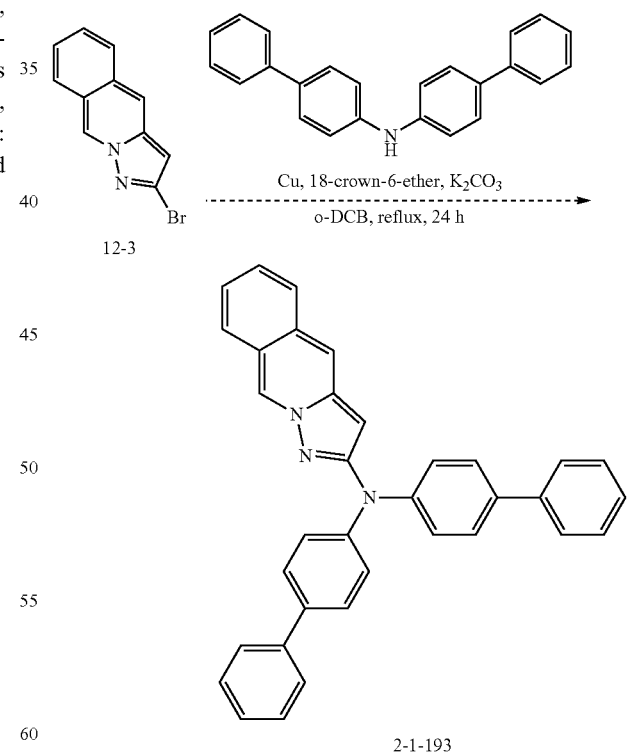

2-1-193

A mixture of 12-3 (6.0 g, 24.28 mmol), di([1,1'-biphenyl]-4-yl)amine (7.0 g, 21.85 mmol), Cu (0.15 g, 2.43 mmol), 18-crown-6-ether (0.64 g, 2.43 mmol), potassium carbonate (10.1 g, 72.84 mmol), and ortho-dichlorobenzene (80 ml) was refluxed and stirred under nitrogen for 24 hours in a one-neck round bottom flask. Ortho-dichlorobenzene was distilled under reduced pressure and removed, and then separated by column chromatography (SiO₂, hexane:methylene chloride=5:1) to obtain white solid Compound 2-1-193 (6.57 g, 55%).

<Preparation Example 35> Preparation of Compound 2-1-200

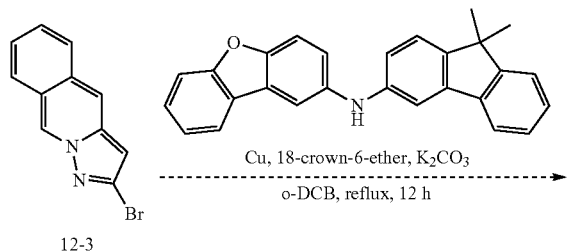

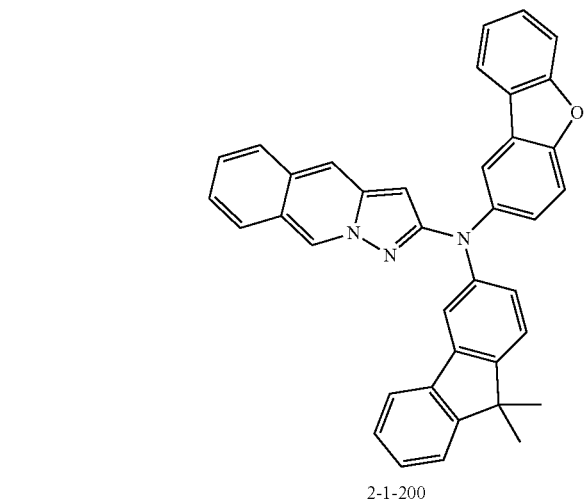

2-1-200

An o-DCB (80 ml) mixture of 12-3 (6.0 g, 24.28 mmol), a reagent (8.2 g, 21.85 mmol), Cu (0.15 g, 2.43 mmol), 18-crown-6-ether (0.79 g, 2.43 mmol), and K₂CO₃ (10.1 g, 72.84 mmol) was refluxed and stirred under nitrogen for 12 hours in a one-neck round bottom flask. o-DCB was distilled under reduced pressure and removed, and then separated by column chromatography (SiO₂, hexane:MC=4:1) to obtain white solid Compound 2-1-200 (7.4 g, 56%).

<Preparation Example 36> Preparation of Compound 2-1-201

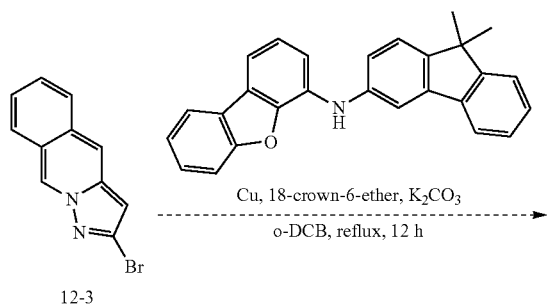

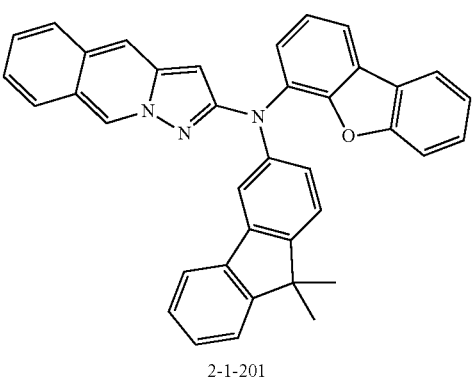

2-1-201

A product (10.1 g, 77%) was prepared in the same manner as in the method for preparing Compound 2-1-200 of Preparation Example 35, except that N-(9,9-dimethyl-9H-fluoren-3-yl)dibenzo[b,d]furan-4-amine was used instead of N-(9,9-dimethyl-9H-fluoren-3-yl)dibenzo[b,d]furan-2-amine in the method.

<Preparation Example 37> Preparation of Compound 2-1-202

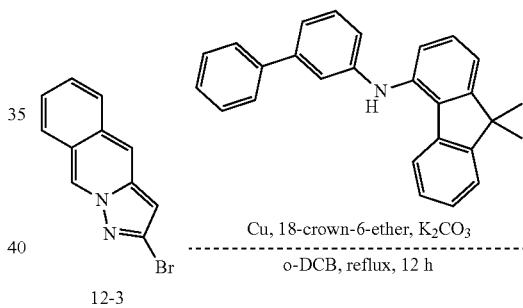

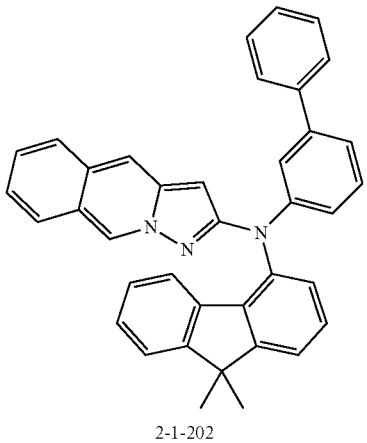

2-1-202

A product (10.4 g, 49%) was produced in the same manner as in the method for preparing Compound 2-1-200 of Preparation Example 35, except that N-([1,1'-biphenyl]-3-yl)-9,9-dimethyl-9H-fluoren-4-amine was used instead of N-(9,9-dimethyl-9H-fluoren-3-yl)dibenzo[b,d]furan-2-amine in the method.

<Preparation Example 38> Preparation of Compound 2-1-203
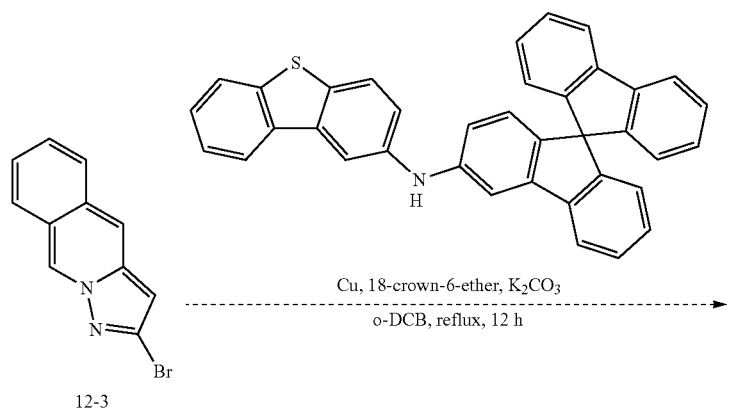
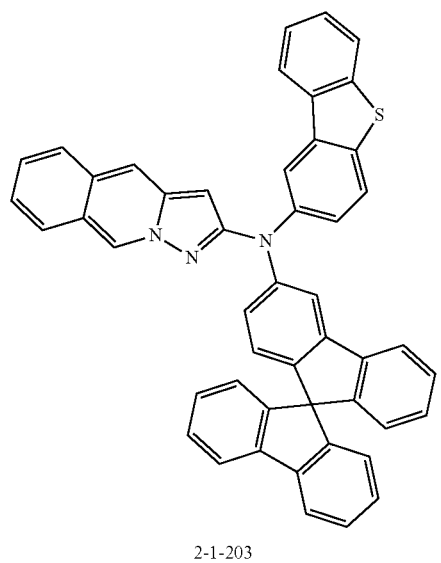
2-1-203
A product (15.1 g, 55%) was prepared in the same manner as in the method for preparing Compound 2-1-200 of Preparation Example 35, except that N-(9,9'-spirobi[fluoren]-3-yl)dibenzo[b,d]thiophen-2-amine was used instead of N-(9,9-dimethyl-9H-fluoren-3-yl)dibenzo[b,d]furan-2-amine in the method.

<Preparation Example 39> Preparation of Compound 2-1-204
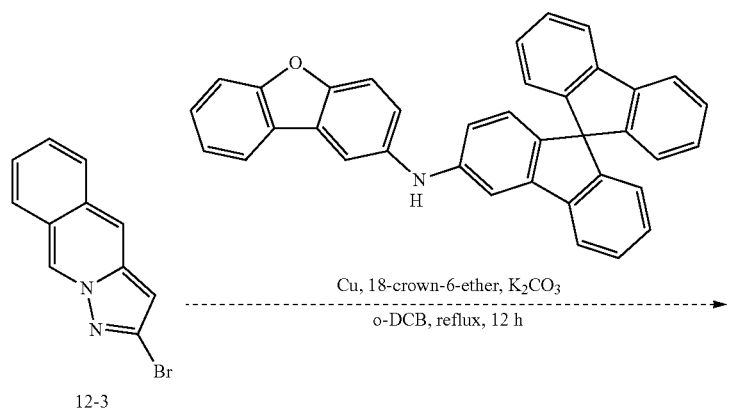
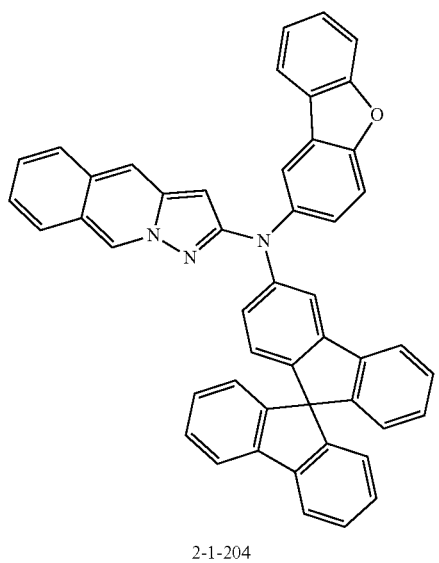
2-1-204
A product (11.8 g, 44%) was prepared in the same manner as in the method for preparing Compound 2-1-200 of Preparation Example 35, except that N-(9,9'-spirobi[fluoren]-3-yl)dibenzo[b,d]furan-2-amine was used instead of N-(9,9-dimethyl-9H-fluoren-3-yl)dibenzo[b,d]furan-2-amine in the method.

<Preparation Example 40> Preparation of Compound 2-1-206

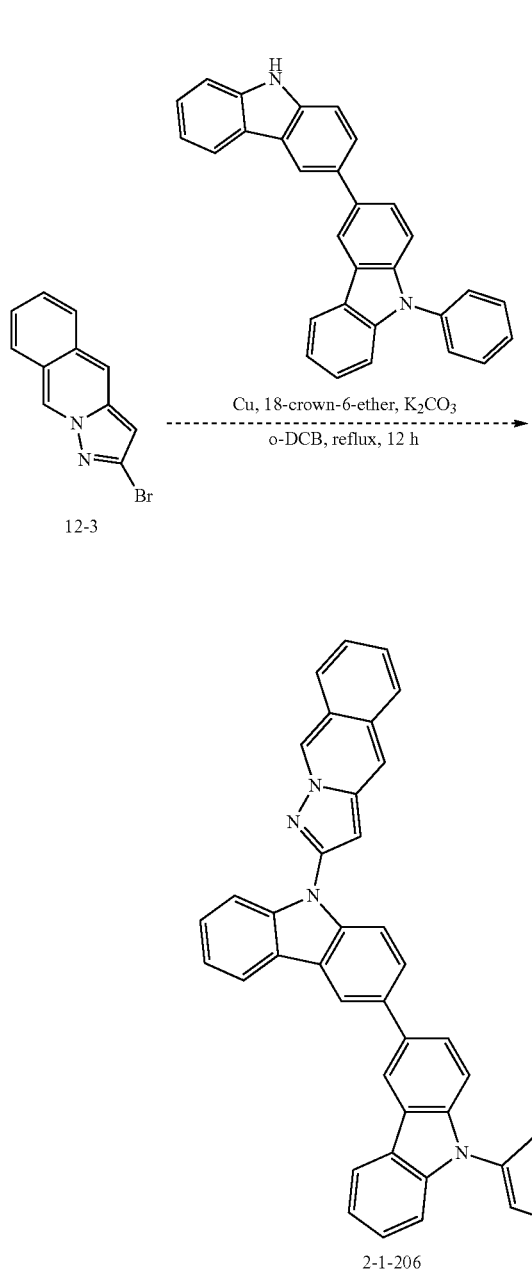

12-3

2-1-206

An o-DCB (80 ml) mixture of 12-3 (6.0 g, 24.28 mmol), a reagent (8.9 g, 21.85 mmol), Cu (0.15 g, 2.43 mmol), 18-crown-6-ether (0.79 g, 2.43 mmol), and K$_2$CO$_3$ (10.1 g, 72.84 mmol) was refluxed and stirred under nitrogen for 12 hours in a one-neck round bottom flask. o-DCB was distilled under reduced pressure and removed, and then separated by column chromatography (SiO$_2$, hexane:MC=4:1) to obtain white solid Compound 2-1-206 (5.7 g, 41%).

<Preparation Example 41> Preparation of Compound 2-1-207

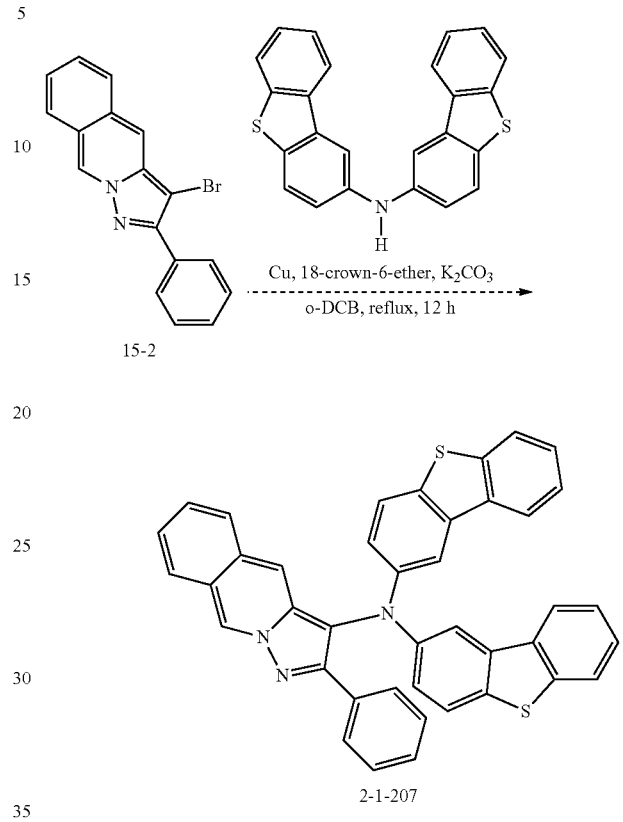

15-2

2-1-207

An o-DCB (80 ml) mixture of 15-2 (10.0 g, 30.94 mmol), a reagent (12.9 g, 34.04 mmol), Cu (0.19 g, 3.09 mmol), 18-crown-6-ether (1.0 g, 3.09 mmol), and K$_2$CO$_3$ (12.8 g, 92.82 mmol) was refluxed and stirred under nitrogen for 12 hours in a one-neck round bottom flask. o-DCB was distilled under reduced pressure and removed, and then separated by column chromatography (SiO$_2$, hexane:MC=3:1) to obtain white solid Compound 2-1-207 (12.2 g, 63%).

<Preparation Example 42> Preparation of Compound 2-1-208

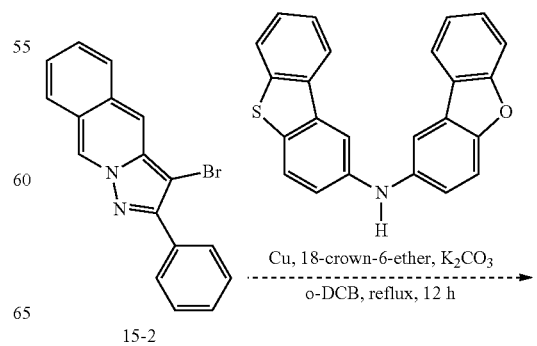

15-2

-continued

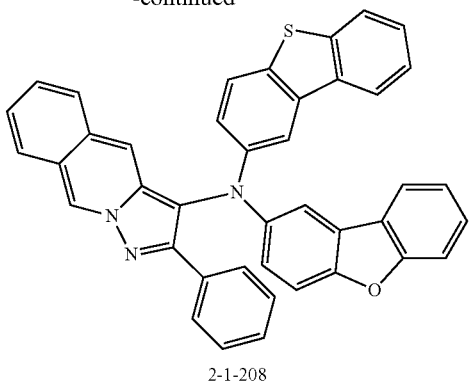

2-1-208

A product (12.4 g, 66%) was prepared in the same manner as in the method for preparing Compound 2-1-207 of Preparation Example 41, except that N-(dibenzo[b,d]thiophen-2-yl)dibenzo[b,d]furan-2-amine was used instead of bis(dibenzo[b,d]thiophen-2-yl)amine in the method.

<Preparation Example 43> Preparation of Compound 2-1-210

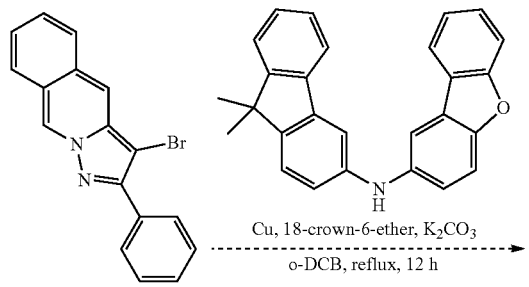

15-2

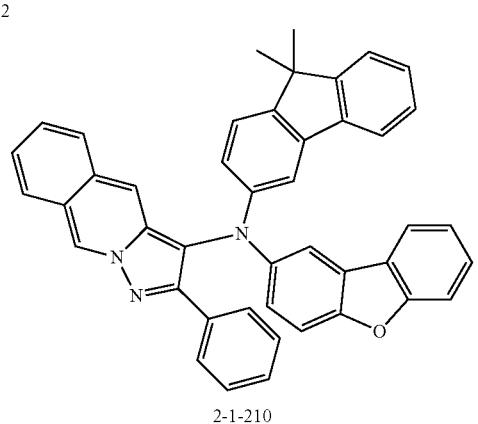

2-1-210

A product (13.6 g, 71%) was prepared in the same manner as in the method for preparing Compound 2-1-207 of Preparation Example 41, except that N-(9,9-dimethyl-9H-fluoren-3-yl)dibenzo[b,d]furan-2-amine was used instead of bis(dibenzo[b,d]thiophen-2-yl)amine in the method.

<Preparation Example 44> Preparation of Compound 2-1-213

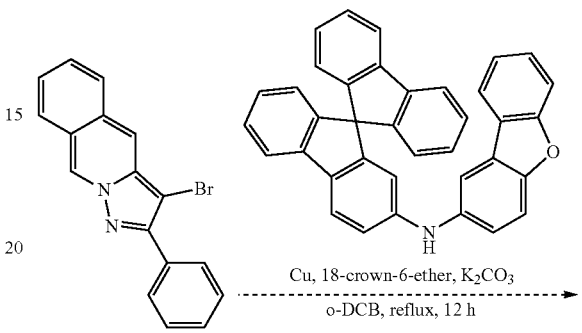

15-2

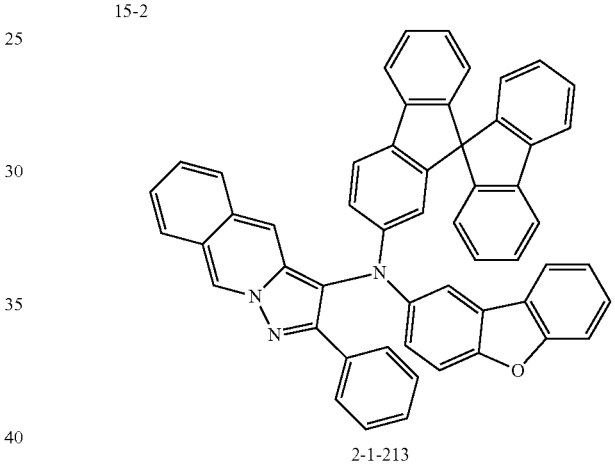

2-1-213

A product (12.1 g, 53%) was prepared in the same manner as in the method for preparing Compound 2-1-207 of Preparation Example 41, except that N-(9,9'-spirobi[fluoren]-2-yl)dibenzo[b,d]furan-2-amine was used instead of bis(dibenzo[b,d]thiophen-2-yl)amine in the method.

Compounds 2-1-1 to 2-1-216 may be prepared by modifying the bonded substituent based on Preparation Examples 23 to 44.

Compounds were prepared in the same manner as in the Preparation Examples, and the synthesis confirmation results thereof are shown in Tables 3 and 4. Table 3 is about the measurement values of $^1$H NMR (CDCl$_3$, 200 Mz), and Table 4 is about the measurement values of field desorption mass spectrometry (FD-MS).

TABLE 3

| Compound | $^1$H NMR(CDCl$_3$, 200 Mz) |
|---|---|
| 2-1-18 | δ = 6.40(1H, s), 7.44~7.51(8H, m), 7.64~7.77(6H, m), 8.11(1H, d), 9.15(1H, s) |
| 2-1-37 | δ = 6.40(1H, s), 7.44~7.68(10H, m), 7.94(4H, m), 8.11(1H, d), 8.73(1H, s), 9.15(1H, s) |
| 2-1-63 | δ = 6.66(1H, s), 7.41~7.50(8H, m), 7.64~7.85(8H, m), 8.04~8.11 (4H, m), 8.30(2H, m), 9.15(1H, s) |
| 2-1-86 | δ = 1.69(6H, s), 6.40(1H, s), 7.20(1H, t), 7.44~7.74(10H, m), 8.11~8.24(3H, m), 9.01(1H, s), 9.15(1H, s) |

TABLE 3-continued

| Compound | ¹H NMR(CDCl₃, 200 Mz) |
|---|---|
| 2-1-109 | δ = 6.66(1H, s), 7.44~7.50(8H, m), 7.64~7.73(3H, m), 7.94(2H, m), 8.11(1H, d), 8.36~8.38(5H, m), 9.15(1H, m) |
| 2-1-120 | δ = 6.66(1H, s), 7.16(2H, m), 7.35~7.68(14H, m), 7.80(1H, d), 7.94(2H < m), 8.11~8.12(2H, m), 8.21(1H, s), 8.55(2H, m), 9.15(1H, s) |
| 2-1-154 | δ = 7.50~7.53(11H, m), 7.64~7.68(2H, m), 7.84(2H, m), 8.11(1H, d), 8.36(4H, m), 9.15(1H, s) |
| 2-1-180 | δ = 6.66(1H, s), 7.16~7.20(4H, m), 7.44~7.64(11H, m), 7.85~7.94(4H, m), 8.11~8.19(5H, m), 8.30(1H, d), 8.55(2H, m), 9.15(1H, s) |
| 2-1-186 | δ = 6.66(2H, d), 7.44~7.50(4H, m), 7.64~7.68(4H, m), 8.11(2H, m), 8.30(4H, s), 9.15(2H, s) |
| 2-1-190 | δ = 6.66(1H, s), 7.38~7.50(17H, m), 7.65~7.68(4H, m), 7.87(2H, m), 8.11(1H, s), 9.15(1H, s) |
| 2-1-192 | δ = 6.40(2H, s), 7.44~7.68(8H, m), 8.11~8.12(3H, m), 8.50(2H, m), 9.15(2H,s) |
| 2-1-193 | δ = 6.40(1H, s), 7.41~7.75(22H, m), 8.11(1H, d), 9.15(1H, s) |
| 2-1-200 | δ = 1.69(6H, s), 6.40(1H, s), 6.97(1H, d), 7.06(1H, d), 7.44~7.68(13H, m), 7.90(1H, d), 7.98(1H, d), 8.11(1H, d), 8.22(1H, s), 9.15(1H, s) |
| 2-1-206 | δ = 6.40(1H, s), 7.16~7.20(2H, m), 7.34~7.58(13H, m), 7.89~7.99(4H, m), 8.13~8.19(3H, m), 8.30(1H, d), 8.55(1H, d), 9.15(1H, s) |
| 2-1-207 | δ = 7.44~7.68(13H, m), 7.84~7.93(8H, m), 8.11(1H, d), 8.45(2H, d), 9.15(1H, s) |

TABLE 4

| Compound | FD-MS | Compound | FD-MS |
|---|---|---|---|
| 2-1-1 | m/z = 399.15 (C26H17N5 = 399.46) | 2-1-2 | m/z = 448.17 (C31H20N4 = 448.53) |
| 2-1-3 | m/z = 474.18 (C33H22N4 = 474.57) | 2-1-4 | m/z = 398.15 (C27H18N4 = 398.47) |
| 2-1-5 | m/z = 487.18 (C33H21N5 = 487.57) | 2-1-6 | m/z = 321.13 (C22H15N3 = 321.38) |
| 2-1-7 | m/z = 321.13 (C22H15N3 = 321.38) | 2-1-8 | m/z = 396.16 (C29H20N2 = 396.49) |
| 2-1-9 | m/z = 398.15 (C27H18N4 = 398.47) | 2-1-10 | m/z = 496.19 (C37H24N2 = 496.61) |
| 2-1-11 | m/z = 470.18 (C35H22N2 = 470.57) | 2-1-12 | m/z = 334.12 (C22H14N4 = 334.38) |
| 2-1-13 | m/z = 398.15 (C27H18N4 = 398.47) | 2-1-14 | m/z = 484.19 (C36H24N2 = 484.63) |
| 2-1-15 | m/z = 574.22 (C41H26N4 = 574.69) | 2-1-16 | m/z = 436.17 (C30H20N4 = 436.52) |
| 2-1-17 | m/z = 436.17 (C30H20N4 = 436.52) | 2-1-18 | m/z = 368.11 (C23H17N2OP = 368.38) |
| 2-1-19 | m/z = 344.13 (C25H16N2 = 344.42) | 2-1-20 | m/z = 361.12 (C24H15N3O = 361.40) |
| 2-1-21 | m/z = 377.10 (C24H15N3S = 377.47) | 2-1-22 | m/z = 295.11 (C20H13N3 = 295.34) |
| 2-1-23 | m/z = 295.11 (C20H13N3 = 295.34) | 2-1-24 | m/z = 295.11 (C20H12N4 = 295.33) |
| 2-1-25 | m/z = 295.11 (C20H12N4 = 295.33) | 2-1-26 | m/z = 388.13 (C25H16N4O = 388.43) |
| 2-1-27 | m/z = 334.11 (C23H14N2O = 334.38) | 2-1-28 | m/z = 350.09 (C23H14N2S = 350.44) |
| 2-1-29 | m/z = 397.16 (C28H19N3 = 397.48) | 2-1-30 | m/z = 397.16 (C28H19N3 = 397.48) |
| 2-1-31 | m/z = 420.16 (C31H20N2 = 420.51) | 2-1-32 | m/z = 551.21 (C38H25N5 = 551.65) |
| 2-1-33 | m/z = 551.21 (C38H25N5 = 551.65) | 2-1-34 | m/z = 497.19 (C36H23N2 = 497.60) |
| 2-1-35 | m/z = 551.21 (C38H25N5 = 551.65) | 2-1-36 | m/z = 551.21 (C38H25N5 = 551.65) |
| 2-1-37 | m/z = 398.15 (C27H18N4 = 398.47) | 2-1-38 | m/z = 474.18 (C33H22N4 = 474.57) |
| 2-1-39 | m/z = 498.18 (C35H22N4 = 198.59) | 2-1-40 | m/z = 552.21 (C37H24N6 = 552.64) |
| 2-1-41 | m/z = 398.15 (C27H18N4 = 398.47) | 2-1-42 | m/z = 498.18 (C35H22N4 = 198.59) |
| 2-1-43 | m/z = 448.17 (C31H20N4 = 448.53) | 2-1-44 | m/z = 399.15 (C26H17N5 = 399.46) |
| 2-1-45 | m/z = 499.18 (C34H21N5 = 499.58) | 2-1-46 | m/z = 551.21 (C38H25N5 = 551.65) |
| 2-1-47 | m/z = 401.14 (C24H15N7 = 401.43) | 2-1-48 | m/z = 401.14 (C24H15N7 = 401.43) |
| 2-1-49 | m/z = 553.20 (C36H23N7 = 553.63) | 2-1-50 | m/z = 555.19 (C34H21N9 = 555.61) |

TABLE 4-continued

| Compound | FD-MS | Compound | FD-MS |
| --- | --- | --- | --- |
| 2-1-51 | m/z = 555.19 (C34H21N9 = 555.61) | 2-1-52 | m/z = 555.19 (C34H21N9 = 555.61) |
| 2-1-53 | m/z = 555.19 (C34H21N9 = 555.61) | 2-1-54 | m/z = 487.18 (C33H21N5 = 487.57) |
| 2-1-55 | m/z = 410.15 (C28H18N4 = 410.48) | 2-1-56 | m/z = 370.15 (C27H18N2 = 370.45) |
| 2-1-57 | m/z = 370.15 (C27H18N2 = 370.45) | 2-1-58 | m/z = 396.19 (C29H20N2 = 396.49) |
| 2-1-59 | m/z = 396.19 (C29H20N2 = 396.49) | 2-1-60 | m/z = 397.16 (C28H19N3 = 397.48) |
| 2-1-61 | m/z = 397.16 (C28H19N3 = 397.48) | 2-1-62 | m/z = 397.16 (C28H19N3 = 397.48) |
| 2-1-63 | m/z = 427.19 (C35H24N2 = 427.59) | 2-1-64 | m/z = 474.18 (C33H22N4 = 474.57) |
| 2-1-65 | m/z = 572.23 (C43H28N2 = 572.72) | 2-1-66 | m/z = 546.21 (C41H26N2 = 546.67) |
| 2-1-67 | m/z = 672.26 (C51H32N2 = 672.83) | 2-1-68 | m/z = 436.19 (C32H24N2 = 436.56) |
| 2-1-69 | m/z = 560.23 (C42H28N2 = 560.70) | 2-1-70 | m/z = 558.21 (C42H26N2 = 558.68) |
| 2-1-71 | m/z = 436.17 (C30H20N4 = 436.52) | 2-1-72 | m/z = 360.14 (C24H16N4 = 360.42) |
| 2-1-73 | m/z = 368.11 (C32H17N2OP = 368.38) | 2-1-74 | m/z = 520.17 (C35H25N2OP = 250.57) |
| 2-1-75 | m/z = 285.09 (C18H11N3O = 280.31) | 2-1-76 | m/z = 301.07 (C18H11N3S = 301.37) |
| 2-1-77 | m/z = 295.11 (C20H13N3 = 295.34) | 2-1-78 | m/z = 295.11 (C20H13N3 = 295.34) |
| 2-1-79 | m/z = 296.11 (C19H12N4 = 296.33) | 2-1-80 | m/z = 296.11 (C19H12N4 = 296.33) |
| 2-1-81 | m/z = 312.10 (C19H12N4O = 312.33) | 2-1-82 | m/z = 334.11 (C23H14N2O = 334.38) |
| 2-1-83 | m/z = 350.09 (C23H14N2S = 350.44) | 2-1-84 | m/z = 379.16 (C28H19N3 = 379.48) |
| 2-1-85 | m/z = 379.16 (C28H19N3 = 379.48) | 2-1-86 | m/z = 449.19 (C32H23N3 = 449.56) |
| 2-1-87 | m/z = 573.22 (C42H27N3 = 573.70) | 2-1-88 | m/z = 439.11 (C29H17N3S = 439.53) |
| 2-1-89 | m/z = 423.14 (C29H17N3O = 423.48) | 2-1-90 | m/z = 498.18 (C35H22N4 = 498.59) |
| 2-1-91 | m/z = 505.16 (C34H23N3S = 505.64) | 2-1-92 | m/z = 629.19 (C44H27N3S = 629.78) |
| 2-1-93 | m/z = 495.09 (C31H17N3S2 = 495.62) | 2-1-94 | m/z = 479.11 (C31H17N3OS = 479.56) |
| 2-1-95 | m/z = 554.16 (C37H22N4S = 554.67) | 2-1-96 | m/z = 505.16 (C34H23N3S = 505.64) |
| 2-1-97 | m/z = 629.19 (C44H27N3S = 629.78) | 2-1-98 | m/z = 495.09 (C31H17N3S2 = 495.62) |
| 2-1-99 | m/z = 497.11 (C31H147N3OS = 497.56) | 2-1-100 | m/z = 554.16 (C37H22N4S = 554.67) |
| 2-1-101 | m/z = 573.22 (C42H27N3 = 573.70) | 2-1-102 | m/z = 627.24 (C44H29N5 = 627.75) |
| 2-1-103 | m/z = 627.24 (C44H29N5 = 627.75) | 2-1-104 | m/z = 573.22 (C43H27N3 = 573.70) |
| 2-1-105 | m/z = 627.24 (C44H29N5 = 627.75) | 2-1-106 | m/z = 474.18 (C33H22N4 = 474.57) |
| 2-1-107 | m/z = 574.22 (C41H26N4 = 574.69) | 2-1-108 | m/z = 524.20 (C37H24N4 = 524.63) |
| 2-1-109 | m/z = 475.18 (C32H21N5 = 475.55) | 2-1-110 | m/z = 575.21 (C40H25N5 = 575.67) |
| 2-1-111 | m/z = 631.22 (C40H25N9 = 631.70) | 2-1-112 | m/z = 631.22 (C40H25N9 = 631.70) |
| 2-1-113 | m/z = 631.22 (C40H25N9 = 631.70) | 2-1-114 | m/z = 563.21 (C39H25N5 = 563.66) |
| 2-1-115 | m/z = 486.18 (C34H22N4 = 486.58) | 2-1-116 | m/z = 525.22 (C38H27N3 = 525.65) |
| 2-1-117 | m/z = 649.25 (C48H31N3 = 649.80) | 2-1-118 | m/z = 515.15 (C35H21N3S = 515.63) |
| 2-1-119 | m/z = 499.17 (C35H21N3O = 499.57) | 2-1-120 | m/z = 574.22 (C41H26N4 = 574.69) |
| 2-1-121 | m/z = 581.19 (C40H27N3S = 581.74) | 2-1-122 | m/z = 705.22 (C50H31N3S = 705.88) |
| 2-1-123 | m/z = 571.12 (C37H21N3S2 = 571.72) | 2-1-124 | m/z = 555.14 (C37H21N3OS = 555.65) |
| 2-1-125 | m/z = 630.19 (C43H26N4S = 630.77) | 2-1-126 | m/z = 581.19 (C40H27N3S = 581.74) |
| 2-1-127 | m/z = 705.22 (C50H31N3S = 705.88) | 2-1-128 | m/z = 571.12 (C37H21N3S2 = 571.72) |

TABLE 4-continued

| Compound | FD-MS | Compound | FD-MS |
|---|---|---|---|
| 2-1-129 | m/z = 555.14 (C37H21N3OS = 555.65) | 2-1-130 | m/z = 630.19 (C43H26N4S = 630.77) |
| 2-1-131 | m/z = 470.18 (C35H22N2 = 470.57) | 2-1-132 | m/z = 596.23 (C45H28N2 = 596.73) |
| 2-1-133 | m/z = 360.16 (C26H20N0 = 360.46) | 2-1-134 | m/z = 484.19 (C36H24N2 = 484.60) |
| 2-1-135 | m/z = 482.18 (C36H22N2 = 482.59) | 2-1-136 | m/z = 436.17 (C30H20N4 = 436.52) |
| 2-1-137 | m/z = 360.14 (C24H16N4 = 360.42) | 2-1-138 | m/z = 368.11 (C23H17N2OP = 368.38) |
| 2-1-139 | m/z = 444.14 (C29H21N2OP = 444.47) | 2-1-140 | m/z = 361.12 (C24H15N3O = 361.40) |
| 2-1-141 | m/z = 524.20 (C37H24N4 = 524.63) | 2-1-142 | m/z = 550.22 (C39H26N4 = 550.66) |
| 2-1-143 | m/z = 474.18 (C33H22N4 = 474.57) | 2-1-144 | m/z = 563.21 (C39H25N5 = 563.66) |
| 2-1-145 | m/z = 371.14 (C26H17N3 = 371.44) | 2-1-146 | m/z = 410.15 (C28H18N4 = 410.48) |
| 2-1-147 | m/z = 512.20 (C36H24N4 = 512.62) | 2-1-148 | m/z = 474.18 (C33H22N4 = 474.57) |
| 2-1-149 | m/z = 444.14 (C29H21N2OP = 444.47) | 2-1-150 | m/z = 512.20 (C36H24N4 = 512.62) |
| 2-1-151 | m/z = 650.25 (C47H30N4 = 650.78) | 2-1-152 | m/z = 420.16 (C31H20N2 = 420.51) |
| 2-1-153 | m/z = 496.19 (C37H24N2 = 496.61) | 2-1-154 | m/z = 475.18 (C32H21N5 = 475.55) |
| 2-1-155 | m/z = 470.18 (C35H22N2 = 470.57) | 2-1-156 | m/z = 468.18 (C34H22N4 = 468.58) |
| 2-1-157 | m/z = 486.18 (C34H22N4 = 486.58) | 2-1-158 | m/z = 481.12 (C29H15N3F4 = 481.45) |
| 2-1-159 | m/z = 369.11 (C23H13N3F2 = 369.37) | 2-1-160 | m/z = 497.28 (C35H35N3 = 497.69) |
| 2-1-161 | m/z = 486.18 (C34H22N4 = 486.58) | 2-1-162 | m/z = 481.12 (C29H15N3F4 = 481.45) |
| 2-1-163 | m/z = 369.11 (C23H13N3F2 = 369.37) | 2-1-164 | m/z = 497.28 (C35H35N3 = 497.69) |
| 2-1-165 | m/z = 574.22 (C41H26N4 = 574.69) | 2-1-166 | m/z = 409.16 (C29H19N3 = 409.49) |
| 2-1-167 | m/z = 485.19 (C35H23N3 = 485.59) | 2-1-168 | m/z = 410.15 (C28H18N4 = 410.48) |
| 2-1-169 | m/z = 487.18 (C33H21N5 = 487.57) | 2-1-170 | m/z = 487.18 (C33H21N5 = 487.57) |
| 2-1-171 | m/z = 562.22 (C40H26N4 = 562.68) | 2-1-172 | m/z = 562.22 (C40H26N4 = 562.68) |
| 2-1-173 | m/z = 557.15 (C35H19N3F4 = 557.55) | 2-1-174 | m/z = 445.14 (C29H17N3F2 = 445.47) |
| 2-1-175 | m/z = 573.31 (C41H39N3 = 574.78) | 2-1-176 | m/z = 562.22 (C40H26N4 = 562.68) |
| 2-1-177 | m/z = 557.15 (C35H19N3F4 = 557.55) | 2-1-178 | m/z = 445.14 (C29H17N3F2 = 445.47) |
| 2-1-179 | m/z = 573.31 (C41H39N3 = 573.78) | 2-1-180 | m/z = 650.25 (C47H30N4 = 650.78) |
| 2-1-181 | m/z = 485.19 (C35H23N3 = 485.59) | 2-1-182 | m/z = 561.22 (C41H27N3 = 561.69) |
| 2-1-183 | m/z = 485.19 (C35H23N3 = 485.59) | 2-1-184 | m/z = 563.21 (C39H25N5 = 563.66) |
| 2-1-185 | m/z = 563.21 (C39H25N5 = 563.66) | 2-1-186 | m/z = 334.12 (C22H14N4 = 334.38) |
| 2-1-187 | m/z = 410.15 (C28H18N4 = 410.48) | 2-1-188 | m/z = 410.15 (C28H18N4 = 410.48) |
| 2-1-189 | m/z = 486.18 (C34H22N4 = 486.58) | 2-1-190 | m/z = 502.19 (C35H26N2Si = 502.69) |
| 2-1-191 | m/z = 411.15 (C27H17N5 = 411.47) | 2-1-192 | m/z = 411.15 (C27H17N5 = 411.47) |
| 2-1-193 | m/z = 487.20 (C35H25N3 = 487.61) | 2-1-194 | m/z = 527.24 (C38H29N3 = 527.67) |
| 2-1-195 | m/z = 517.16 (C35H23N3S = 517.65) | 2-1-196 | m/z = 444.14 (C29H21N2OP = 444.46) |
| 2-1-197 | m/z = 547.12 (C35H21N3S2 = 547.69) | 2-1-198 | m/z = 531.14 (C35H21N3SO = 531.63) |
| 2-1-199 | m/z = 515.16 (C35H21N3O2 = 515.57) | 2-1-200 | m/z = 541.22 (C38H27N3O = 541.65) |
| 2-1-201 | m/z = 541.22 (C38H27N3O = 541.65) | 2-1-202 | m/z = 527.24 (C38H29N3 = 527.67) |
| 2-1-203 | m/z = 679.21 (C48H29N3S = 679.84) | 2-1-204 | m/z = 663.23 (C48H29N3O = 663.78) |
| 2-1-205 | m/z = 383.12 (C25H13N5 = 383.41) | 2-1-206 | m/z = 574.22 (C41H26N4 = 574.69) |

TABLE 4-continued

| Compound | FD-MS | Compound | FD-MS |
|---|---|---|---|
| 2-1-207 | m/z = 623.15 (C41H25N3S2 = 623.79) | 2-1-208 | m/z = 607.17 (C41H25N3SO = 607.73) |
| 2-1-209 | m/z = 591.19 (C41H25N3O2 = 591.67) | 2-1-210 | m/z = 617.25 (C44H31N3O = 617.75) |
| 2-1-211 | m/z = 617.25 (C44H31N3O = 617.75) | 2-1-212 | m/z = 603.27 (C44H33N3 = 603.77) |
| 2-1-213 | m/z = 739.26 (C54H33N3O = 739.88) | 2-1-214 | m/z = 755.24 (C54H33N3S = 755.94) |
| 2-1-215 | m/z = 459.15 (C31H17N5 = 459.51) | 2-1-216 | m/z = 650.25 (C47H30N4 = 650.78) |

<Experimental Example> Manufacture of Organic Electroluminescence Device

Comparative Example 1

A glass substrate, in which ITO was thinly coated to have a thickness of 1,500 Å, was ultrasonically washed with distilled water. When the washing with distilled water is finished, the glass substrate was ultrasonically washed with a solvent such as acetone, methanol, and isopropyl alcohol, dried and then was subjected to uvo treatment for 5 minutes by using UV in a UV washing machine. Thereafter, the substrate was transferred to a plasma washing machine (PT), and then was subjected to plasma treatment for an ITO work function in a vacuum state and in order to remove a residual film, and thus, was transferred to a thermal deposition apparatus for organic deposition.

A hole transport layer was formed by thermally depositing N,N'-bis(α-naphthyl)-N,N'-diphenyl-4,4'-diamine (NPB) under vacuum to have a thickness of 400 Å on the ITO transparent electrode (positive electrode) prepared as described above.

A hole injection layer and a hole transport layer, which are common layers, were formed, and then a light emitting layer was thermally deposited under vacuum thereon as follows. The light emitting layer was deposited to have a thickness of 200 Å by using 4,4'-N,N'-dicarbazole-biphenyl (CBP) as a host and Ir(ppy)$_3$ as a green phosphorus dopant to dope the CBP with Ir(ppy)$_3$ at a concentration of 7%. Thereafter, 2,9-dimethyl-4,7-diphenyl-1,10-phenanthroline (BCP) was deposited to have a thickness of 60 Å as a hole blocking layer, and tris(8-hydroxyquinoline)aluminum (Alq$_3$) was deposited thereon to have a thickness of 200 Å as an electron transport layer. Finally, an organic electroluminescence device was manufactured by depositing lithium fluoride (LiF) to have a thickness of 10 Å on the electron transport layer to form an electron injection layer, and then depositing an aluminum (Al) negative electrode to have a thickness of 1,200 Å on the electron injection layer to form a negative electrode.

Meanwhile, all the organic compounds required for manufacturing an OLED device were subjected to vacuum sublimed purification under $10^{-6}$ to $10^{-8}$ torr for each material, and used for the manufacture of OLED.

Example 1

An organic electroluminescence device was manufactured in the same manner as in Comparative Example 1, except that Compound 1-1-18 was used instead of Alq$_3$ used during the formation of an electron transport layer in Comparative Example 1.

Example 2

An organic electroluminescence device was manufactured in the same manner as in Comparative Example 1, except that Compound 1-1-20 was used instead of Alq$_3$ used during the formation of an electron transport layer in Comparative Example 1.

Example 3

An organic electroluminescence device was manufactured in the same manner as in Comparative Example 1, except that Compound 1-1-27 was used instead of Alq$_3$ used during the formation of an electron transport layer in Comparative Example 1.

Example 4

An organic electroluminescence device was manufactured in the same manner as in Comparative Example 1, except that Compound 1-1-37 was used instead of Alq$_3$ used during the formation of an electron transport layer in Comparative Example 1.

Example 5

An organic electroluminescence device was manufactured in the same manner as in Comparative Example 1, except that Compound 1-1-38 was used instead of Alq$_3$ used during the formation of an electron transport layer in Comparative Example 1.

Example 6

An organic electroluminescence device was manufactured in the same manner as in Comparative Example 1, except that Compound 1-1-63 was used instead of Alq$_3$ used during the formation of an electron transport layer in Comparative Example 1.

Example 7

An organic electroluminescence device was manufactured in the same manner as in Comparative Example 1, except that Compound 1-1-66 was used instead of Alq$_3$ used during the formation of an electron transport layer in Comparative Example 1.

Example 8

An organic electroluminescence device was manufactured in the same manner as in Comparative Example 1, except that Compound 1-1-97 was used instead of Alq$_3$ used during the formation of an electron transport layer in Comparative Example 1.

Example 9

An organic electroluminescence device was manufactured in the same manner as in Comparative Example 1, except that Compound 1-1-102 was used instead of Alq$_3$ used during the formation of an electron transport layer in Comparative Example 1.

Example 10

An organic electroluminescence device was manufactured in the same manner as in Comparative Example 1, except that Compound 1-1-109 was used instead of Alq$_3$ used during the formation of an electron transport layer in Comparative Example 1.

Example 11

An organic electroluminescence device was manufactured in the same manner as in Comparative Example 1, except that Compound 1-1-154 was used instead of Alq$_3$ used during the formation of an electron transport layer in Comparative Example 1.

Example 12

An organic electroluminescence device was manufactured in the same manner as in Comparative Example 1, except that Compound 1-1-155 was used instead of Alq$_3$ used during the formation of an electron transport layer in Comparative Example 1.

Example 13

An organic electroluminescence device was manufactured in the same manner as in Comparative Example 1, except that Compound 1-1-156 was used instead of Alq$_3$ used during the formation of an electron transport layer in Comparative Example 1.

Example 14

An organic electroluminescence device was manufactured in the same manner as in Comparative Example 1, except that Compound 1-1-166 was used instead of Alq$_3$ used during the formation of an electron transport layer in Comparative Example 1.

Example 15

An organic electroluminescence device was manufactured in the same manner as in Comparative Example 1, except that Compound 1-1-167 was used instead of Alq$_3$ used during the formation of an electron transport layer in Comparative Example 1.

Example 16

An organic electroluminescence device was manufactured in the same manner as in Comparative Example 1, except that Compound 1-1-186 was used instead of Alq$_3$ used during the formation of an electron transport layer in Comparative Example 1.

Example 17

An organic electroluminescence device was manufactured in the same manner as in Comparative Example 1, except that Compound 1-1-192 was used instead of Alq$_3$ used during the formation of an electron transport layer in Comparative Example 1.

Example 18

An organic electroluminescence device was manufactured in the same manner as in Comparative Example 1, except that Compound 1-1-193 was used instead of Alq$_3$ used during the formation of an electron transport layer in Comparative Example 1.

Example 19

An organic electroluminescence device was manufactured in the same manner as in Comparative Example 1, except that Compound 1-1-86 was used instead of CBP used during the formation of a light emitting layer in Comparative Example 1.

Example 20

An organic electroluminescence device was manufactured in the same manner as in Comparative Example 1, except that Compound 1-1-180 was used instead of CBP used during the formation of a light emitting layer in Comparative Example 1.

Example 21

An organic electroluminescence device was manufactured in the same manner as in Comparative Example 1, except that Compound 1-1-120 was used instead of CBP used during the formation of a light emitting layer in Comparative Example 1.

Example 22

An organic electroluminescence device was manufactured in the same manner as in Comparative Example 1, except that Compound 1-1-190 was used instead of CBP used during the formation of a light emitting layer in Comparative Example 1.

Examples 23 to 42

An organic electroluminescence device was manufactured in the same manner as in Comparative Example 1, except that any one of Compounds 1-1-197 to 1-1-216 was used instead of NPB used during the formation of a hole transport layer in Comparative Example 1.

Example 43

An organic electroluminescence device was manufactured in the same manner as in Comparative Example 1, except that Compound 2-1-18 was used instead of Alq$_3$ used during the formation of an electron transport layer in Comparative Example 1.

Example 44

An organic electroluminescence device was manufactured in the same manner as in Comparative Example 1,

Example 45

An organic electroluminescence device was manufactured in the same manner as in Comparative Example 1, except that Compound 2-1-27 was used instead of Alq$_3$ used during the formation of an electron transport layer in Comparative Example 1.

Example 46

An organic electroluminescence device was manufactured in the same manner as in Comparative Example 1, except that Compound 2-1-37 was used instead of Alq$_3$ used during the formation of an electron transport layer in Comparative Example 1.

Example 47

An organic electroluminescence device was manufactured in the same manner as in Comparative Example 1, except that Compound 2-1-38 was used instead of Alq$_3$ used during the formation of an electron transport layer in Comparative Example 1.

Example 48

An organic electroluminescence device was manufactured in the same manner as in Comparative Example 1, except that Compound 2-1-63 was used instead of Alq$_3$ used during the formation of an electron transport layer in Comparative Example 1.

Example 49

An organic electroluminescence device was manufactured in the same manner as in Comparative Example 1, except that Compound 2-1-66 was used instead of Alq$_3$ used during the formation of an electron transport layer in Comparative Example 1.

Example 50

An organic electroluminescence device was manufactured in the same manner as in Comparative Example 1, except that Compound 2-1-86 was used instead of Alq$_3$ used during the formation of an electron transport layer in Comparative Example 1.

Example 51

An organic electroluminescence device was manufactured in the same manner as in Comparative Example 1, except that Compound 2-1-97 was used instead of Alq$_3$ used during the formation of an electron transport layer in Comparative Example 1.

Example 52

An organic electroluminescence device was manufactured in the same manner as in Comparative Example 1, except that Compound 2-1-102 was used instead of Alq$_3$ used during the formation of an electron transport layer in Comparative Example 1.

Example 53

An organic electroluminescence device was manufactured in the same manner as in Comparative Example 1, except that Compound 2-1-109 was used instead of Alq$_3$ used during the formation of an electron transport layer in Comparative Example 1.

Example 54

An organic electroluminescence device was manufactured in the same manner as in Comparative Example 1, except that Compound 2-1-120 was used instead of Alq$_3$ used during the formation of an electron transport layer in Comparative Example 1.

Example 55

An organic electroluminescence device was manufactured in the same manner as in Comparative Example 1, except that Compound 2-1-154 was used instead of Alq$_3$ used during the formation of an electron transport layer in Comparative Example 1.

Example 56

An organic electroluminescence device was manufactured in the same manner as in Comparative Example 1, except that Compound 2-1-155 was used instead of Alq$_3$ used during the formation of an electron transport layer in Comparative Example 1.

Example 57

An organic electroluminescence device was manufactured in the same manner as in Comparative Example 1, except that Compound 2-1-156 was used instead of Alq$_3$ used during the formation of an electron transport layer in Comparative Example 1.

Example 58

An organic electroluminescence device was manufactured in the same manner as in Comparative Example 1, except that Compound 2-1-166 was used instead of Alq$_3$ used during the formation of an electron transport layer in Comparative Example 1.

Example 59

An organic electroluminescence device was manufactured in the same manner as in Comparative Example 1, except that Compound 2-1-167 was used instead of Alq$_3$ used during the formation of an electron transport layer in Comparative Example 1.

Example 60

An organic electroluminescence device was manufactured in the same manner as in Comparative Example 1, except that Compound 2-1-180 was used instead of Alq$_3$ used during the formation of an electron transport layer in Comparative Example 1.

Example 61

An organic electroluminescence device was manufactured in the same manner as in Comparative Example 1, except that Compound 2-1-186 was used instead of Alq$_3$ used during the formation of an electron transport layer in Comparative Example 1.

Example 62

An organic electroluminescence device was manufactured in the same manner as in Comparative Example 1, except that Compound 2-1-190 was used instead of Alq$_3$ used during the formation of an electron transport layer in Comparative Example 1.

Example 63

An organic electroluminescence device was manufactured in the same manner as in Comparative Example 1, except that Compound 2-1-192 was used instead of Alq$_3$ used during the formation of an electron transport layer in Comparative Example 1.

Example 64

An organic electroluminescence device was manufactured in the same manner as in Comparative Example 1, except that Compound 2-1-193 was used instead of Alq$_3$ used during the formation of an electron transport layer in Comparative Example 1.

Examples 65 to 84

An organic electroluminescence device was manufactured in the same manner as in Comparative Example 1, except that any one of Compounds 2-1-197 to 2-1-216 was used instead of NPB used during the formation of a hole transport layer in Comparative Example 1.

<Experimental Example 1> Driving Voltage, Light Emitting Efficiency, and Service Life of Organic Electroluminescence Device For the organic electroluminescence devices manufactured in Comparative Example 1 and Examples 1 to 18, when the light emitting brightness was 1,000 cd/m$^2$, the driving voltage and light emitting efficiency were measured, and the service life was measured as an average value of times taken for the brightness to be decreased to a brightness corresponding to 90% of the brightness at the time of starting the driving according to the elapse of the driving time of the device at 2,000 cd/m$^2$, and the results are shown in the following Table 5.

In this case, electroluminescence (EL) characteristics were measured by using an IVL measurement apparatus (M7000) manufactured by McScience Inc., to measure the light emitting efficiency. As a result of the measurement, the service life of T90 was measured by using M6000PMX manufactured by McScience Inc., at a reference brightness of 300 cd/m$^2$.

TABLE 5

|  | Material for Electron transport layer | Driving voltage (V) | Light emitting efficiency (cd/A) | T = 90%/hr |
| --- | --- | --- | --- | --- |
| Example 1 | Compound 1-1-18 | 4.5 | 55 | 55 |
| Example 2 | Compound 1-1-20 | 4.2 | 54 | 60 |
| Example 3 | Compound 1-1-27 | 4.3 | 57 | 57 |
| Example 4 | Compound 1-1-37 | 4.7 | 52 | 57 |
| Example 5 | Compound 1-1-38 | 4.3 | 56 | 58 |
| Example 6 | Compound 1-1-63 | 4.8 | 53 | 53 |
| Example 7 | Compound 1-1-66 | 4.2 | 52 | 55 |
| Example 8 | Compound 1-1-97 | 4.0 | 59 | 56 |
| Example 9 | Compound 1-1-102 | 4.1 | 55 | 55 |
| Example 10 | Compound 1-1-109 | 4.6 | 54 | 56 |
| Example 11 | Compound 1-1-154 | 4.7 | 53 | 58 |
| Example 12 | Compound 1-1-155 | 4.1 | 55 | 59 |
| Example 13 | Compound 1-1-156 | 4.2 | 55 | 61 |
| Example 14 | Compound 1-1-166 | 4.4 | 52 | 52 |
| Example 15 | Compound 1-1-167 | 4.2 | 56 | 56 |
| Example 16 | Compound 1-1-186 | 5.0 | 50 | 59 |
| Example 17 | Compound 1-1-192 | 5.0 | 51 | 60 |
| Example 18 | Compound 1-1-193 | 4.8 | 51 | 54 |
| Comparative Example 1 | Alq$_3$ | 5.2 | 48 | 50 |

As a result of the experiments, it can be confirmed that the organic electroluminescence devices manufactured by Examples 1 to 18 in which the compound according to the present application was used had a lower driving voltage, higher light emitting efficiency, and better service life characteristics than the organic electroluminescence device of Comparative Example 1 in the related art where Alq$_3$ was used.

That is, when the compounds according to the present application are used as a material for the electron transport layer of the organic electroluminescence device because the core structure has a structure in which two N's are disposed adjacent to each other, the electron transfer capability is excellent and driving characteristics may be improved. Further, due to the hole blocking function according to a low HOMO value of the compound, the number of holes transferring from the light emitting layer to a layer including the compound according to the present application is decreased, and thus the light emitting efficiency and service life thereof may be improved.

<Experimental Example 2> Driving Voltage, Light Emitting Efficiency, and Service Life of Organic Electroluminescence Device For the organic electroluminescence devices manufactured in Comparative Example 1 and Examples 19 to 22, when the light emitting brightness was 1,000 cd/m$^2$, the driving voltage and light emitting efficiency were measured, and the service life was measured as an average value of times taken for the brightness to be decreased to a brightness corresponding to 90% of the brightness at the time of starting the driving according to the elapse of the driving time of the device at 2,000 cd/m$^2$, and the results are shown in the following Table 6.

In this case, electroluminescence (EL) characteristics were measured by using an IVL measurement apparatus (M7000) manufactured by McScience Inc., to measure the light emitting efficiency. As a result of the measurement, the service life of T90 was measured by using M6000PMX manufactured by McScience Inc., at a reference brightness of 300 cd/m$^2$.

TABLE 6

|  | Host material | Driving voltage (V) | Light emitting efficiency (cd/A) | T = 90%/hr |
|---|---|---|---|---|
| Example 19 | Compound 1-1-86 | 4.1 | 53 | 54 |
| Example 20 | Compound 1-1-180 | 4.2 | 57 | 52 |
| Example 21 | Compound 1-1-120 | 4.0 | 58 | 53 |
| Example 22 | Compound 1-1-190 | 4.4 | 50 | 55 |
| Comparative Example 1 | CBP | 5.2 | 48 | 50 |

As a result of the experiments, it can be confirmed that the organic electroluminescence devices manufactured by Examples 19 to 22 in which the compound according to the present application was used had a lower driving voltage, higher light emitting efficiency, and better service life characteristics than the organic electroluminescence device of Comparative Example 1 in the related art where CBP was used.

That is, since the hole mobility and the electron mobility in the compound are appropriately maintained due to a structure which includes both an electron transport group and a hole transport group of the compounds according to the present application, the driving voltage is lowered, and the light emitting efficiency and service life characteristics may be improved.

<Experimental Example 3> Driving Voltage, Light Emitting Efficiency, and Service Life of Organic Electroluminescence Device For the organic electroluminescence devices manufactured in Comparative Example 1 and Examples 23 to 42, when the light emitting brightness was 1,000 cd/m$^2$, the driving voltage and light emitting efficiency were measured, and the service life was measured as an average value of times taken for the brightness to be decreased to a brightness corresponding to 90% of the brightness at the time of starting the driving according to the elapse of the driving time of the device at 2,000 cd/m$^2$, and the results are shown in the following Table 7.

In this case, electroluminescence (EL) characteristics were measured by using an IVL measurement apparatus (M7000) manufactured by McScience Inc., to measure the light emitting efficiency. As a result of the measurement, the service life of T90 was measured by using M6000PMX manufactured by McScience Inc., at a reference brightness of 300 cd/m$^2$.

TABLE 7

|  | Material for hole transport layer | Driving voltage (V) | Light emitting efficiency (cd/A) | T = 90%/hr |
|---|---|---|---|---|
| Example 23 | Compound 1-1-197 | 4.0 | 50 | 51 |
| Example 24 | Compound 1-1-198 | 4.3 | 51 | 59 |
| Example 25 | Compound 1-1-199 | 4.4 | 51 | 51 |
| Example 26 | Compound 1-1-200 | 4.0 | 53 | 52 |
| Example 27 | Compound 1-1-201 | 4.1 | 55 | 55 |
| Example 28 | Compound 1-1-202 | 3.9 | 55 | 56 |
| Example 29 | Compound 1-1-203 | 4.7 | 57 | 54 |
| Example 30 | Compound 1-1-204 | 4.4 | 51 | 53 |
| Example 31 | Compound 1-1-205 | 4.7 | 52 | 51 |
| Example 32 | Compound 1-1-206 | 4.1 | 54 | 50 |
| Example 33 | Compound 1-1-207 | 4.2 | 50 | 51 |
| Example 34 | Compound 1-1-208 | 4.2 | 55 | 51 |
| Example 35 | Compound 1-1-209 | 4.2 | 56 | 51 |
| Example 36 | Compound 1-1-210 | 4.4 | 54 | 53 |
| Example 37 | Compound 1-1-211 | 4.2 | 53 | 55 |
| Example 38 | Compound 1-1-212 | 4.9 | 51 | 55 |
| Example 39 | Compound 1-1-213 | 4.2 | 59 | 57 |
| Example 40 | Compound 1-1-214 | 5.0 | 51 | 51 |
| Example 41 | Compound 1-1-215 | 4.1 | 55 | 55 |
| Example 42 | Compound 1-1-216 | 4.1 | 54 | 57 |
| Comparative Example 1 | NPB | 5.2 | 48 | 50 |

As a result of the experiments, it can be confirmed that the organic electroluminescence devices manufactured by Examples 23 to 42 in which the compound according to the present application was used had a lower driving voltage, higher light emitting efficiency, and better service life characteristics than the organic electroluminescence device of Comparative Example 1 in the related art where CBP was used.

<Experimental Example 4> Driving Voltage, Light Emitting Efficiency, and Service Life of Organic Electroluminescence Device For the organic electroluminescence devices manufactured in Comparative Example 1 and Examples 43 to 64, when the light emitting brightness was 1,000 cd/m$^2$, the driving voltage and light emitting efficiency were measured, and the service life was measured as an average value of times taken for the brightness to be decreased to a brightness corresponding to 90% of the brightness at the time of starting the driving according to the elapse of the driving time of the device at 2,000 cd/m$^2$, and the results are shown in the following Table 8.

In this case, electroluminescence (EL) characteristics were measured by using an IVL measurement apparatus (M7000) manufactured by McScience Inc., to measure the light emitting efficiency. As a result of the measurement, the service life of T90 was measured by using M6000PMX manufactured by McScience Inc., at a reference brightness of 300 cd/m$^2$.

TABLE 8

|  | Material for Electron transport layer | Driving voltage (V) | Light emitting efficiency (cd/A) | T = 90%/hr |
|---|---|---|---|---|
| Example 43 | Compound 2-1-18 | 4.8 | 55 | 62 |
| Example 44 | Compound 2-1-20 | 4.1 | 55 | 55 |
| Example 45 | Compound 2-1-27 | 4.1 | 55 | 59 |
| Example 46 | Compound 2-1-37 | 4.6 | 51 | 58 |
| Example 47 | Compound 2-1-38 | 4.2 | 55 | 61 |
| Example 48 | Compound 2-1-63 | 4.3 | 52 | 57 |
| Example 49 | Compound 2-1-66 | 4.4 | 52 | 52 |
| Example 50 | Compound 2-1-86 | 4.5 | 53 | 58 |
| Example 51 | Compound 2-1-97 | 4.5 | 55 | 57 |
| Example 52 | Compound 2-1-102 | 4.1 | 55 | 55 |
| Example 53 | Compound 2-1-109 | 4.5 | 53 | 56 |
| Example 54 | Compound 2-1-120 | 4.6 | 55 | 58 |
| Example 55 | Compound 2-1-154 | 5.0 | 52 | 57 |
| Example 56 | Compound 2-1-155 | 4.1 | 55 | 57 |
| Example 57 | Compound 2-1-156 | 4.3 | 53 | 61 |
| Example 58 | Compound 2-1-166 | 4.1 | 53 | 57 |
| Example 59 | Compound 2-1-167 | 4.1 | 55 | 57 |
| Example 60 | Compound 2-1-180 | 4.7 | 54 | 58 |
| Example 61 | Compound 2-1-186 | 4.7 | 51 | 55 |
| Example 62 | Compound 2-1-190 | 4.3 | 52 | 57 |
| Example 63 | Compound 2-1-192 | 4.3 | 51 | 54 |

TABLE 8-continued

| | Material for Electron transport layer | Driving voltage (V) | Light emitting efficiency (cd/A) | T = 90%/hr |
|---|---|---|---|---|
| Example 64 | Compound 2-1-193 | 4.2 | 51 | 57 |
| Comparative Example 1 | Alq$_3$ | 5.2 | 48 | 50 |

As a result of the experiments, it can be confirmed that the organic electroluminescence devices manufactured by Examples 43 to 64 in which the compound according to the present application was used had a lower driving voltage, higher light emitting efficiency, and better service life characteristics than the organic electroluminescence device of Comparative Example 1 in the related art where Alq$_3$ was used.

That is, when the compounds according to the present application are used as a material for the electron transport layer of the organic electroluminescence device because the core structure has a structure in which two N's are disposed adjacent to each other, the electron transfer capability is excellent and driving characteristics may be improved. Further, due to the hole blocking function according to a low HOMO value of the compound, the number of holes transferring from the light emitting layer to a layer including the compound according to the present application is decreased, and thus the light emitting efficiency and service life thereof may be improved.

<Experimental Example 5> Driving Voltage, Light Emitting Efficiency, and Service Life of Organic Electroluminescence Device For the organic electroluminescence devices manufactured in Comparative Example 1 and Examples 65 to 84, when the light emitting brightness was 1,000 cd/m$^2$, the driving voltage and light emitting efficiency were measured, and the service life was measured as an average value of times taken for the brightness to be decreased to a brightness corresponding to 90% of the brightness at the time of starting the driving according to the elapse of the driving time of the device at 2,000 cd/m$^2$, and the results are shown in the following Table 9.

In this case, electroluminescence (EL) characteristics were measured by using an IVL measurement apparatus (M7000) manufactured by McScience Inc., to measure the light emitting efficiency. As a result of the measurement, the service life of T90 was measured by using M6000PMX manufactured by McScience Inc., at a reference brightness of 300 cd/m$^2$.

TABLE 9

| | Material for hole transport layer | Driving voltage (V) | Light emitting efficiency (cd/A) | T = 90%/hr |
|---|---|---|---|---|
| Example 65 | Compound 2-1-197 | 4.4 | 50 | 53 |
| Example 66 | Compound 2-1-198 | 4.7 | 55 | 51 |
| Example 67 | Compound 2-1-199 | 4.1 | 56 | 50 |
| Example 68 | Compound 2-1-200 | 4.4 | 56 | 50 |
| Example 69 | Compound 2-1-201 | 4.2 | 55 | 55 |
| Example 70 | Compound 2-1-202 | 4.2 | 55 | 56 |
| Example 71 | Compound 2-1-203 | 4.4 | 57 | 54 |
| Example 72 | Compound 2-1-204 | 4.2 | 51 | 53 |
| Example 73 | Compound 2-1-205 | 4.9 | 52 | 51 |
| Example 74 | Compound 2-1-206 | 4.2 | 54 | 50 |
| Example 75 | Compound 2-1-207 | 4.3 | 57 | 51 |

TABLE 9-continued

| | Material for hole transport layer | Driving voltage (V) | Light emitting efficiency (cd/A) | T = 90%/hr |
|---|---|---|---|---|
| Example 76 | Compound 2-1-208 | 4.2 | 55 | 51 |
| Example 77 | Compound 2-1-209 | 4.2 | 55 | 59 |
| Example 78 | Compound 2-1-210 | 4.4 | 57 | 51 |
| Example 79 | Compound 2-1-211 | 4.2 | 51 | 52 |
| Example 80 | Compound 2-1-212 | 4.9 | 52 | 55 |
| Example 81 | Compound 2-1-213 | 4.4 | 54 | 56 |
| Example 82 | Compound 2-1-214 | 4.2 | 50 | 54 |
| Example 83 | Compound 2-1-215 | 4.9 | 55 | 53 |
| Example 84 | Compound 2-1-216 | 4.1 | 57 | 55 |
| Comparative Example 1 | NPB | 5.2 | 48 | 50 |

As a result of the experiments, it can be confirmed that the organic electroluminescence devices manufactured by Examples 65 to 42 in which the compound according to the present application was used had a lower driving voltage, higher light emitting efficiency, and better service life characteristics than the organic electroluminescence device of Comparative Example 1 in the related art where NPB was used.

From the foregoing, preferred exemplary embodiments of the present application have been described, but the present application is not limited thereto, and it is natural that the exemplary embodiments can be variously modified and implemented within the scope of the claims and the detailed description of the invention, and the modifications also fall within the scope of the present application.

The invention claimed is:

1. A hetero-cyclic compound represented by the following Formula 1:

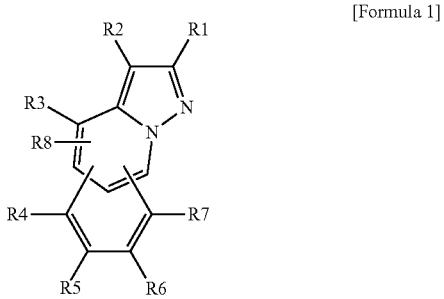

[Formula 1]

in Formula 1,
at least one of R1 and R2 is -(L)m-(Z)n,
L is a substituted or unsubstituted, monocyclic or polycyclic C$_6$ to C$_{60}$ arylene group; or a substituted or unsubstituted, monocyclic or polycyclic C$_2$ to C$_{60}$ heteroarylene group,
m is an integer of 0 to 3,
n is an integer of 1 to 5,
Z is selected from the group consisting of a substituted or unsubstituted, monocyclic or polycyclic C$_6$ to C$_{60}$ aryl group; a substituted or unsubstituted, monocyclic or polycyclic C$_2$ to C$_{60}$ heteroaryl group; —SiRR'R''; —P(=O)RR'; and NRR',
in case that m is an integer of 0, Z is selected from the group consisting of a substituted or unsubstituted, polycyclic C$_{10}$ to C$_{60}$ aryl group; a substituted or unsubstituted, monocyclic or polycyclic C$_2$ to C$_{60}$ heteroaryl group; —SiRR'R''; —P(=O)RR'; and NRR', the other of R1 and R2, and R3 to R8 are the same as or different from each other, and are each independently selected from the group consisting of hydrogen; deuterium; a halogen group; —CN; a substituted or unsubstituted, straight-chained or branched $C_1$ to $C_{60}$ alkyl group; a substituted or unsubstituted, straight-chained or branched $C_2$ to $C_{60}$ alkynyl group; a substituted or unsubstituted, monocyclic or polycyclic $C_3$ to $C_{60}$ cycloalkyl group; a substituted or unsubstituted, monocyclic or polycyclic $C_2$ to $C_{60}$ heterocycloalkyl group; a substituted or unsubstituted, monocyclic or polycyclic $C_6$ to $C_{60}$ aryl group; a substituted or unsubstituted, monocyclic or polycyclic $C_2$ to $C_{60}$ heteroaryl group; —SiRR'R''; —P(=O)RR'; and —NRR', and R, R', and R'' are the same as or different from each other, and are each independently selected from the group consisting of a substituted or unsubstituted, straight-chained or branched $C_1$ to $C_{60}$ alkyl group; a substituted or unsubstituted, monocyclic or polycyclic $C_3$ to $C_{60}$ cycloalkyl group; a substituted or unsubstituted, monocyclic or polycyclic $C_6$ to $C_{60}$ aryl group; and a substituted or unsubstituted, monocyclic or polycyclic $C_2$ to $C_{60}$ heteroaryl group.

2. The hetero-cyclic compound of claim 1, wherein Formula 1 is represented by the following Formula 2:

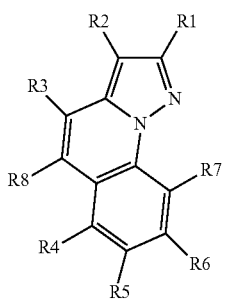

[Formula 2]

in Formula 2, R1 to R8 are the same as those defined in Formula 1.

3. The hetero-cyclic compound of claim 1, wherein Formula 1 is represented by the following Formula 3:

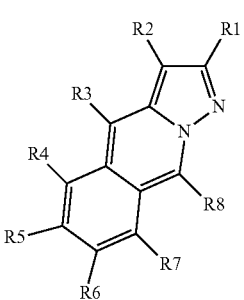

[Formula 3]

in Formula 3, R1 to R8 are the same as those defined in Formula 1.

4. The hetero-cyclic compound of claim 1, wherein at least one of R1 and R2 is a substituted or unsubstituted, polycyclic $C_6$ to $C_{60}$ aryl group; a substituted or unsubstituted, monocyclic or polycyclic $C_2$ to $C_{60}$ heteroaryl group; —SiRR'R''; —P(=O)RR' or —NRR', and R, R', and R'' are the same as or different from each other, and are each independently selected from the group consisting of a substituted or unsubstituted, straight-chained or branched $C_1$ to $C_{60}$ alkyl group; a substituted or unsubstituted, monocyclic or polycyclic $C_3$ to $C_{60}$ cycloalkyl group; a substituted or unsubstituted, monocyclic or polycyclic $C_6$ to $C_{60}$ aryl group; and a substituted or unsubstituted, monocyclic or polycyclic $C_2$ to $C_{60}$ heteroaryl group.

5. The hetero-cyclic compound of claim 1, wherein Z is

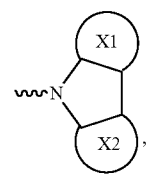

and

X1 and X2 are the same as or different from each other, and are each independently a substituted or unsubstituted, monocyclic or polycyclic $C_6$ to $C_{60}$ aromatic hydrocarbon ring; or a substituted or unsubstituted, monocyclic or polycyclic $C_2$ to $C_{60}$ aromatic hetero ring.

6. The hetero-cyclic compound of claim 5, wherein

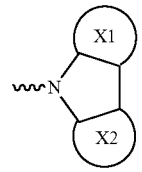

is represented by any one of the following structural formulae:

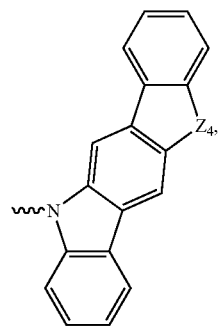 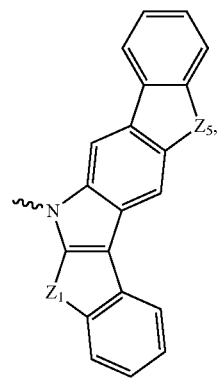

-continued

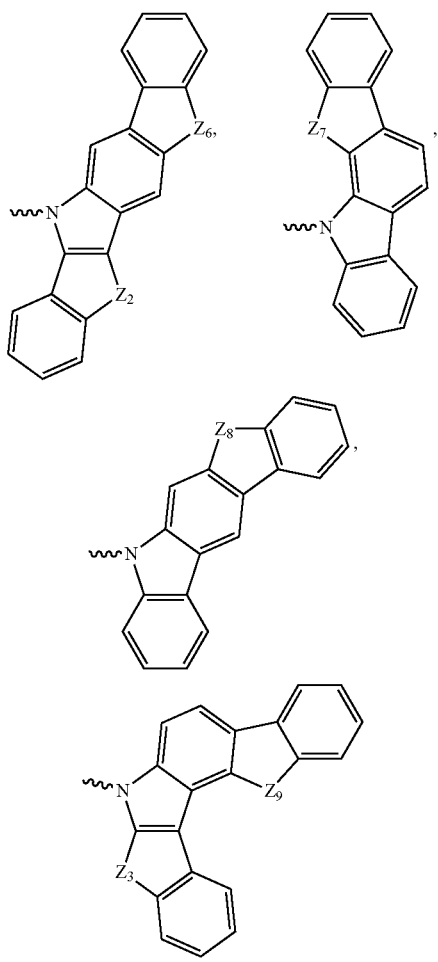

in the structural formulae, $Z_1$ to $Z_3$ are the same as or different from each other, and are each independently S or O, $Z_4$ to $Z_9$ are the same as or different from each other, and are each independently CY'Y", NY', S, or O, and Y' and Y" are the same as or different from each other, and are each independently hydrogen; deuterium; a substituted or unsubstituted, straight-chained or branched $C_1$ to $C_{60}$ alkyl group; or a substituted or unsubstituted, monocyclic or polycyclic $C_6$ to $C_{60}$ aryl group.

7. The hetero-cyclic compound of claim 1, wherein R3 to R8 are each independently hydrogen or deuterium.

8. The hetero-cyclic compound of claim 1, wherein Formula 1 is represented by the following Formula 4 or 5:

[Formula 4]

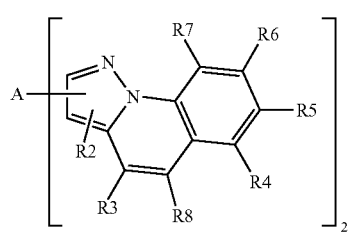

-continued

[Formula 5]

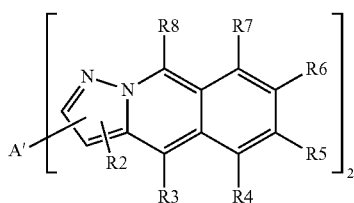

in Formulae 4 and 5,

A and A' are each independently selected from the group consisting of a direct bond; a substituted or unsubstituted, straight-chained or branched $C_2$ to $C_{60}$ alkylene group; a substituted or unsubstituted, straight-chained or branched $C_2$ to $C_{60}$ alkynylene group; a substituted or unsubstituted, monocyclic or polycyclic $C_3$ to $C_{60}$ cycloalkylene group; a substituted or unsubstituted, monocyclic or polycyclic $C_2$ to $C_{60}$ heterocycloalkylene group; a substituted or unsubstituted, monocyclic or polycyclic $C_6$ to $C_{60}$ arylene group; and a substituted or unsubstituted, monocyclic or polycyclic $C_2$ to $C_{60}$ heteroarylene group, and R2 to R8 are the same as those defined in Formula 1.

9. The hetero-cyclic compound of claim 1, wherein Formula 1 is represented by any one of the following compounds:

Compound 1-1-1

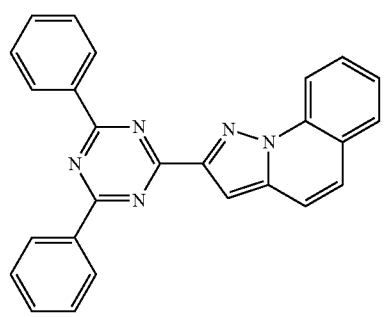

Compound 1-1-2

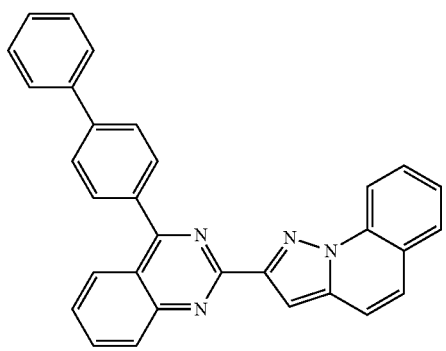

Compound 1-1-3
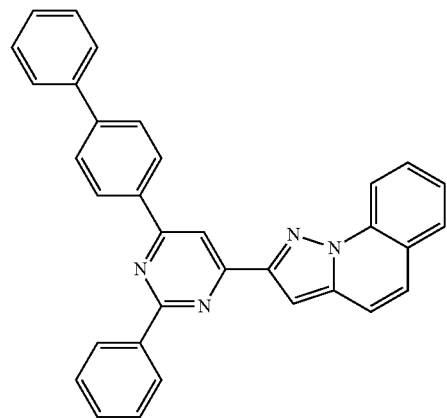
Compound 1-1-7
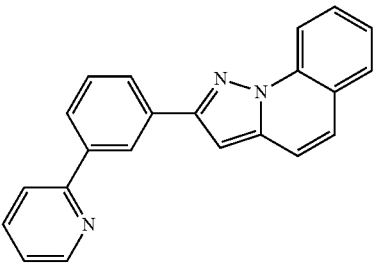
Compound 1-1-4
Compound 1-1-8
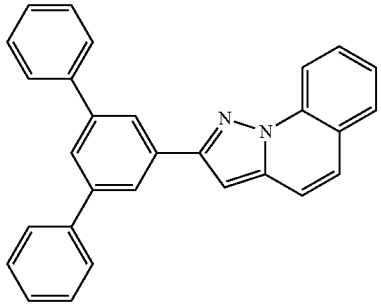
Compound 1-1-9
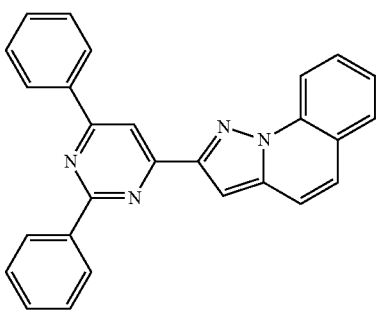
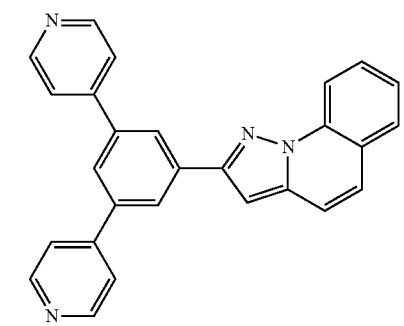
Compound 1-1-5
Compound 1-1-10
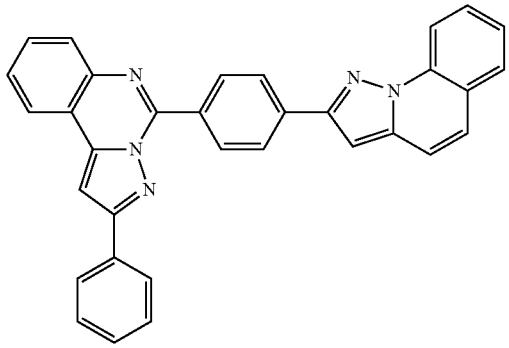
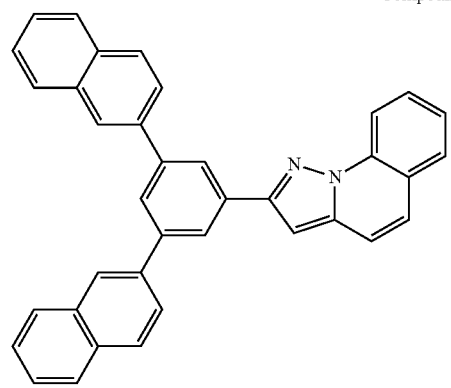
Compound 1-1-6
Compound 1-1-11
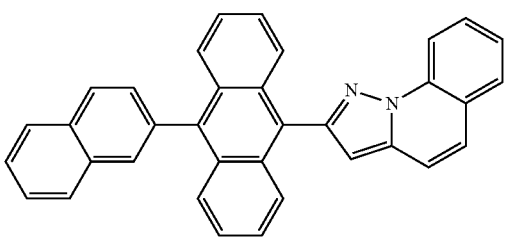

Compound 1-1-12
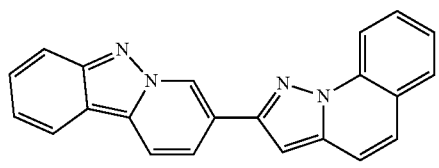
Compound 1-1-13
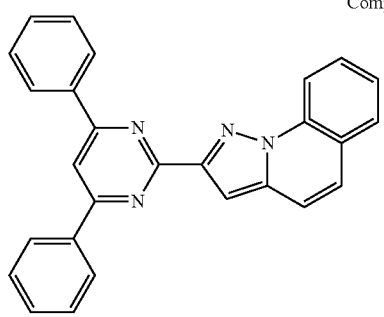
Compound 1-1-14
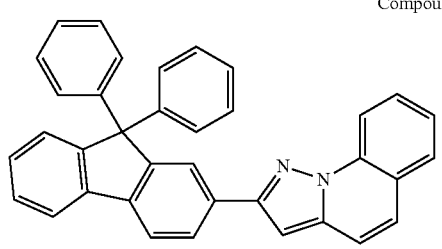
Compound 1-1-15
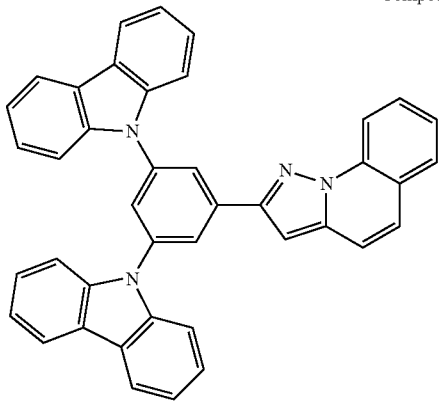
Compound 1-1-16
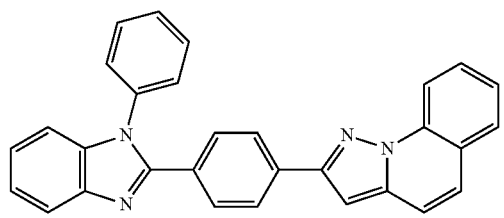
Compound 1-1-17
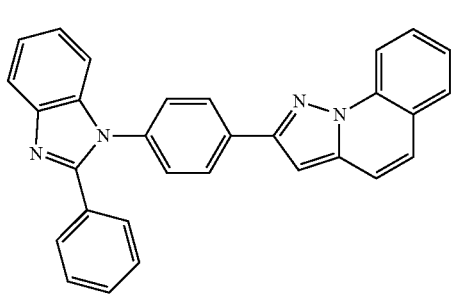
Compound 1-1-18
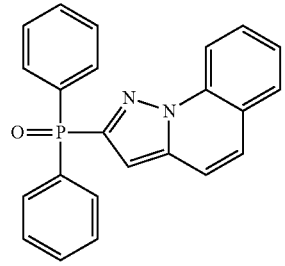
Compound 1-1-19
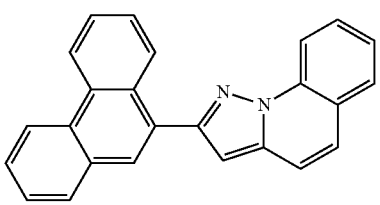
Compound 1-2-20
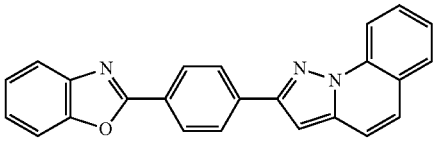
Compound 1-2-21
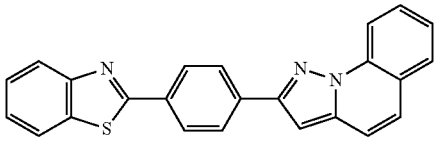
Compound 1-2-22
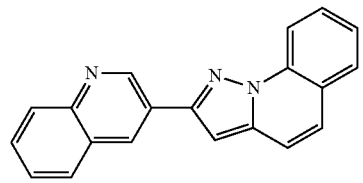
Compound 1-2-23
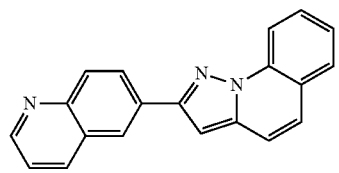

Compound 1-2-24
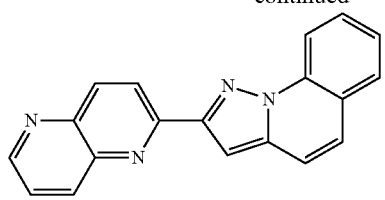
Compound 1-2-25
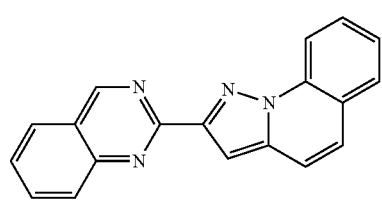
Compound 1-2-26
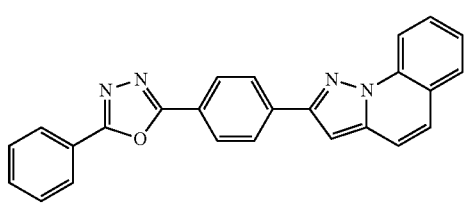
Compound 1-2-27
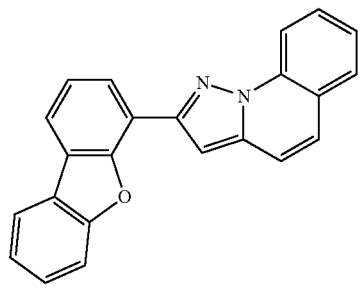
Compound 1-2-28
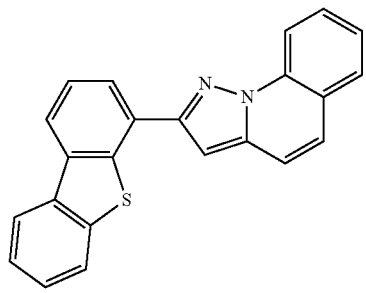
Compound 2-1-29
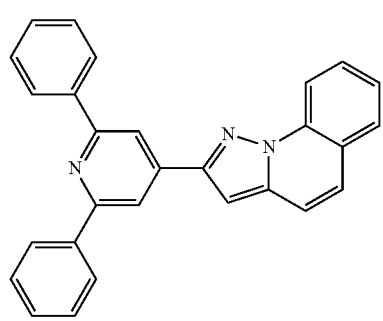
Compound 2-1-30
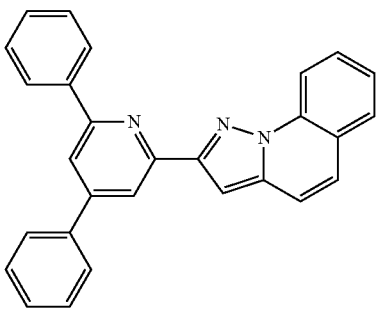
Compound 2-1-31
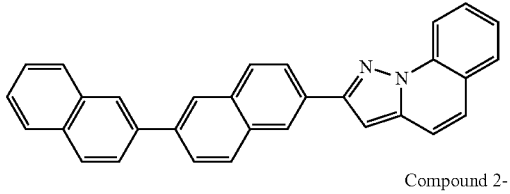
Compound 2-1-32
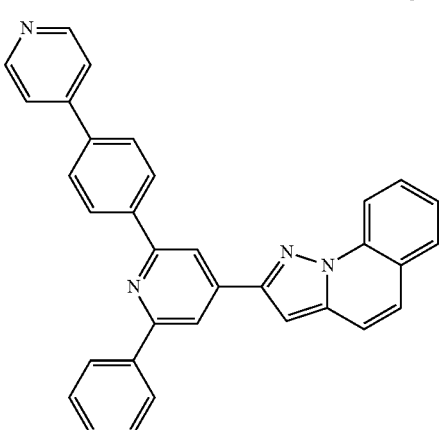
Compound 1-1-33
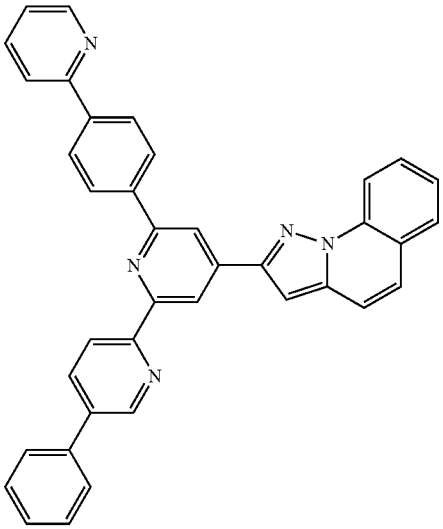

Compound 1-1-34
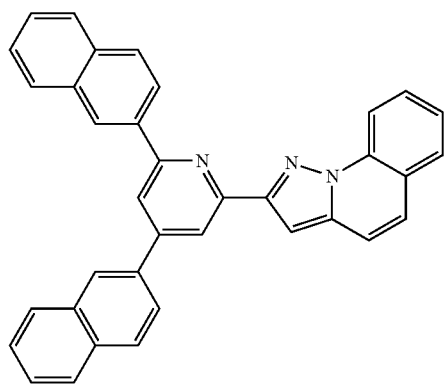
Compound 1-1-35
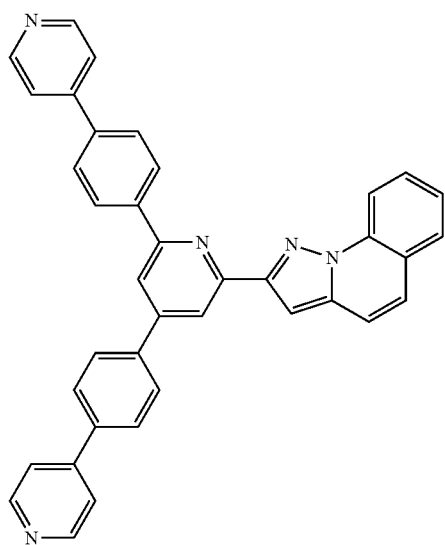
Compound 1-1-36
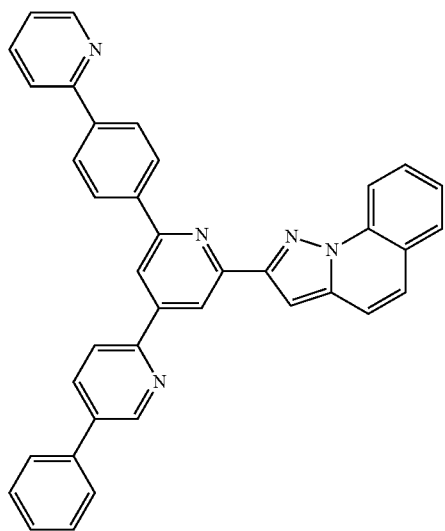
Compound 1-1-37
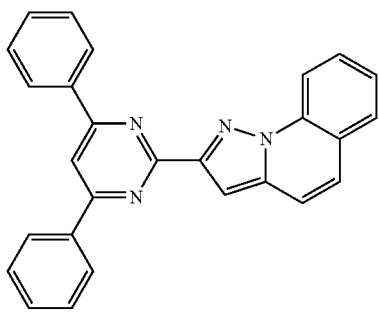
Compound 1-1-38
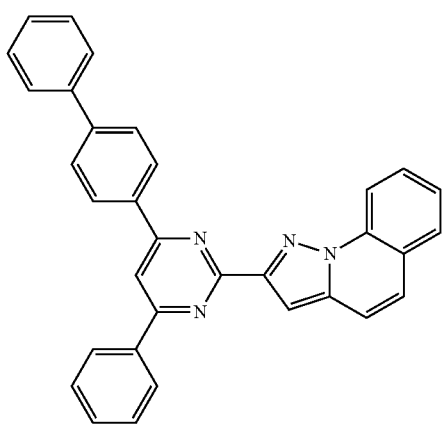
Compound 1-1-39
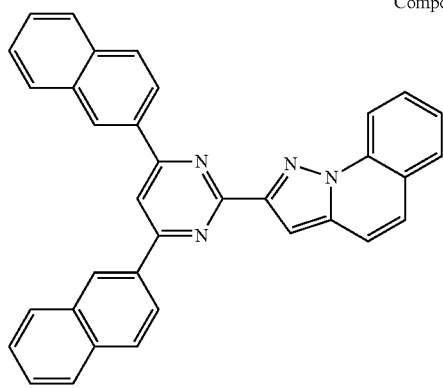

Compound 1-1-40
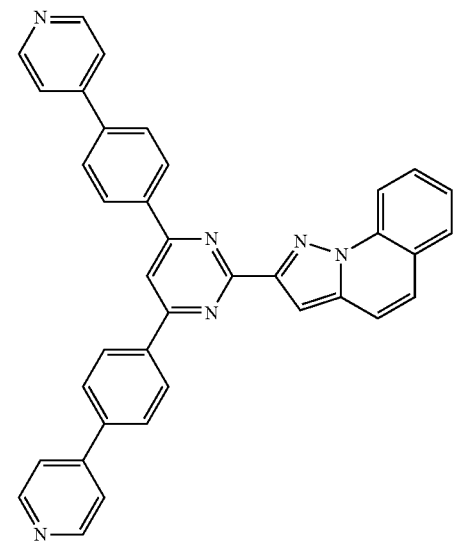
Compound 1-1-41
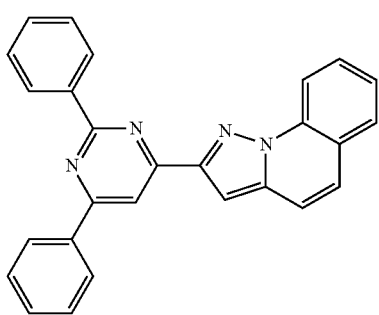
Compound 1-1-42
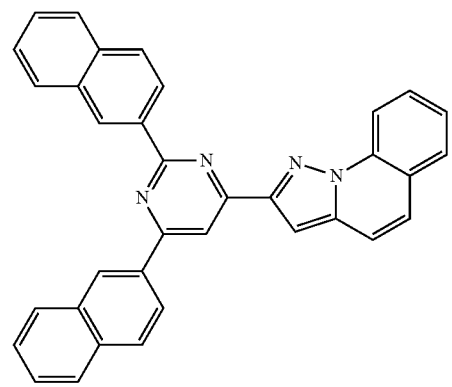
Compound 1-1-43
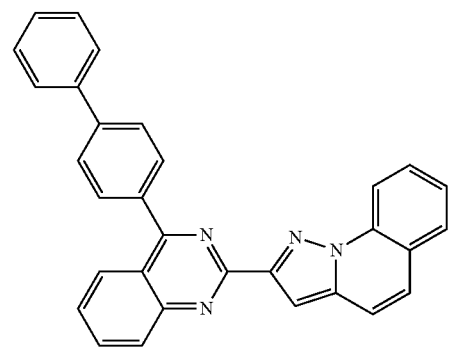
Compound 1-1-44
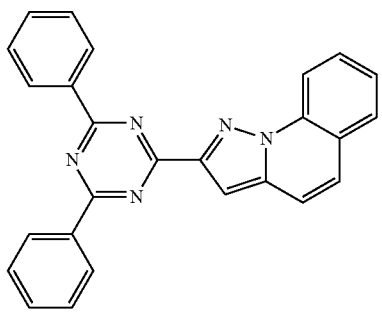
Compound 1-1-45
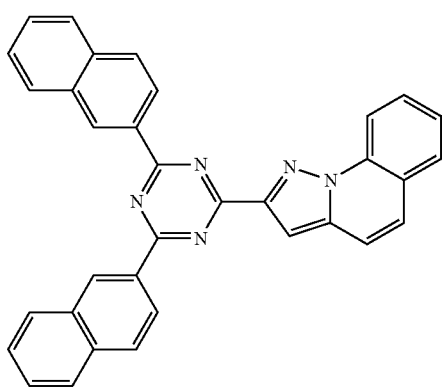
Compound 1-1-46
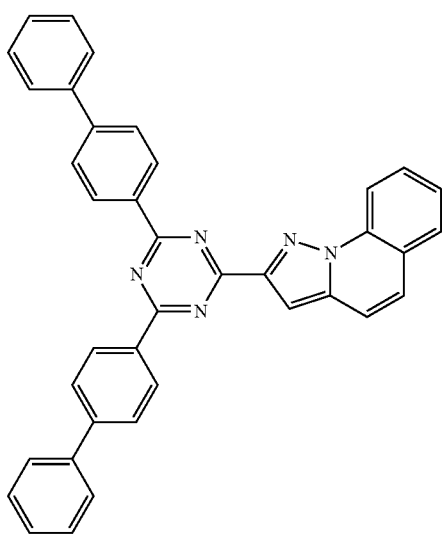
Compound 1-1-47
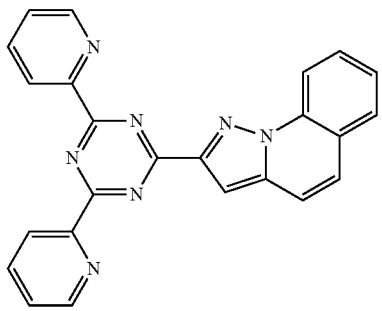

Compound 1-1-48
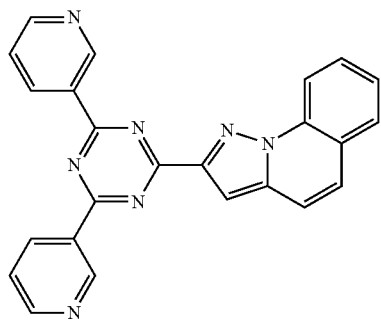
Compound 1-1-49
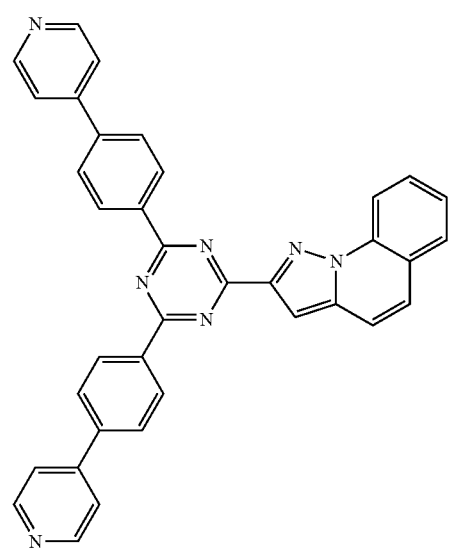
Compound 1-1-50
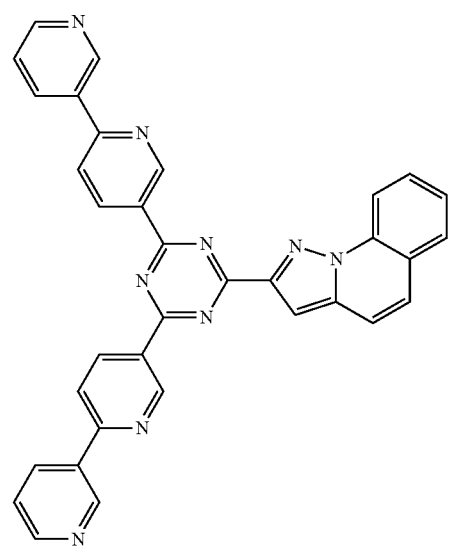
Compound 1-1-51
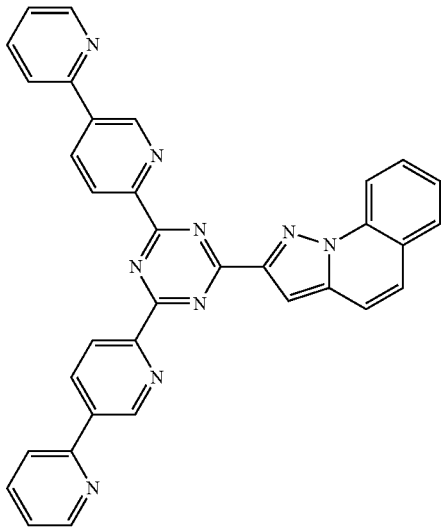
Compound 1-1-52
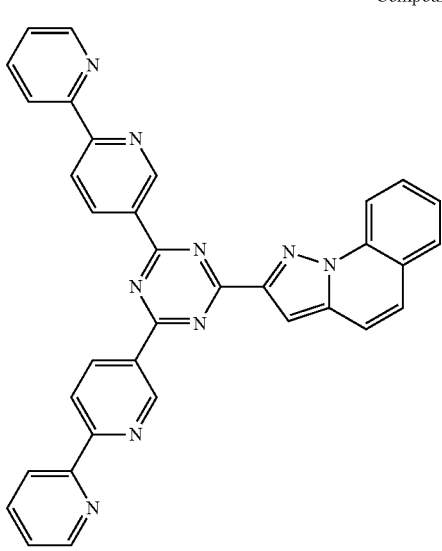
Compound 1-1-53
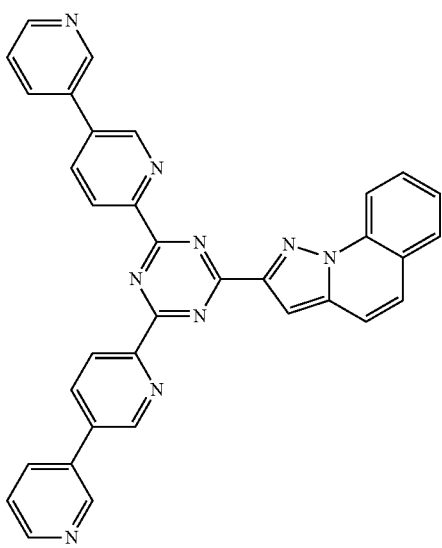

Compound 1-1-54
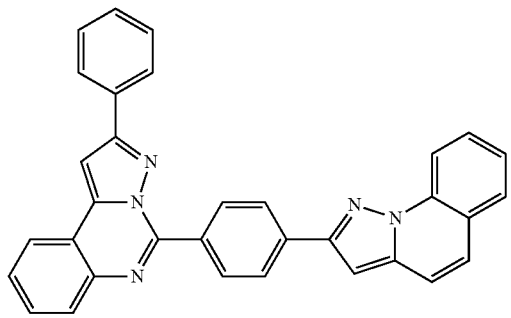
Compound 1-1-55
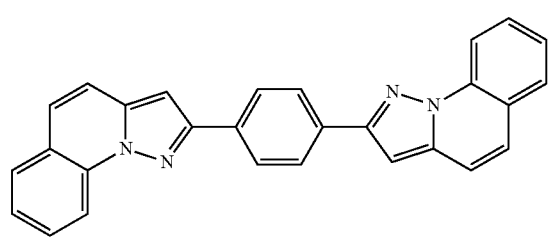
Compound 1-1-56
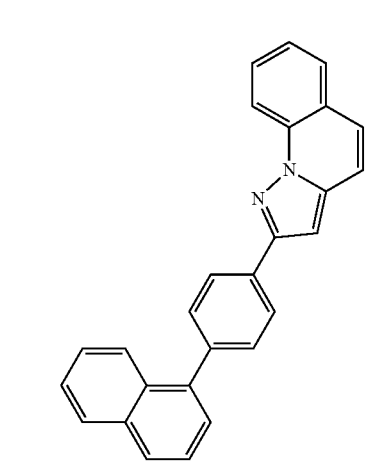
Compound 1-1-57
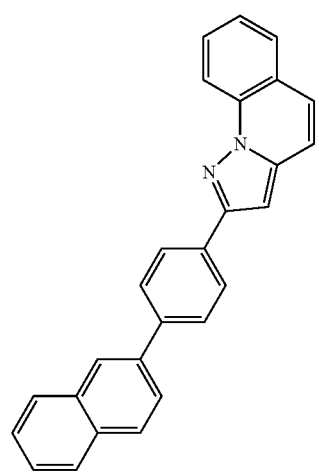
Compound 1-1-58
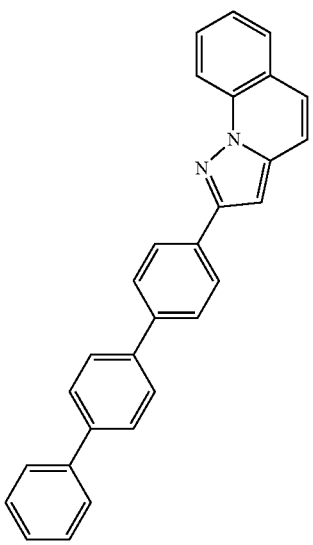
Compound 1-1-59
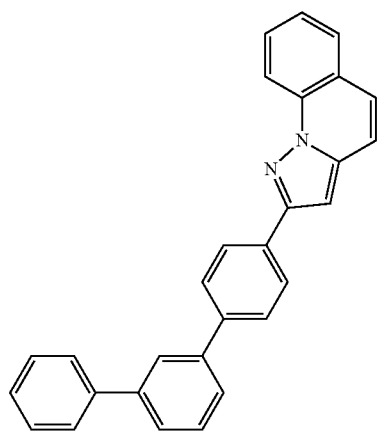
Compound 1-1-60
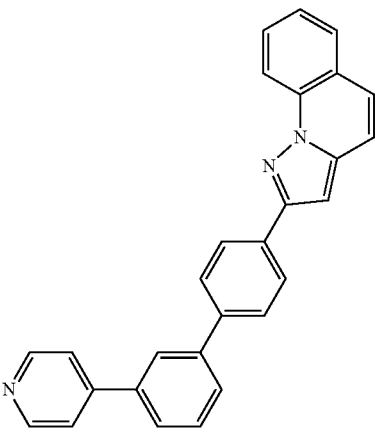

Compound 1-1-61
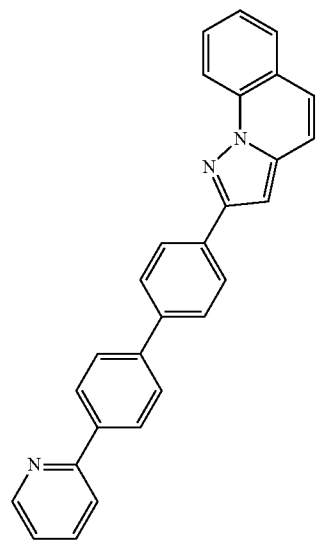
Compound 1-1-62
Compound 1-1-63
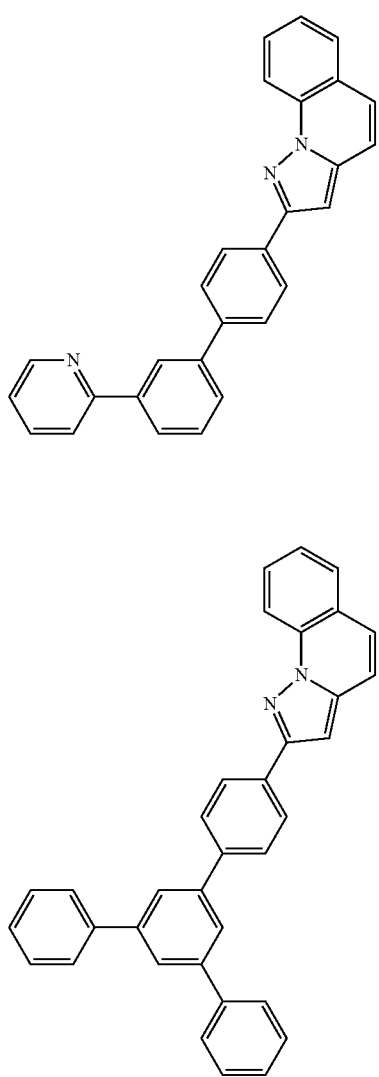
Compound 1-1-64
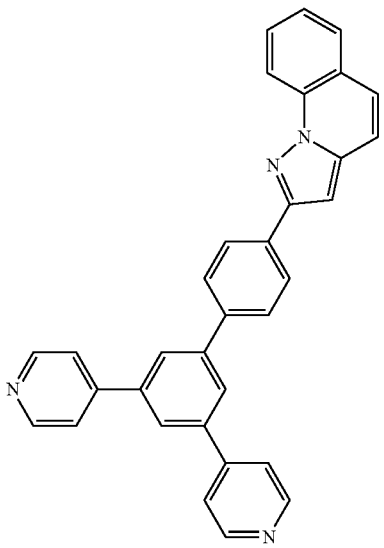
Compound 1-1-65
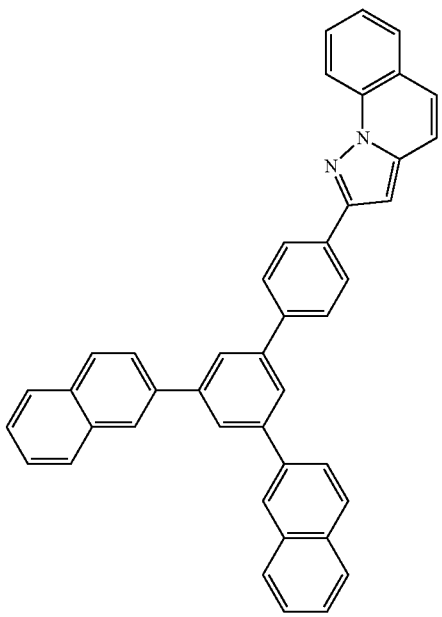

Compound 1-1-66
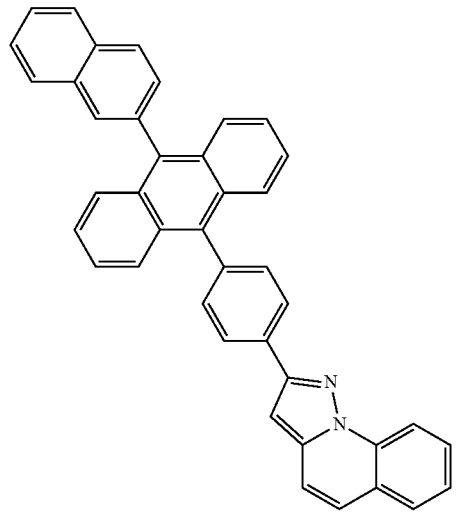
Compound 1-1-67
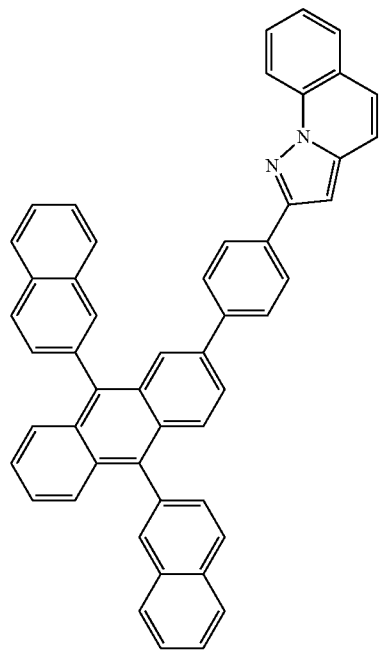
Compound 1-1-68
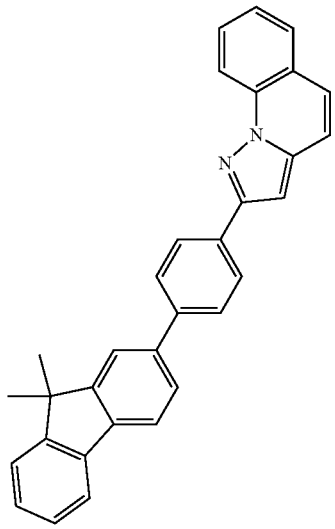
Compound 1-1-69
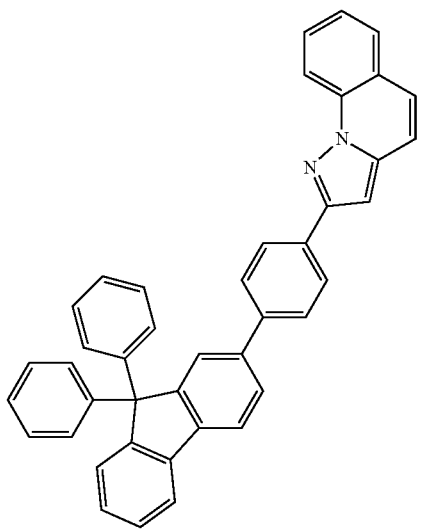
Compound 1-1-70
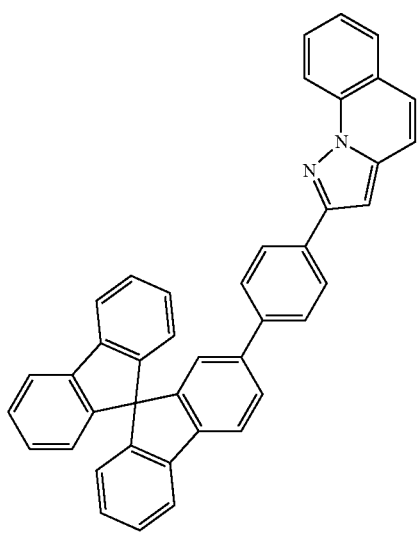

Compound 1-1-71
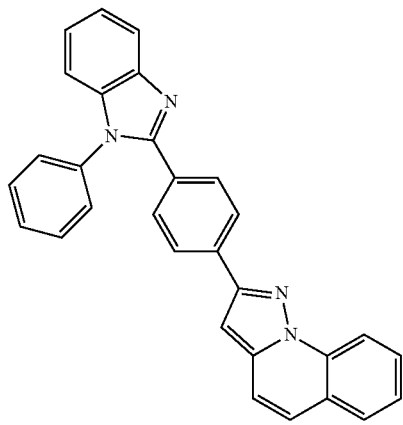
Compound 1-1-72
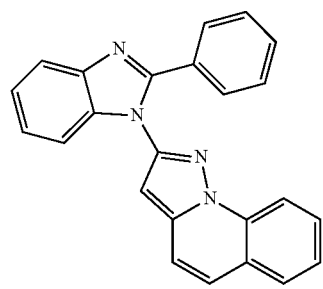
Compound 1-1-73
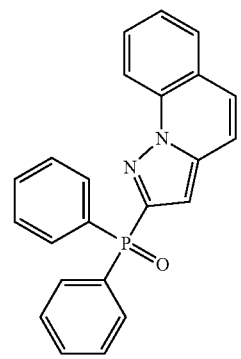
Compound 1-1-74
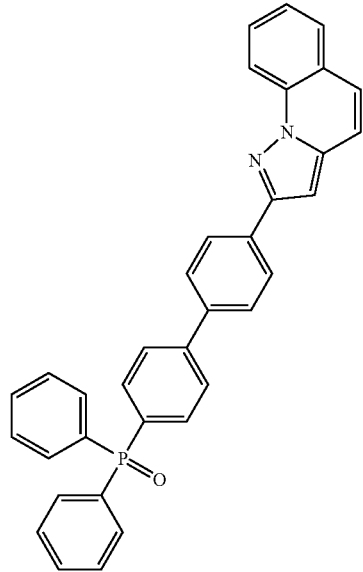
Compound 1-1-75
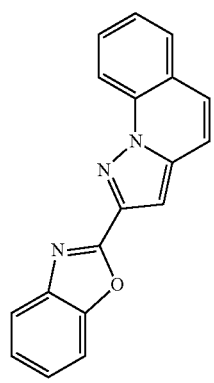
Compound 1-1-76
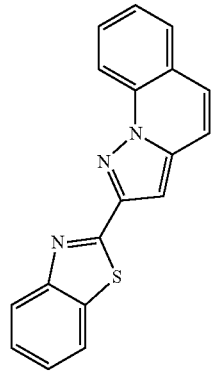
Compound 1-1-77
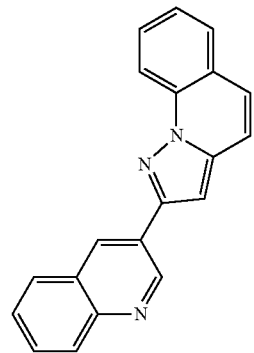
Compound 1-1-79
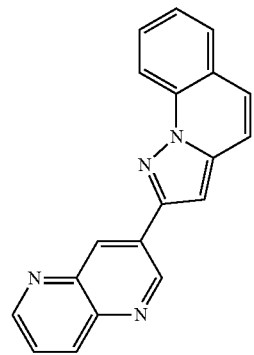

Compound 1-1-80
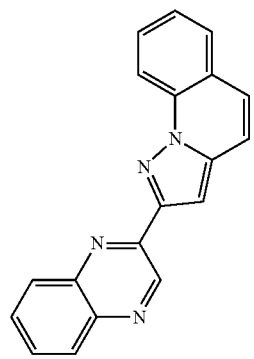
Compound 1-1-81
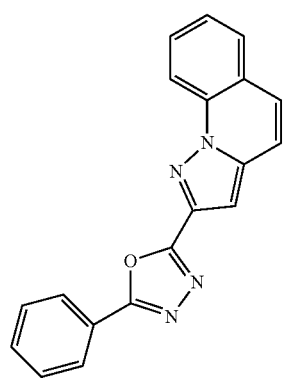
Compound 1-1-82
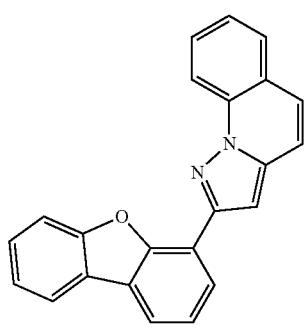
Compound 1-1-83
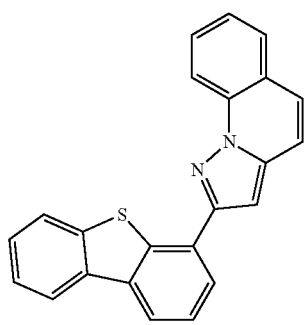
Compound 1-1-84
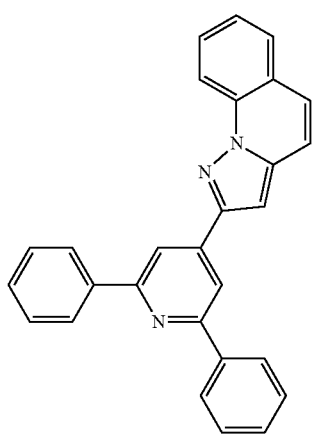
Compound 1-1-85
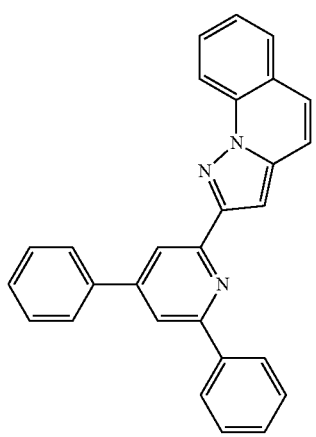
Compound 1-1-86
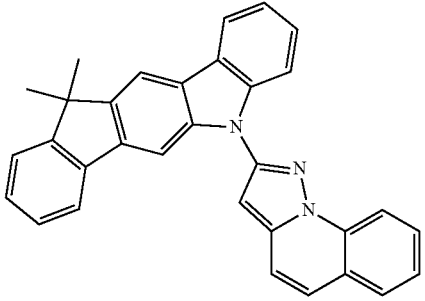
Compound 1-1-87
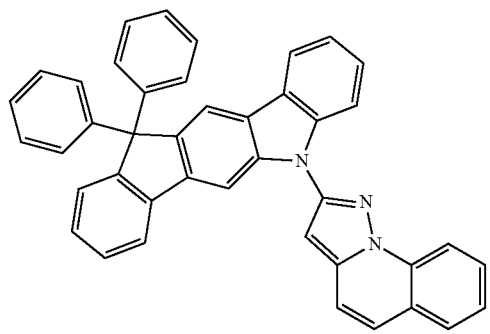

Compound 1-1-88
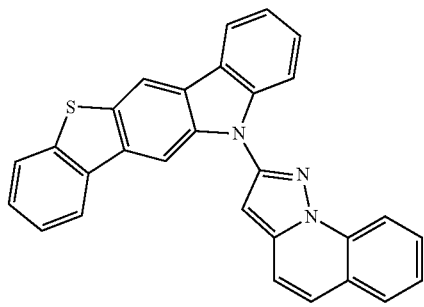
Compound 1-1-89
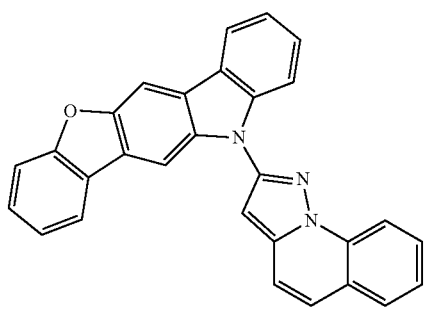
Compound 1-1-90
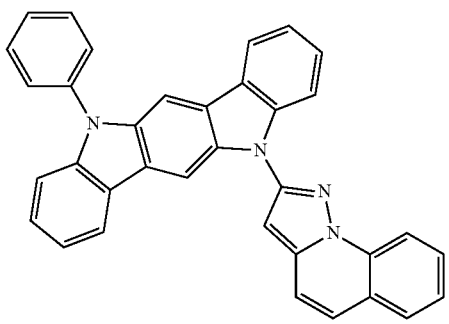
Compound 1-1-91
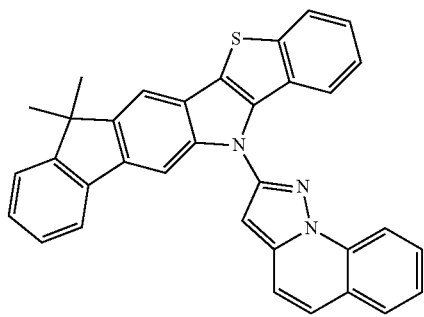
Compound 1-1-92
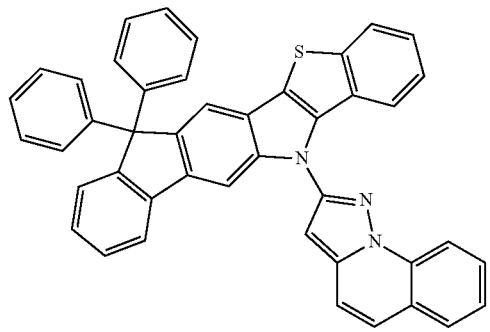
Compound 1-1-93
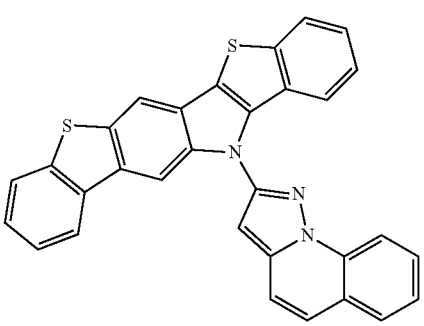
Compound 1-1-94
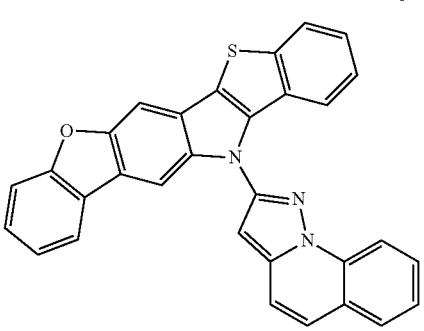
Compound 1-1-95
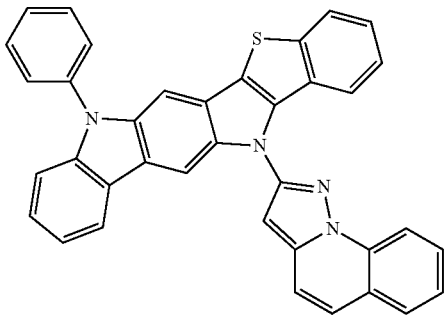

Compound 1-1-96
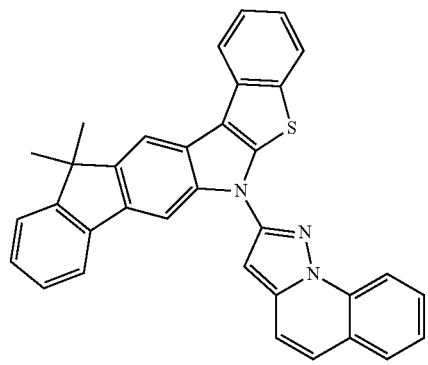
Compound 1-1-97
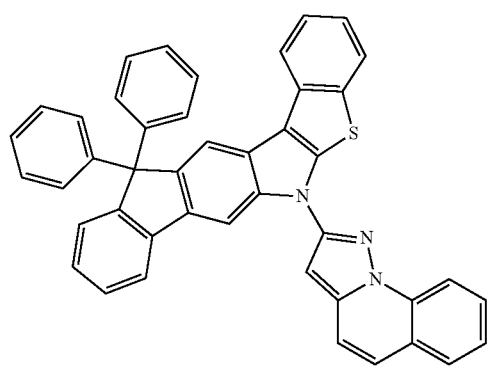
Compound 1-1-98
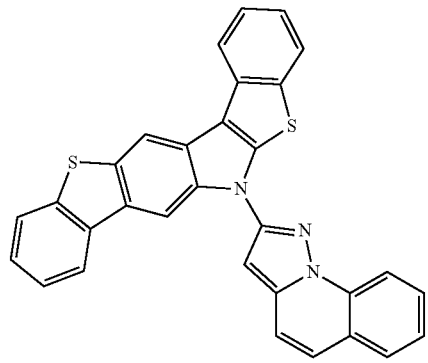
Compound 1-1-99
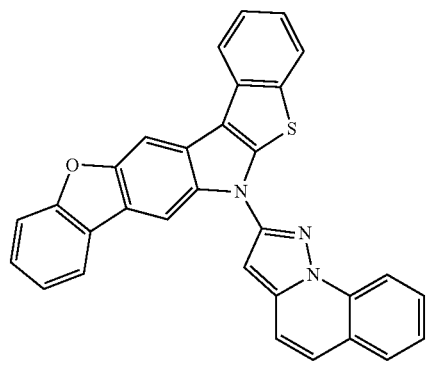
Compound 1-1-100
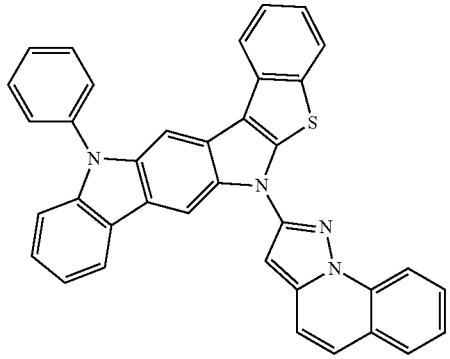
Compound 1-1-101
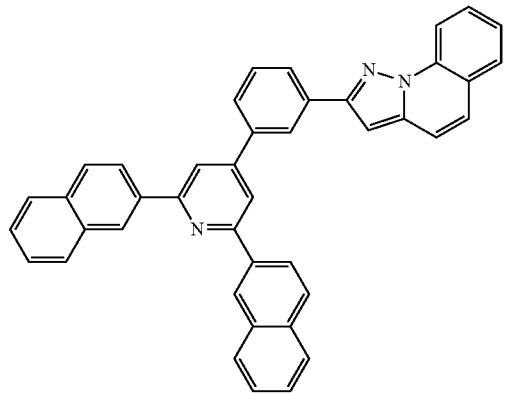
Compound 1-1-102
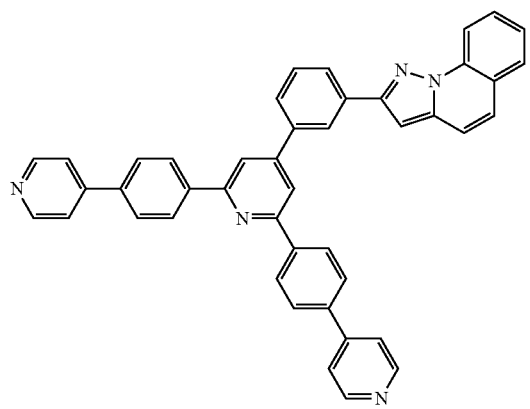
Compound 1-1-103
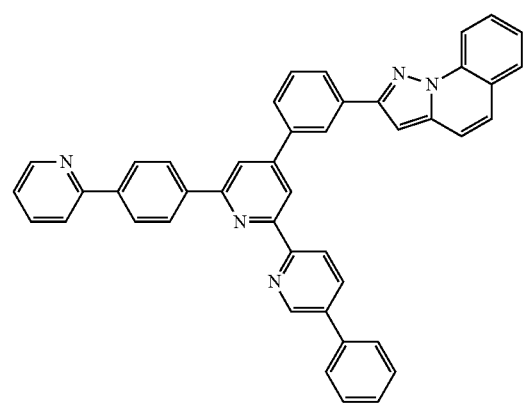

Compound 1-1-104
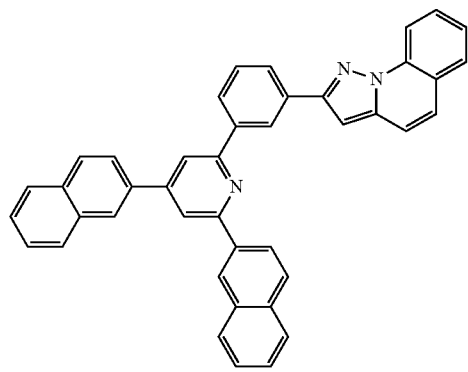
Compound 1-1-104
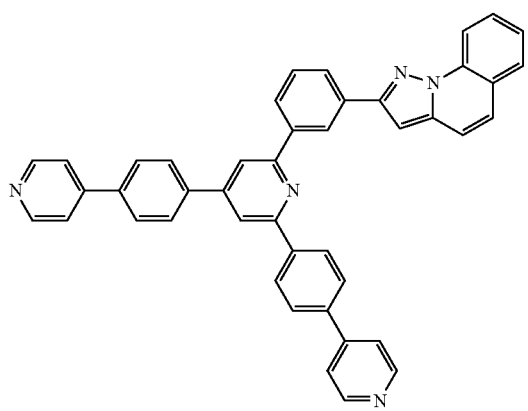
Compound 1-1-106
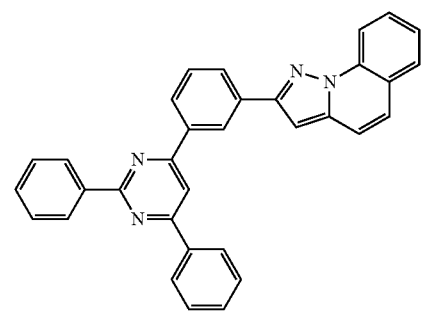
Compound 1-1-107
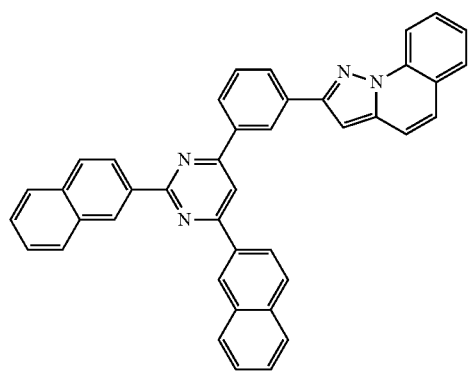
Compound 1-1-108
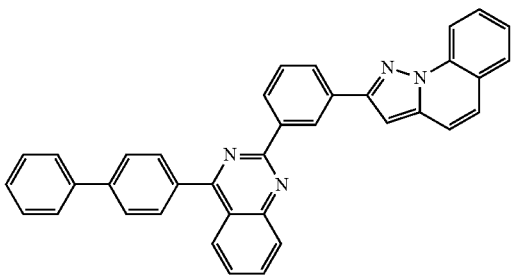
Compound 1-1-109
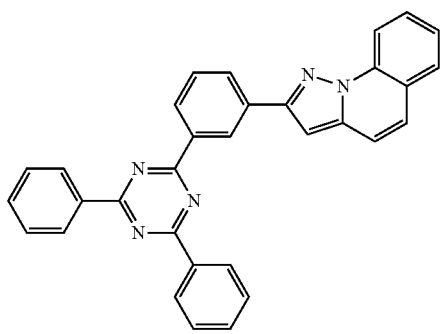
Compound 1-1-110
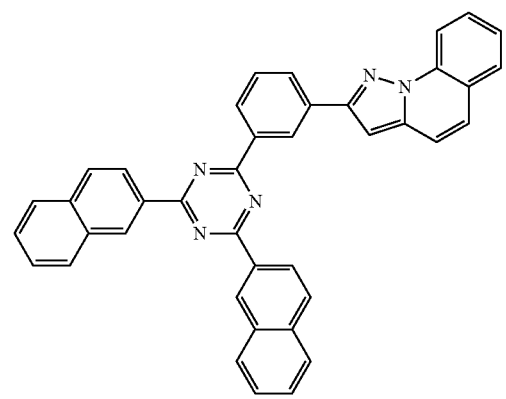
Compound 1-1-11
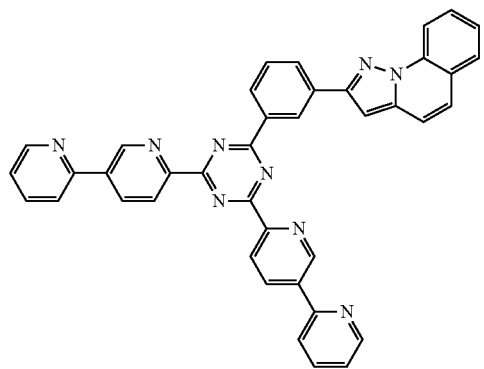

Compound 1-1-112
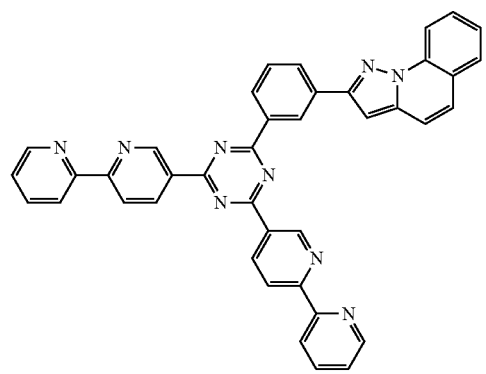
Compound 1-1-116
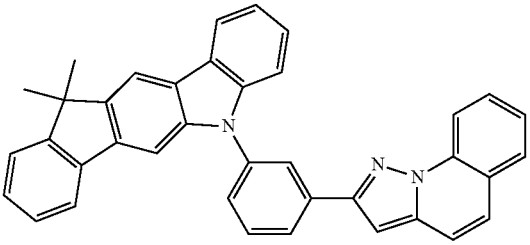
Compound 1-1-113
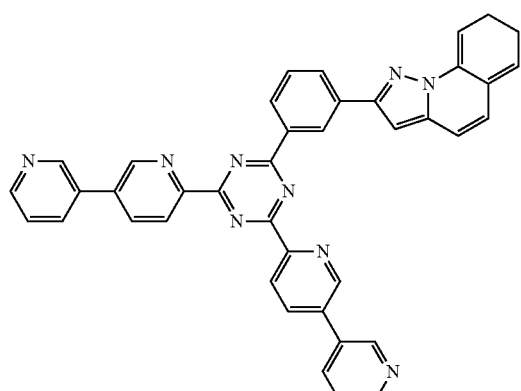
Compound 1-1-117
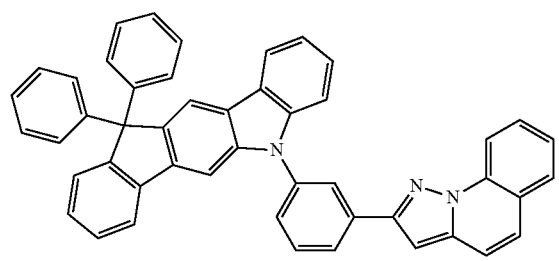
Compound 1-1-118
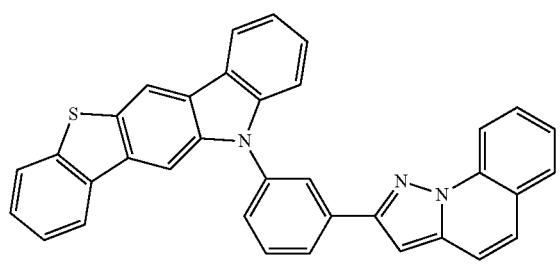
Compound 1-1-114
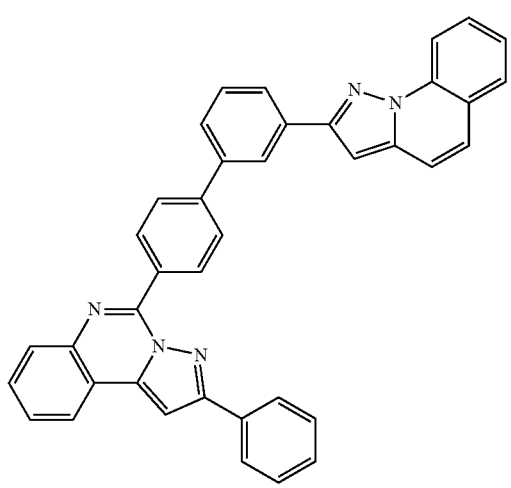
Compound 1-1-119
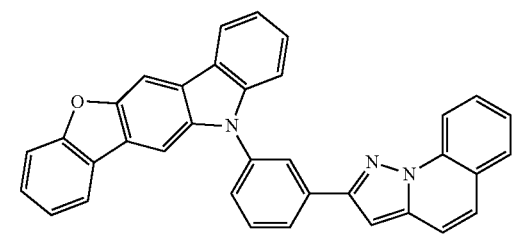
Compound 1-1-115
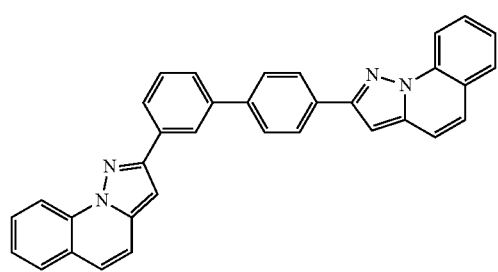
Compound 1-1-120
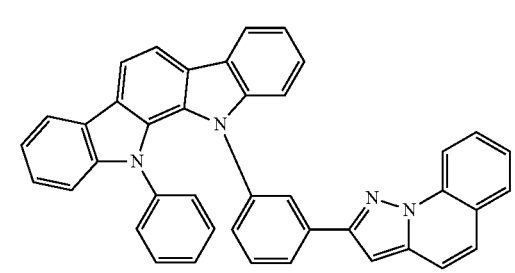

-continued
Compound 1-1-121
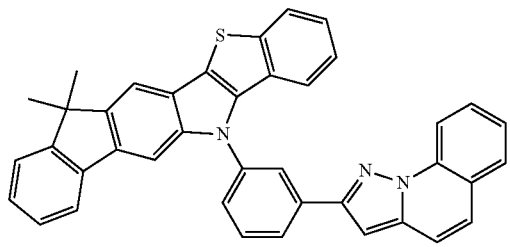
Compound 1-1-122
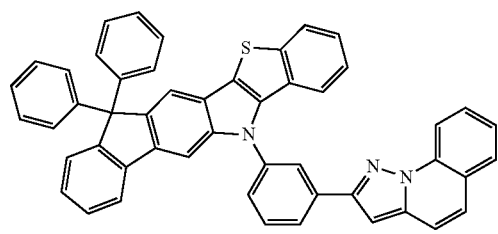
Compound 1-1-123
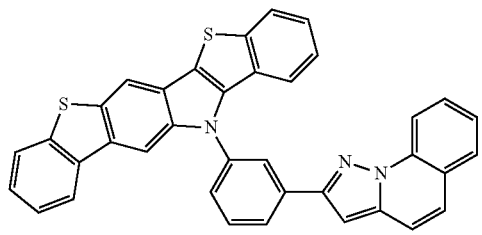
Compound 1-1-124
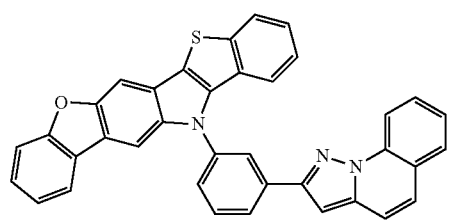
Compound 1-1-125
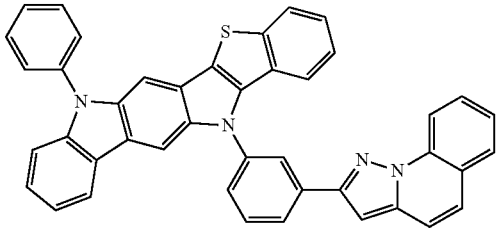
Compound 1-1-126
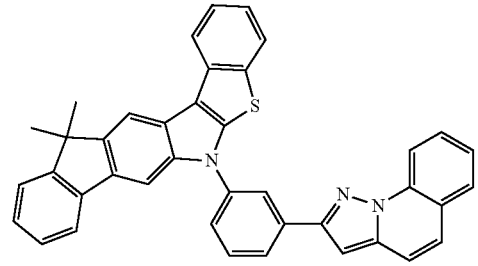
-continued
Compound 1-1-127
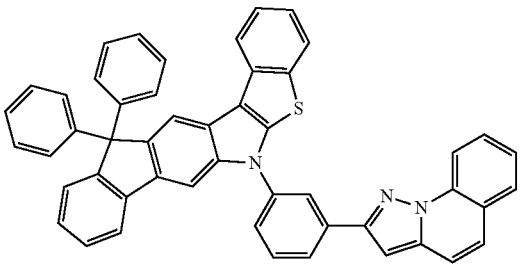
Compound 1-1-128
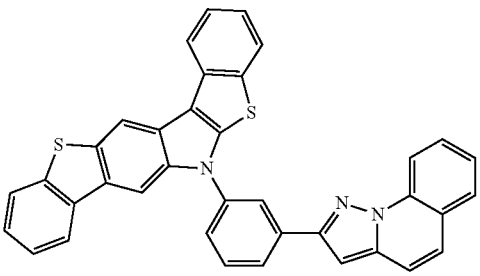
Compound 1-1-129
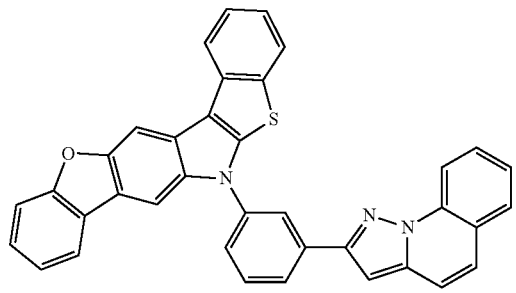
Compound 1-1-130
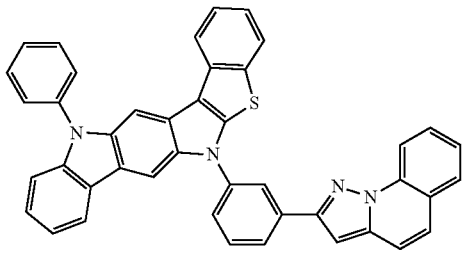
Compound 1-1-131
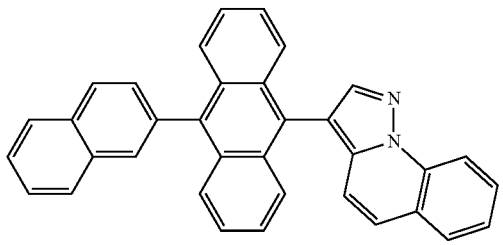

Compound 1-1-132
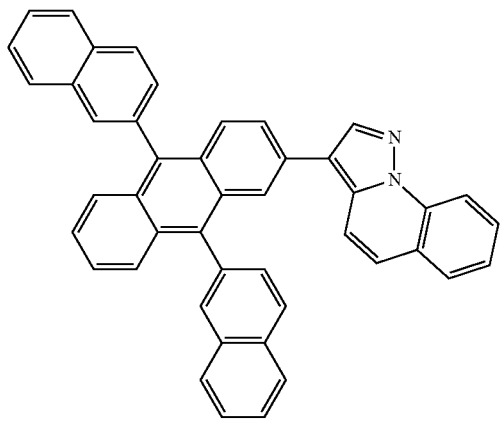
Copound 1-1-133
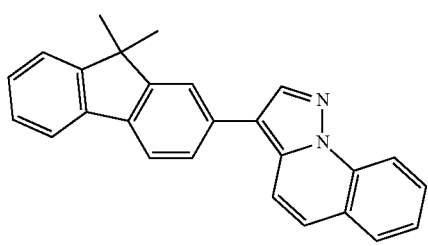
Compound 1-1-134
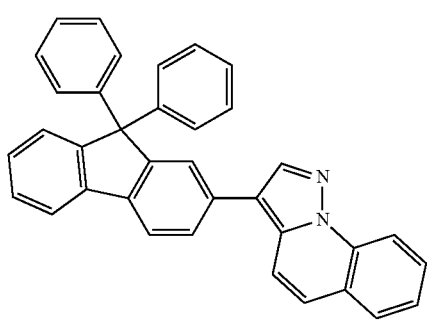
Compound 1-1-135
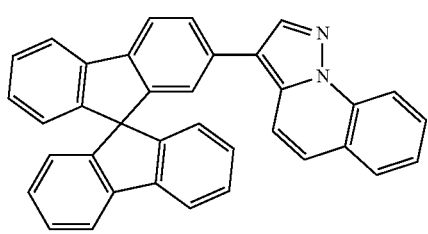
Compound 1-1-136
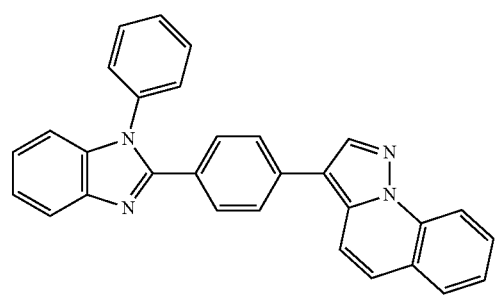
Compound 1-1-137
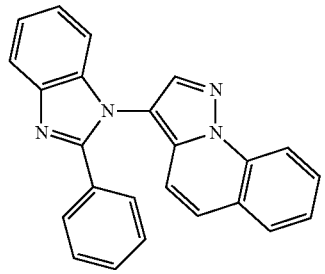
Compound 1-1-138
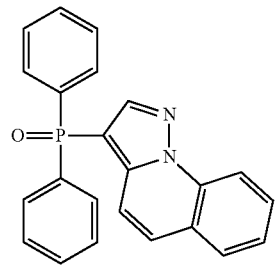
Compound 1-1-139
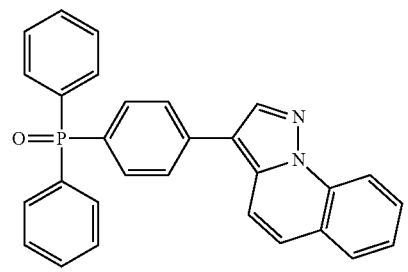
Compound 1-1-140
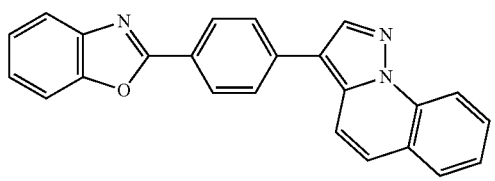
Compound 1-1-141
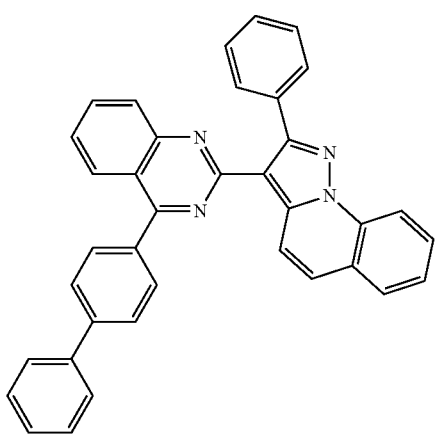

Compound 1-1-142
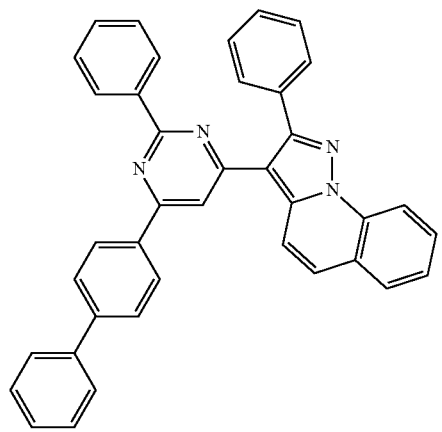
Compound 1-1-143
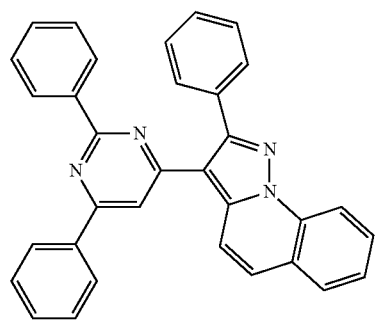
Compound 1-1-144
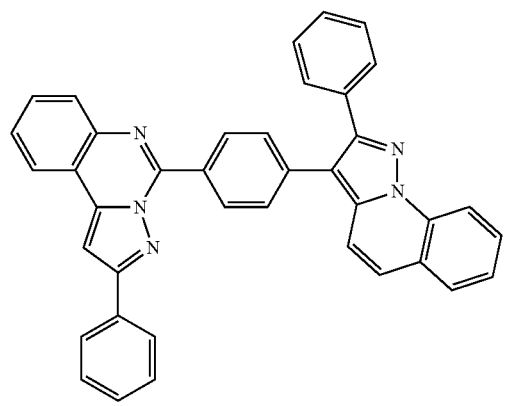
Compound 1-1-145
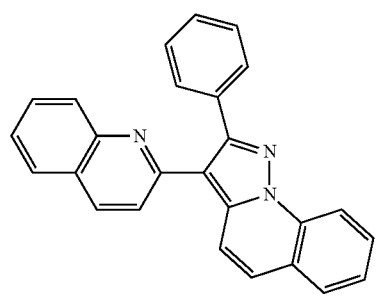
Compound 1-1-146
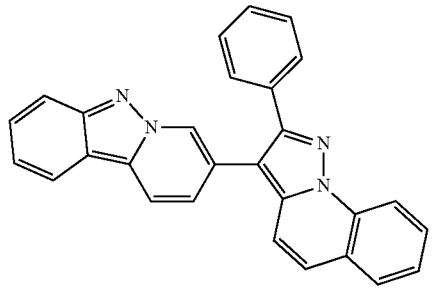
Comppound 1-1-147
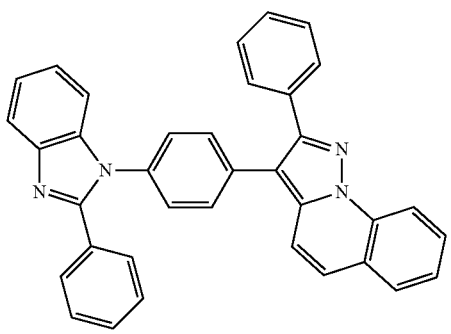
Compound 1-1-148
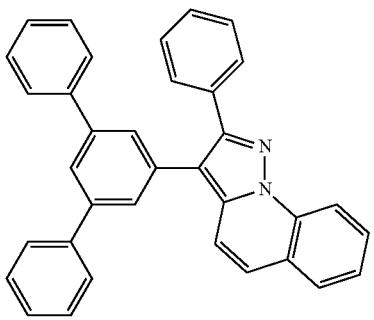
Compound 1-1-149
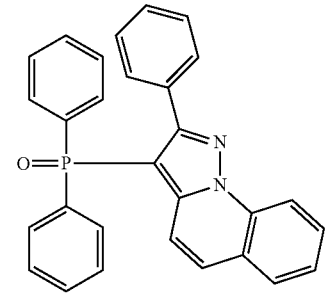
Compound 1-1-150
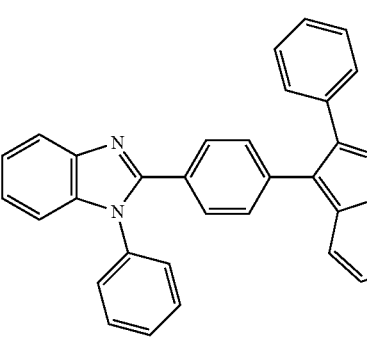

Compond 1-1-151
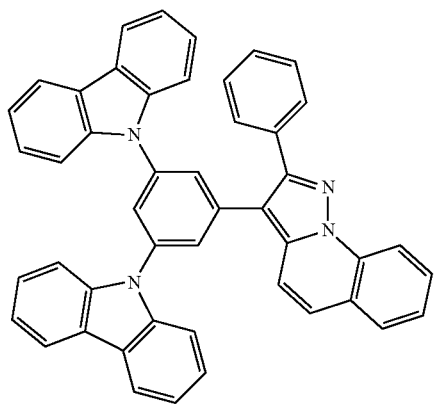
Compound 1-1-152
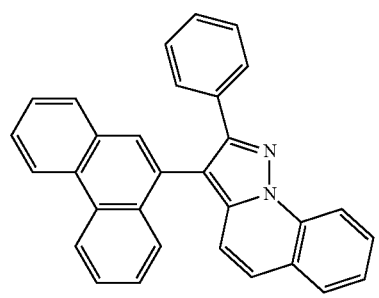
Compound 1-1-153
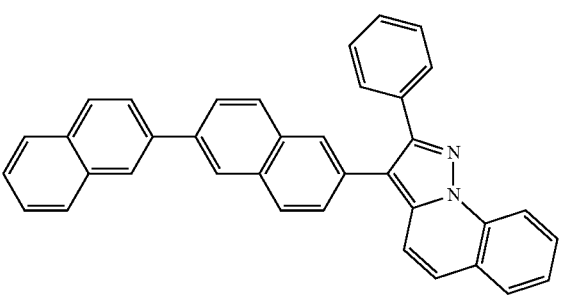
Compound 1-1-154
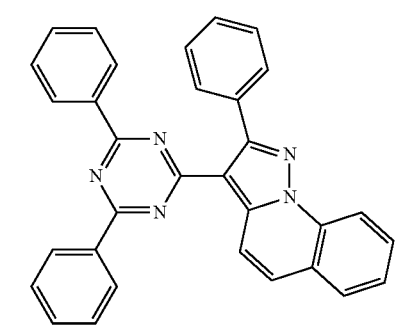
Compound 1-1-155
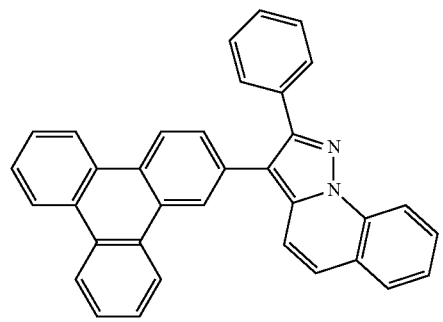
Compound 1-1-156
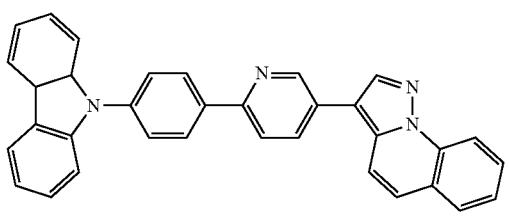
Compound 1-1-157
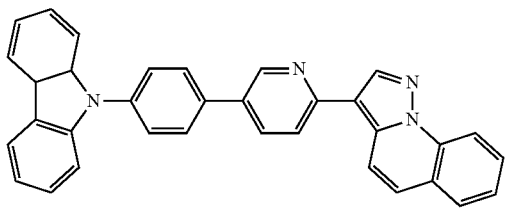
Compound 1-1-158
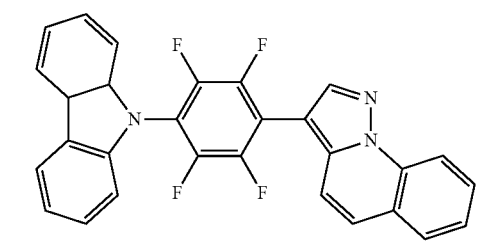
Compound 1-1-159
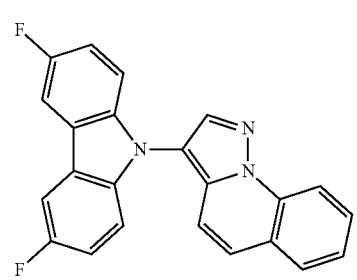

Compound 1-1-160
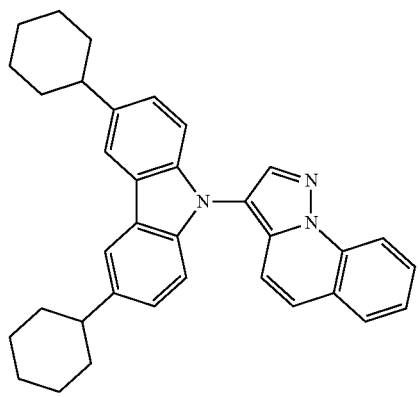
Compound 1-1-161
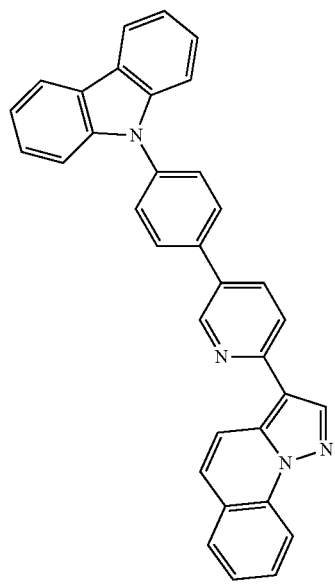
Compound 1-1-162
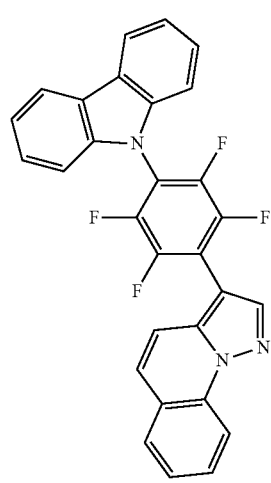
Compound 1-1-163
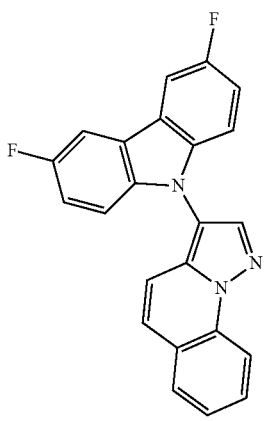
Compound 1-1-164
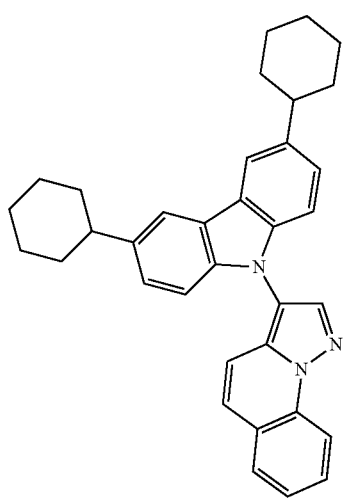
Compound 1-1-165
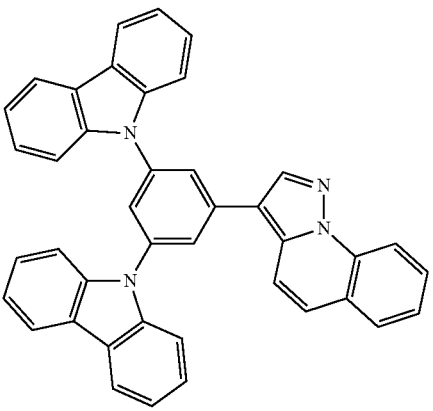

-continued
Compound 1-1-166
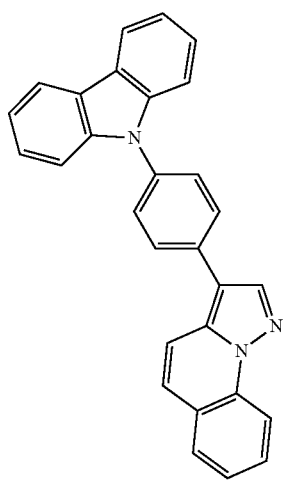
Compound 1-1-167
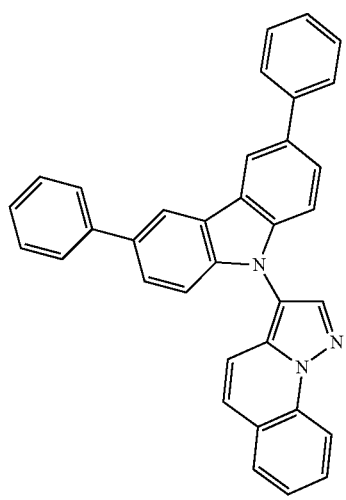
Compound 1-1-168
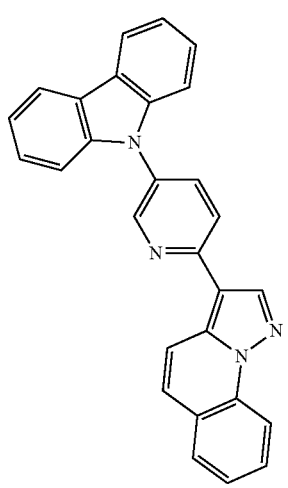
-continued
Compound 1-1-169
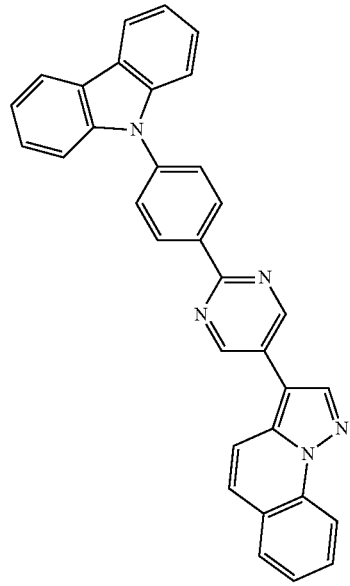
Compound 1-1-170
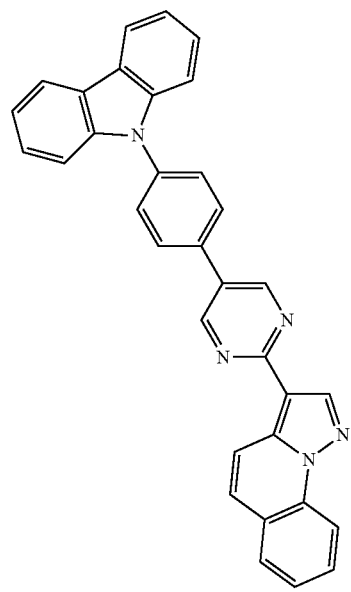
Compound 1-1-171
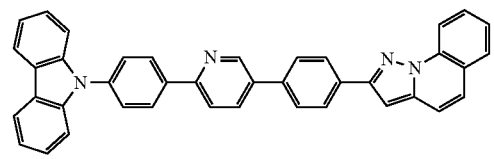
Compound 1-1-172
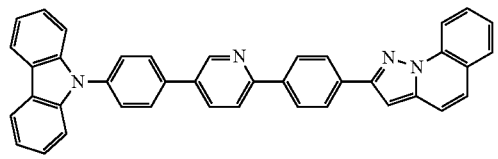

Compound 1-1-173
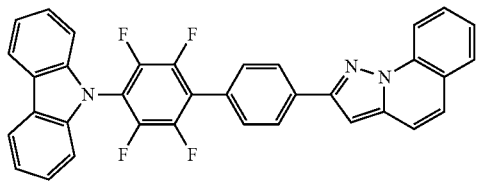
Compound 1-1-174
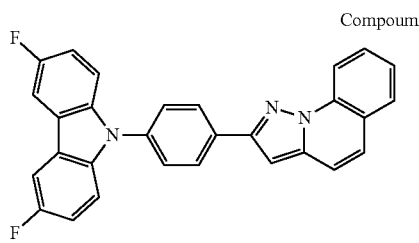
Compound 1-1-175
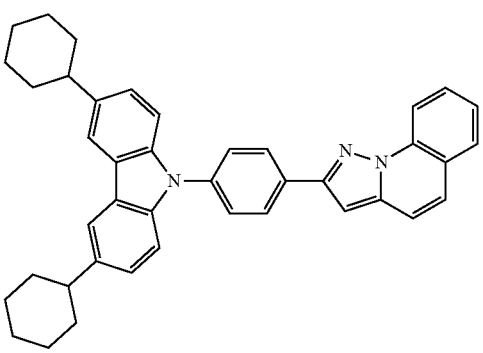
Compound 2-1-176
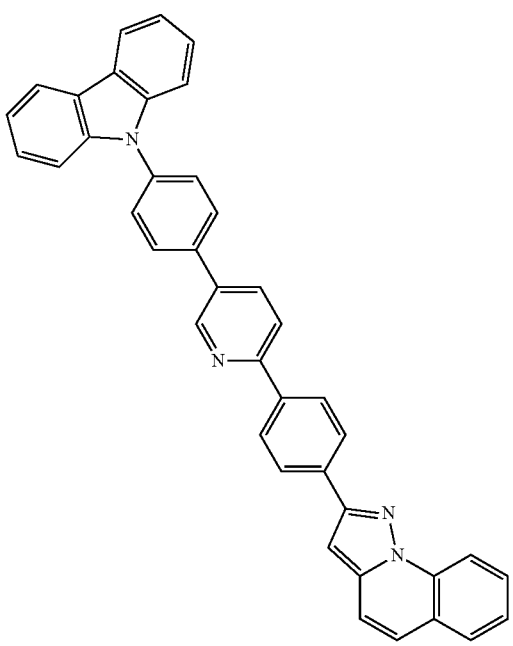
Compound 1-1-177
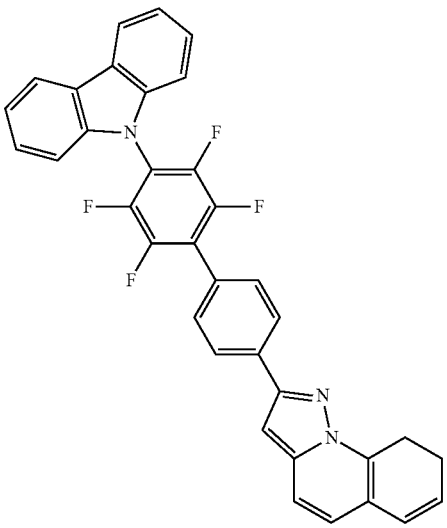
Compound 1-1-178
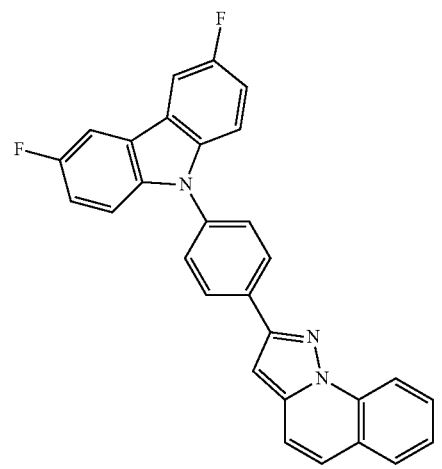
Compound 1-1-179
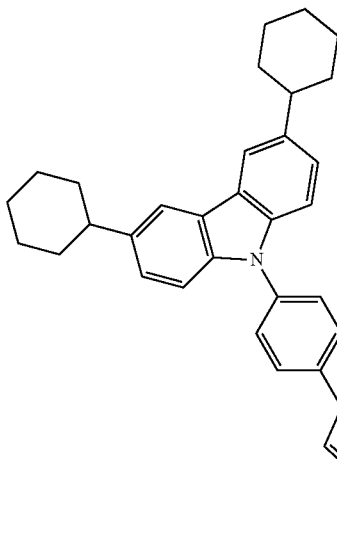

Compound 1-1-180
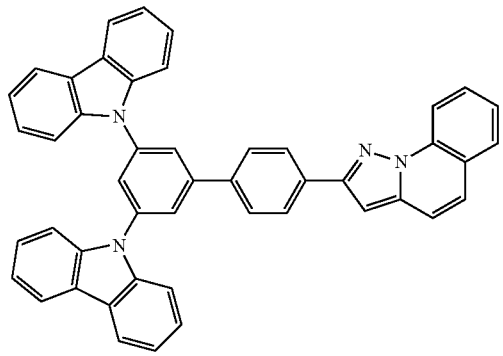
Compound 2-1-181
Compound 1-1-182
Compound 1-1-183
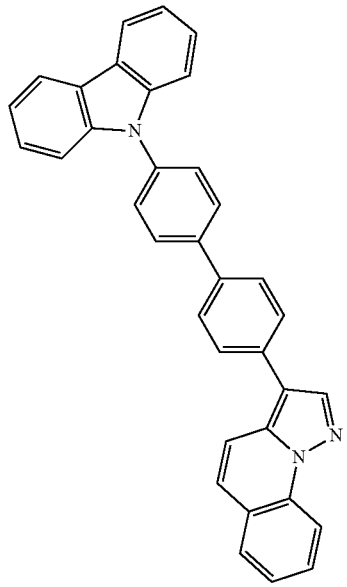
Compound 1-1-184
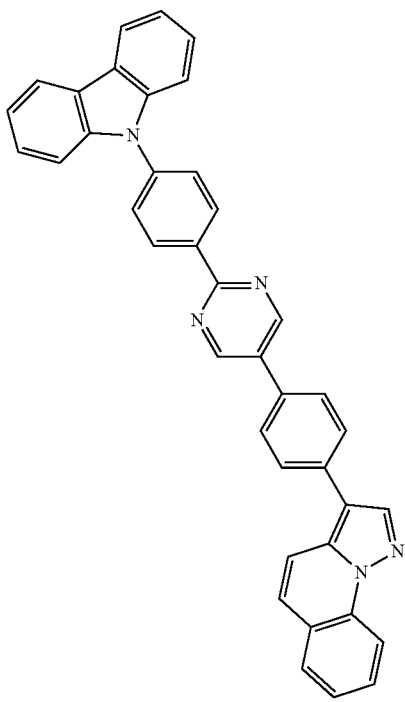

Compound 1-1-185
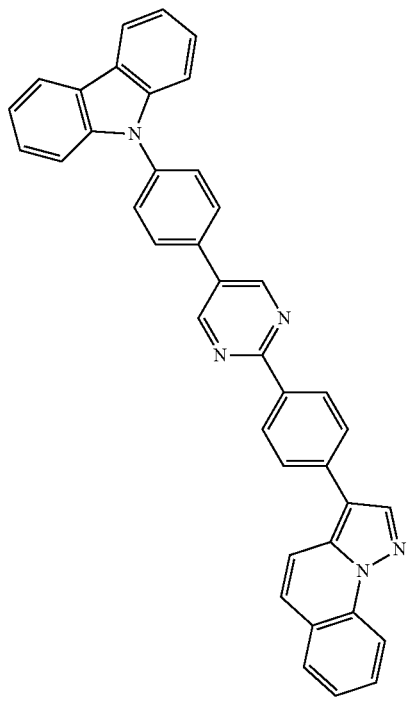
Compound 1-1-186
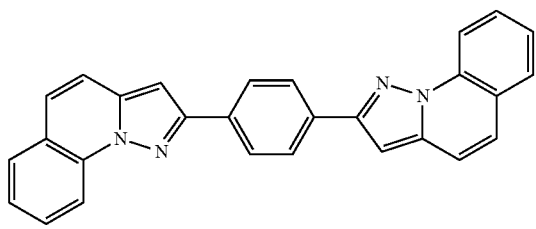
Compound 1-1-187
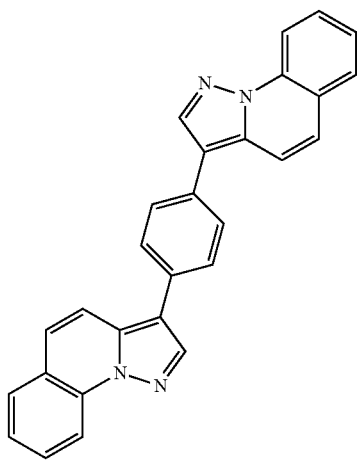
Compound 1-1-188
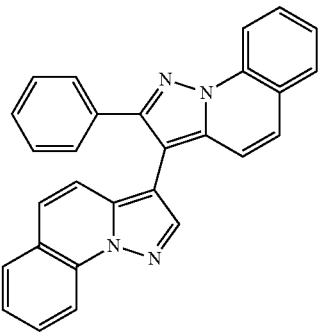
Compound 1-1-189
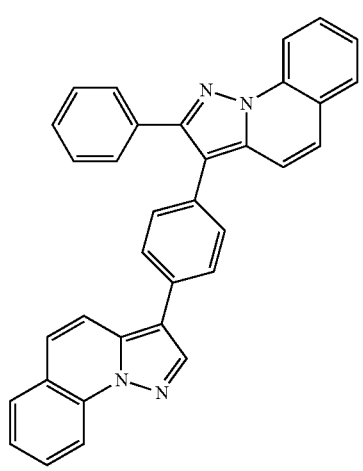
Compound 1-1-190
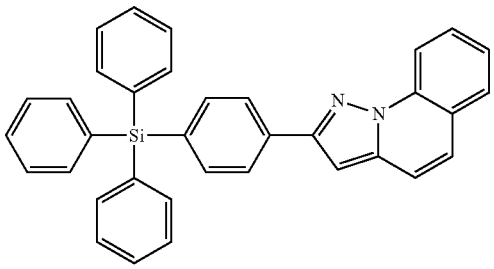
Compound 1-1-191
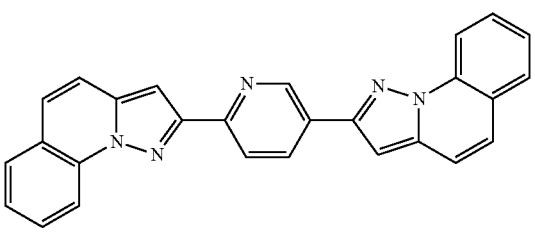

Compound 1-1-192
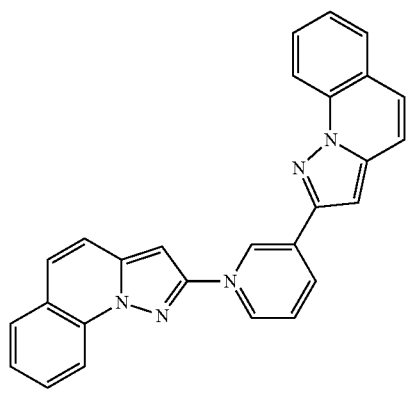
Compound 1-1-193
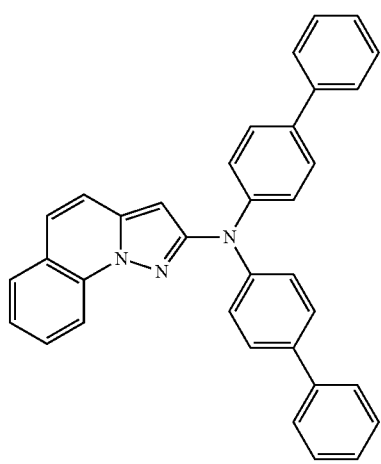
Compound 1-1-194
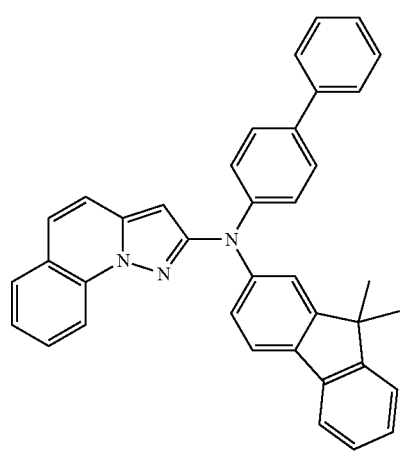
Compound 1-1-195
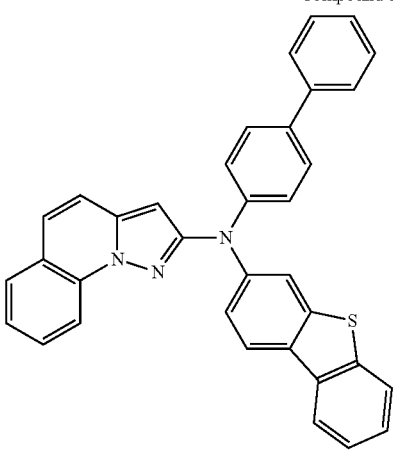
Compound 1-1-196
Compound 1-1-197
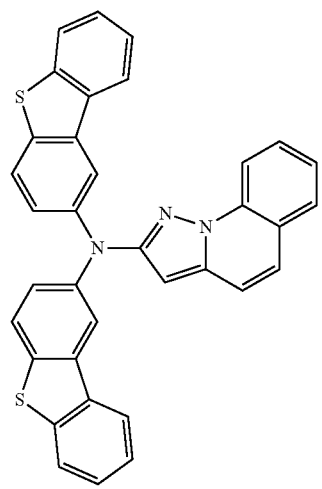

Comppind 1-1-198
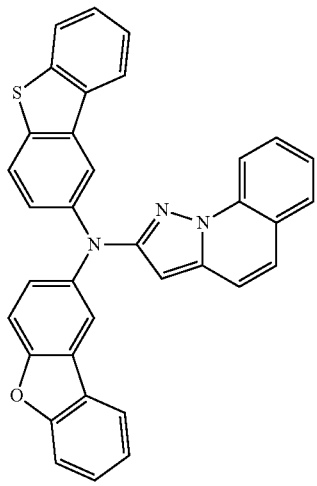
Comppind 1-1-199
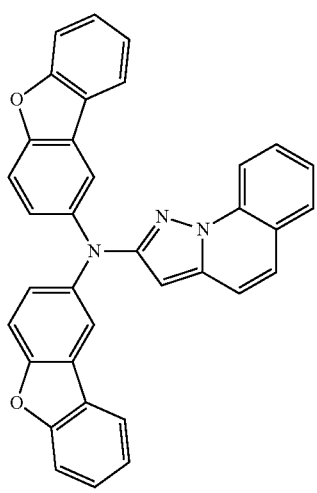
Comppind 1-1-200
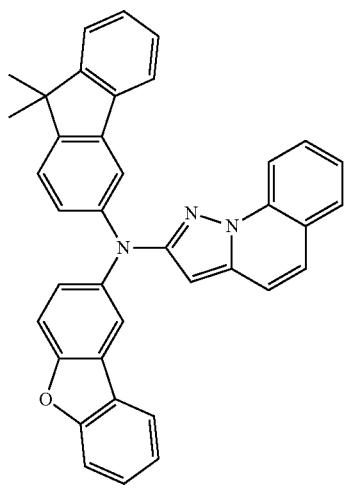
Compound 1-1-201
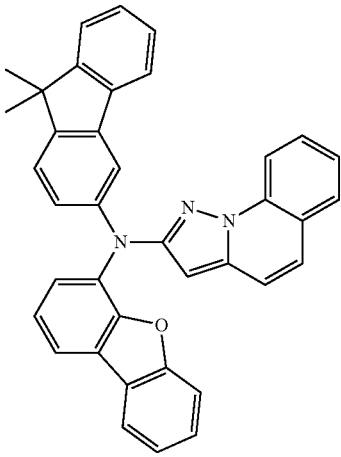
Compound 1-1-202
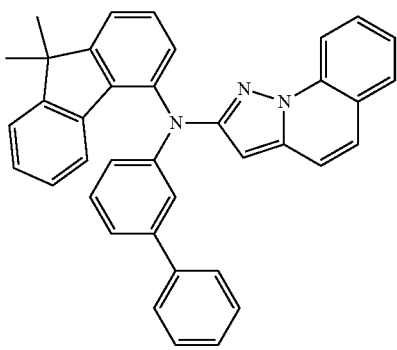
Compound 2-1-203

Compound 1-1-203
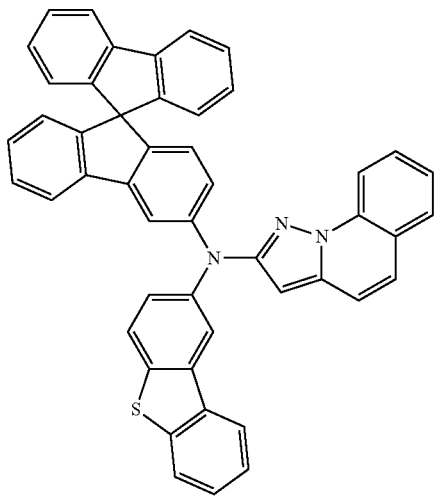
Compound 1-1-204
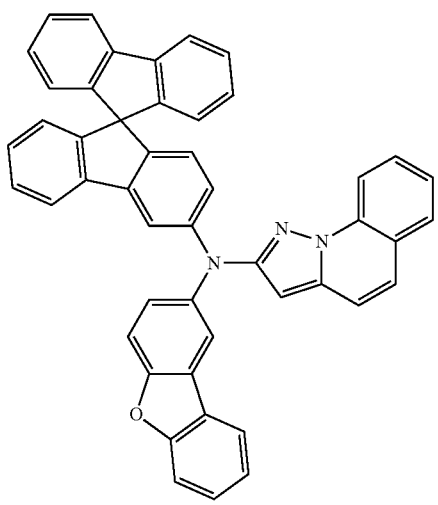
Compound 1-1-205
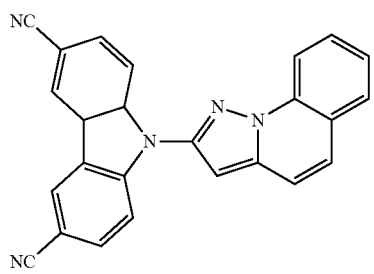
Compound 1-1-206
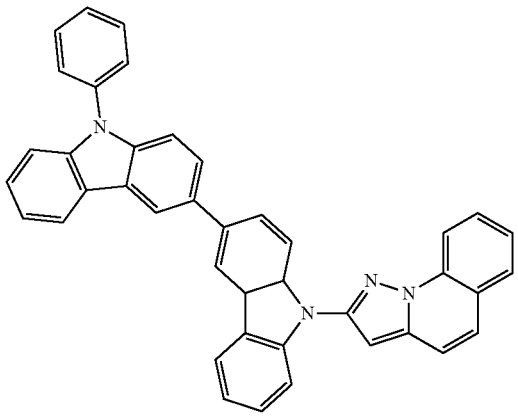
Compound 1-1-207
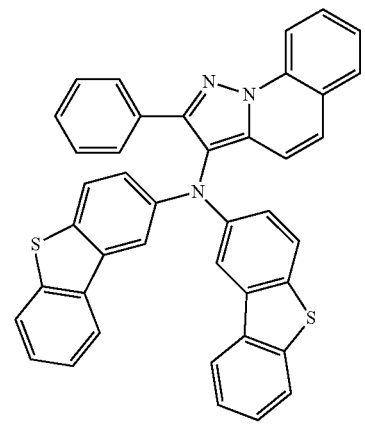
Compound 1-1-208
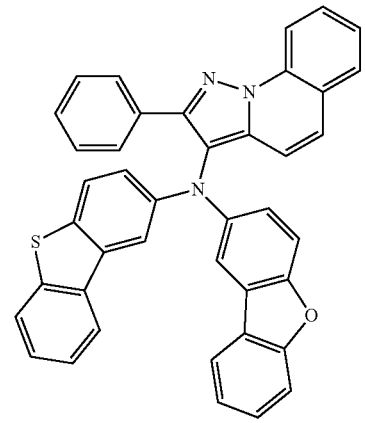

Compound 1-1-209
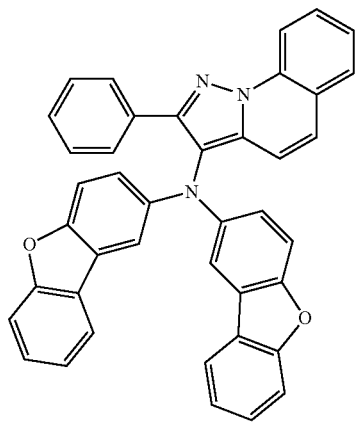
Compound 1-1-210
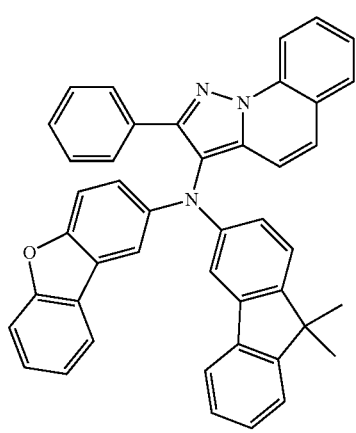
Compound 1-1-211
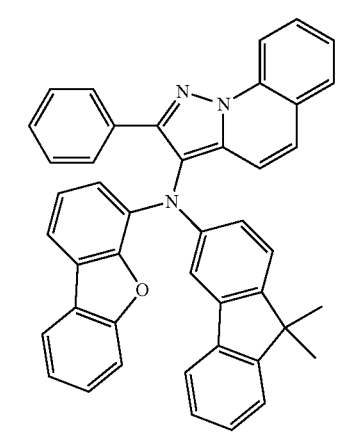
Compound 1-1-212
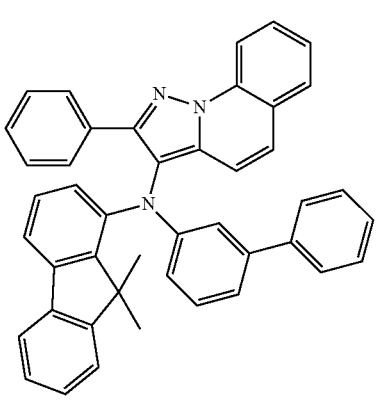
Compound 1-1-213
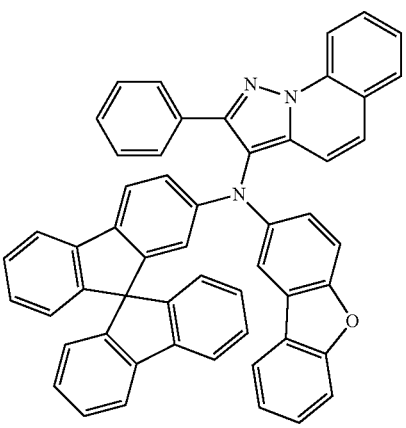
Compound 1-1-214
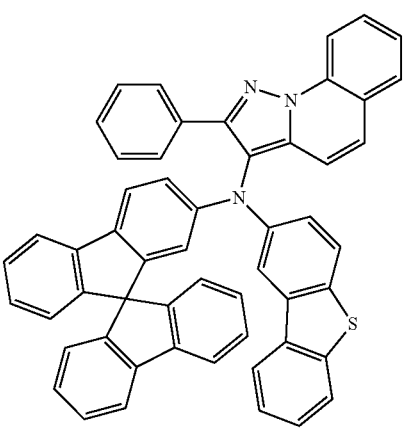
Compound 1-1-215
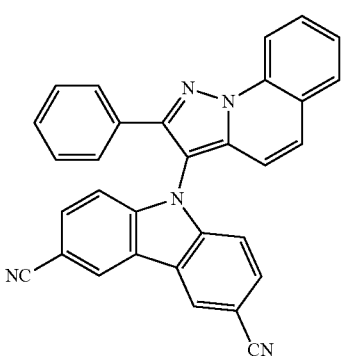

Compound 1-1-216
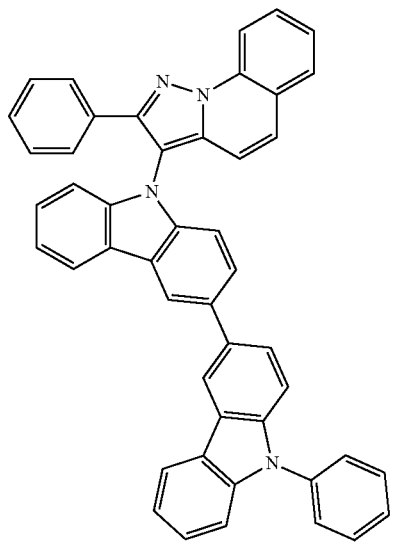
10. The hetero-cyclic compound of claim 1, wherein Formula 1 is represented by any one of the following compounds:
Compound 2-1-1
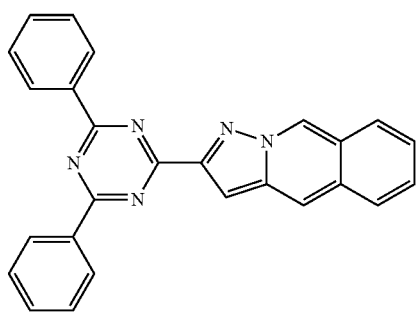
Compound 2-1-2
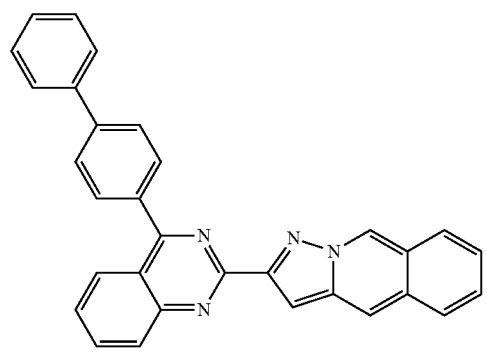
Compound 2-1-3
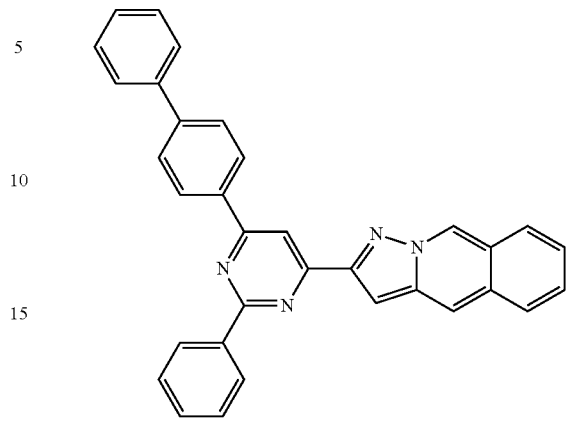
Compound 2-1-4
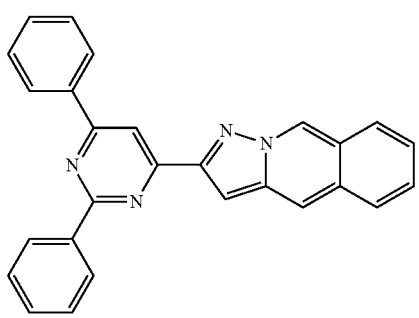
Compound 2-1-5
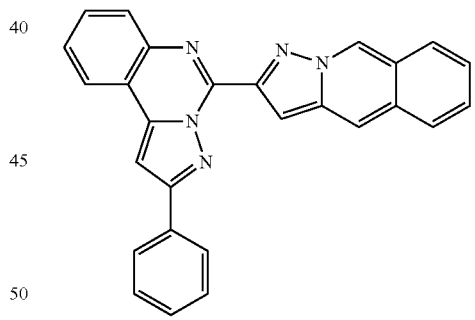
Compound 2-1-6
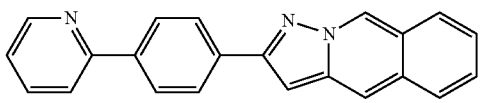
Compound 2-1-7
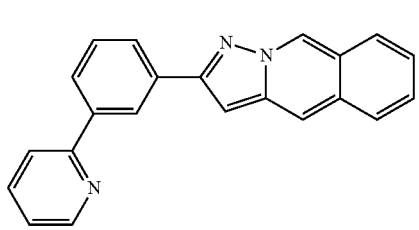

Compound 2-1-8
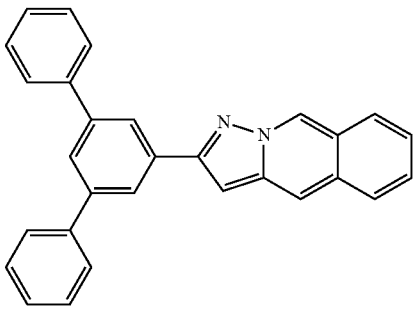
Compound 2-1-9
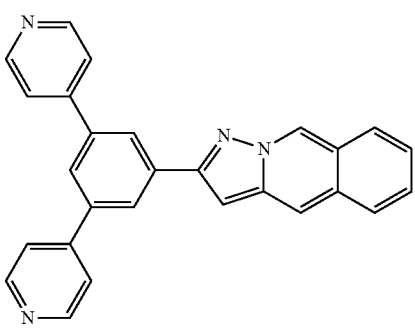
Compound 2-1-10
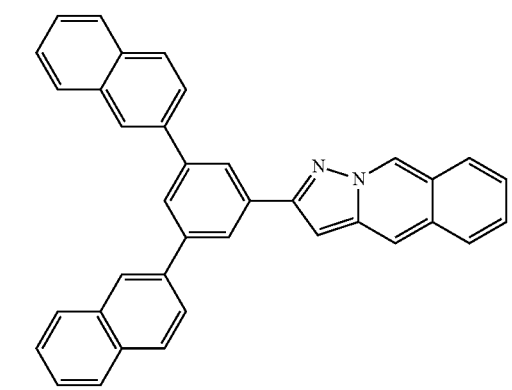
Compound 2-1-11
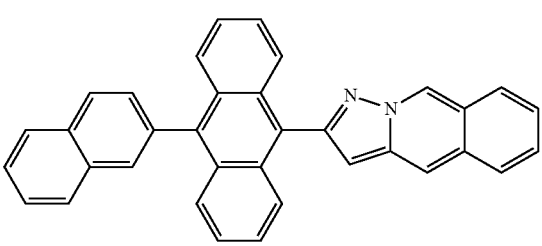
Compound 2-1-12
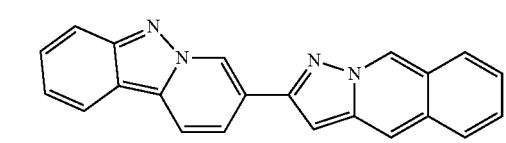
Compound 2-1-13
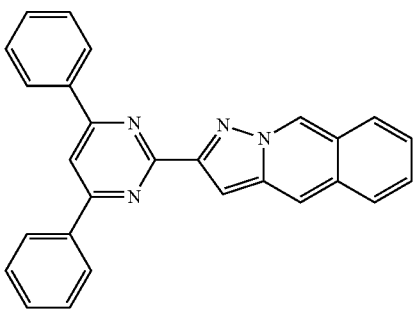
Compound 2-1-14
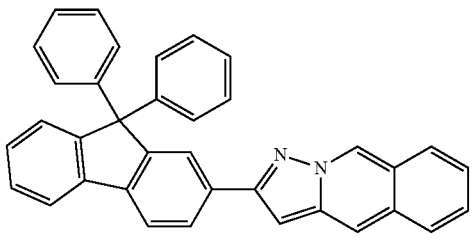
Compound 2-1-15
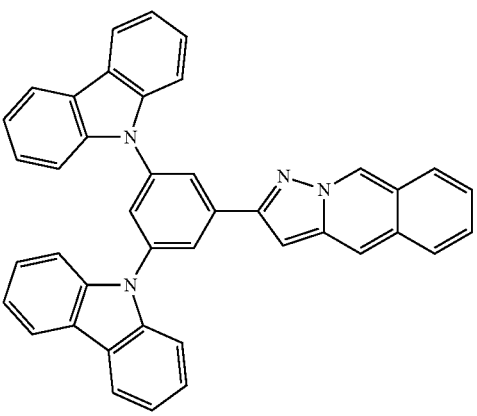
Compound 2-1-16
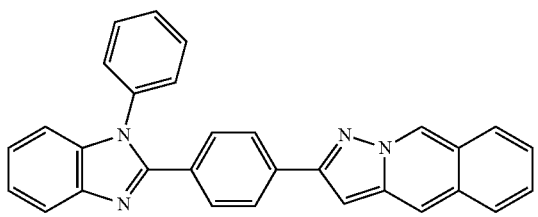
Compound 2-1-17
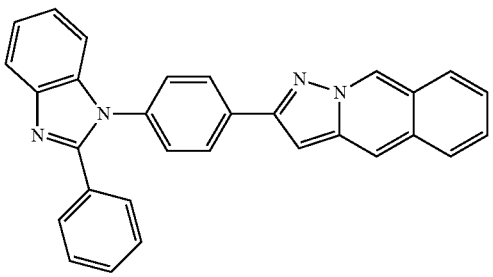

Compound 2-1-18
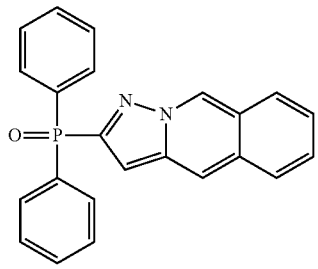
Compound 2-1-19
Compound 2-1-20
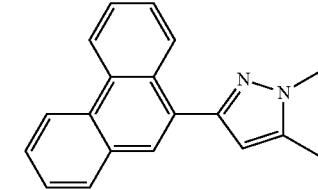
Compound 2-1-21
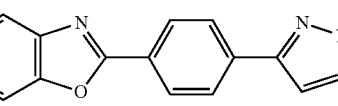
Compound 2-1-22
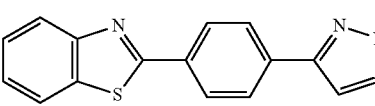
Compound 2-1-23
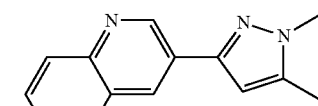
Compound 2-1-24
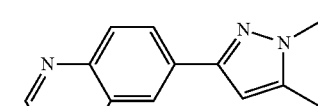
Compound 2-1-25
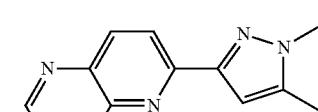
Compound 2-1-26
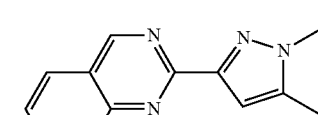
Compound 2-1-27
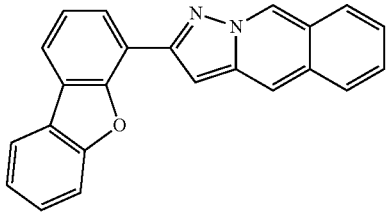
Compound 2-1-28
Compound 2-1-29
Compound 2-1-30
Compound 2-1-31
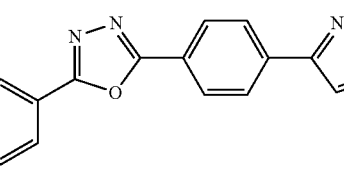

Compound 2-1-32
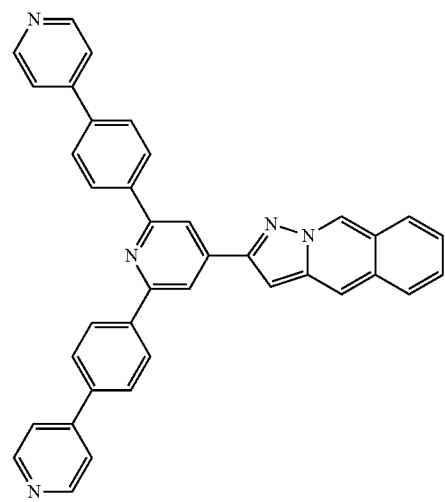
Compound 2-1-35
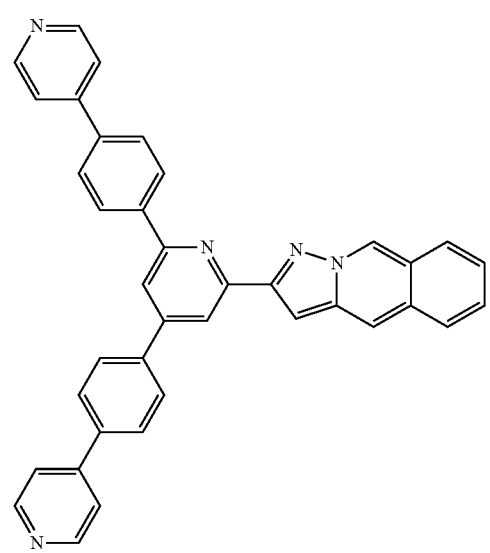
Compound 2-1-33
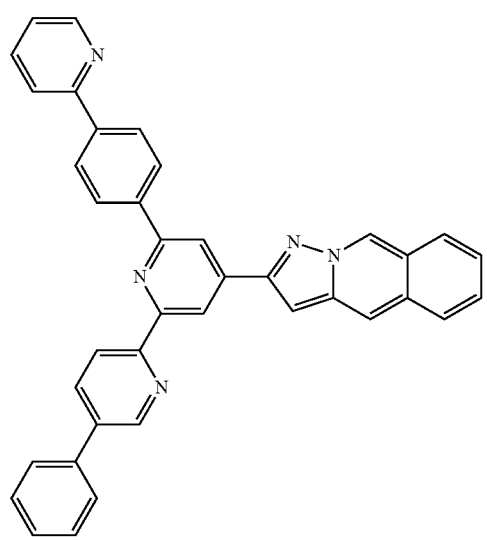
Compound 2-1-36
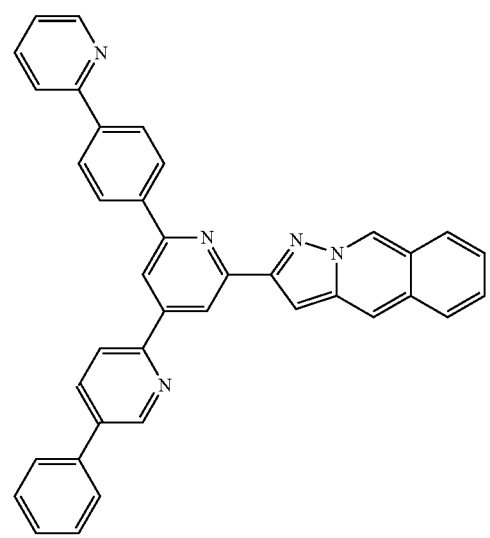
Compound 2-1-34
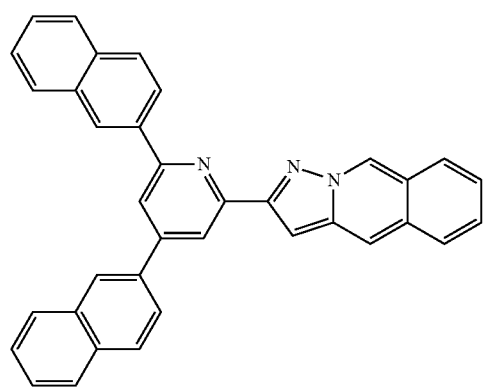
Compound 2-1-37
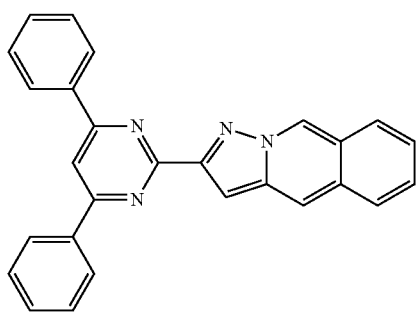

Compound 2-1-38
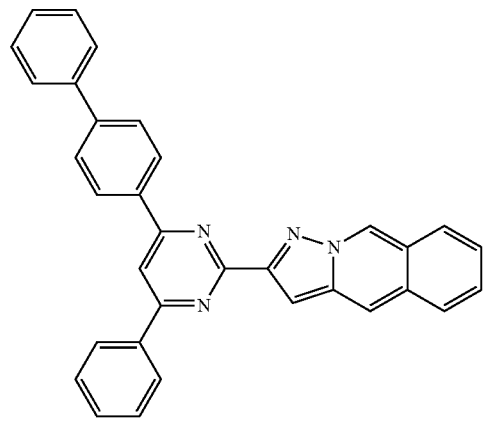
Compound 2-1-41
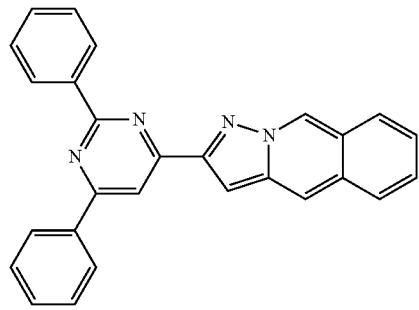
Compound 2-1-42
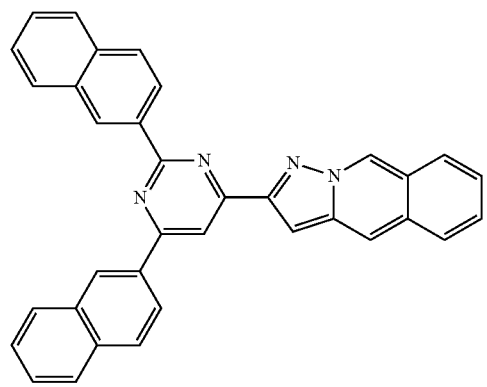
Compound 2-1-39
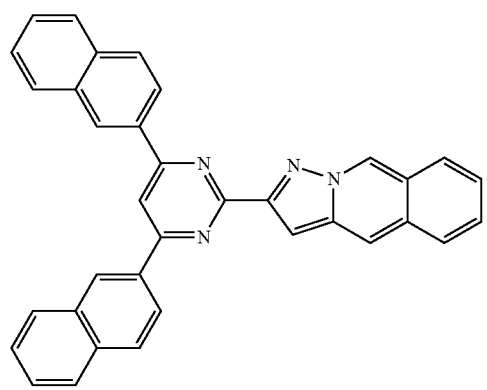
Compound 2-1-43
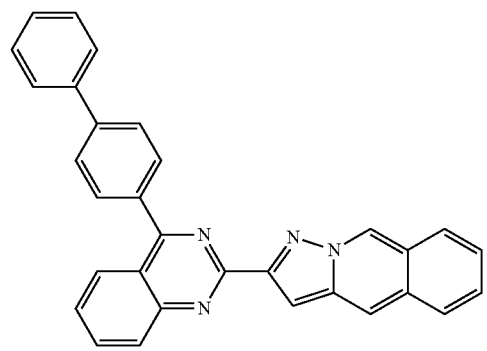
Compound 2-1-40
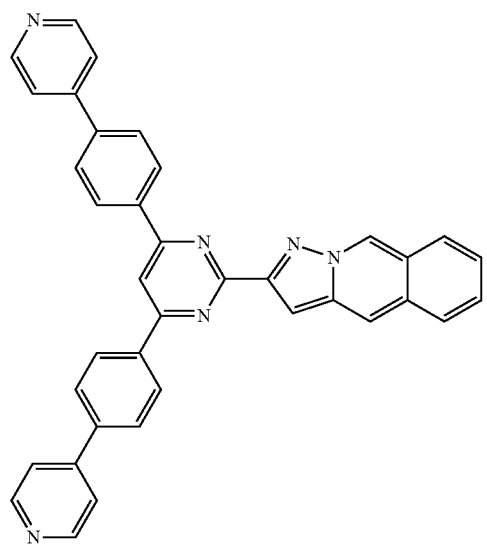
Compound 2-1-44
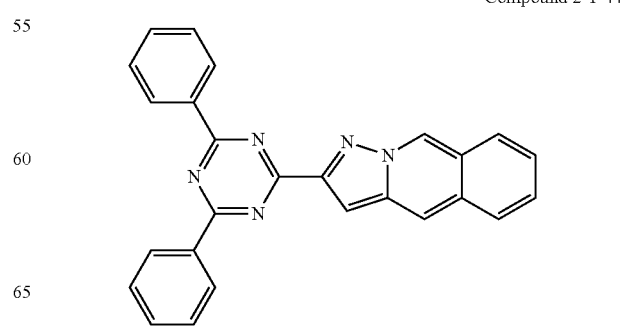

Compound 2-1-45
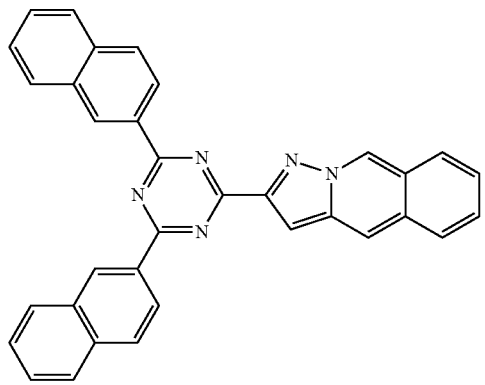
Compound 2-1-46
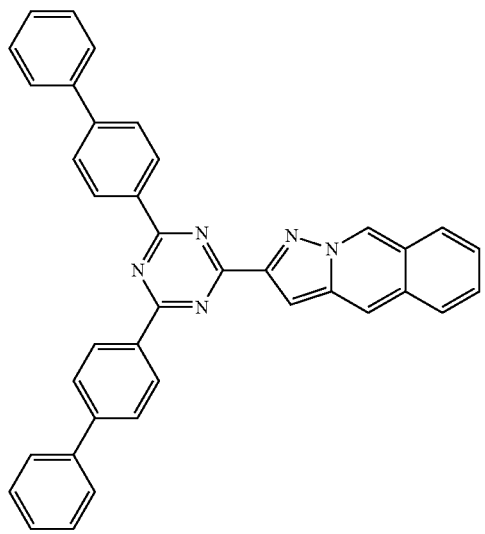
Compound 2-1-47
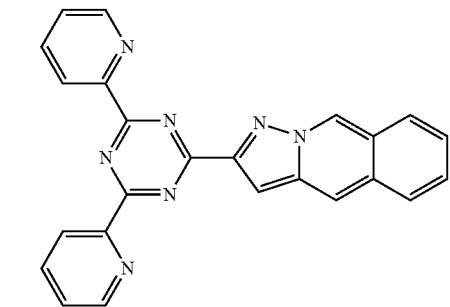
Compound 2-1-48
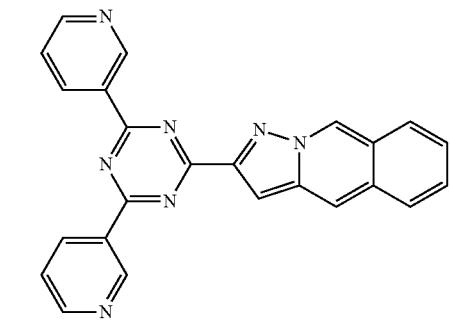
Compound 2-1-49
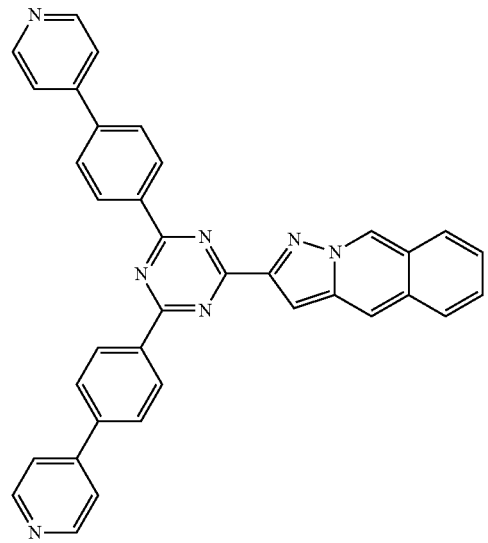
Compound 2-1-50
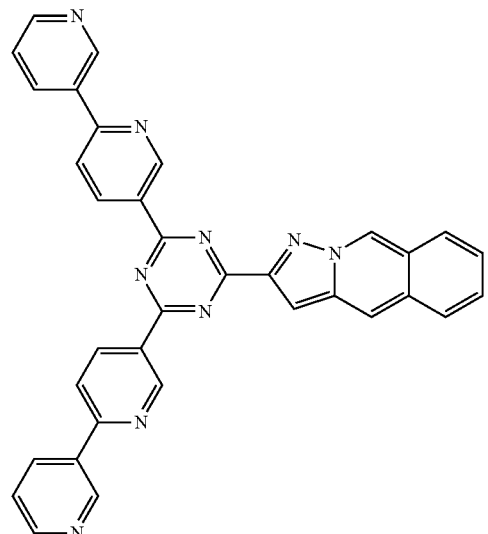
Compound 2-1-51
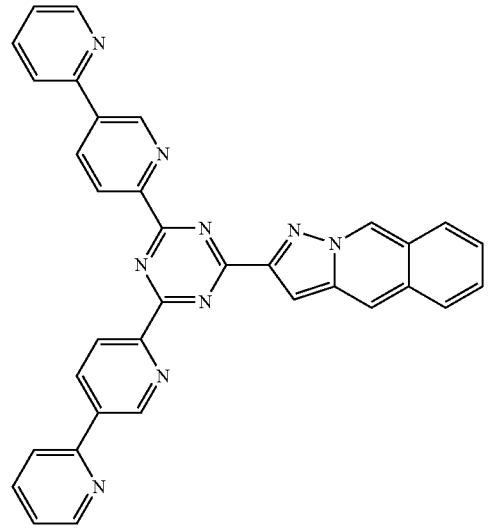

Compound 2-1-52
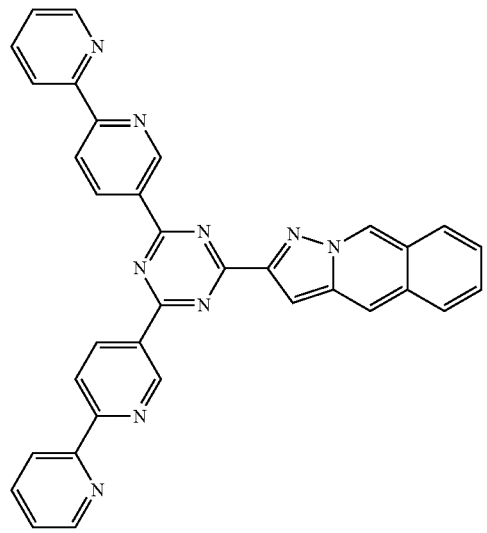
Compound 2-1-53
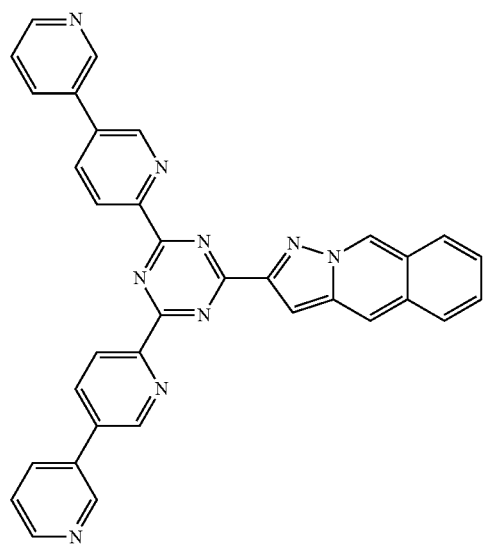
Compound 2-1-54
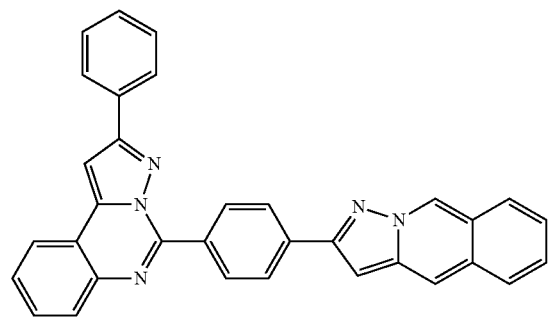
Compound 2-1-55
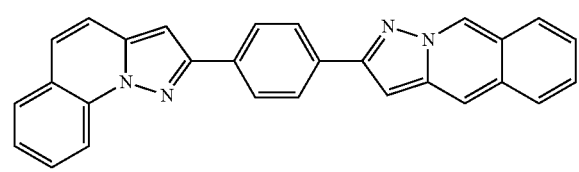
Compound 2-1-56
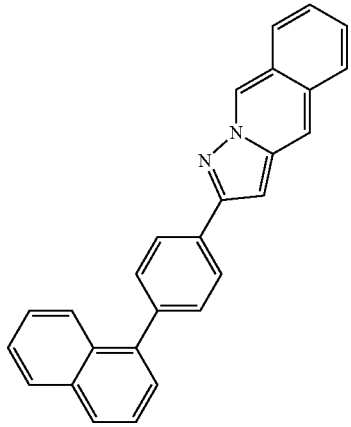
Compound 2-1-57
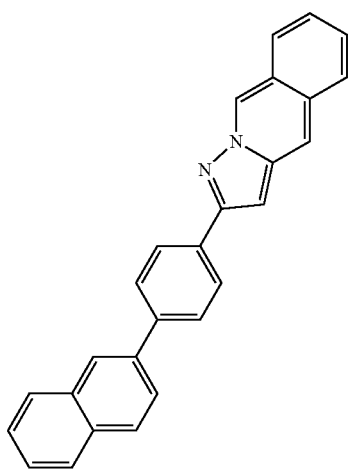
Compound 2-1-58
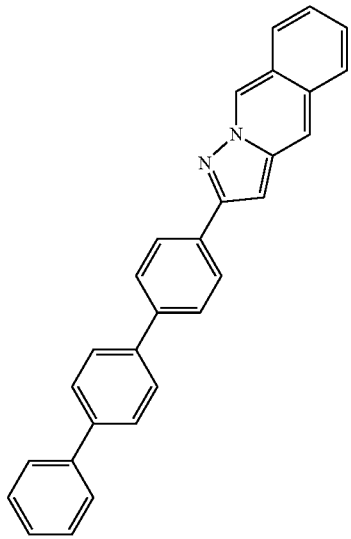

Compound 2-1-59
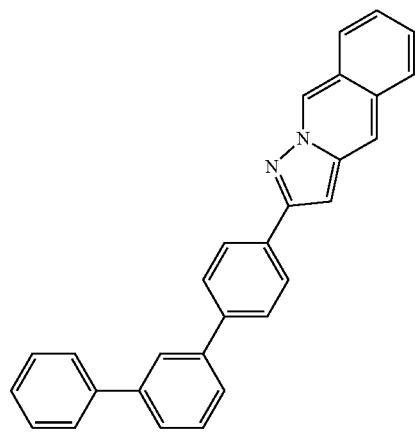
Compound 2-1-60
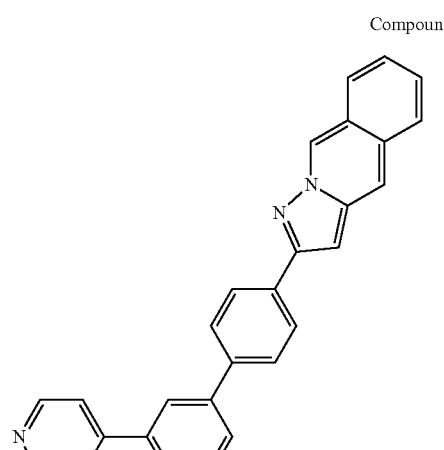
Compound 2-1-61
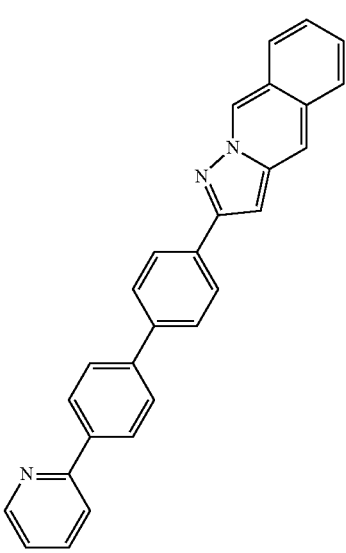
Compound 2-1-62
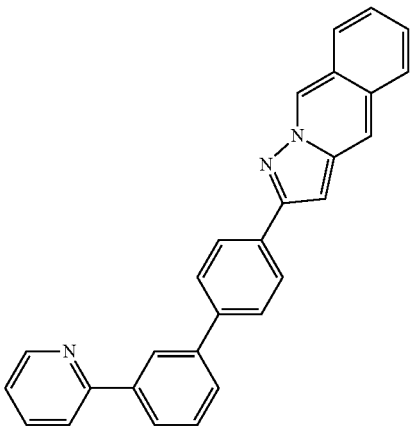
Compound 2-1-63
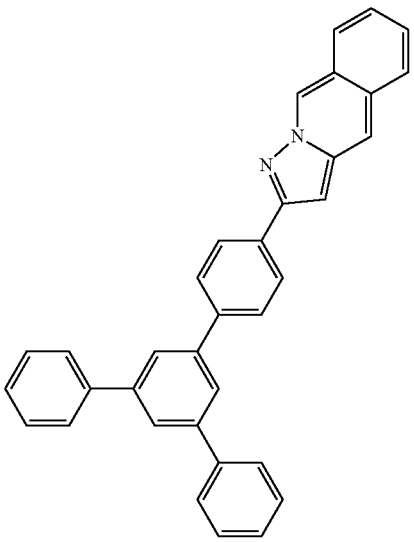
Compound 2-1-64
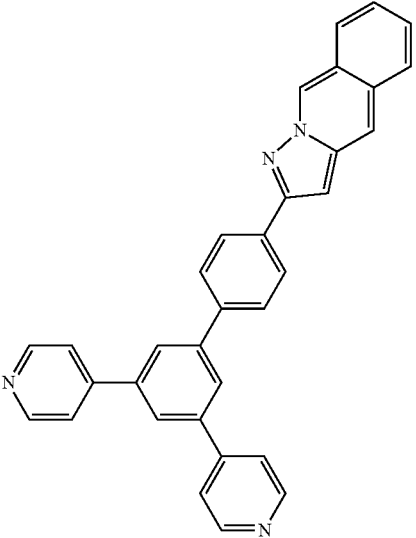

Compound 2-1-65
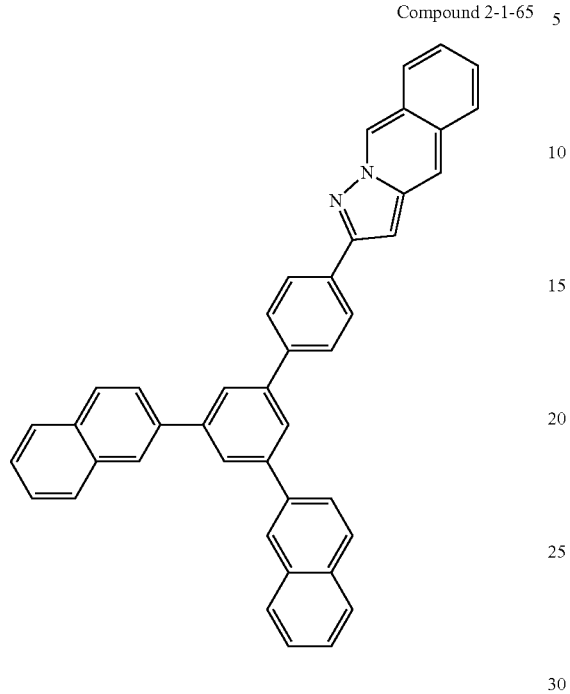
Compound 2-1-66
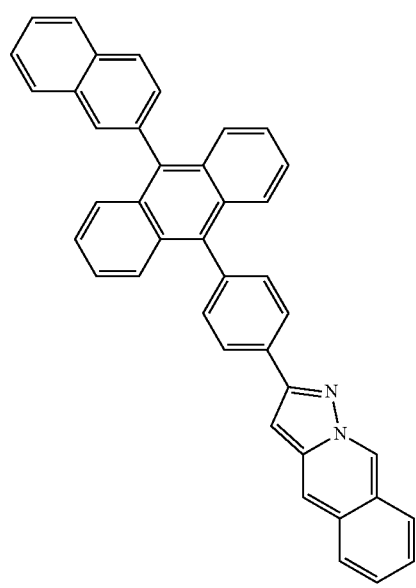
Compound 2-1-67
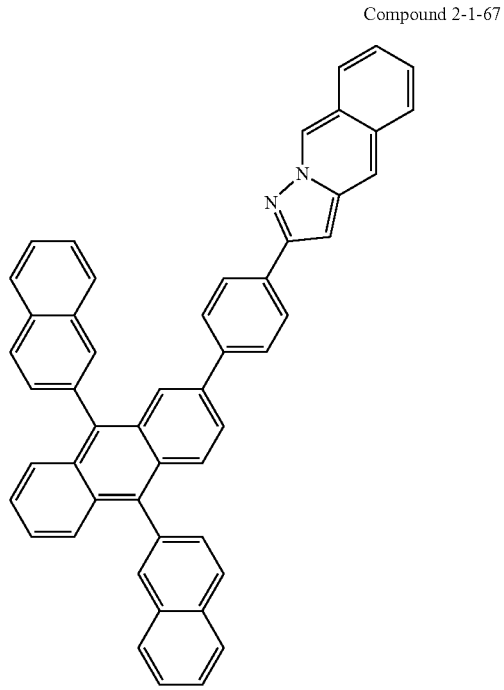
Compound 2-1-68
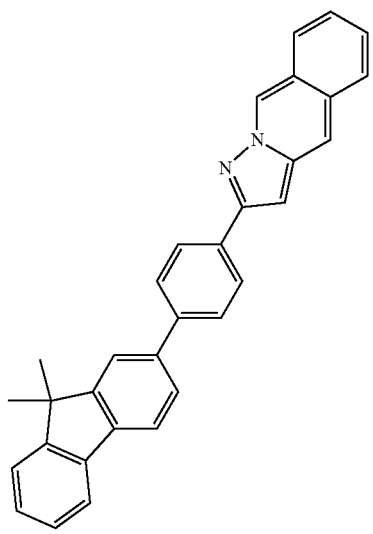

Compound 2-1-69
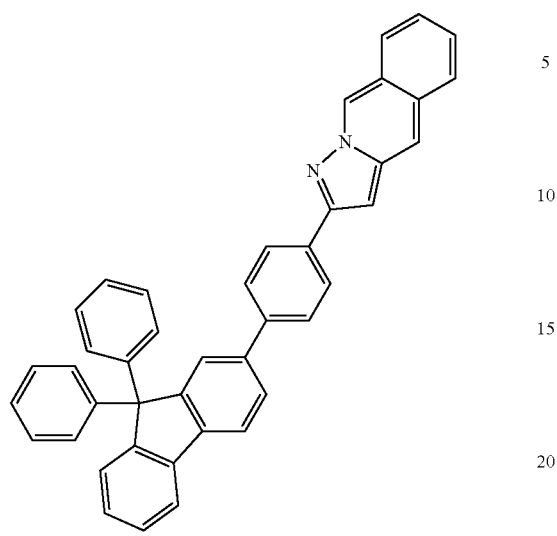
Compound 2-1-70
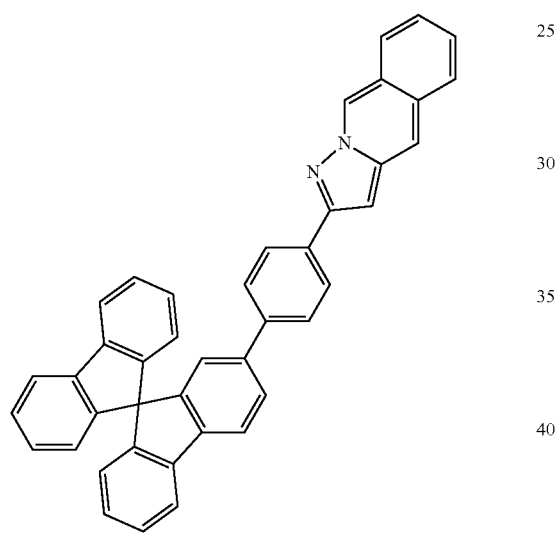
Compound 2-1-71
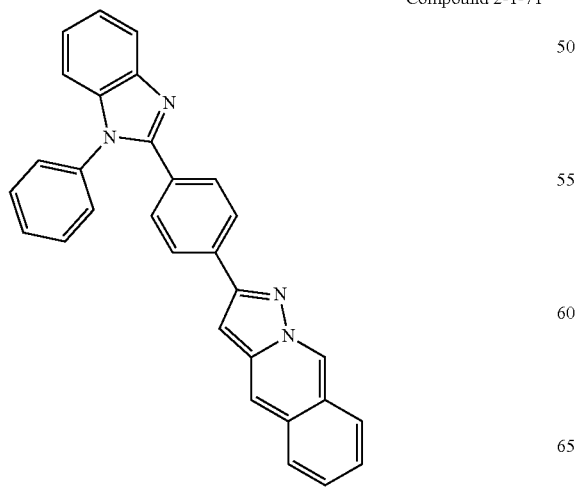
Compound 2-1-72
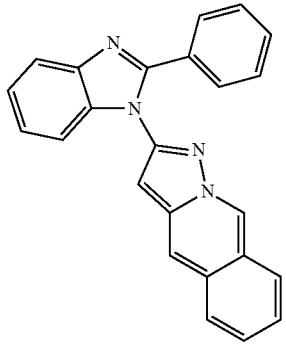
Compound 2-1-73
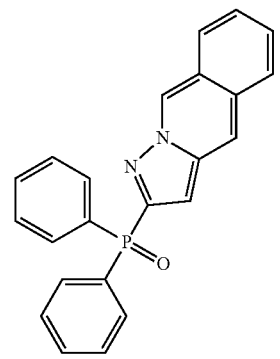
Compound 2-1-74
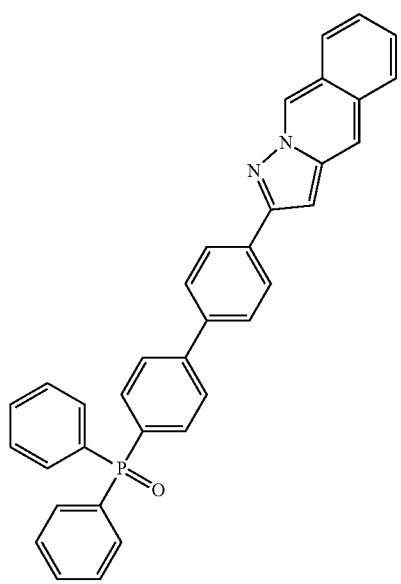

Compound 2-1-75
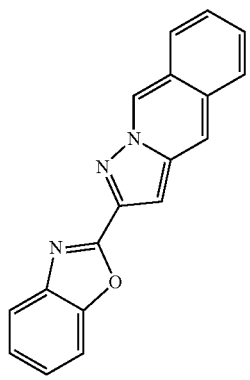
Compound 2-1-76
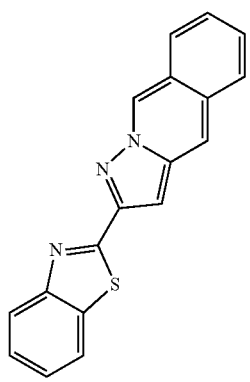
Compound 2-1-77
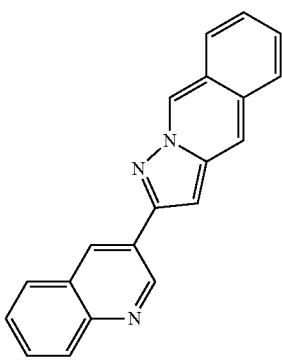
Compound 2-1-78
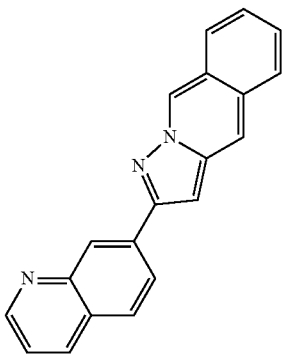
Compound 2-1-79
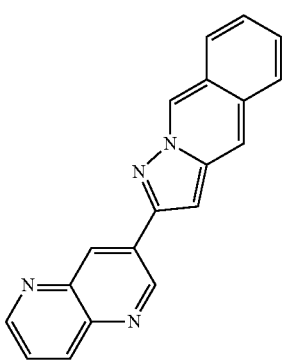
Compound 2-1-80
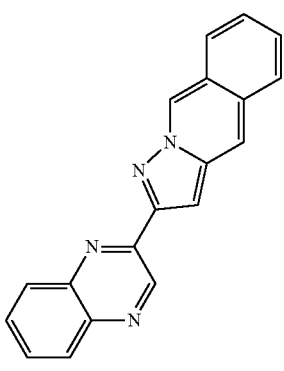
Compound 2-1-81
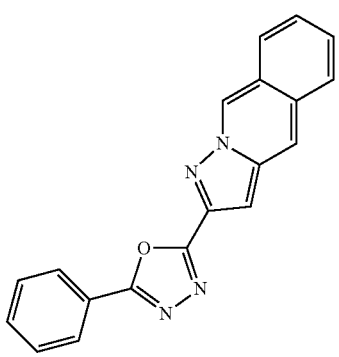
Compound 2-1-82
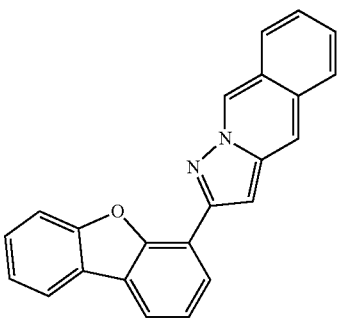

Compound 2-1-83
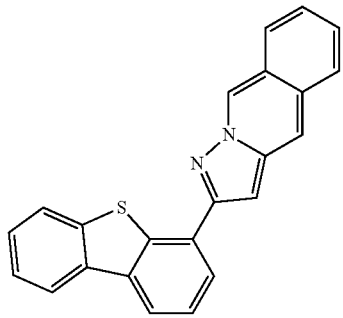
Compound 2-1-84
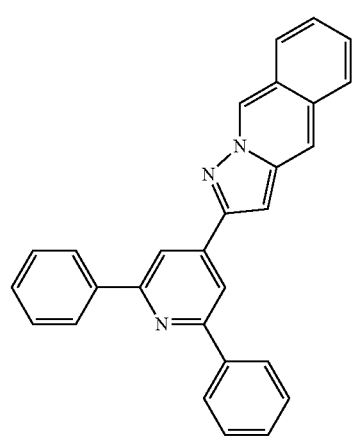
Compound 2-1-85
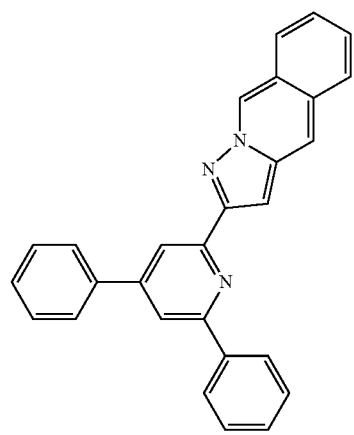
Compound 2-1-86
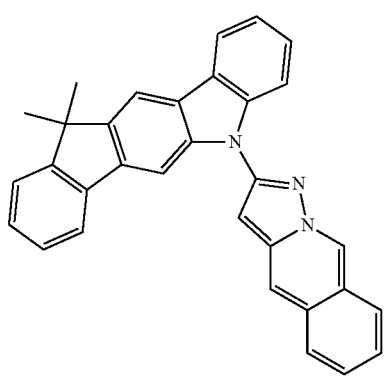
Compound 2-1-87
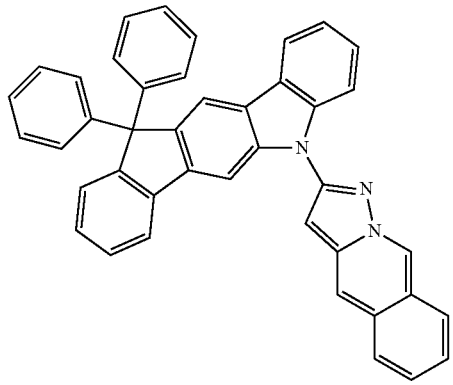
Compound 2-1-88
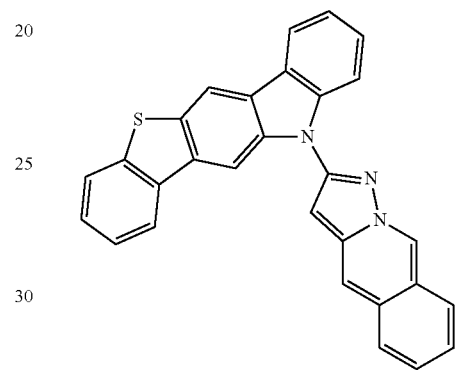
Compound 2-1-89
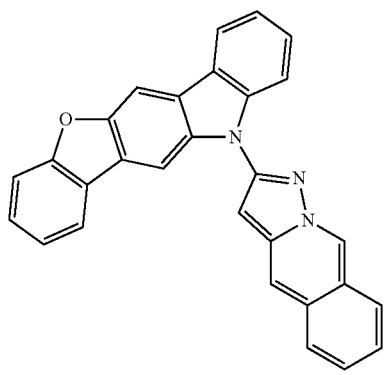
Compound 2-1-90
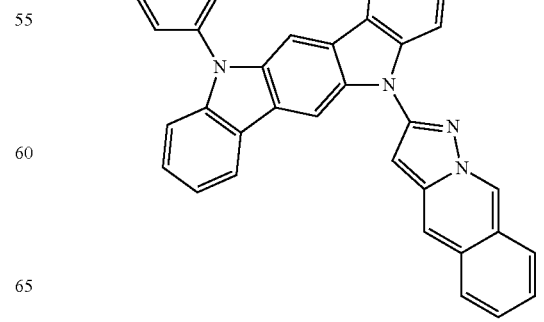

-continued
Compound 2-1-91
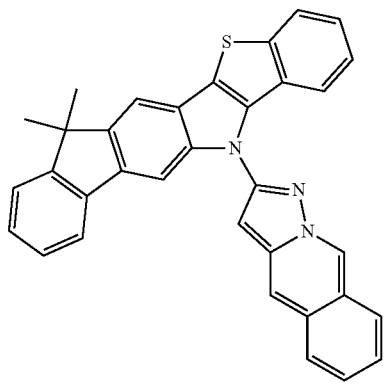
Compound 2-1-92
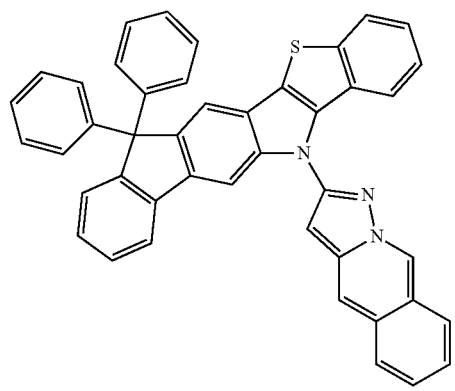
Compound 2-1-93
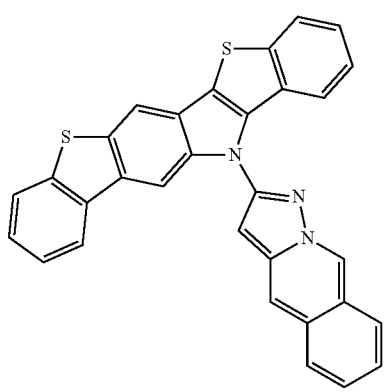
Compound 2-1-94
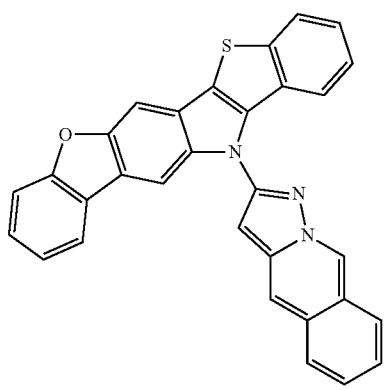
-continued
Compound 2-1-95
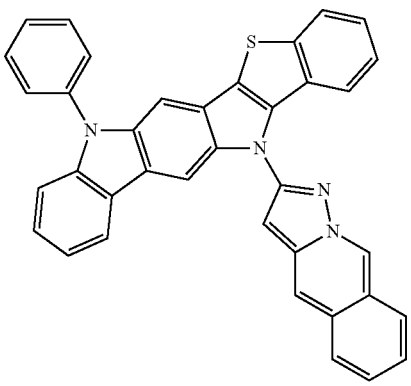
Compound 2-1-96
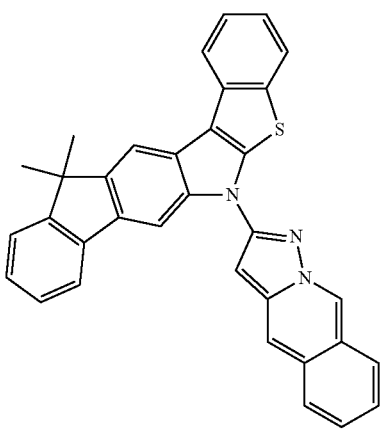
Compound 2-1-97
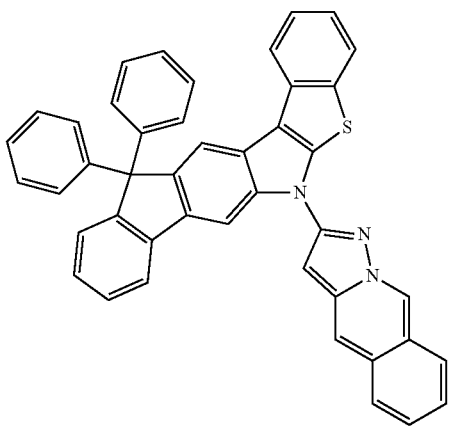

Compound 2-1-98
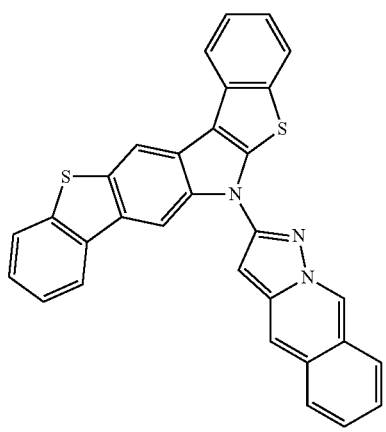
Compound 2-1-99
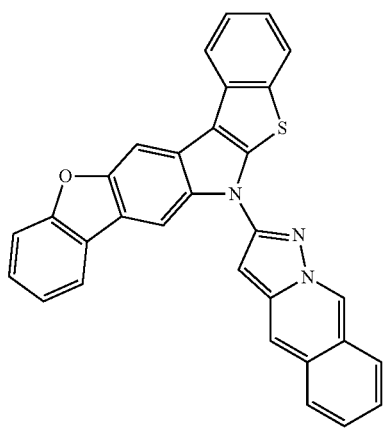
Compound 2-1-100
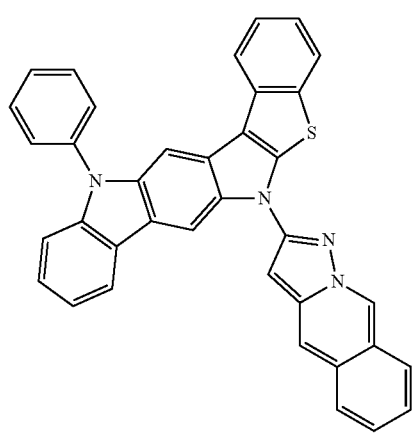
Compound 2-1-101
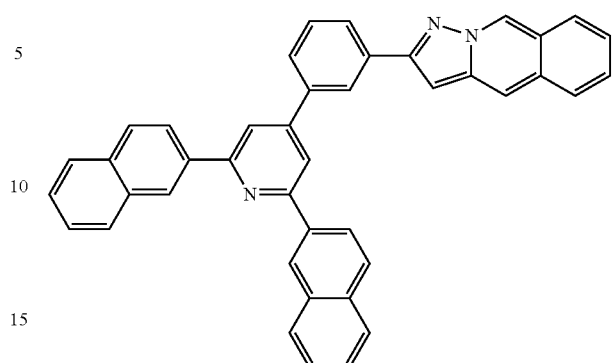
Compound 2-1-102
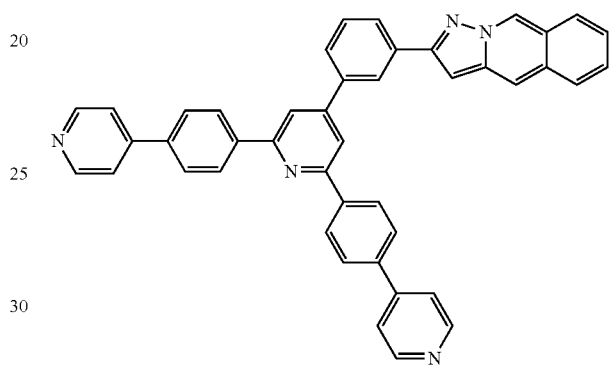
Compound 2-1-103
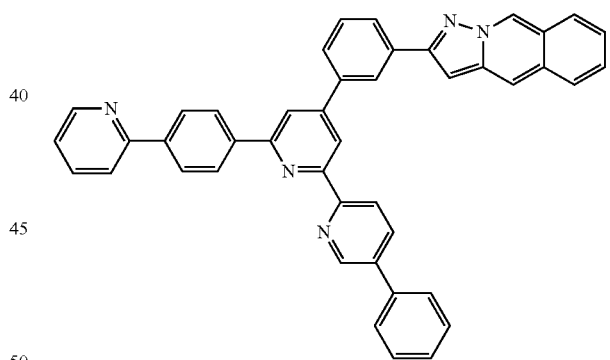
Compound 2-1-104
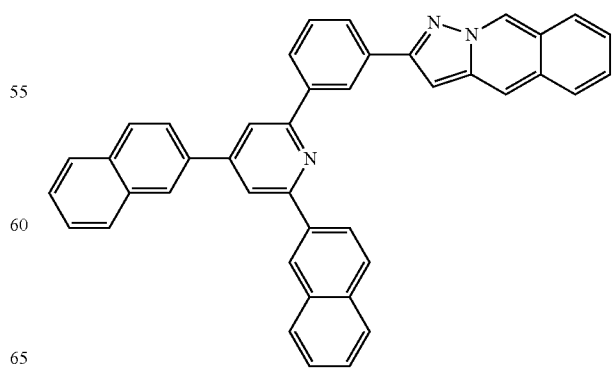

Compound 2-1-105
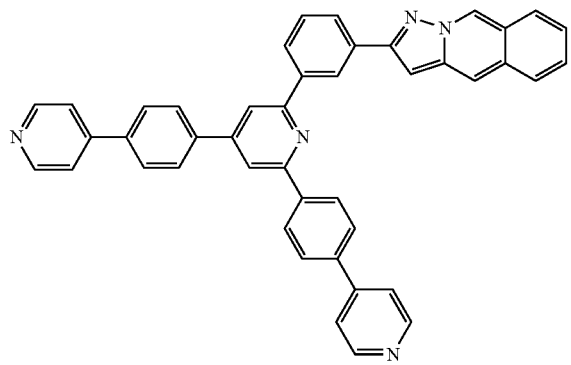
Compound 2-1-106
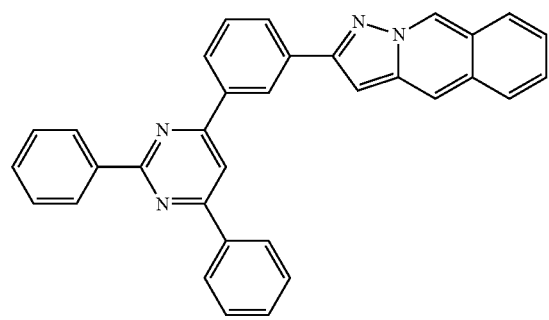
Compound 2-1-107
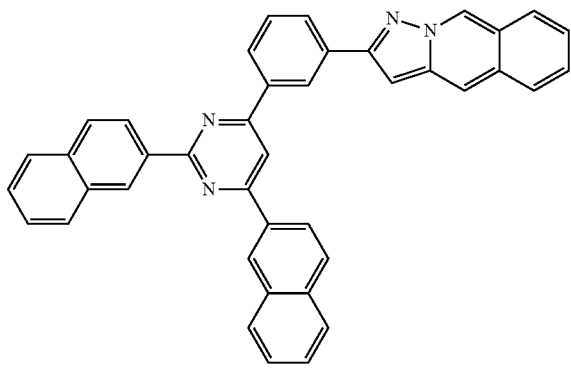
Compound 2-1-108
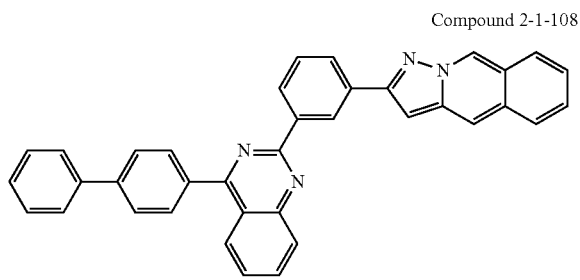
Compound 2-1-109
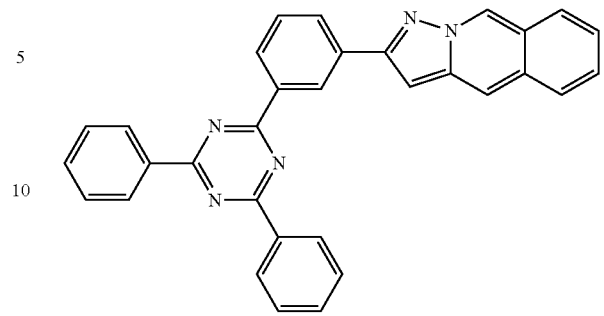
Compound 2-1-110
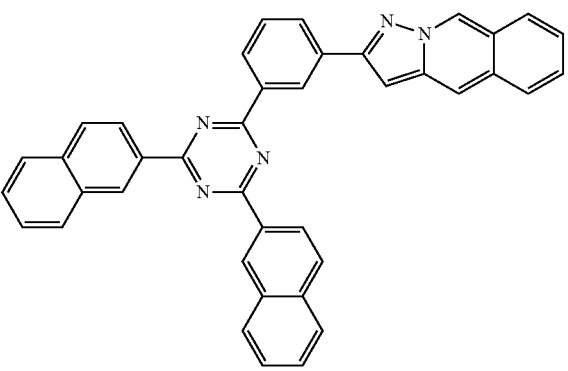
Compound 2-1-111
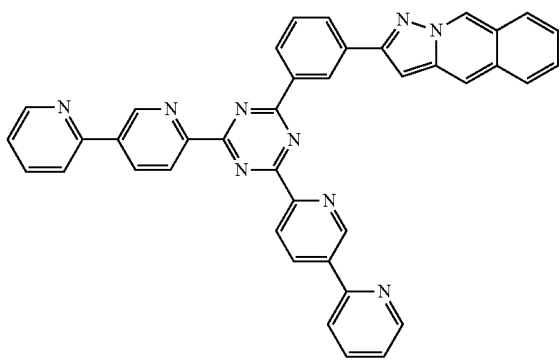
Compound 2-1-112

Compound 2-1-113
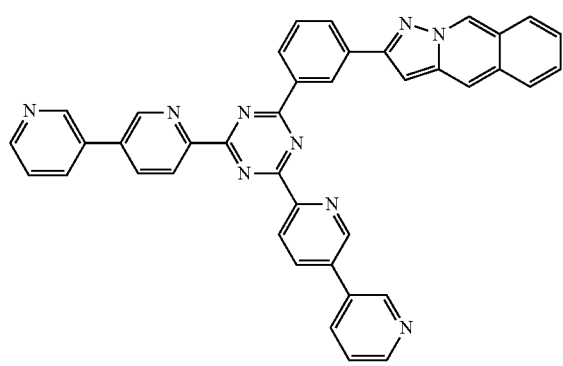
Compound 2-1-114
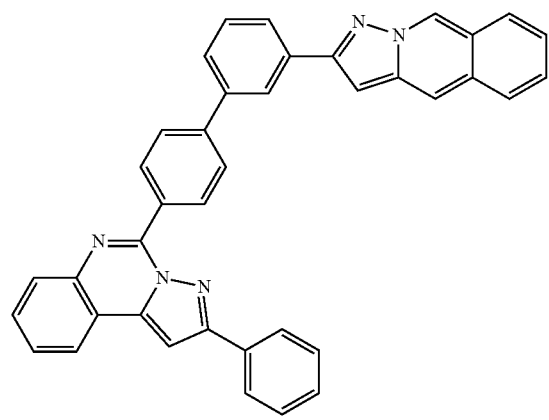
Compound 2-1-115
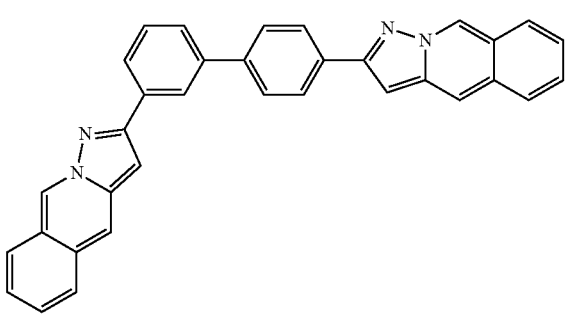
Compound 2-1-116
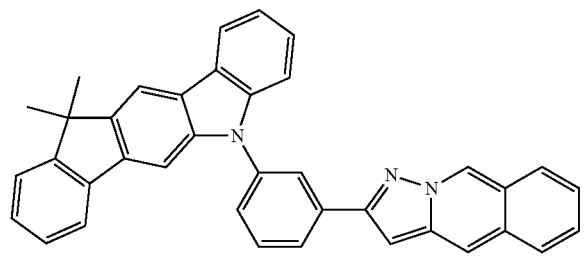
Compound 2-1-117
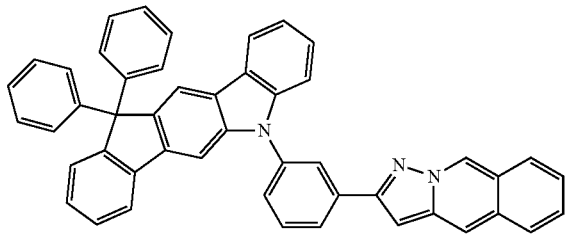
Compound 2-1-118
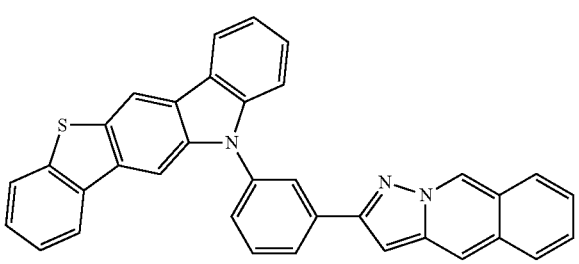
Compound 2-1-119
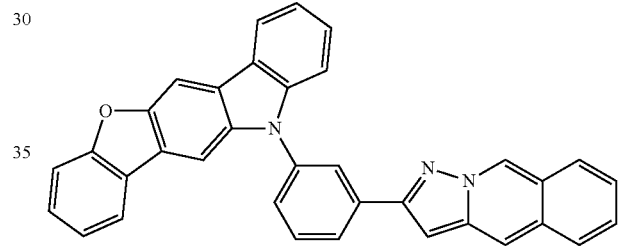
Compound 2-1-120
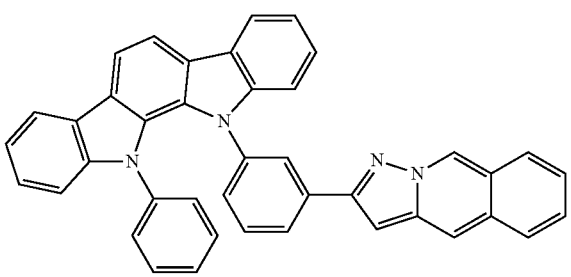
Compound 2-1-121
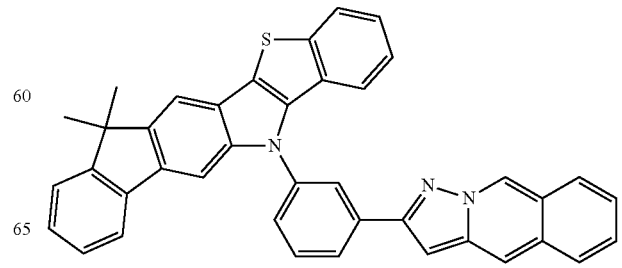

Compound 2-1-122
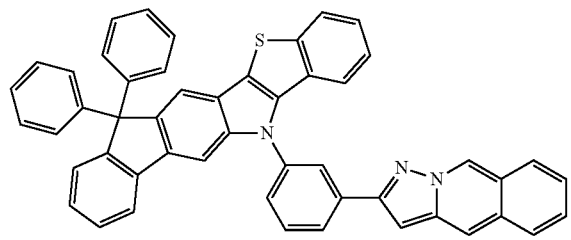
Compound 2-1-123
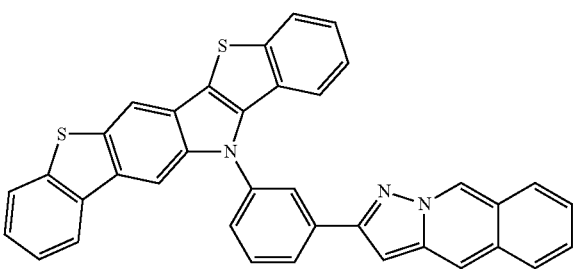
Compound 2-1-124
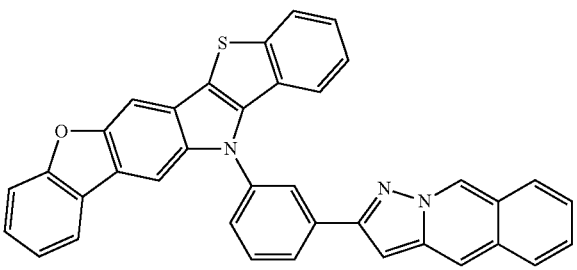
Compound 2-1-125
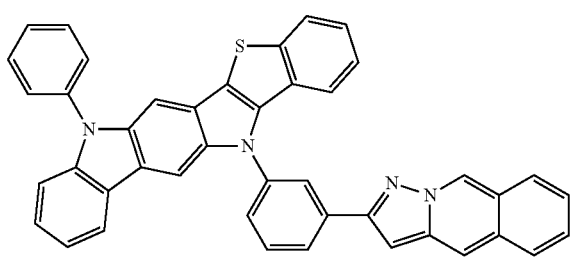
Compound 2-1-126
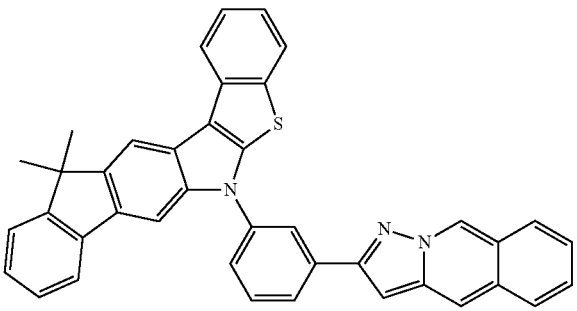
Compound 2-1-127
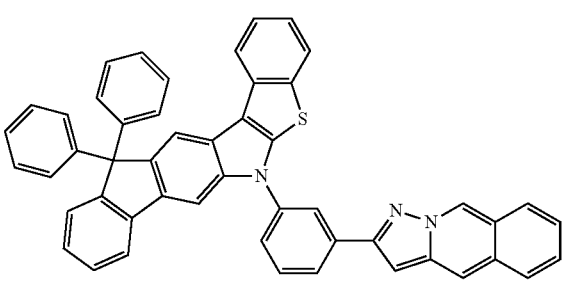
Compound 2-1-128
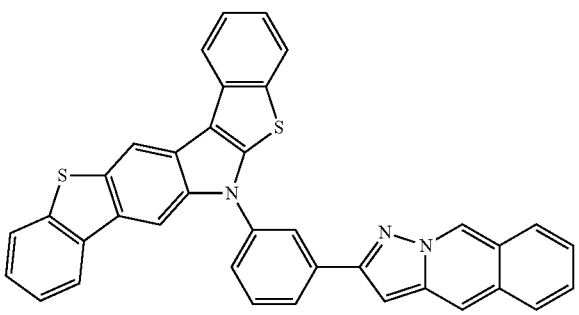
Compound 2-1-129
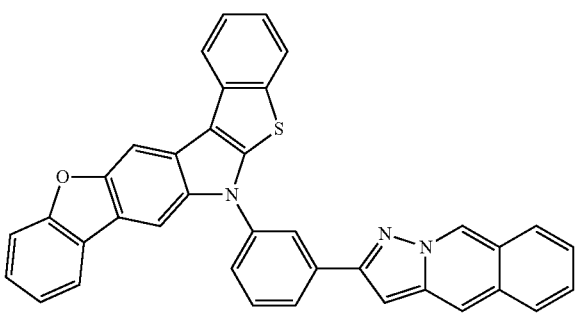
Compound 2-1-130
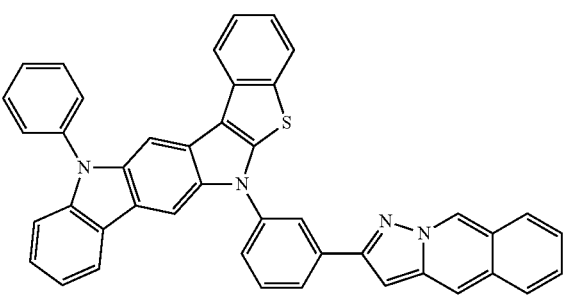
Compound 2-1-131
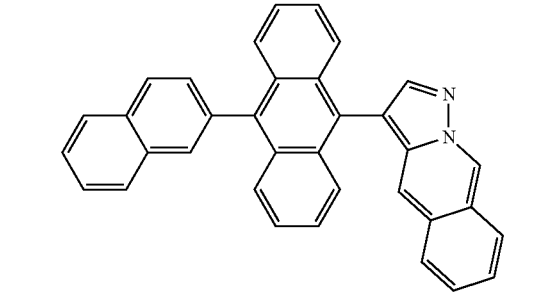

Compound 2-1-132
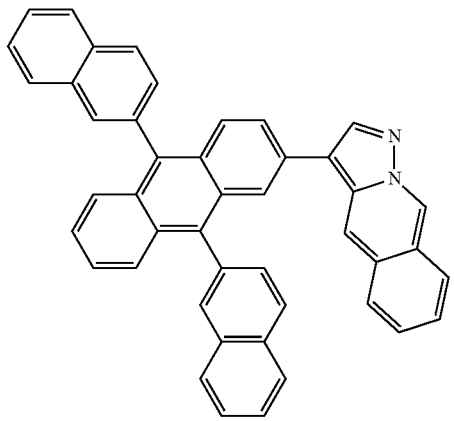
Compound 2-1-133
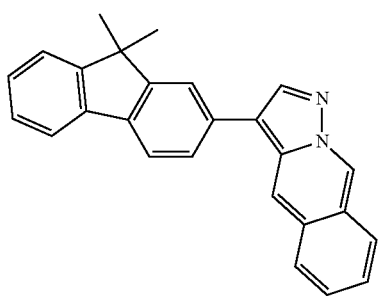
Compound 2-1-134
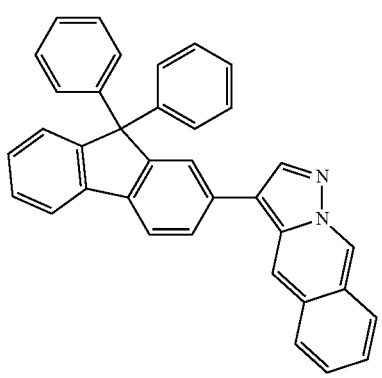
Compound 2-1-135
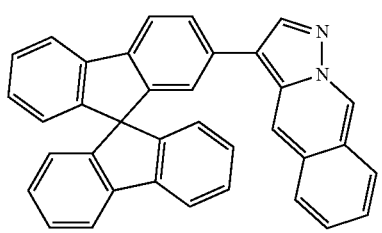
Compound 2-1-136
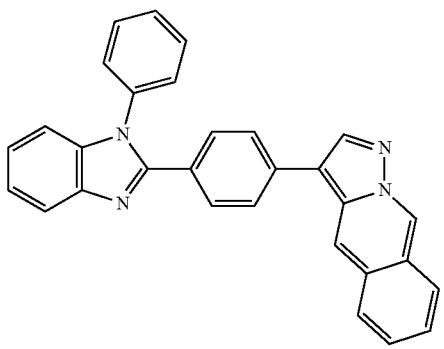
Compound 2-1-137
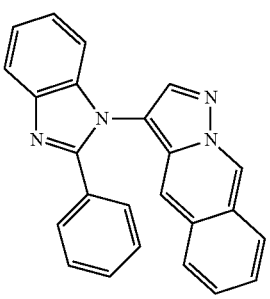
Compound 2-1-138
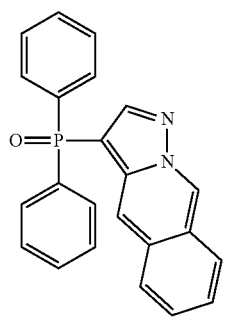
Compound 2-1-139
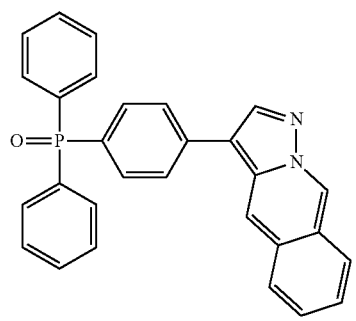
Compound 2-1-140
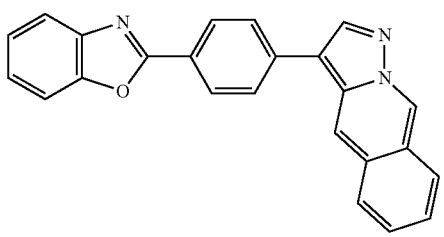

Compound 2-1-141
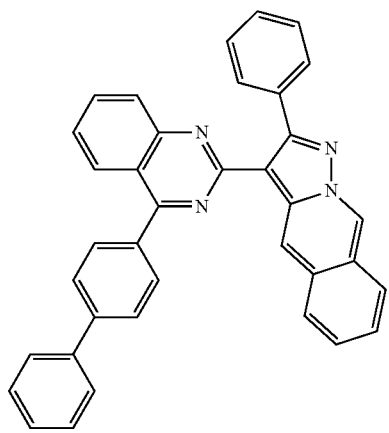
Compound 2-1-144
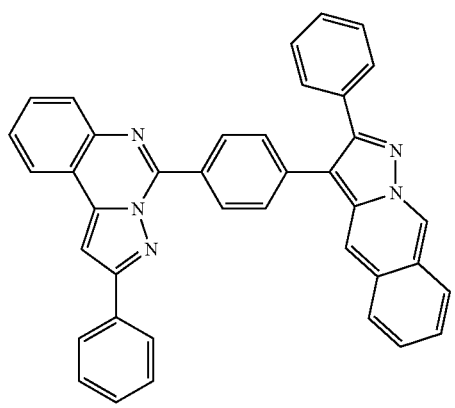
Compound 2-1-145
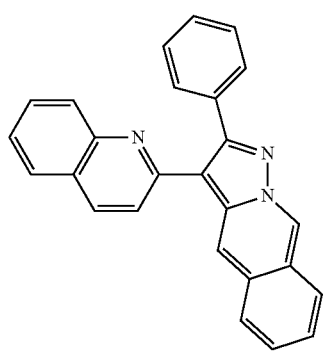
Compound 2-1-142
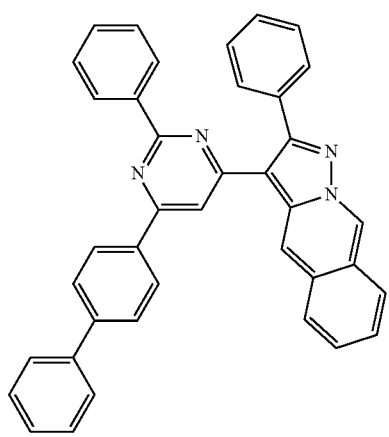
Compound 2-1-146
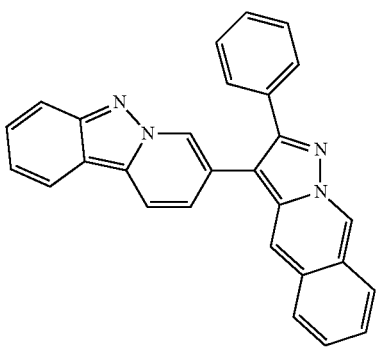
Compound 2-1-143
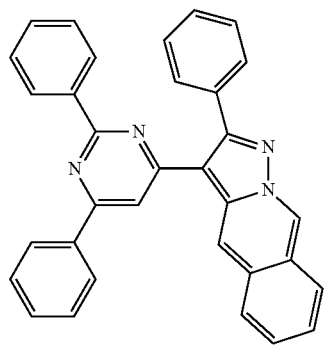
Compound 2-1-147
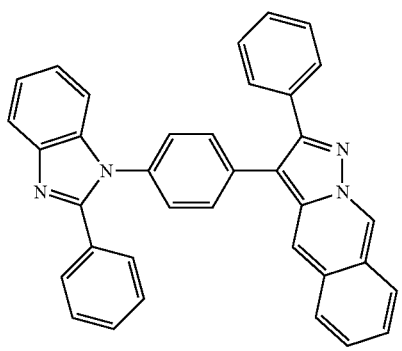

Compound 2-1-148
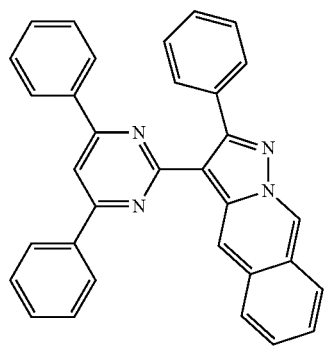
Compound 2-1-152
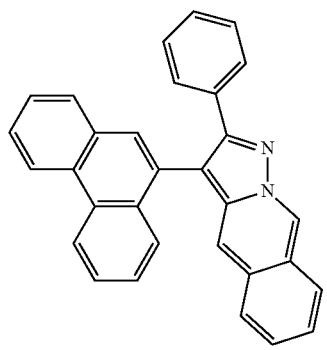
Compound 2-1-149
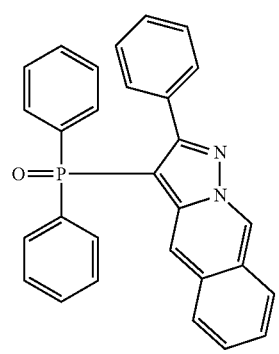
Compound 2-1-153
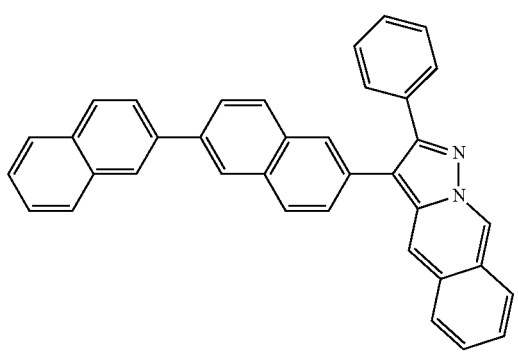
Compound 2-1-150
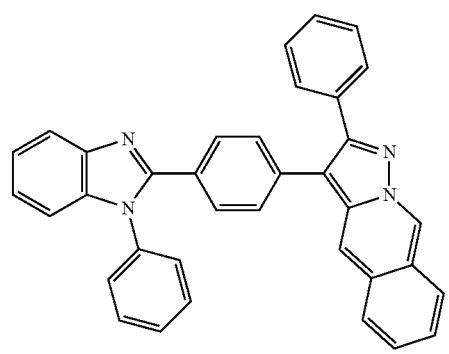
Compound 2-1-154
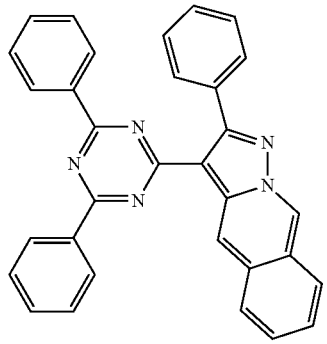
Compound 2-1-151
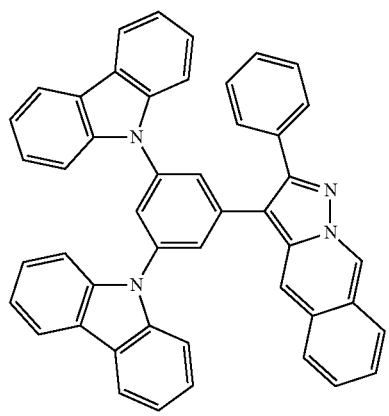
Compound 2-1-155
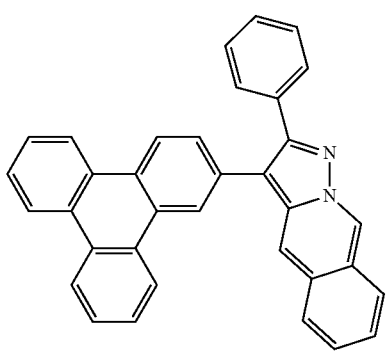

Compound 2-1-156
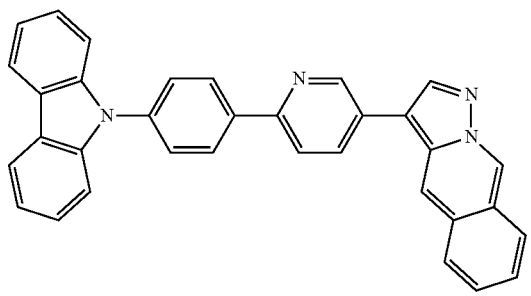
Compound 2-1-157
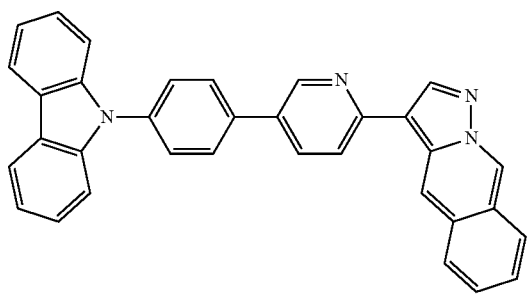
Compound 2-1-158
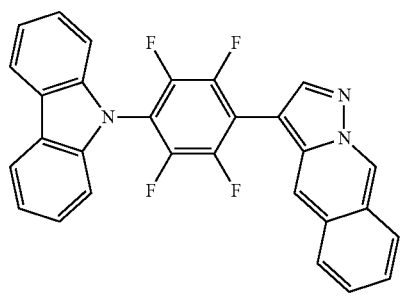
Compound 2-1-159
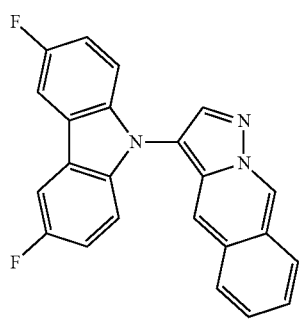
Compound 2-1-160
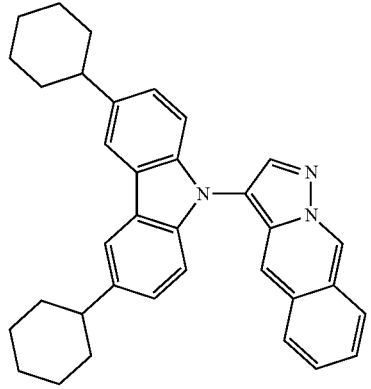
Compound 2-1-161
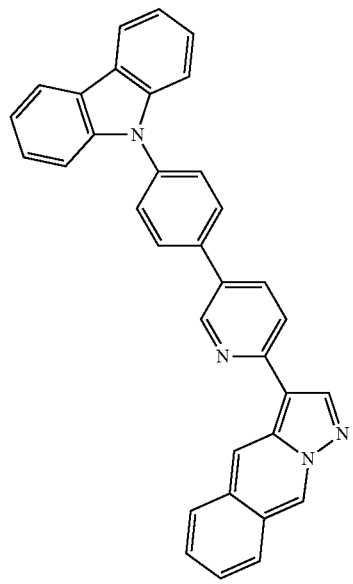
Compound 2-1-162
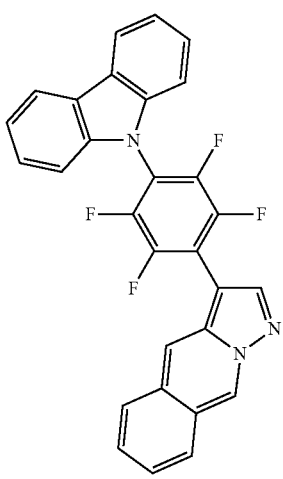

-continued
Compound 2-1-163
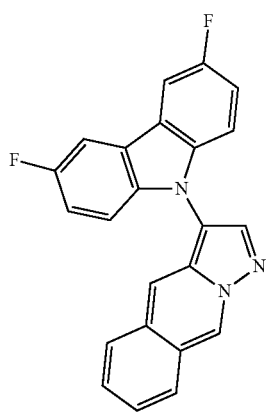
Compound 2-1-164
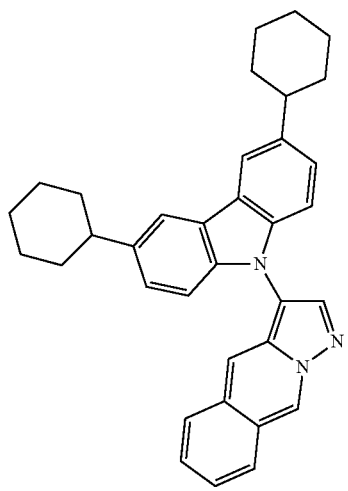
Compound 2-1-165
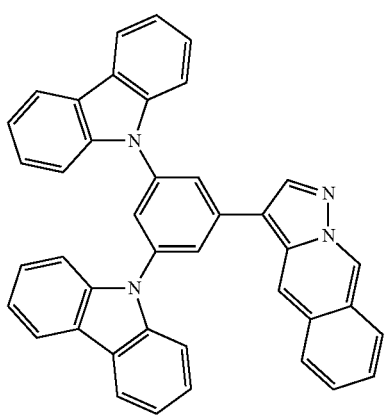
Compound 2-1-166
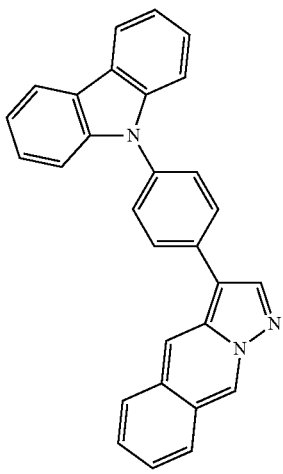
Compound 2-1-167
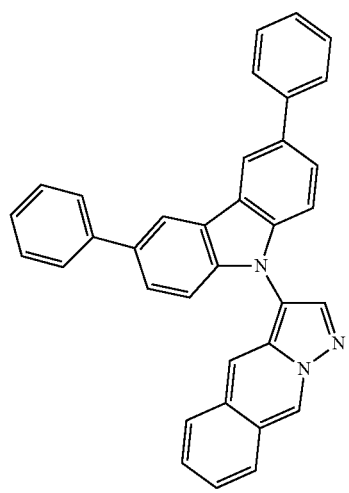
Compound 2-1-168
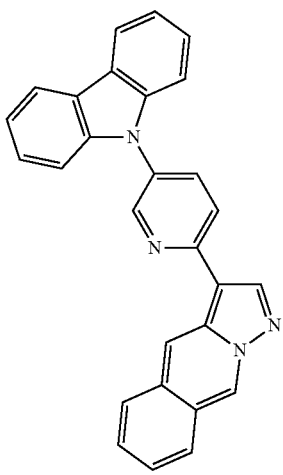

Compound 2-1-169
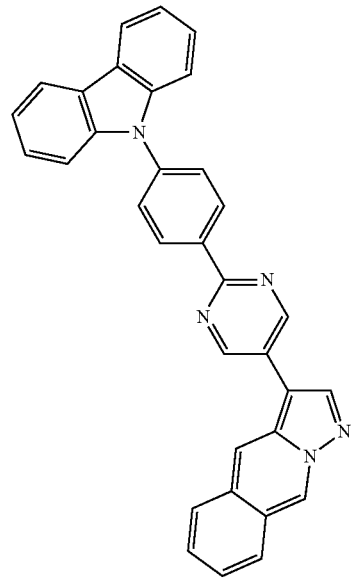
Compound 2-1-170
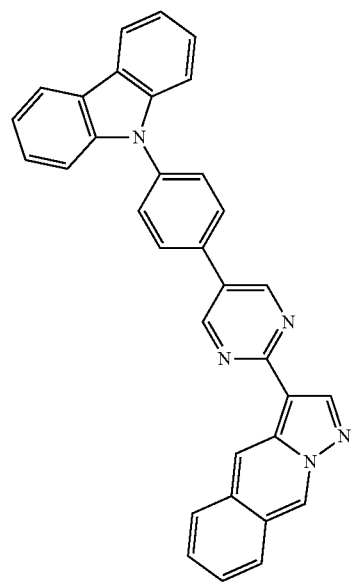
Compound 2-1-171
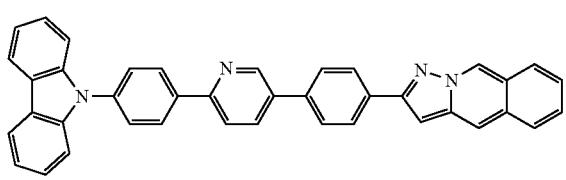
Compound 2-1-172
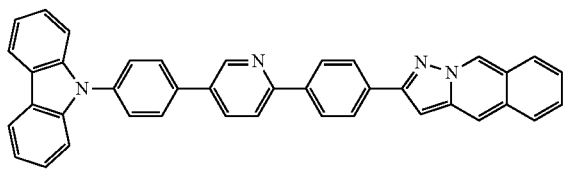
Compound 2-1-173
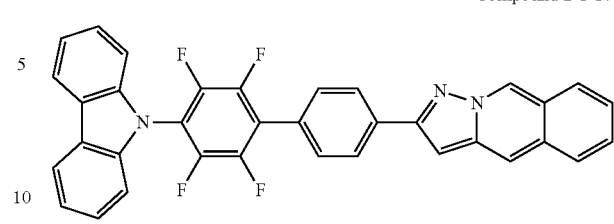
Compound 2-1-174
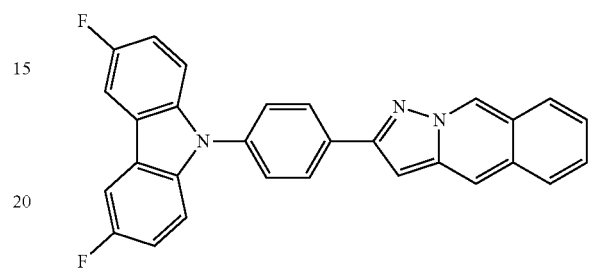
Compound 2-1-175
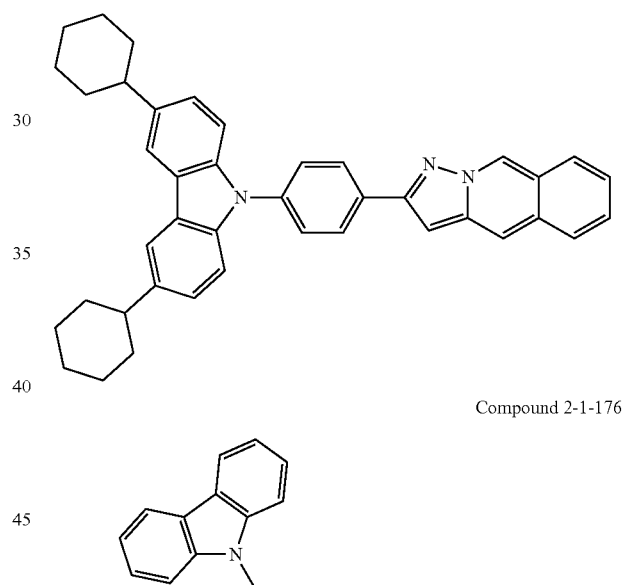
Compound 2-1-176
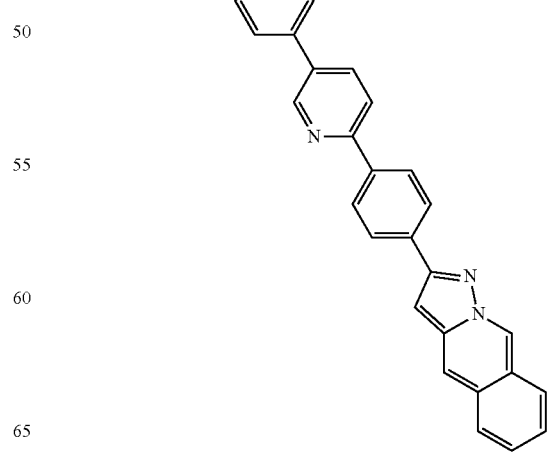

Compound 2-1-177
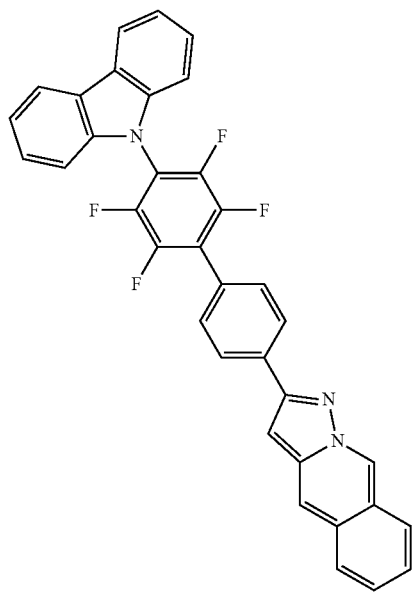
Compound 2-1-178
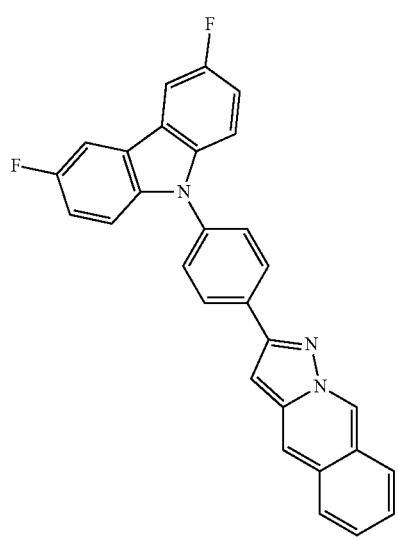
Compound 2-1-179
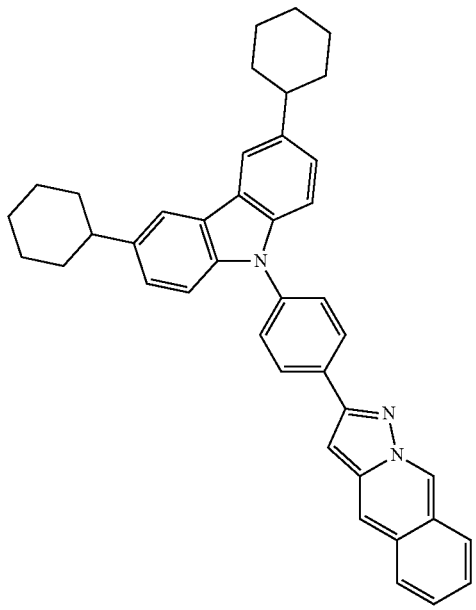
Compound 2-1-180
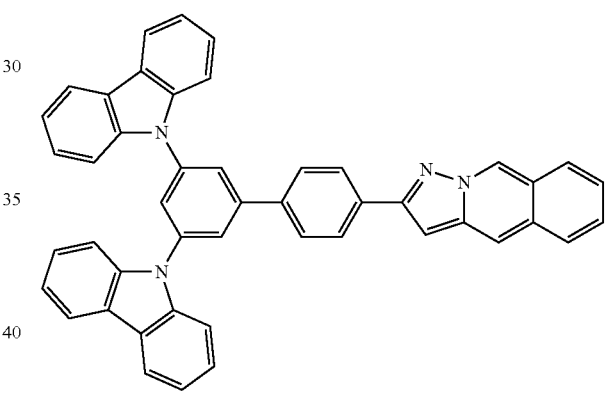
Compound 2-1-181
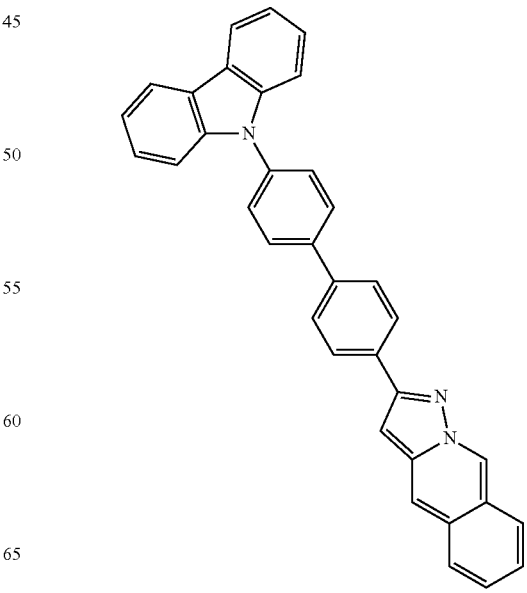

Compound 2-1-182
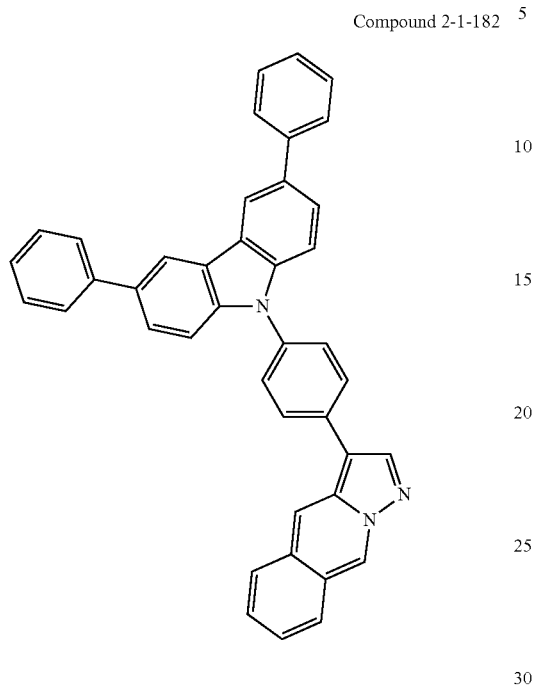
Compound 2-1-184
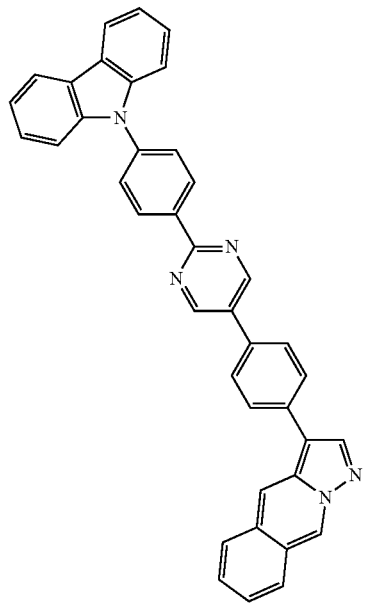
Compound 2-1-183
Compound 2-1-185
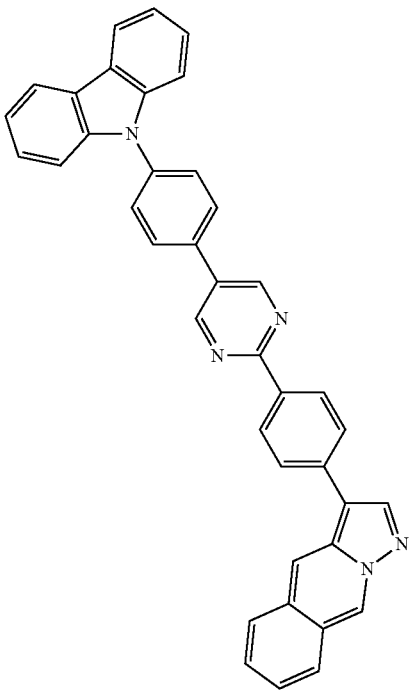

Compound 2-1-186
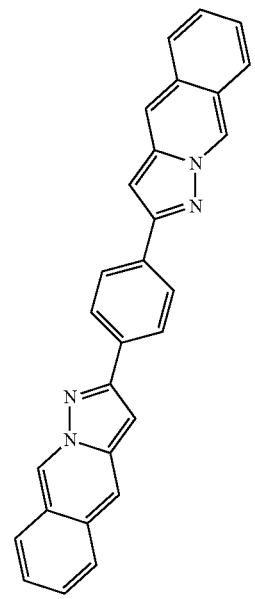
Compound 2-1-187
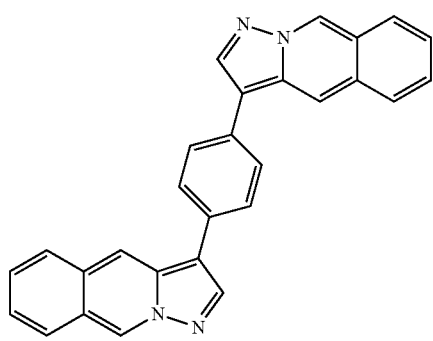
Compound 2-1-188
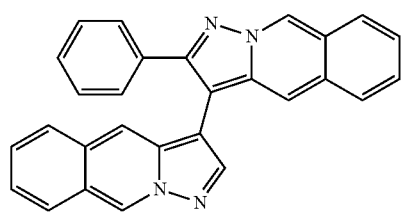
Compound 2-1-189
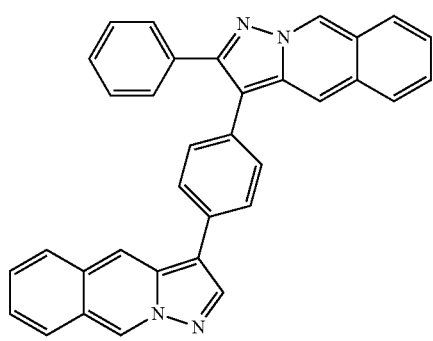
Compound 2-1-190
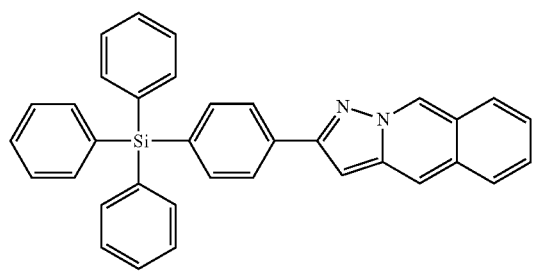
Compound 2-1-191
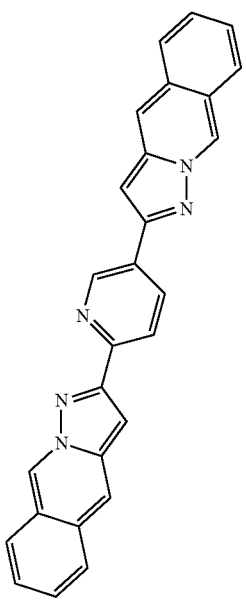
Compound 2-1-192
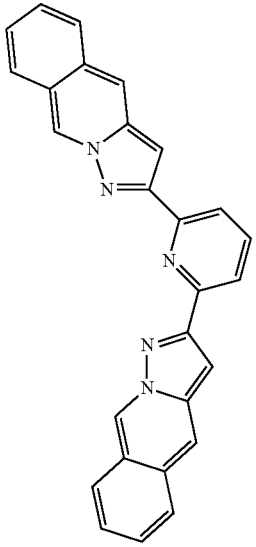

Compound 2-1-193
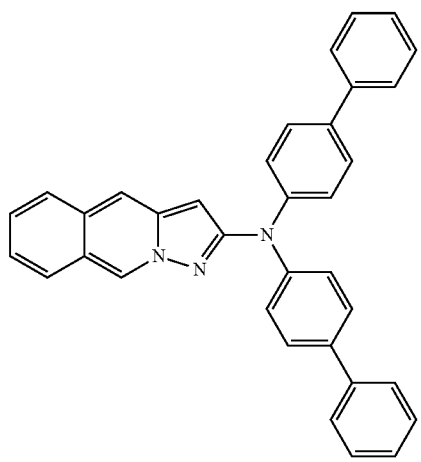
Compound 2-1-194
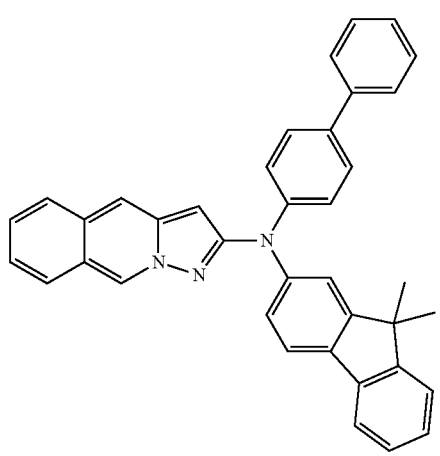
Compound 2-1-195
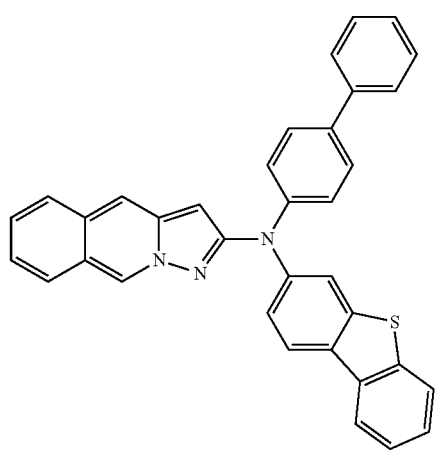
Compound 2-1-196
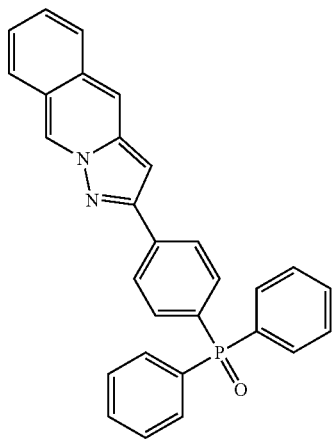
Compound 2-1-197
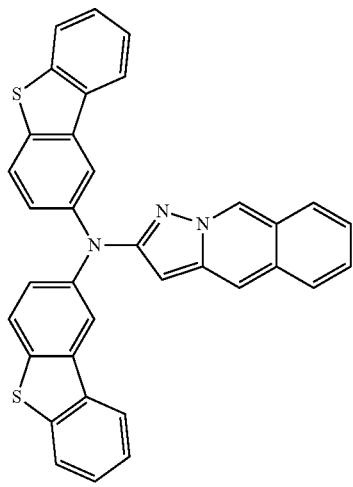
Compound 2-1-198
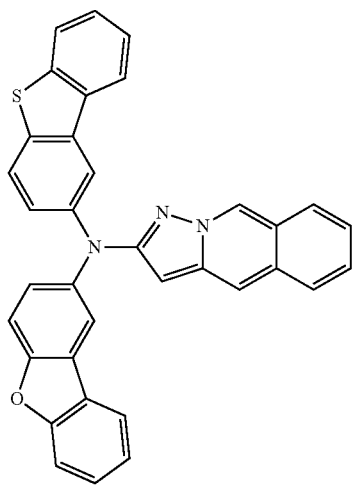

Compound 2-1-199
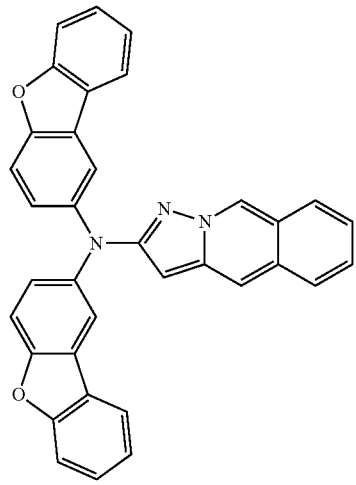
Compound 2-1-200
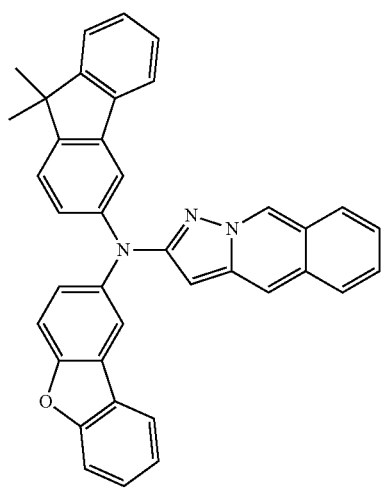
Compound 2-1-201
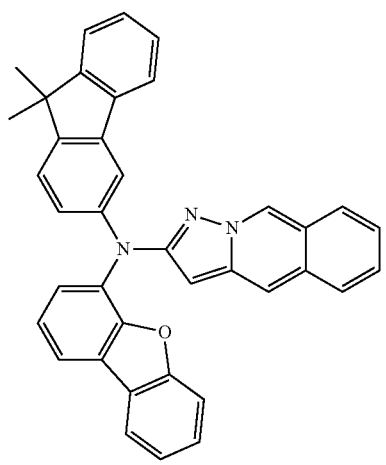
Compound 2-1-202
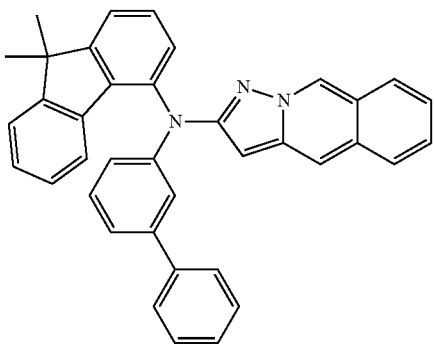
Compound 2-1-203
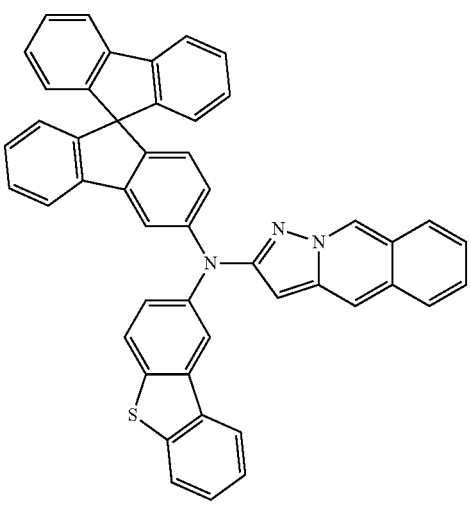
Compound 2-1-204
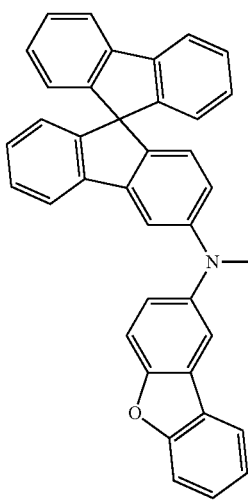

Compound 2-1-205
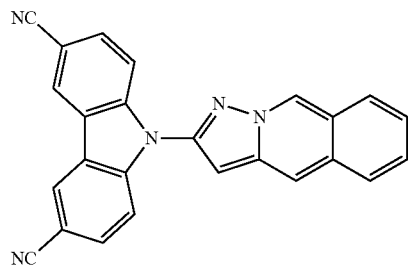
Compound 2-1-206
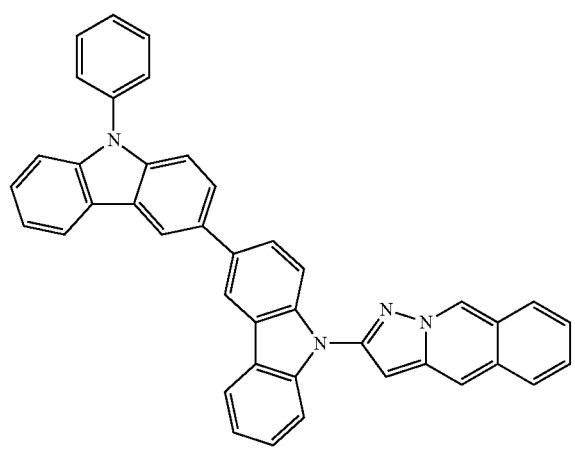
Compound 2-1-207
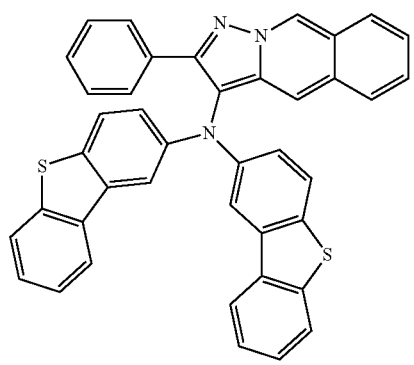
Compound 2-1-208
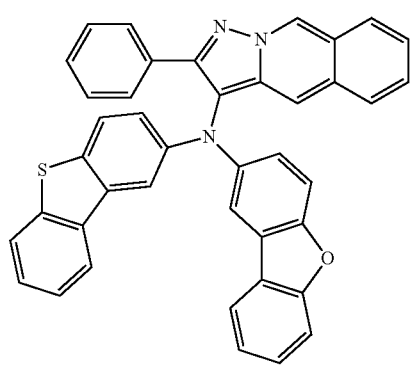
Compound 2-1-209
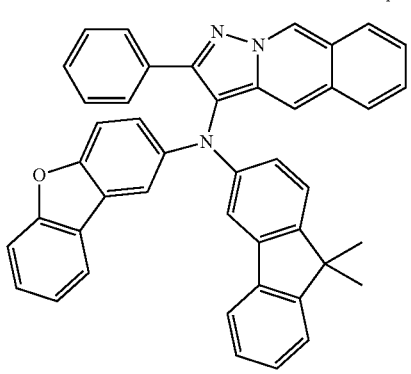
Compound 2-1-210
Compound 2-1-211
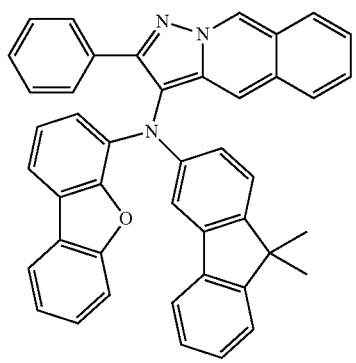
Compound 2-1-212
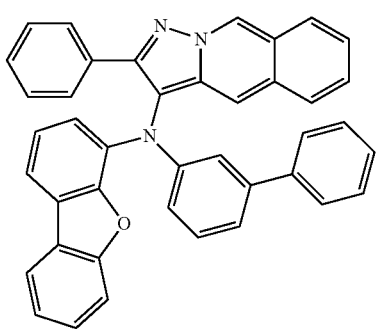

Compound 2-1-213

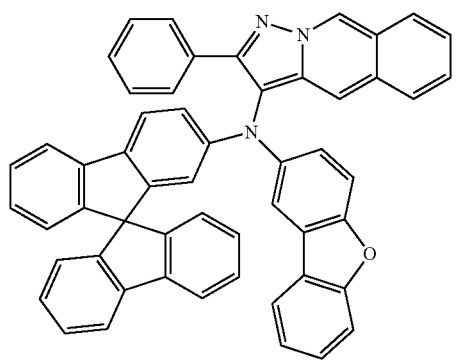

Compound 2-1-214

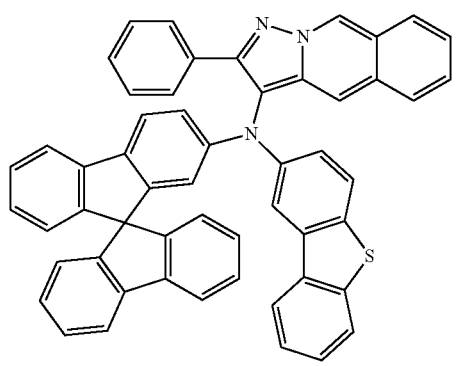

Compound 2-1-215

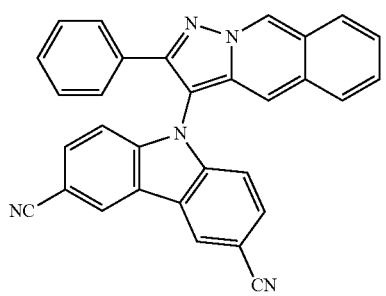

Compound 2-1-216

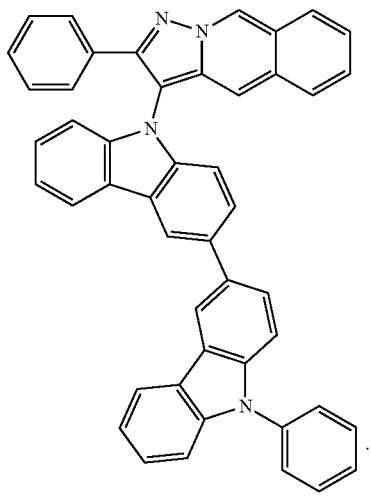

11. An organic light emitting device comprising:
a positive electrode;
a negative electrode; and
one or more organic material layers provided between the positive electrode and the negative electrode,
wherein one or more layers of the organic material layers comprise the hetero-cyclic compound of claim 1.

12. The organic light emitting device of claim 11, wherein the organic material layer comprise at least one layer of a hole blocking layer, an electron injection layer, and an electron transport layer, and at least one layer of the hole blocking layer, the electron injection layer, and the electron transport layer comprises the hetero-cyclic compound.

13. The organic light emitting device of claim 11, wherein the organic light emitting layer comprises a light emitting layer, and the light emitting layer comprises the hetero-cyclic compound.

14. The organic light emitting device of claim 11, wherein the organic material layer comprises one or more layers of a hole injection layer, a hole transport layer, and a layer which injects and transports holes simultaneously, and one layer of the layers comprises the hetero-cyclic compound.

* * * * *